US012790593B2

(12) United States Patent
Wagner et al.

(10) Patent No.: US 12,790,593 B2
(45) Date of Patent: Nov. 10, 2026

(54) SYSTEMS AND METHODS FOR CELL MANUFACTURING

(71) Applicant: Cellino Biotech, Inc., Cambridge, MA (US)

(72) Inventors: Matthias Wagner, Cambridge, MA (US); Suvi Aivio, Arlington, MA (US); Catherine Pilsmaker, Arlington, MA (US); Mariangela Amenduni, Arlington, MA (US); Arnaldo Pereira, Cambridge, MA (US); Sangkyun Lee, Newton, MA (US); Scott Luro, Somerville, MA (US); Stefanie Morgan, Hanover, MA (US); Matthew Sullivan, Westwood, MA (US); Maya Berlin-Udi, Acton, MA (US); Deniz Aksel, Cambridge, MA (US); Jason Natale, Cambridge, MA (US)

(73) Assignee: Cellino Biotech, Inc., Cambridge, MA (US)

( * ) Notice: Subject to any disclaimer, the term of this patent is extended or adjusted under 35 U.S.C. 154(b) by 622 days.

(21) Appl. No.: 18/234,321

(22) Filed: Aug. 15, 2023

(65) Prior Publication Data

US 2024/0067916 A1 Feb. 29, 2024

Related U.S. Application Data

(60) Provisional application No. 63/521,223, filed on Jun. 15, 2023, provisional application No. 63/472,370,
(Continued)

(51) Int. Cl.
*C12N 5/074* (2010.01)
*C12M 1/00* (2006.01)
(Continued)

(52) U.S. Cl.
CPC ........... *C12N 5/0696* (2013.01); *C12M 23/22* (2013.01); *C12M 23/40* (2013.01); *C12M 25/04* (2013.01);
(Continued)

(58) Field of Classification Search
CPC ...... C12M 23/16; C12M 23/22; C12M 23/40; C12M 25/04; C12M 33/00; C12M 33/02;
(Continued)

(56) References Cited

U.S. PATENT DOCUMENTS

| | | | |
|---|---|---|---|
| 8,802,435 B2 | 8/2014 | Qian et al. | |
| 2004/0077073 A1* | 4/2004 | Schindler | C12M 47/04 604/20 |

(Continued)

FOREIGN PATENT DOCUMENTS

| | | |
|---|---|---|
| JP | 6543954 B2 | 7/2019 |
| WO | WO-2020/033871 A1 | 2/2020 |

(Continued)

OTHER PUBLICATIONS

Invitation to Pay Additional Fees for Application No. PCT/US23/30293 dated Nov. 9, 2023.

(Continued)

*Primary Examiner* — Michael L Hobbs
(74) *Attorney, Agent, or Firm* — Foley Hoag LLP; David P. Halstead; Erik A. Huestis

(57) ABSTRACT

Systems and methods are disclosed for processes related to cell culture and generation. A system for culturing cells a cell culture container comprises a first surface, the first surface being configured for a plurality of cell colonies to continuously adhere thereto throughout a cell culture process; an image sensor configured to capture one or more time-series images of the plurality of cell colonies during the cell culture process; a cell removal tool configured to
(Continued)

remove one or more cells from the first surface of the cell culture container during the cell culture process; and a computing subsystem configured to: track one or more characteristics of the plurality of cell colonies based on the one or more time-series images, and control the cell removal tool to remove cells based on the one or more characteristics.

26 Claims, 99 Drawing Sheets

Related U.S. Application Data filed on Jun. 12, 2023, provisional application No. 63/374,899, filed on Sep. 7, 2022, provisional application No. 63/373,026, filed on Aug. 19, 2022, provisional application No. 63/373,029, filed on Aug. 19, 2022, provisional application No. 63/371,844, filed on Aug. 18, 2022, provisional application No. 63/371,730, filed on Aug. 17, 2022, provisional application No. 63/371,614, filed on Aug. 16, 2022, provisional application No. 63/371,491, filed on Aug. 15, 2022.

(51) Int. Cl.

| | |
|---|---|
| ***C12M 1/12*** | (2006.01) |
| ***C12M 1/26*** | (2006.01) |
| ***C12M 1/30*** | (2006.01) |
| ***C12M 1/34*** | (2006.01) |
| ***C12M 1/36*** | (2006.01) |
| ***C12M 1/42*** | (2006.01) |
| *C12N 5/07* | (2010.01) |

(52) U.S. Cl.

CPC ............ *C12M 33/02* (2013.01); *C12M 33/04* (2013.01); *C12M 35/02* (2013.01); *C12M 41/10* (2013.01); *C12M 41/46* (2013.01); *C12M 41/48* (2013.01); *C12M 47/04* (2013.01); *C12N 5/06* (2013.01)

(58) Field of Classification Search

CPC ...... C12M 33/04; C12M 25/02; C12M 41/10; C12M 41/46; C12M 41/48; C12M 47/04; C12N 5/06; C12N 5/0696

See application file for complete search history.

(56) References Cited

U.S. PATENT DOCUMENTS

| | | | |
|---|---|---|---|
| 2011/0297950 A1 | 12/2011 | Kato et al. | |
| 2014/0360576 A1 | 12/2014 | Plotnikov et al. | |
| 2017/0183627 A1 | 6/2017 | Fossati et al. | |
| 2021/0403942 A1 | 12/2021 | Wang et al. | |
| 2023/0051840 A1* | 2/2023 | Kelso | C12M 45/07 |
| 2024/0052321 A1 | 2/2024 | Wagner et al. | |
| 2024/0067914 A1 | 2/2024 | Wagner et al. | |
| 2024/0067917 A1 | 2/2024 | Wagner et al. | |

FOREIGN PATENT DOCUMENTS

| | | |
|---|---|---|
| WO | WO-2021/150631 A1 | 7/2021 |
| WO | WO-2021/243203 A1 | 12/2021 |
| WO | WO-2024/039688 A2 | 2/2024 |

OTHER PUBLICATIONS

Case et al., "In vitro clonal analysis of murine pluripotent stem cells isolated from skeletal muscle and adipose stromal cells" Exp Hematol, 36(2): 224-234 (2008).
International Search Report and Written Opinion for International Application No. PCT/US23/30293 dated Feb. 16, 2024.
Kawata, "Plasmonics for Nanoimaging and Nanospectroscopy" Focal Point Review, vol. 67, No. 2 (2013).
Wang et al., "Rapid and efficient reprogramming of somatic cells to induced pluripotent stem cells by retinoic acid receptor gamma and liver receptor homolog 1" PNAS, vol. 108, No. 45 (2011).
Ye et al., "Induced Pluripotent Stem Cells and Their Potential for Basic and Clinical Sciences" Current Cardiology Reviews, vol. 9, p. 63-72 (2013).

* cited by examiner

4000

4100

4300

4400

7900

7902a
7902b
7902c
7902d 7902a
7902b
7902c
7902d

7902d

7902d

7904

7904

7906

SPATIAL COLONY EXPANSION

SPATIAL COLONY EXPANSION

SYSTEMS AND METHODS FOR CELL MANUFACTURING

RELATED APPLICATION(S)

This application claims the benefit of priority to U.S. Provisional Application No. 63/371,491, filed Aug. 15, 2022, U.S. Provisional Application No. 63/371,614, filed Aug. 16, 2022, U.S. Provisional Application No. 63/371,730, filed Aug. 17, 2022, U.S. Provisional Application No. 63/371,844, filed Aug. 18, 2022, U.S. Provisional Application No. 63/373,026, filed Aug. 19, 2022, U.S. Provisional Application No. 63/373,029, filed Aug. 19, 2022, U.S. Provisional Application No. 63/374,899, filed Sep. 7, 2022, U.S. Provisional Application No. 63/472,370, filed Jun. 12, 2023, and U.S. Provisional Application No. 63/521,223, filed Jun. 15, 2023, each of which are incorporated herein by reference in their entirety.

TECHNICAL FIELD

The disclosure is generally directed to automated cell culture systems, and in particular, to quickly and accurately producing output cell products scalable to enable large scale biological manufacturing.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

The stochastic nature of cell processes has long plagued biological manufacturing efforts. This has been particularly true of processes in mammalian cells that involve phenotype transitions, for example induced pluripotent stem cell (iPSC) reprogramming or stem cell differentiation into targets cells or trans-differentiation. Additionally, processes including gene editing, which may be combined with the above processes, add yet more process variability. Finally, patient-specific processes, such as those for autologous cell therapies or patient-specific drug discovery, are notoriously unpredictable. As a result, many cell processes are so variable, low-yielding, and/or labor intensive that they do not reach the clinic. Even if they do, the low yields, labor requirements, required purification and sorting steps, and multiple transfers between cell culture containers make the process extremely expensive and unscalable to a large patient population.

One current approach for large scale biological manufacturing involves the use of large bioreactors, such as stirred bioreactors, in which cells are cultured in suspension, often in clumps/aggregates or on microcarriers. However, yields from such bulk processes are typically inefficient, manually managed 2-dimensional cell culture vessels. The advantage of the bioreactor approach is sheer volume of cells, but the process has virtually no feedback control to account for lot-to-lot, patient-to-patient or clone-to-clone variability. Filtration steps may be added to refine the cell product, but these often reduce the viability or functionality of the cell product and can have enormous yield impacts. A deviation in cell behavior early in the process may cause catastrophically low yield or performance on quality control (QC) assays and is almost never detectable until the end of the process.

The manual approach in 2D cell culture vessels seeks to address this variability by adding a highly-trained operator or scientist to make observations and "edits" to the cell culture. Most often these edits take the form of selective transfer from one culture container/vessel to another, repeated on a regular basis as the cell culture grows to maximum density, often due to the growth of undesirable cells alongside the target cells. While this manual process can eliminate gross deviations in the cell culture process, the subjective decision making (often based on single timepoint views through a dissection microscope), manual mechanical manipulation of cells and colonies, and frequent transfer between cell culture containers make this process expensive, unscalable, and prone to a high degree of variability and subject to contamination unless performed in dedicated, expensive, high-grade cleanroom facilities. Automation would solve some of these issues, but objective evaluation of the quality of cell cultures during the cell culture process is lacking. Thus, a fast, accurate, automated, and scalable system for biological manufacturing is needed.

SUMMARY

According to certain aspects of the present disclosure, systems and methods for including an automated cell culture system to quickly and accurately produce output cell products and that is easily scalable to enable large scale biological manufacturing are disclosed.

In an embodiment, a system for culturing cells comprises a cell culture container comprising a first surface, the first surface being configured for a plurality of cell colonies to continuously adhere thereto throughout a cell culture process; an image sensor configured to capture one or more time-series images of the plurality of cell colonies during the cell culture process; a cell removal tool configured to remove one or more cells from the first surface of the cell culture container during the cell culture process; and a computing subsystem configured to: track one or more characteristics of the plurality of cell colonies based on the one or more time-series images, and control the cell removal tool to remove cells based on the one or more characteristics.

In some embodiments, the cell culture process comprises manufacturing a plurality of clonal induced pluripotent stem cells (iPSCs) from a plurality of somatic cells.

In some embodiments, the cell culture process further comprises: reprogramming the plurality of somatic cells to form a plurality of iPSC colonies and wherein the computing subsystem is further configured to: maintain a cell density of the plurality of iPSC cell colonies below a first threshold; select a first clonal iPSC cell colony from the plurality of iPSC cell colonies; remove the plurality of iPSC cell colonies from the first surface except for the first clonal iPSC cell colony; and maintain a cell density of the first clonal iPSC cell colony below a second threshold amount while the first clonal iPSC colony expands.

In some embodiments, the first threshold is one of 750,000 cells/cm$^2$, 500,000 cells/cm$^2$, 400,000 cells/cm$^2$, 300,000 cells/cm$^2$, or 250,000 cells/cm$^2$.

In some embodiments, the second threshold is one of 750,000 cells/cm$^2$, 500,000 cells/cm$^2$, 400,000 cells/cm$^2$, 300,000 cells/cm$^2$, or 250,000 cells/cm$^2$.

In some embodiments, the cell culture process has a duration of one of: at least 7 days, at least 10 days, at least 20 days, at least 30 days, at least 45 days, or at least 60 days.

In some embodiments, maintaining the cell density of the plurality of iPSC cell colonies below the first threshold comprises iteratively removing portions of the plurality of iPSC cell colonies and expanding a remainder of the plurality of iPSC cell colonies.

In some embodiments, selecting the first clonal iPSC cell colony is based on the one or more characteristics.

In some embodiments, the first clonal iPSC cell colony has a highest clonal quality among the plurality of iPSC cell colonies based on the one or more characteristics.

In some embodiments, the cell culture process further comprises extracting a portion of the first clonal iPSC cell colony from the first cell culture container.

In some embodiments, the cell culture process further comprises: profiling the portion of the first clonal iPSC cell colony; and providing a resulting profile to the computing subsystem.

In some embodiments, the computing subsystem is configured to provide the one or more characteristics to a machine learning model and receive therefrom an indication of which cells to remove.

In some embodiments, the cell removal tool comprises a pulsed laser.

In some embodiments, the pulsed laser comprises one or more visible light lasers.

In some embodiments, the first surface comprises a laser film.

In some embodiments, the laser film is semi-transparent and has wavelength-selective absorption.

In some embodiments, the laser film is a plasmonic film.

In some embodiments, the laser film is configured to enable light-based cell imaging.

In some embodiments, the light-based cell imaging is within an imaging wavelength range detectible by the image sensor.

In some embodiments, the laser film is further configured to enable light-based cell removal within a removal wavelength range emitted by the pulsed laser, the removal wavelength range different from the imaging wavelength range.

In some embodiments, the laser film is absorptive of optical energy from the pulsed laser, thereby removing the one or more cells from the first surface.

In some embodiments, the laser film is at least partially absorptive of optical energy from the pulsed laser within a first range of wavelengths and at least partially transmissive of optical energy to the imaging sensor within a second range of wavelengths.

In some embodiments, the one or more characteristics are selected from: cell proliferation rate, cell count, colony surface area, colony area growth rate, colony morphology, and fluorescent marker expression.

In some embodiments, the cell removal tool comprises a continuous wave laser.

In some embodiments, the first surface comprises a laser film and a biocoating and wherein the continuous wave laser is configured to ablate the biocoating.

In an embodiment, a method for culturing cells, comprises introducing a plurality of cell colonies to a first surface of a cell culture container; capturing one or more time-series images of the plurality of cell colonies by an image sensor during a cell culture process; tracking, by a computing subsystem, one or more characteristics of the plurality of cell colonies based on the one or more time-series images; and controlling, by the computing subsystem, a cell removal tool to remove one or more cell colony from the first surface of the cell culture container during the cell culture process based on the one or more characteristics.

In an embodiment, a computer program product for culturing cells comprises a computer readable storage medium having program instructions embodied therewith, the program instructions executable by a processor to cause the processor to perform a method comprising: receiving one or more time-series images of a plurality of cell colonies captured during a cell culture process; tracking, by a computing subsystem, one or more characteristics of the plurality of cell colonies based on the one or more time-series images; and controlling, by the computing subsystem, a cell removal tool to remove one or more cell colony from a substrate during the cell culture process based on the one or more characteristics.

In an embodiment, a system for culturing cells, comprises a cell culture container comprising a first surface, the first surface being configured for one or more cell colonies to adhere thereto; an image sensor configured to capture one or more time-series images of a first cell colony in the one or more cell colonies; a computing subsystem configured to iteratively manage a surface area of the first cell colony according to a method comprising: calculating the surface area of the first cell colony as the first cell colony proliferates, selecting a portion of the first cell colony to remove to reduce the surface area of the first cell colony when its surface area is above a predetermined threshold, and removing, using a cell removal tool, the selected portion of the first cell colony from the first surface.

In some embodiments, the surface area is calculated based on the one or more time-series images of the first cell colony.

In some embodiments, iteratively managing the surface area of the first cell colony comprises increasing clonality of the first cell colony over time.

In some embodiments, the portion of the first cell colony is selected such that a remainder of the first cell colony translates across the first surface as it proliferates In some embodiments, the first surface comprises an extracellular matrix and wherein cell removal tool is configured to remove the extracellular matrix from under the selected portion of the first cell colony.

In some embodiments, an absence of the extracellular matrix over a region inhibits cells from proliferating in the region.

In some embodiments, the cell removal tool comprises a continuous wave laser system.

In some embodiments, the cell removal tool comprises a pulsed laser system.

In some embodiments, the first surface comprises a laser film.

In some embodiments, the laser film is absorptive of optical energy from the pulsed laser, thereby removing one or more cells adhered to the laser film.

In some embodiments, the laser film is at least partially absorptive of optical energy from the pulsed laser within a first range of wavelengths and at least partially transmissive of optical energy to the imaging sensor within a second range of wavelengths.

In some embodiments, the laser film is semi-transparent and has wavelength selective absorption.

In some embodiments, the laser film is a plasmonic film.

In some embodiments, the laser film is configured to enable light-based cell imaging.

In some embodiments, the light-based cell imaging is within an imaging wavelength range emitted by the image sensor.

In some embodiments, the laser film is further configured to enable light-based cell removal within a removal wavelength range emitted by the source of electromagnetic radiation, the removal wavelength range different from the imaging wavelength range.

In some embodiments, the first surface is configured for the first cell colony to remain continuously adhered thereto during said iterative management.

In some embodiments, iteratively managing the surface area of the first cell colony comprises managing a cell density of the first cell colony.

In some embodiments, the predetermined threshold is an increase in surface area that is one of 5, 10, 20, 30, 50, or 100 times an initial surface area of the first cell colony.

In an embodiment, a method for culturing cells comprises: introducing a plurality of cell colonies to a first surface of a cell culture container; capturing one or more time-series images of a first cell colony in the one or more cell colonies; calculating a surface area of the first cell colony as the first cell colony proliferates; selecting a portion of the first cell colony to remove to reduce the surface area of the first cell colony when its surface area is above a predetermined threshold, and removing, using a cell removal tool, the selected portion of the first cell colony from the first surface.

In an embodiment, a computer program product comprises a computer readable storage medium having program instructions embodied therewith, the program instructions executable by a processor to cause the processor to perform a method comprising: capturing one or more time-series images of a first cell colony; calculating a surface area of the first cell colony as the first cell colony proliferates; selecting a portion of the first cell colony to remove to reduce the surface area of the first cell colony when its surface area is above a predetermined threshold; and removing, using a cell removal tool, the selected portion of the first cell colony from the surface area.

In an embodiment, a system for culturing cells, comprises: a cell culture container comprising a closed cell culture chamber enclosing a fluid media and a first surface configured for a cell culture to adhere thereto; a cell removal tool configured to selectively remove one or more cells from the first surface of the cell culture container; and a controller configured to iteratively remove one or more cells using the cell removal tool and thereby maintain the cell culture below a threshold density throughout a cell culture process, wherein the cell culture chamber is configured to seal during the cell culture process.

In some embodiments, the cell culture comprises one or more cell colonies.

In some embodiments, iterative removal of one or more cells comprises removing a portion of a first cell colony of the one or more cell colonies.

In some embodiments, the portion is selected such that a remainder of the first cell colony after removal of the portion of the first cell colony translates across the first surface.

In some embodiments, iterative removal of one or more cells comprises splitting a first cell colony in the one or more cell colonies into a plurality of sub-colonies.

In some embodiments, the cell removal tool is further configured to detach a first sub-colony in the plurality of sub-colonies from the first surface.

In some embodiments, the cell culture container further comprises a fluid port configured to remove the first sub-colony.

In some embodiments, the cell removal tool is further configured to translate the first sub-colony to a first region of the first surface, wherein the fluid media flushes cells from the first region through the fluid port.

In some embodiments, the iterative removal of the one or more cells comprises increasing a size and a confluence of the cell culture.

In some embodiments, the cell removal tool comprises a continuous wave laser.

In some embodiments, the cell removal tool comprises a pulsed laser.

In some embodiments, the pulsed laser comprises one or more ultraviolet visible light lasers.

In some embodiments, the first surface comprises a laser film.

In some embodiments, the laser film is absorptive of optical energy from the pulsed laser, thereby removing the one or more cells from the first surface.

In some embodiments, the laser film is at least partially absorptive of optical energy from the pulsed laser within a first range of wavelengths and at least partially transmissive of optical energy within a second range of wavelengths.

In some embodiments, the first surface is configured for the cell culture to remain continuously adhered thereto throughout the cell culture process.

In some embodiments, the cell culture process comprises reprogramming and expanding of induced pluripotent stem cells.

In some embodiments, the threshold density is one of 750,000 cells/cm$^2$, 500,000 cells/cm$^2$, 400,000 cells/cm$^2$, 300,000 cells/cm$^2$, or 250,000 cells/cm$^2$.

In some embodiments, the cell culture process has a duration of one of: at least 7 days, at least 10 days, at least 20 days, at least 30 days, at least 45 days, or at least 60 days.

In some embodiments,

In an embodiment, a method of culturing cells, comprising: introducing a plurality of cell colonies to a first surface of a cell culture container, the cell culture container comprising a cell culture chamber enclosing a fluid media and the first surface; sealing the cell culture chamber throughout a cell culture process; and iteratively removing one or more cells from the first surface using a cell removal tool and thereby maintaining the cell culture below a threshold density throughout the cell culture process.

In an embodiment, a computer program product for culturing cells comprises a computer readable storage medium having program instructions embodied therewith, the program instructions executable by a processor to cause the processor to perform a method comprising: iteratively removing one or more cells from a first surface of a cell culture container, the cell culture container comprising a cell culture chamber enclosing a fluid media and the first surface, using a cell removal tool and thereby maintaining the cell culture below a threshold density throughout a cell culture process.

In an embodiment, a method of manufacturing gene-edited cells comprises: seeding a plurality of gene-edited cells into a cell culture container; culturing, by a cell culture system, the plurality of gene-edited cells into a plurality of gene-edited cell colonies; clonalizing, by the cell culture system, the plurality of gene-edited cell colonies by iterative spatially-selective removal of one or more portions from the plurality of gene-edited cell colonies as the colonies proliferate; tracking, by the cell culture system, one or more characteristics of the plurality of gene-edited clonal cell colonies; maintaining, by the cell culture system, a cell density of the plurality of gene-edited clonal cell colonies based on the tracked characteristics; selecting, by the cell culture system, a first gene-edited clonal cell colony from the plurality of gene-edited clonal cell colonies; removing, by the cell culture system, the plurality of gene-edited clonal cell colonies from the cell culture container except for the first gene-edited clonal cell colony; and expanding, by the cell culture system, the first gene-edited clonal cell colony.

In some embodiments, the method further comprises harvesting, by the cell culture system, at least a portion of the first gene-edited clonal cell colony.

In some embodiments, the method further comprises using the harvested portion of the first gene-edited clonal cell colony in a cell therapy.

In some embodiments, the plurality of gene-edited cells comprises gene-edited induced pluripotent stem cells.

In some embodiments, clonalizing comprises: a) expanding, by the cell culture system, the plurality of gene-edited cell colonies; b) removing, by the cell culture system, a portion of each of the plurality of cell colonies; and c) repeating steps a) to b), wherein each iteration increases a percentage of clonal cells in each of the plurality of gene-edited cell colonies.

In some embodiments, the one or more characteristics comprise at least one of cell proliferation rate, colony surface area, colony area growth rate, colony morphology, and fluorescent marker expression.

In some embodiments, tracking comprises: capturing, by the cell culture system, a plurality of time-series images of the plurality of gene-edited clonal cell colonies; and determining, by the cell culture system, the tracked characteristics from the plurality of time-series images.

In some embodiments, maintaining comprises: a) expanding, by the cell culture system, the plurality of gene-edited clonal cell colonies; b) determining, by the cell culture system, a region of each of the plurality of gene-edited clonal cell colonies to remove based on the one or more characteristics to maintain the cell density of the plurality of gene-edited clonal cell colonies below a threshold; c) removing, by the cell culture system, the region of each of the plurality of gene-edited clonal cell colonies; and d) repeating steps a) through c) until a target confluence is reached.

In some embodiments, the cell culture system selects the first gene-edited clonal cell colony based on the one or more characteristics.

In some embodiments, the cell culture system comprises at least one of an imaging sensor, a computing subsystem, and a source of electromagnetic radiation.

In some embodiments, the source of electromagnetic radiation comprises a continuous wave laser.

In some embodiments, the source of electromagnetic radiation comprises a pulsed laser.

In some embodiments, the cell culture container comprises a laser film, wherein the plurality of gene-edited cells are cultured on the laser film.

In some embodiments, the laser film is absorptive of optical energy from the pulsed laser, thereby removing cells adhered to the laser film.

In some embodiments, the pulsed laser comprises one or more visible light lasers.

In some embodiments, the laser film is semi-transparent and has wavelength selective absorption.

In some embodiments, the laser film is a plasmonic film.

In some embodiments, the laser film is configured to enable light-based cell imaging.

In some embodiments, the light-based cell imaging is within an imaging wavelength range emitted by the image sensor.

In some embodiments, the laser film is further configured to enable light-based cell removal within a removal wavelength range emitted by the source of electromagnetic radiation, the removal wavelength range different from the imaging wavelength range In some embodiments, the plurality of gene-edited cells, the plurality of gene-edited cell colonies, and the plurality of gene-edited clonal cell colonies are continuously adhered to a first surface of the cell culture container.

In some embodiments, the method has a duration of one of: at least 7 days, at least 10 days, at least 20 days, at least 30 days, at least 45 days, or at least 60 days.

In an embodiment, a system for manufacturing gene-edited cells comprises: a closed cell culture chamber enclosing a fluid media and a first surface configured for a cell culture to adhere thereto; and a cell removal tool configured to selectively remove one or more cells from the first surface, wherein the cell removal tool is further configured to perform a method according to any of the above embodiments.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative implementations, in which the principles of the disclosure are utilized, and the accompanying drawings of which:

Figure 1:
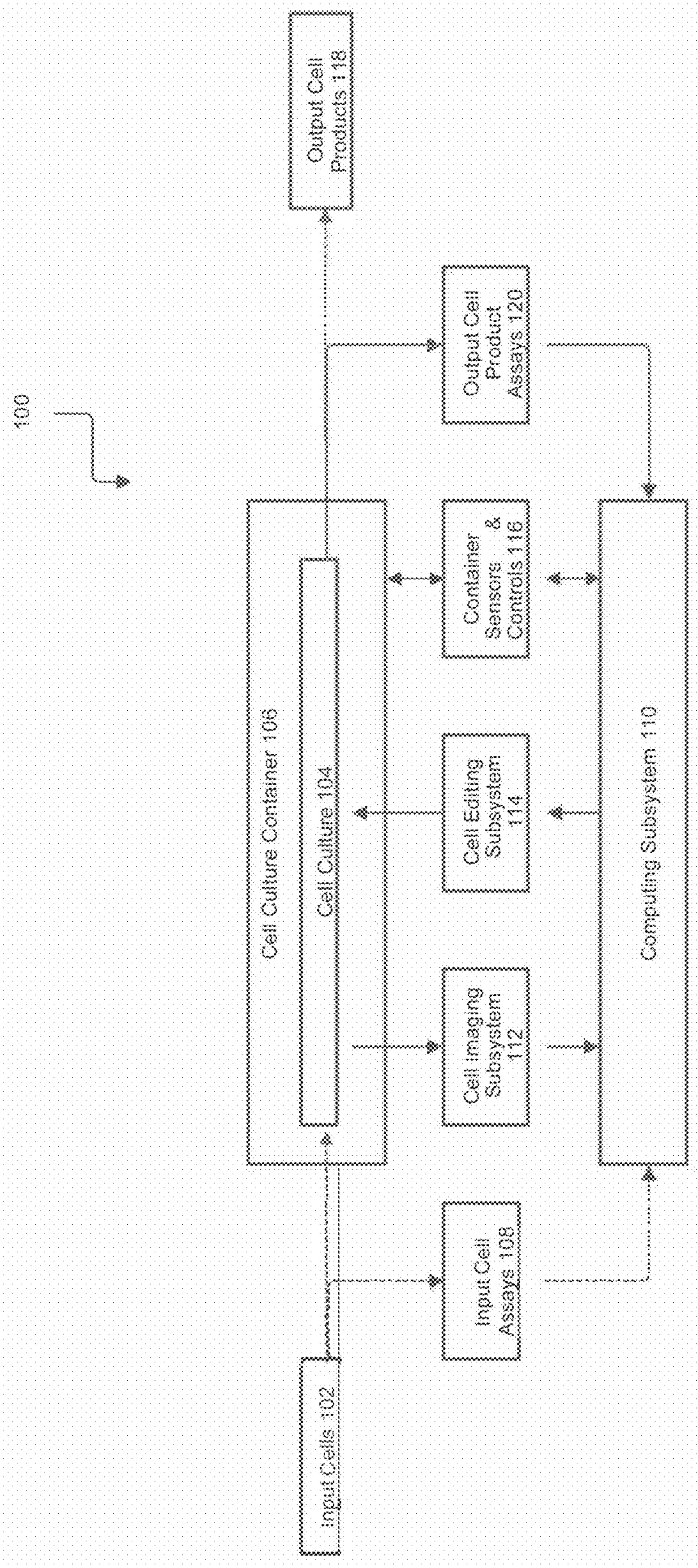
FIG. 1 is a block diagram of a cell culture system in accordance with various implementations.

These and other features of the present implementations will be understood better by reading the following detailed description, taken together with the figures herein described. The accompanying drawings are not intended to be drawn to scale. For purposes of clarity, not every component may be labeled in every drawing.

DETAILED DESCRIPTION

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term “exemplary” is used in the sense of “example,” rather than “ideal.” Moreover, the terms “a” and “an” herein do not denote a limitation of quantity, but rather denote the presence of one or more of the referenced items.

Disclosed herein are systems and methods including an automated cell culture system that may quickly and accurately produce output cell products and that is easily scalable to enable large scale biological manufacturing. The system may include cell imaging subsystems to acquire images of a cell culture, a cell editing subsystem to edit (e.g., remove) one or more cells during the cell culture process, a computing subsystem that controls the cell editing subsystem based on the acquired images, or any combination thereof. The computing subsystem may apply machine learning to data collected by the system (e.g., imaging data, sensor data, input, and output assay data) to determine how to effectively edit the cell culture to reach the desired output. This allows for dynamic monitoring and control of how the cell culture develops from input cells to output cell products. The automated nature of the system removes the need for manual human intervention at many stages of cell culture development, thus reducing the time and cost of making output cell products. It also allows for easy scalability, as the computing subsystem may monitor and control multiple cell culture processes at the same time.

FIG. 1 is a block diagram of a cell culture system 100 in accordance with various implementations. The cell culture system 100 receives input cells 102 as “source” cells upon which the cell culture system 100 performs various cell culture processes. The input cells 102 may be sorted, expanded, or otherwise modified prior to the cell culture performed by the cell culture system 100. Input cell types may include, but are not limited to, somatic cells (including but not limited to fibroblasts, mature blood and progenitor cells, such as CD34+ cells and erythroblasts, keratinocytes, epithelial cells, including blood and urine-derived epithelial cells, Sertoli cells, endothelial cells, granulosa epithelial, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other muscle cells, and generally any live somatic cells. The term “somatic cells,” as used herein, also includes adult stem cells and pluripotent stem cells (including but not limited to induced pluripotent stem cells and embryonic stem cells).

The input cells 102 may be analyzed with one or more input cell assays 108 which serve to quantify the state of the input cells 102. The input cell assays 108 may be nondestructive (such as cell counting) or a sample may be extracted for tests including, but not limited to, genomic profiling, gene expression assays such as PCR, qPCR, microarray, single-cell RNA sequencing, whole exome sequencing (WES), whole genome sequencing (WGS), karyotyping, short tandem repeat (STR) analysis, sterility testing (testing for bacteria and viruses), or other phenotype analysis including but not limited to cell surface antigen or intracellular staining-based immunofluorescence or flow analysis, and cell viability, morphology and migration assays, or any other implementations known to persons of ordinary skill in the art. The sample extraction can be performed using automated or semi-automated processes within a closed cell culture environment to enable continued propagation of the cell culture within a sterile environment. The results of these assays are transmitted to a computing subsystem 110, which may use the results in various software applications to monitor, predict, and control the cell culture process performed by the cell culture system 100.

The input cells 102 are placed into a cell culture 104, where they will remain for the duration of the processes performed by the cell culture system 100. The cell culture 104 may reside in a cell culture container 106. The cell culture container 106 may include one or more chambers to hold the cell cultures, and may take the form of microwell plates, flasks, stackable cell culture containers, closed cassette systems, microfluidic chambers, purpose-built bioreactor vessels, or any other implementations known to persons of ordinary skill in the art. The cell culture container 106 may be a closed/sealed sterile environment for the cell culture 104 and fluid media used in cell culture processes.

The cell culture 104 may be used for a number of cell processes performed and monitored by the cell culture system 100, including but not limited to: cell reprogramming (into pluripotent or multipotent forms), cell differentiation, cell trans-differentiation, cell expansion, cell sorting, clonal isolation, cell gene editing, cell-based protein production, cell-based viral production, combinations thereof, or any other implementations known to persons of ordinary skill in the art.

The cell culture container 106 may be in a format that allows for observation of the cell culture 104 at regular intervals using an imaging subsystem 112. For example, the cell culture container 106 may include a closed cassette system having at least one transparent or semi-transparent surface that allows for light or laser-based imaging and editing. The imaging subsystem 112 may be configured to provide label-free imaging suitable for long-term cell culture observation, although some implementations may include fluorescent imaging capability for immunofluorescent or other labeled images. Label-free modalities employed by the imaging subsystem 112 may include, but are not limited to, brightfield imaging, phase imaging, darkfield imaging, transmission imaging, reflection imaging, quantitative phase imaging, holographic imaging, two-photon imaging, autofluorescence imaging, Fourier ptychographic imaging, defocus imaging or any other implementations known to persons of ordinary skill in the art. The imaging subsystem 112 may be shared between one or more of the cell culture containers 106.

The cell culture system 100 further includes a cell editing subsystem 114 for editing the cell culture 104. The cell editing subsystem 114 may edit the cell culture 104 at a regional, colony-specific, and/or cell-specific level. Editing, in this context, may include selective destruction and/or removal of cells or cell regions, and non-destructive operations on cells (including intracellular delivery of compounds into cells or extraction of compounds from cells). The cell editing subsystem 114 may edit the cell culture 104 through a variety of directed energy mechanisms. In other words, the cell editing subsystem 114 may generate energy that is directly used to edits cells and/or converts energy of one form (e.g., light, mechanical) into energy of another form to achieve cell editing. The mechanism by which the cell editing subsystem 114 acts upon cells in the cell culture may include, but not be limited to, robotic systems that mechanically actuate a tip or tool across the cell culture, magnetic actuators in conjunction with magnetic tools that interact with the cell culture, systems that are configured to selectively apply an electric field across portions of the cell culture, ultrasound systems that are configured to apply ultrasonic energy to portions of the cell culture, droplet or particle ejection/acceleration systems that are designed to impact droplets or particles on portions of the cell culture, optical systems that are designed to deliver optical energy to portions of the cell culture, combinations thereof, or any other implementations known to persons of ordinary skill in the art. The cell editing subsystem 114 may be shared between one or more of the cell culture containers 106.

Optical mechanisms for cell editing may include, but are not limited to, optical systems that direct energy directly into cells or surrounding media in the cell culture, optical systems that direct energy into particles or dyes that are added to the cell culture media (including but not limited to particles functionalized in a manner to attach to specific cells, or that are taken up by cells), or optical systems that direct energy into particles or films that are on surfaces proximate to portions of the cell culture, or any other implementations known to persons of ordinary skill in the art. Optical mechanisms may operate on the cell culture by a number of approaches including, but not limited to, elevating the local temperature to a point where cells are destroyed due to heat damage, elevating local temperature to cause boiling and/or bubble formation to cause portions of the cell culture to detach from a surface, or elevating local temperature rapidly in order to cause rapid bubble formation and then subsequent collapse to affect mechanical forces on the local cell membranes, or combinations thereof.

The cell culture system 100 may also include a number of sensors and controls 116 which may measure or act upon the cell culture 104. For example, the sensors and controls 116 may carry out functions such as measuring media conditions within the cell culture 104, causing fresh media to be supplied, or adding reagents or gases in order to adjust media conditions for optimal cell culture growth. Sensors that sense the state of the cell culture 104, cell culture media, and/or surrounding cell culture container 106 may include, but are not limited to, temperature sensors, humidity sensors, gas composition sensors including but not limited to O2 and CO2 concentration sensors, gas flow rate sensors, dissolved gas sensors including but not limited to dissolved O2 sensors, liquid flow rate sensors, and sensors to measure cell culture media constituents (such as nutrients, waste products, vitamins, metabolites, proteins, extracellular vesicles, cell mass, or cell debris) including but not limited to optical absorption sensors, optical scattering sensors, mass spectroscopic sensor systems, optical or electrical pH sensors, and viscosity sensors.

Controls that may interact with the cell culture 104 or the cell culture container 106 may include, but are not limited to, liquid handling systems that inject or extract various liquids to/from the cell culture 104 or the cell culture container 106, environmental control systems that control the temperature or other environmental parameters of the cell culture 104 or the cell culture container 106, power systems that provide electrical power to the cell culture container 106, and mechanical or robotic systems that may move or manipulate the cell culture container 106 or portions thereof.

The computing subsystem 110 may be configured to control the other components of the cell culture system 100 to perform the specified cell culture process on the cell culture 104 to produce output cell products 118. The output cell products 118 may include both cells and cell-derived products, and may be harvested from the cell culture 104. Output cell products 118 that may be produced by the computing subsystem 110 may include, but are not limited to, induced pluripotent stem cells, proteins (e.g., cytokines, antibodies, hormones), lipid particles (e.g., exosomes), viral particles, somatic cells (including but not limited to fibroblasts, mature blood and progenitor cells, such as CD34+ cells and erythroblasts, keratinocytes, epithelial cells, including blood and urine-derived epithelial cells, Sertoli cells, endothelial cells, granulosa epithelial, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other muscle cells, generally any live somatic cells, and the combination of any of the above. The term "somatic cells," as used herein, also includes adult stem cells.

The output cell products 118 may be measured by output cell product assays 120 in order to determine critical product parameters such as phenotype distribution, protein production, gene activation, genomic makeup (including but not limited to genomic profiling assays such as PCR, qPCR, microarray, single-cell RNA sequencing, whole exome sequencing (WES), whole genome sequencing (WGS), karyotyping, short tandem repeat (STR) analysis, sterility testing (testing for bacteria and viruses)), or other phenotype analysis including but not limited to cell surface antigen or intracellular staining and immunofluorescence or flow analysis and cell viability, morphology and migration assays, or potency assays such as self-renewal and teratoma formation assays, and germ-layer differentiation assays. The output assay data may be conveyed to the computing subsystem 110 in order to refine predictive models (based on image data, sensor data, information from prior cell culture processes, and other information sources) for cell culture monitoring and control. Output cell product assays 120 may include, but not be limited to, viability assays, cell counting, flow cytometry, immunostained imaging assays, PCR assays (including but not limited qPCR, ddPCR), RNA sequencing assays including single-cell RNA assays, cell differentiation assays, embryoid body formation assays, trilineage differentiation assays, karyotyping assays, DNA sequencing, or any other implementations known to persons of ordinary skill in the art.

The computing subsystem 110 is configured to gather data from a range of sources, organizes the data in a manner that allows it to make predictions of success/quality/functionality of the cell culture 104, and in many cases do so on a cell-by-cell, colony-by-colony, or region-by-region basis. For example, using local cell density and proliferation rate data obtained through analysis of the time series of label-free images provided by the imaging subsystem 112, in conjunction with data regarding the input cells (in order to control for patient-specific factors, for instance), and based on a large number of observed histories and corresponding cell quality data measured by the output cell product assays 120, the computing subsystem 110 may predict which regions of cells are most likely to yield superior cell products, and which regions are less likely to yield good product. In situations where cell media is limited or there is competition between cells for space in the cell culture container 106, the computing subsystem 110 may instruct the cell editing subsystem 114 to remove the regions or even individual cells predicted to underperform.

Another function of the computing subsystem 110 is to use cell data derived from imaging in conjunction with environmental parameters and sensor data from the sensors and controls 116 and assay data from the input cells 102 and/or the output cell products 118 in order to pre-emptively adjust cell culture conditions according to cell count, proliferation rate, differentiation status, phenotype, or other factors in addition to real-time cell media readings. Using a model trained on previous iterations, the computing subsystem 110 may adjust media conditions such as fresh media feed, media type, temperature, pH, dissolved Oxygen levels, reagent or vitamin levels or other global cell culture properties using the controls 116. Similarly, the computing subsystem 110 may use cell data obtained from imaging, potentially in conjunction with cell media sensor data, to determine when the cell culture 104 is ready for harvest. Actuators utilized by the controls 116 may include, but are not limited to: liquid handling robots, liquid circulation systems including valves and pumps, temperature control elements, pH controllers, gas exchange mechanisms to control dissolved gases or any other implementations known to persons of ordinary skill in the art.

The computing subsystem 110 may control the cell editing subsystem 114 to make edits to the cell culture 104 according to cell management algorithms (for example, to maintain a certain cell density, to maintain certain exclusion areas within the cell culture container), in a timed manner (for example, delivering gene-activating or gene-editing compounds to cells at a specific interval), and/or as a result of predictions made by the computing subsystem 110 (for example, removal of cells predicted not to yield the desired phenotype or optimal level of function). "Editing" may include both destruction of cells and/or colonies (including inducing apoptosis, lysing, physically removing) as well as selective delivery of compounds into cells and/or regions of cells via intracellular delivery mechanisms, or selective extraction of compounds from the cells via intracellular delivery mechanisms, or other types of cell manipulation.

The computing system 110 may include elements that perform conventional image processing (including but not limited to filtering, normalization, contrast enhancement, z-stack processing, thresholding, histogram transformations, edge detection, correlations, convolutions, frequency space operations, blob detection, morphological operations, registration, warping, object detection, object tracking or combinations thereof), deep learning based image processing (including but not limited to convolutional neural networks, fully-connected neural networks, semantic and instance-level segmentation, encoder-decoder networks, multi-scale algorithms, recurrent networks, visual attention models, vision transformers, generative adversarial models, U-Nets, ResU-Net, SegNet, X-Net, ENet, BoxENet, long short-term memory neural networks, and combinations thereof), statistical models, pattern recognition, statistical learning (including but not limited to linear regression, non-linear regression, hierarchical regression, generalized linear models, logistic regression, log-linear models, non-parametric models), machine learning (including but not limited to decision trees, random forest, support vector machines, neural nets, deep learning, association models, sequence modeling, genetic modeling), clustering techniques including hierarchical and non-hierarchical clustering, supervised machine learning models, unsupervised machine learning models, databases (including but not limited to SQL databases and NoSQL databases), visualization tools for image, cell, colony, clone and other data, combinations of these elements, or any other implementations known to persons of ordinary skill in the art.

The computing subsystem 110 may also include data storage for storing image data, sensor data, the results of data analysis, and program code that the computing subsystem 110 executes. The computing subsystem 110 may also include input/output devices to allow users to view data and monitor and control the cell culture system 100, or to transfer data in and out of the cell culture system 100. For example, the computing subsystem 110 may include display screens, monitors, communications/interface ports, keyboards, audio systems, and the like. The computing subsystem 110 may be proximate to the other components in the cell culture system 100 (e.g., a local computer) or may be remote from the other components in the cell culture system 100 (e.g., a cloud server). In some implementations, the computing subsystem 110 may have one or more components proximate the other components in the cell culture system 100 and some components remote from the other components in the cell culture system 100. The computing subsystem 110 may be configured to communicate with the other components in the cell culture system 100 utilizing a wired and/or wireless connection (e.g., Ethernet cables, optical fiber, Wi-Fi, Bluetooth), and may be configured to communicate with external components utilizing a wired and/or wireless connection. The computing subsystem 110 may have additional functionality and components not disclosed herein, but would be apparent to a person of ordinary skill in the art.

The cell culture system 100 may be configured to allow extended cell culture processes to be performed within a single cell culture container 106 using the cell editing subsystem 114. Because the cell editing subsystem 114, as directed by the computing subsystem 110, can selectively remove cells from cell culture, the cell culture does not overgrow the cell culture container, and therefore does not require frequent transfers ("passaging") which are stressful on cell populations, disrupt cell processes, introduce potential sterility and contamination issues, and make time series tracking of cell-, region-, colony- or clone-specific behavior impossible. Thus, the combination of continuous monitoring via image and sensor data—enabled by the single-container process—may allow the computing subsystem 110 to predict the optimal regions or cells to remove in order to maintain low enough cell density to remain in the single cell culture container 106. In the process the cell culture system 100 may also perform in-place "sorting" of cells in order to enrich the population according to real-time measurements.

Figure 2:
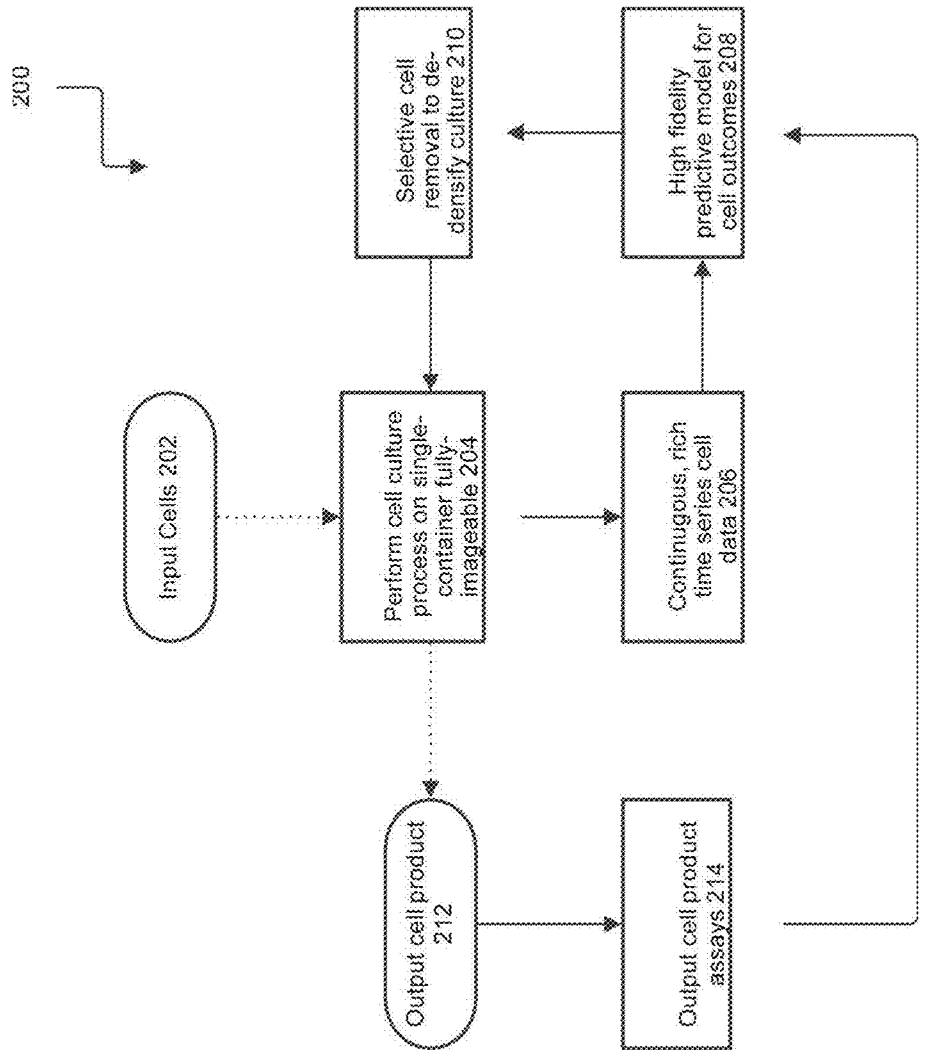
FIG. 2 is a flow chart of a method of operating a cell culture system in accordance with various implementations.

FIG. 2 is a flow chart of an example method 200 of operating a cell culture system in accordance with various implementations. The method 200 may be performed by a cell culture system, such as cell culture system 100. In block 202, input cells are seeded into a cell culture container that is fully imageable and able to support a cell culture for the duration of the cell process. This results in a single-container, fully-imageable cell culture. The cell culture container may provide a closed, sterile environment for cell culture processes. In block 204, a cell culture process may be performed on the single-container, fully-imageable cell culture. The cell culture process may be sustained within a single container for the duration of the process (as opposed to transferring, sometimes selectively, cells from container to container to maintain property density). The cell culture process may be monitored and controlled by a computing subsystem in the cell culture system.

In block 206, the cells may be observed with an imaging subsystem to acquire unbroken, contiguous, rich time series of cell data. In block 208, the computing subsystem may analyze the cell data to develop a high fidelity predictive model for cell outcomes. The computing subsystem may utilize the predictive model to adjust the cell culture process dynamically. For example, in block 210, the computing subsystem may control a cell editing subsystem to selectively remove cells from the cell culture in order to de-densify the cell culture. The selective removal, in turn, is optimally configured to improve the predicted yield, functionality, phenotype, or other properties of the output cell product. The method 200 may iterate through the steps of collecting imaging data, refining the predictive model, and editing the cell culture until the output cell product is produced in block 212.

In block 214, output cell product assay 214 may be performed on the output cell product at the end of a cell culture operation. The results of the assays may be used in conjunction with the time series cell data to adjust the predictive model in block 208. In some cases, the output cell product may be harvested dynamically from the process (for example, a subset of cells may be selected and removed from the cell culture, or cell products within the media are removed from the cell culture) and the corresponding assay results immediately fed back into the predictive model. In this manner, the method 200 allows for a completely automated method for dynamically processing and editing cell cultures, from input cells to output cell products. This allows for faster, more accurate cell culture processes without the time and expense of manual human intervention, which in turn reduces the time and cost for producing output cell products. This approach is also easily scalable to enable large scale biological manufacturing.

Clonally Reprogrammed iPSCs

Induced pluripotent stem cells (iPSCs) have the potential to revolutionize regenerative medicine. Their capacity for self-renewal, ability to differentiate into any cell type in the body, and ability to be manufactured from small volumes of patient tissue samples make them the ideal starting material for personalized cell and tissue therapies. The same genetic plasticity that allows for these cells to be used to make biologics also makes the cell vulnerable to selective pressure and can potentially put the product and process at risk when changes are made.

However, there are several hurdles to creating cost-effective, safe, and efficient hiPSC-derived cell therapies. Creation of a master cell bank (MCB) of hiPSCs with current protocols is extremely labor- and time-intensive (up to 4 months), with estimates for the cost of generating a clinical-grade iPSC line going as high as US $1.2M. A majority of these costs include labor and quality control (QC) measures required for ensuring the safety and efficacy of the end product. Any methods aimed to reduce the cost involved in these would significantly help enable cost-effective manufacturing of hiPSC-derived cell therapy products.

One factor to the low numbers of hiPSC-lines passing the QC assays is the heterogeneous nature of the iPSC culture. There is variability both within and across iPSC lines, in terms of differentiation potential, tumorigenicity, epigenetic profile, and other parameters. The exact reason behind this remains unclear, and could be related to differences in source material, protocols, or operator technique. Nevertheless, this indicates a need for more standardization and automation across iPSC manufacturing and characterization techniques, which can help minimize the heterogeneity within the MCB and allow for well-controlled processes capable of consistent manufacturing of a product. When cell banks are nonclonal, every potential change made to the upstream process (raw materials, process parameters, manufacturing site, etc.) may put selective pressure on the cultures, which may result in changes to the manufacturing process or the final product. Clonality is a crucial step in stable cell line development (CLD) for biotherapeutic workflows and it is closely monitored by government regulators. If clonality is not sufficiently evidenced, regulatory bodies such as the US Food and Drug Administration (FDA) and the European Medicines Agency (EMA) will require additional manufacturing controls, increasing the cost of clinical trials and delaying drugs from reaching patients.

There are a number of iPSC reprogramming methods, including genome integration, non-genome integration, minicircle vectors, the Sendai protocol, mRNA, self-replicating RNA, CRISPR activators, and recombinant proteins. Each of these are summarized herein.

Genome integrating methods: one of the most commonly used methods for reprogramming is the integration of the reprogramming factors into the genome by lentiviral or retroviral transduction. This method is highly efficient but poses the threat of generating permanent random integrations of exogenous genes into the genome that can potentially have oncogenic potential and are therefore less suitable for use in therapeutic approaches.

Non-genome integrating methods: non-genome integrating methods (footprint-free) include a number of methods to exogenously express reprogramming factors and RNA components, from either episomal DNA vectors, RNA viruses, or messenger RNAs (mRNAs). Among integration-free methods, the episomal method is a technically simple, fast, convenient, and reproducible approach for generating iPSCs. However, episomal vectors have low reprogramming efficiency in comparison with viral vectors. Furthermore, in many studies that used the episomal system, the transcription factors were delivered individually by nucleofection. However, due to differences in vector uptake by nucleofection, gene expression levels between cells are highly variable.

Minicircle vectors: minicircles are DNA vectors with eliminated bacterial backbones and transcription units commonly used in episomal plasmids. Therefore, they have a relatively small size compared to other commercial vectors. The small size and the ability to avoid immune reactions leads to the high expression of the foreign gene, both in vitro and in vivo. Minicircles also show potential in pre-clinical gene therapy research and proof-of-concept studies combining minicircle vectors and stem cells suggest a potential regenerative tool for clinical applications.

Sendai: the Sendai virus is a single chain RNA virus that does not integrate into the host genome or alter the genetic information of the host cells. The virus remains in the cytoplasm and is therefore diluted out of the host cells after approximately ten passages after virus infection. The Sendai virus can infect a wide range of cell types in proliferative and quiescent states with high transduction efficiency. Expression of transgenes delivered by the Sendai virus is detectable as early as 6-10 hours after transduction, with maximum expression detected more than 24 hours after transduction. Sendai-based reprogramming vectors have been used to successfully reprogram neonatal and adult fibroblasts as well as blood cells with high efficiency.

CRISPR activation (CRISPRa): CRISPRa uses a catalytically inactivated CRISPR-Cas9 system (dCas9) fused to a transactivator domain for transcriptional activation of endogenous genes without editing DNA. High efficiency, multiplexed, fibroblast CRISPRa reprogramming has recently been reported with improved fidelity. Activation of reprogramming gene endogenous promoters with CRISPRa improves the quality of human pluripotent reprogramming.

mRNA: expression of reprogramming factors using mRNA provides another method to make transgene-free iPSCs. It was shown that in vitro transcribed mRNAs were able to efficiently express reprogramming factors when transfected into human fibroblasts. Although reprogramming factor mRNAs are commercially available, this method suffers from the limitations that it is labor-intensive, requires daily transfection of mRNA for 7 successive days, and there are no successful reports regarding the reprogramming of blood cells. However, despite the great advances in the development of synthetic mRNA-based reprogramming approaches, one of the main obstacles of this method is still the induction of an innate immune response following multiple daily mRNA transfections, resulting in increased cellular stress and severe cytotoxicity.

Self-replicating mRNA (srRNA): an alternative to mRNA-based reprogramming is the use of srRNA. Structurally, srRNA mimics its synthetic mRNA counterpart, and contains the coding sequences of the "Yamanaka" transcription factors Oct4, Klf4, Sox2, and cMyc, and four nonstructural proteins enabling its replication. The application of srRNA enables an extended duration of protein expression without the need of multiple daily transfections to maintain the protein expression required to reprogram cells.

Recombinant proteins: protein-based hiPS technology offers a new and potentially safe method for generating patient-specific stem cells that does not require the destruction of ex utero embryos. This system completely eliminates genome manipulation and DNA transfection, resulting in human iPS cells suitable for drug discovery, disease modeling, and future clinical translation. However, the generation of p-hiPS cells is very slow and inefficient, and requires further optimization. In particular, the whole protein extracts that are used limits the concentrations of factors delivered into the target cells, thus suggesting that p-hiPS cells may be more efficiently generated using purified reprogramming proteins.

Due to the plastic nature of somatic cells upon reprogramming, hiPSCs can be created from several cell sources that may be classified into two groups: adherent and suspension. Each comes with different sets of challenges and benefits, which are discussed herein.

Fibroblasts and other adherent cells: Fibroblasts are the most commonly used primary somatic cell type for the generation of iPSCs. Various characteristics of fibroblasts supported their utilization for the groundbreaking experiments of iPSC generation. One major advantage is the high availability of fibroblasts which can be easily isolated from skin biopsies. Furthermore, their cultivation, propagation, and cryoconservation properties are uncomplicated with respect to nutritional requirements and viability in culture. However, the required skin biopsy remains an invasive approach, representing a major drawback for using fibroblasts as the starting material. Additionally, it has been shown that skin fibroblasts in particular accumulate mutations during the person's lifetime that might negatively affect the outcome of the reprogramming process. Other adherent cell types used for reprogramming include keratinocytes from hair follicles and skin biopsies, epithelial cells derived from urine and blood, synovial cells, and beta islet cells. The compatibility of all the potential somatic cell types with the existing and emerging reprogramming methods will need to be evaluated by persons of skill in the art.

Suspension cells: CD34+ blood stem cells and erythroblasts purified from peripheral blood mononucleated cells (PBMCs) are one of the most studied cell types as a starting material for reprogramming. This is mainly due to their easy harvest via blood withdrawal, and the low number of mutations these cells accumulate over the lifetime that might negatively affect the outcome. All reprogramming methods minus mRNA electroporation have been successfully used to reprogram these cell types.

Assurance of clonality is part of the overall control strategy for cell-based products. It improves the consistency of the process and directly affects the quality and safety of the products. However, for cell-based biologics entering clinical phase, there exists no single regulatory document that explicitly states that the cell banks should be monoclonal, mainly reflecting the inability of the current technologies to ensure monoclonality. However, starting with a monoclonal population would maximize the potential to optimize the manufacturing process by reducing variables associated with heterogeneous cell behavior within the culture.

The sole method currently able to distinguish a monoclonal population from a polyclonal one in an already established cell line is Fluorescent In Situ Hybridization (FISH).

It relies on random monoallelic expression of genes (so-called allelic exclusion), in which a subset of human genes are normally expressed at a single allele in a fixed fraction of cells within a tissue, independent of the parental origin of the allele. It is hypothesized that application of FISH to assess the allelic expression patterns among one or more of these genes should be able to distinguish a monoclonal population of cells from a polyclonal on. However, although fairly successful in determining the clonality of B and T-cell lines due to the specific recombination events occurring in them, applying FISH to other cell types (such as hiPSCs) that do not naturally undergo genetic recombination has proven to be technically challenging and incompatible with reliable high-throughput analysis of samples. Therefore, due to lack of biological assays, the current methods to assess clonality of hiPSCs rely on image-based assurance of single-cell origin of the culture and/or statistical methods to reduce the probability of cells originating from multiple cells within the culture. Several clonality strategies are described herein.

Single-cell plating (limiting dilution): in order to create a more uniform, homogeneous population of hiPSCs, many laboratories opt for clonal derivation of the cell lines. By plating a single hiPSC per growth area for expansion, the resulting product is a clonal population of cells where each cell is genetically and phenotypically more similar to the other cells in the same culture than in hiPSC-cultures with non-clonal origin. Single-cell plating can be done by several methods from limiting dilution to cell sorting. Single-cell origin of the culture is specifically critical for gene-edited hiPSCs, where each cell in the culture must carry the edited version of the gene. Unfortunately, the process of creating clonal cultures from single cells poses a significant challenge to the cells that require contact with neighboring cells to survive. Due to this, the survival rate of hiPSCs after single-cell plating is very low, and the cells that do manage to proliferate and expand often have acquired mutations beneficial for single-cell survival, but that result in failure during the end QC.

Low-density plating (repeated colony picking): to avoid having to plate hiPSCs at single cells, many laboratories and publications rely on statistical probability modeling and derive "clonal" populations by plating hiPSCs at low density and picking and replating pieces from a single colony several times either manually or with technologies such as ClonePix. This has been shown to result in highly homogenous hiPSC cultures, yet does not provide an absolute proof of clonality. This is mainly due to the probability of plated cells to reside within 150 μm distance from each other, which has been shown to cause cells to migrate and form a polyclonal colony.

Clonality assays: currently, there are no assays to address the clonality of an existing hiPSC-culture. To ensure absolute clonal origin, imaging-based techniques are suggested by the FDA to track the single cell during the expansion and MCB creation.

One of the quality aspects required from hiPSC-derived cell therapy products is the assurance of complete elimination of the reprogramming material. For integrating methods this requires the use of excisable gene cassettes (e.g., Cre-lox system) engineered into the viral vectors encoding reprogramming factors. Upon activation, an exogenous enzyme (e.g., Cre-recombinase) cuts the DNA around the insertion site and removes the cassette containing the reprogramming factor. After this the cells' own DNA repair systems repair the remaining cut in the genome and the cell is considered "safe" and ready for downstream applications, including cell therapies. To ensure the complete excision of the cassette, sequencing of the cell population is required.

For non-integrating reprogramming methods, it suffices to prove that the DNA, mRNA, or viral vector (e.g., Sendai) is no longer detected by qPCR. The mechanism of DNA elimination in the episomal and microcircle methods rely on cell-proliferation-based dilution of reprogramming plasmid in the progeny of cells. Additionally, the elimination is dependent on the type of origin of replication used to drive the replication of these plasmids and directly affects how quickly they will be diluted below the threshold of detection.

The time for complete elimination of DNA-based non-integrating reprogramming materials varies significantly between methods and clones and can take anywhere between 40-120 days, significantly slowing down the manufacturing process. Any methods allowing for a faster and more consistent elimination of the reprogramming methods would allow for more cost-effective and safe manufacturing cell therapies. Using mRNA-based reprogramming has the major advantage of producing footprint-free hiPSCs much faster than other methods. Synthetic mRNA is commonly degraded within 48 hours after its entry into the cell. However, due to its rapid degradation, up to 14 rounds of consecutive transfections is necessary to retain sufficient level of protein expression to reprogram cells. Therefore, synthetic mRNA-based reprogramming is better suitable for reprogramming hardy cell types, such as fibroblasts and epithelial cells, instead of, for example, blood stem cells sensitive to multiple rounds of transfection. To overcome the challenge of multi-round transfections and yet produce a foot-print free hiPSC line in under 40 days, a novel approach of srRNAs may be used. These synthetic mRNAs have an additional genetic element in their structure that allows them to replicate once inside mammalian cells. Depending on the type of this replicative element, srRNAs can remain in the cells up to 30 days after which they are rapidly removed by the cells' type I interferon activity after the withdrawal of interferon suppressing factor B18R.

All the above mentioned non-integrating methods have been shown to successfully reprogram somatic cells into hiPSCs. However, the high variability between clones derived using these methods is hindering their translation into commercial production. One of the greatest contributors to this variability is the initial reprogramming cargo load being introduced into the cell. There is currently no way to control the load of DNA, RNA, or protein that is delivered into each cell in the culture upon transfection. This depends on several factors such as cell cycle stage, metabolic activity, and cell surface area of the cells being transfected. However, the amount of cargo entering the cells can directly affect several aspects of the reprogramming process, including reprogramming efficiency and elimination speed of exogenous material and thus the manufacturing time. Indeed, partially due to these factors significant variation between clones is often observed, resulting in highly heterogeneous non-clonal culture of hiPSCs. The ability to use image-guided algorithms to track and analyze single cells and ensure clonality during the reprogramming and expansion process can provide a powerful tool to distinguish between fully vs partially reprogrammed clones. Especially when combined with qPCR-based quantification of the remaining reprogramming material in each clone during the early days of reprogramming, a cell culture system for growing hiPSCs may provide great insights into selecting the best clones for accelerated manufacturing of safe hiPSCs.

In summary, the problems facing quick and relatively inexpensive mass reprogramming of iPSCs include low yields and low consistency of high-quality iPSC clones. This is exacerbated by an inability to observe behavior during reprogramming vs outcomes, inconsistent handling of the cells, and frequent passaging that causes variable effects on cells. In addition, it is difficult to ensure clonality on an iPSC cell culture such that monoclonal iPSC output cell products can be reliably manufactured. Low fidelity of QC results and/or high QC volumes/costs, in addition to inconsistent behavior during reprogramming observation, further make consistent monoclonality a challenge.

The systems and methods disclosed herein provide a reliable, automated process for monoclonal reprogramming of iPSCs, and hiPSCs in particular. The cell culture system disclosed herein (e.g., cell culture system 100) may be used to produce iPSCs that are the result of a true clonal reprogramming process, in which a single iPS candidate cell or cell colony is isolated using a cell removal mechanism (e.g., cell editing subsystem 114) that acts on the other cells, and confirmed by imaging. The colony/colonies resulting from proliferation of this single cell are isolated from colonies proliferating from other cells, by use of a cell removal mechanism that acts on potentially clone cross-contaminating cells, the removal coordinated and confirmed by imaging and image analysis. The colony/colonies of a single starting cell are then isolated to form the final clonal output cell product. The entire cell culture process may be conducted in a closed system, such as a closed cassette system. The cell culture container does not need to be opened or otherwise exposed to the external environment for media exchange, imaging, cell editing, and other cell culture process operations. Thus, the cell culture system herein may be configured to grow monoclonal cell colonies (e.g., iPSC colonies) in a closed system.

In some implementations, the isolation of a single clone from multiple clonal colonies is achieved by a cell removal mechanism that acts on the other colonies, the removal coordinated and confirmed by imaging and image analysis. In some implementations, the cell removal mechanism includes at least a pulsed laser system. In some implementations, the entire process up to the output cell product is performed within a single cell culture container. In some implementations, the cells are reprogrammed in a sealed microfluidic environment, such as a closed cassette system.

The cell culture system disclosed herein provides a number of advantages over the prior art for monoclonal reprogramming of iPSCs. For example, the cell culture system may be used to track reprogrammed cells at a single-cell level or cell cluster/colony level, and a precision laser system may be used to remove any unwanted cells in the cell culture. Unwanted cells can be any cells analyzed and predicted by the image-based algorithms during any stage of the reprogramming and expansion stages that, according to the predictions, would not pass the QC or manufacturing requirements at the end of the manufacturing process. QC requirements focus on ensuring the safety and potency of the output cell product and are determined by the regulatory bodies. Manufacturing requirements are specific for the cell culture system and aim to reduce the cost and manufacturing time of the product, and may include but are not limited to eliminating cells that divide too slowly, cells that have high reprogramming cargo load, and migrating, hard to track cells.

The cell culture system is also agnostic to the starting material. The cell culture system may be configured to reprogram fibroblasts or other adherent cells such as keratinocytes, epithelial cells, or synovial cells, independent of the reprogramming method. The system's image-based algorithms can be used to distinguish fibroblasts from newly reprogrammed cells based on an array of phenotypic features specific to pluripotent stem cells, including but not limited to, cell morphology, cell proliferation rate, chromatin condensation, nucleus to cytosol ratio and cell migration patterns. The cell editing subsystem of the cell culture system may then be used to remove unwanted adherent cells.

When the cell culture system disclosed herein is used to reprogram suspension cells, such as CD34+ stem cells or erythroblasts, the number of cells adhering to the cell culture surface is significantly lower after reprogramming. Only at around day 5 after transfection(s), the cells that received sufficient load of reprogramming material will adhere and start to form colonies of fully or partially reprogrammed cells. Similar to the above-mentioned methods with adherent cells, the cell culture system is trained to distinguish the most promising single-cell derived colonies at an early stage and keep them isolated by removing any unwanted cells surrounding the emerging colonies and eventually all other cells in the growth area.

In addition, the cell culture system disclosed herein does not require single-cell plating, limiting dilution or repeated colony picking to create clonal populations of cells. The process of deriving clonal hiPSC-populations from single cells has been shown to be highly ineffective due to increased cell death upon 48 h after plating. The biological mechanism behind this phenomenon is poorly understood. To increase cloning efficiency, low-density plating is commonly used to ensure cell survival, but often at the cost of clonality. Despite the better survival, this method requires frequent imaging to ensure that the cells do not migrate and form a polyclonal colony. Once detected, these wells with polyclonal colonies need to be excluded from the experiment, leading to loss of money. Indeed, it has been shown that when plated closer than 150 μm apart hiPSCs tend to move together to form a colony. To date, there are no technologies able to control the distance of the cells when plated in low density fashion.

However, the cell culture system may be configured to fully reprogram hiPSCs plated at the density most likely to yield in cell separation of at least 150 μm. Due to the random plating location of each cell, the cell editing subsystem may be configured to remove any cell that resides closer than 150 μm from its neighbor, reducing the chances of polyclonal colony formation. To improve the number of monoclonal lines, low-density plating is followed by repeated rounds of hiPSC colony picking, which is not necessary when using the cell culture system. These directly translate into reduced manufacturing costs per clonal hiPSC-line when compared to methods based on single-cell plating or low-density plating followed by repeated clonal picking. An additional advantage of this approach is that the total number of cell divisions is kept to a minimum when compared to post-reprogramming clonality enforcement. It is known that hiPSCs are particularly prone to genetic or karyotypical variations, and that the load of these variations grows with the number of cell divisions (or related, “passages”). By enforcing clonality from the start of reprogramming, the full resulting population of hiPSCs at the end of the reprogramming process may be used for quality control and for the application at hand, rather than as the input to a process that restarts from a single cell.

Figure 3A:
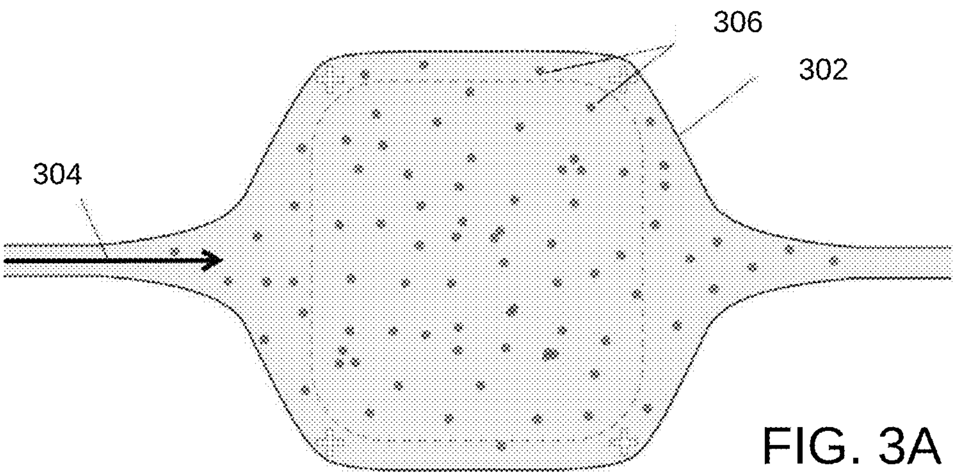
FIGS. 3A-C are diagrams illustrating a portion of a process for iPSC reprogramming in accordance with various implementations.
Figure 3B:
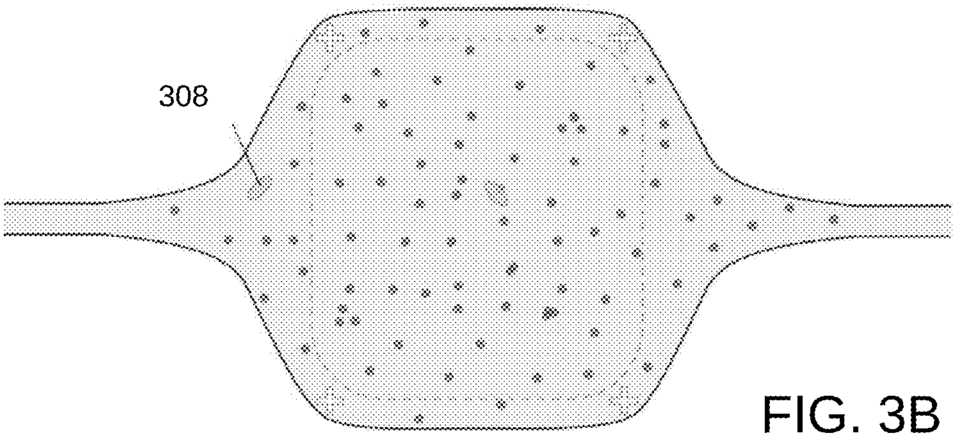
Figure 3C:
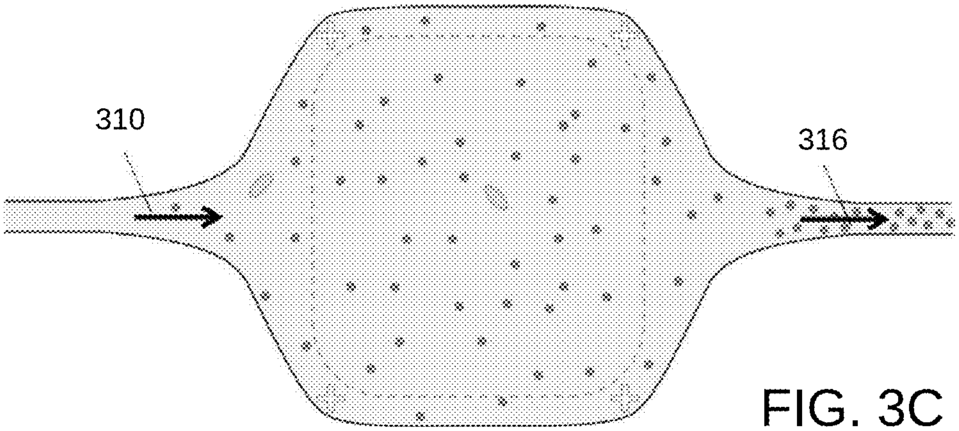

FIGS. 3A-C are diagrams illustrating a portion of a process for iPSC reprogramming in accordance with various implementations. Specifically, FIGS. 3A-C depict the cell seeding and early reprogramming phases in which somatic cells are seeded into a cell culture container, having either had reprogramming factors delivered prior to seeding, or factors delivered in the chamber itself. FIG. 3A shows an example cell culture chamber 302, shown here as a fluidic chamber with two ports for filling/removal, and media circulation. The cell culture chamber 302 is inoculated (shown by arrow 304) and non-reprogrammed input cells 306 then settle in the cell culture chamber 302. For example, the reprogramming process may utilize CD34+ cells that have had episomal vectors delivered prior to inoculation via electroporation. FIG. 3B shows the emergence of pre-IPS cells 308 from a subset of the non-reprogrammed input cells 306 after some period of time. Generally, cells that have some degree of reprogramming will become adherent to a surface that has a supporting matrix. FIG. 3C shows an initial media exchange in the cell culture chamber 302, where fresh media 310 displaces the initial media, and in the process cells that have not become adherent (which exclude the pre-IPS cells 308) are washed out as indicated by arrow 316.

Figure 4A:
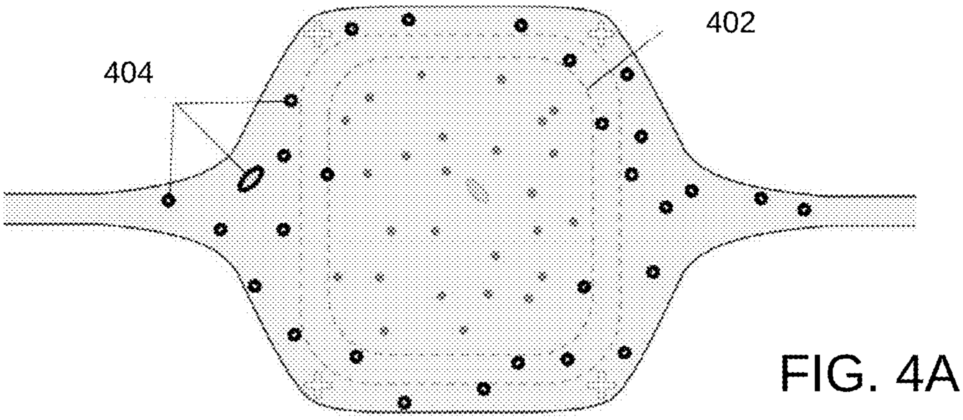
FIGS. 4A-B are diagrams illustrating cell removal during an iPSC reprogramming process in accordance with various implementations.
Figure 4B:
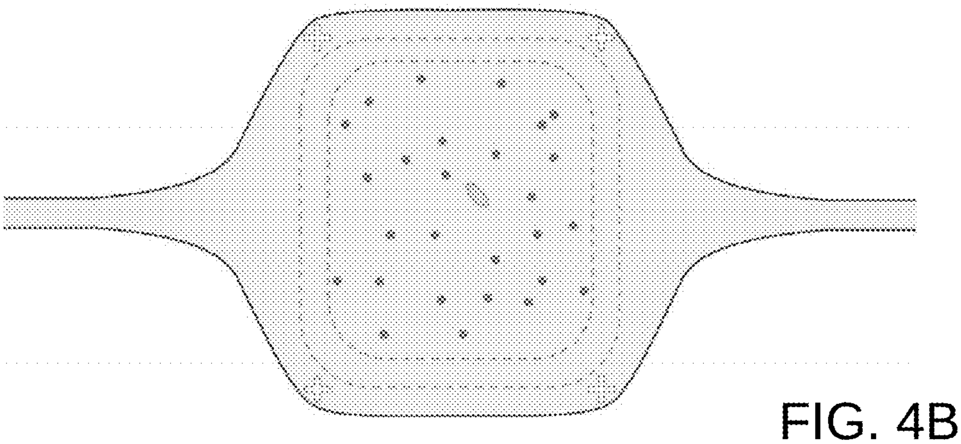

FIGS. 4A-B are diagrams illustrating cell removal during an iPSC reprogramming process in accordance with various implementations. Cell removal may be conducted to limit initial cell attachment and growth to an area where it is not perturbed by cell culture container edges or edge liquid/thermal/chemical gradient effects. FIG. 4A shows a designed area 402 in a cell culture chamber that is designated for initial cell emergence. The designed area 402 may be designed such that colonies that emerge within the designed area 402 have room to grow before hitting the designated boundary away from the cell culture chamber edge (indicated by the outer dashed line). Cells that are outside of this initial boundary, denoted as cells 404, are identified and removed using a cell removal mechanism (e.g., cell editing subsystem 114 in FIG. 1). This cell removal mechanism may be optical (laser), acoustic (focused ultrasound), mechanical, etc., but should be able to lyse, destroy, and/or lift cells off the growth surface. In any case this removal mechanism should be steered by a computing system (e.g., computing subsystem 110 in FIG. 1). Preferably, the cell removal mechanism performs this action without any need to open the cell culture container (i.e., it is compatible with closed containers//media systems). The cell removal mechanism may either target individual cells as identified through imaging, or sweep the entire area outside of the designated boundary. FIG. 4B shows the resulting cell population after removal of out-of-bounds cells, and appropriate washing to remove cell debris.

Figure 5A:
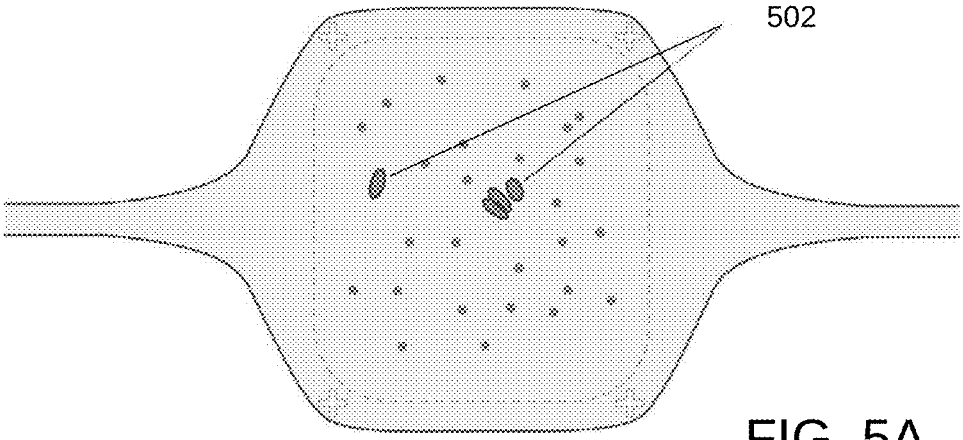
FIGS. 5A-C are diagrams illustrating cell isolation during an iPSC reprogramming process in accordance with various implementations.
Figure 5B:
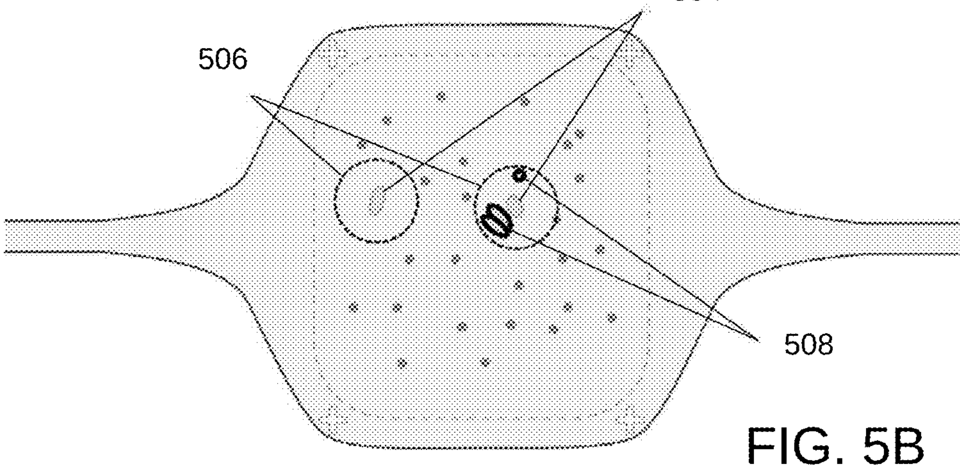
Figure 5C:
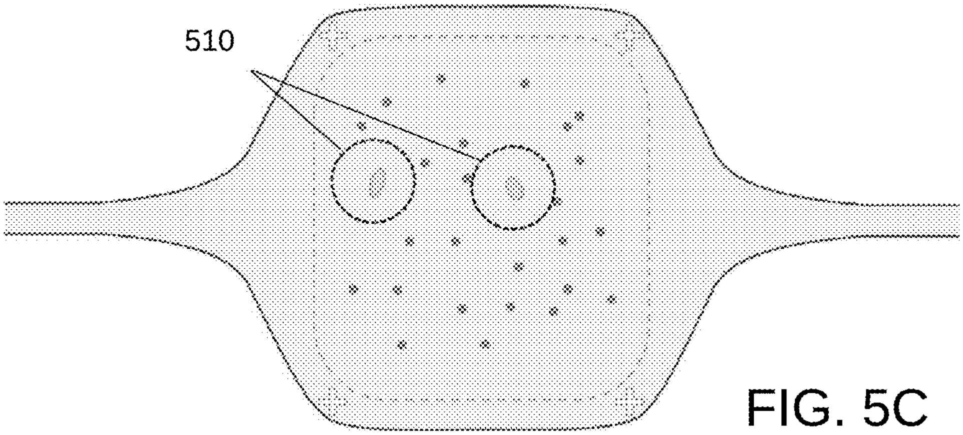

FIGS. 5A-C are diagrams illustrating cell isolation during an iPSC reprogramming process in accordance with various implementations. A cell removal mechanism (e.g., cell editing subsystem 114) may be used to isolate single cells in clusters of emerging iPSC candidates. FIG. 5A shows a cell culture chamber that includes a mix of source somatic (un-reprogrammed) cells and emerging iPS cells in small colonies 502. Each of these colonies 502 often corresponds to a single source cell. For example, in a case where CD34+ cells are being reprogrammed using episomal vectors delivered via electroporation, reprogramming efficiency is approximately 0.05% per cell. Thus, in a container with 10,000 CD34+ cells it would be expected that, on average, 5 cells will emerge as iPSCs. Statistically these cells are unlikely to emerge immediately adjacent to one another, but in some cases, they may be close enough to each other that they may merge into a single colony and lose monoclonality.

The cell culture system disclosed herein may ensure monoclonality using a combination of imaging, image processing from label-free images to determine precise cell location coordinates, a method for computing an optimal set of cell removals, and a mechanism for individually removing or terminally damaging the selected cells. This results in a single viable cell isolated within a sufficiently large area such that there will be no "cross-contamination" between already-emerging iPS clones, nor with yet-to-emerge iPS cells from proximate somatic cells. This selection and deletion process is shown in FIG. 5B. Selected iPS candidate cells 504 are identified and have virtual perimeters 506 drawn around them. Any cells lying within these perimeters that are not the selected iPS candidates are marked for removal//destruction, and the cell removal mechanism lyses//irreparably damages//removes them from the culture as indicated by outlined cell colonies 508. After removal, the selected emerging iPS cells are left as single cells within the perimeters as illustrated in FIG. 5C with "clonal perimeters" 510.

Figure 6A:
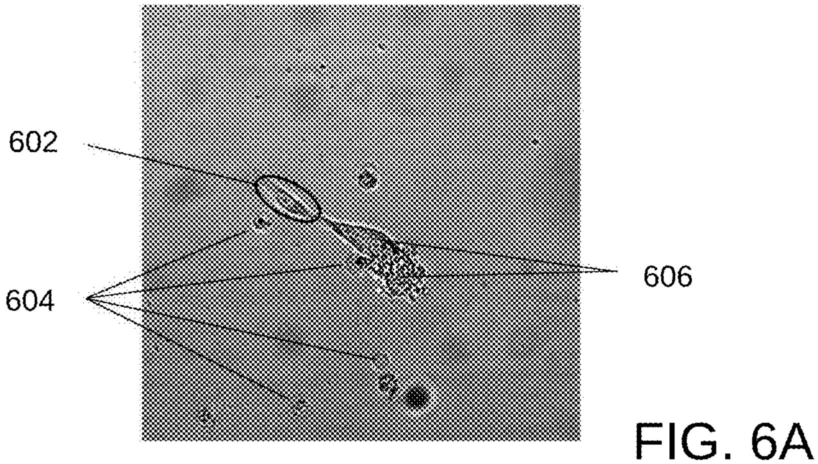
FIGS. 6A-C are images illustrating cell isolation during an iPSC reprogramming process in accordance with various implementations.
Figure 6B:
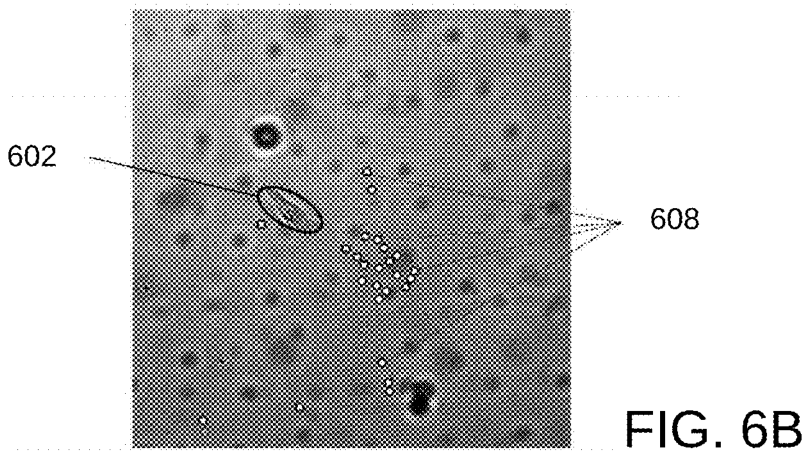
Figure 6C:
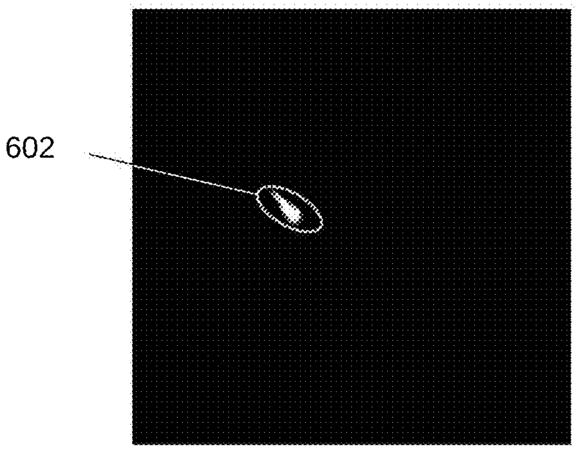

FIGS. 6A-C are images illustrating cell isolation during an iPSC reprogramming process in accordance with various implementations. FIGS. 6A-C show real images taken from a cell culture chamber undergoing the process described with respect to FIGS. 5A-C. The cells in FIGS. 6A-C are iPS cells emerging from CD34+ cells during reprogramming. In FIG. 6A, a number of CD34+ cells 604 (approximate cell diameter 10 microns, for reference) showing no signs of reprogramming are located in the neighborhood of a cluster of cells that show signs of successful reprogramming including a "selected" cell 602 and several connected "unselected" cells 606. As described above, the goal is to isolate the selected cell as the only viable cell in the local region. FIG. 6B shows a pattern of points 608 that were targeted by a cell removal mechanism (e.g., cell editing subsystem 114), which in this case is a nanosecond pulsed laser (<10 ns pulse width, 532 nm) that is focused on a 20 nm Titanium semi-absorbing film on the cell growth surface. The resulting explosive microbubbles lyse and detach the target cells, while inducing little collateral damage in surrounding cells, specifically the selected iPS candidate cell 602. In FIG. 6C, a cell viability stain is used to demonstrate the viability of the selected cell 602, and also to demonstrate that no other viable cells remain within the field of view.

Figure 7A:
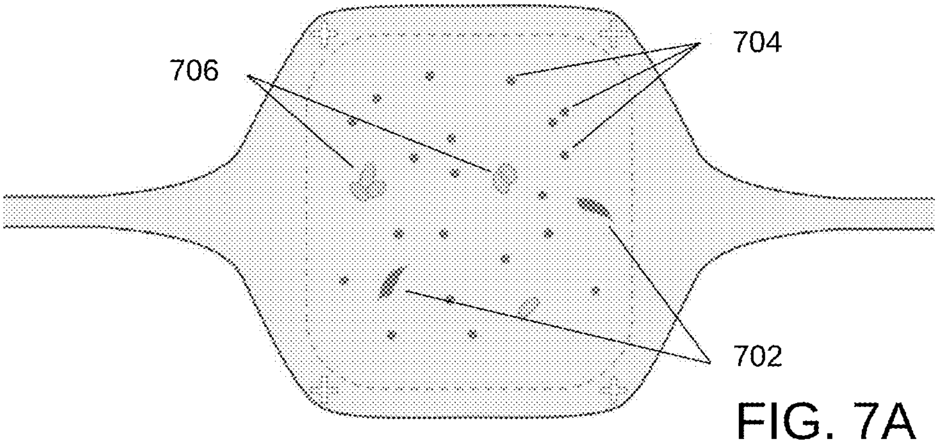
FIGS. 7A-C are diagrams illustrating non-iPS cell removal during an iPSC reprogramming process in accordance with various implementations.
Figure 7B:
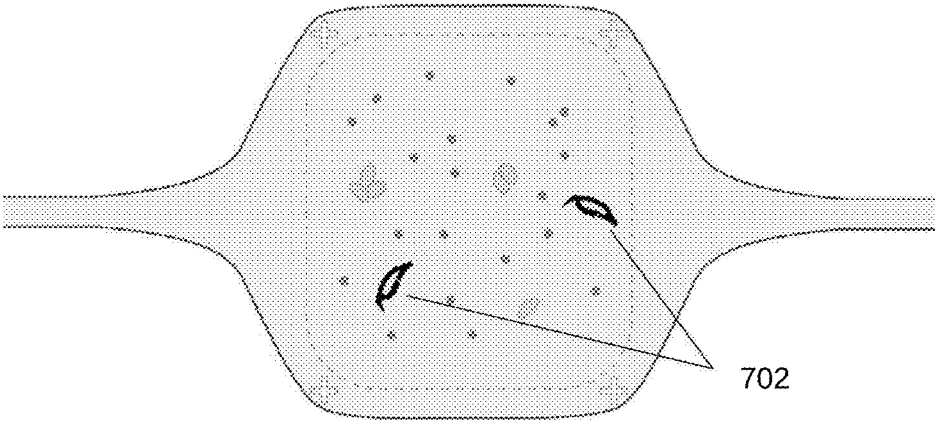
Figure 7C:
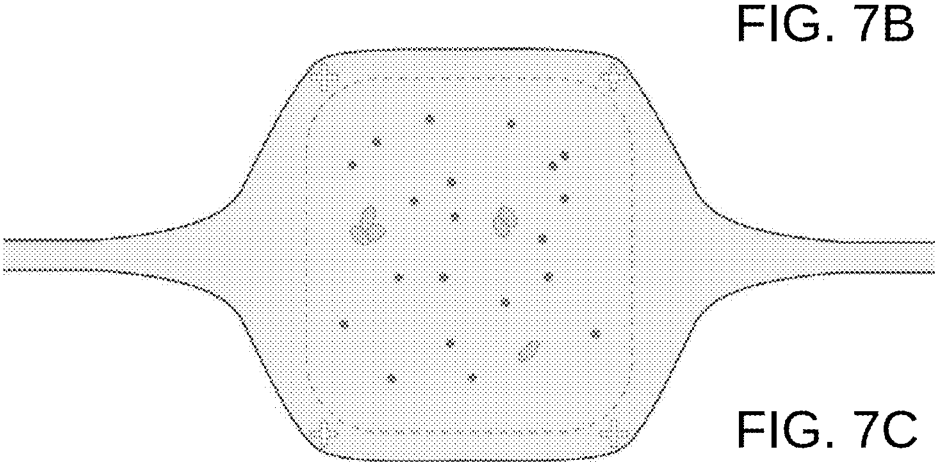

FIGS. 7A-C are diagrams illustrating non-iPS cell removal during an iPSC reprogramming process in accordance with various implementations. For example, certain cells may start differentiating into non-iPS cell types during cell culture and thus should be removed. In some cases, there may be failed partial reprogramming that causes the source somatic cells to differentiate into non-iPS cells 702, which may potentially contaminate the emerging iPSC candidate cells or colonies 706. These cells are located and classified by a computing subsystem as non-source and non-iPS candidates by their distinct morphological characteristics using image analysis. The non-iPS cells may be distinguished from as-yet un-reprogrammed source cells 704 or emerging iPSC candidate cells or colonies 706, which should remain in the cell culture. To prevent non-iPS cells from proliferating and contaminating the iPS cell culture, these errant cells are identified and then removed using a cell removal mechanism (e.g., cell editing subsystem 114), as shown in FIG. 7B. The non-iPS cells may be identified, located, and targeted by the cell removal mechanism. Subsequently, the cell culture chamber contains only source somatic cells and iPS candidate cells as shown in FIG. 7C.

Figure 8A:
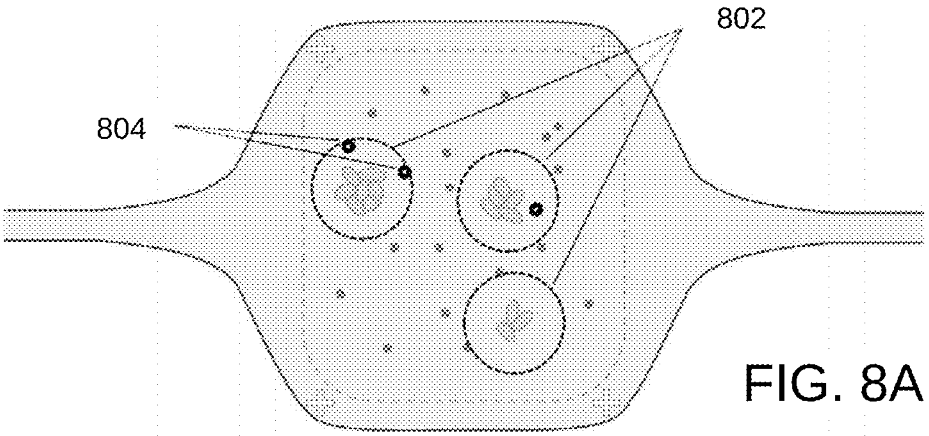
FIGS. 8A-B are diagrams illustrating neighboring cell removal around iPSC colonies during an iPSC reprogramming process in accordance with various implementations.
Figure 8B:
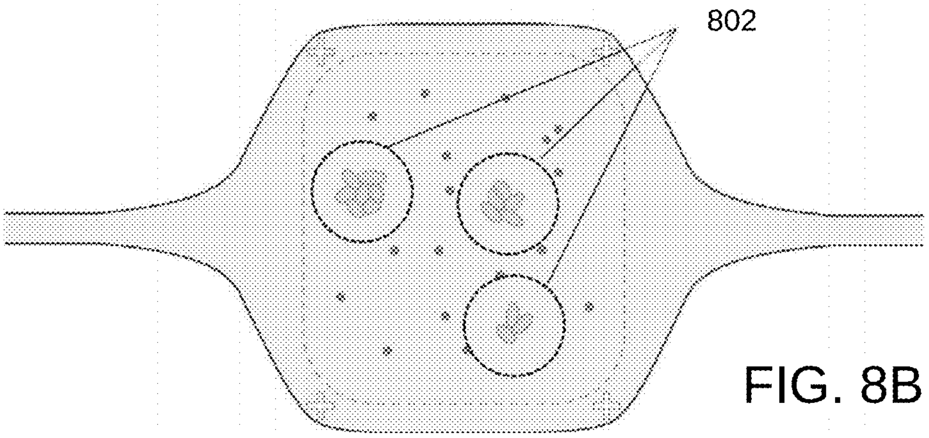

FIGS. 8A-B are diagrams illustrating neighboring cell removal around iPSC colonies during an iPSC reprogramming process in accordance with various implementations. This may ensure continued clonality of the iPSC colonies.

FIG. 8A shows an example where three clonal iPS-like colonies with corresponding exclusion zones 802 are designed to maintain clonality by removing any cells not clearly belonging to the original clonal colony. The size of these zones may be determined by the interval between imaging//selective cell removal, the expected area growth rates of the colonies, and the expected rate of emergence of other iPS candidates from somatic cells. Any neighboring cells 804 not clearly belonging to the clonal colonies that are detected inside these clonal zones may be considered contaminant cells, are marked for deletion, and deleted. After deletion (which may include direct removal, or destruction and subsequent removal through washing), the exclusion zones 802 are again demonstrably clonal in origin. In all the selective removal operations depicted in the current disclosure, re-imaging after removal and washing may be used to confirm removal of target cells. Any cells that remain may be retargeted with a cell removal mechanism (e.g., cell editing subsystem 114) until removal is complete.

Figure 9A:
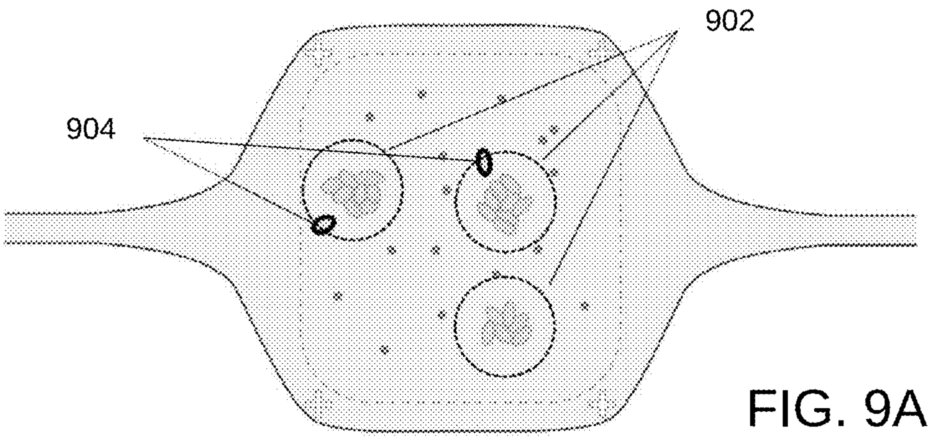
FIGS. 9A-B are diagrams illustrating removal of cells that break off from iPSC colonies during an iPSC reprogramming process in accordance with various implementations.
Figure 9B:
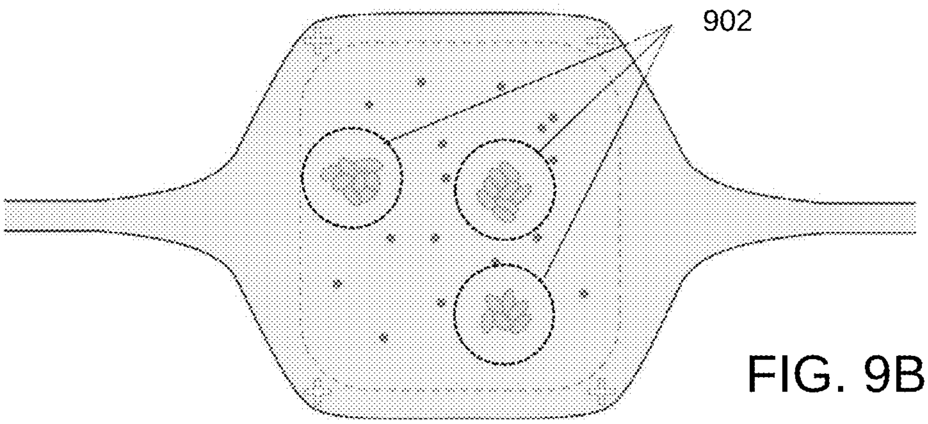

FIGS. 9A-B are diagrams illustrating removal of cells that break off from iPSC colonies during an iPSC reprogramming process in accordance with various implementations. Cells that break off from clonal iPSC candidate colonies and move beyond a defined perimeter around those colonies may endanger clonality of the verified-clonal colonies. This operation is analogous to the process described with respect to FIGS. 8A-B, except applied to cells whose origin cannot be traced to the clone owning the exclusion zones 902. These potentially-escaped cells 904 are considered contaminant cells and should be removed if they cannot be traced back to an originating colony, as it may be a clone of the colony. If the iPS-like cells can be traced to the local clone, then the exclusion zone 902 may be widened to contain the cells instead. Note the circular zones drawn in FIGS. 9A-B are here are only for illustration. In most cases the exclusion zones will be a distanced-based metric from the nearest known cells belonging to the specific clone, to define a polygonal exclusion zone. After a cell removal mechanism (e.g., cell editing subsystem 114) removes the potentially-escaped cells 904, the pure clonal zones are shown in FIG. 9B with no extraneous cells in their exclusive zones 902.

Figure 10A:
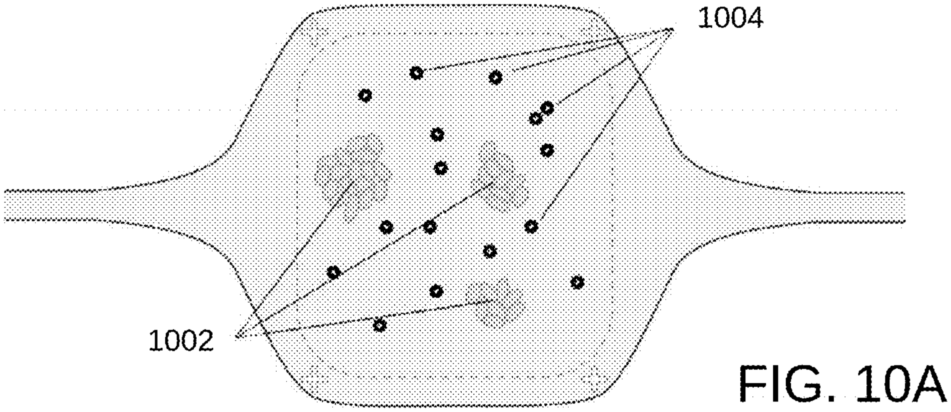
FIGS. 10A-B are diagrams illustrating removal of non-iPS cell candidates during an iPSC reprogramming process in accordance with various implementations.
Figure 10B:
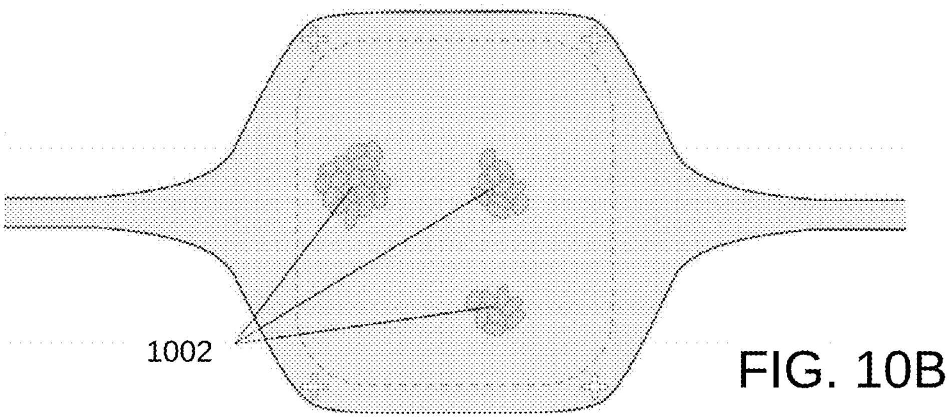

FIGS. 10A-B are diagrams illustrating removal of non-iPS cell candidates during an iPSC reprogramming process in accordance with various implementations. At a timepoint at which new iPS colonies are unlikely to emerge from somatic cells, the remaining somatic cells (for example, CD34+ cells that have had episomal vector delivered) are considered contaminant cells and are actively removed from the cell culture chamber, as shown in FIG. 10A in which non-reprogrammed cells 1004 are targeted and removed while leaving iPSC colonies 1002 alone. After clearing of remaining un-reprogrammed cells, only iPS colonies 1002 remain as shown in FIG. 10B.

Figure 11A:
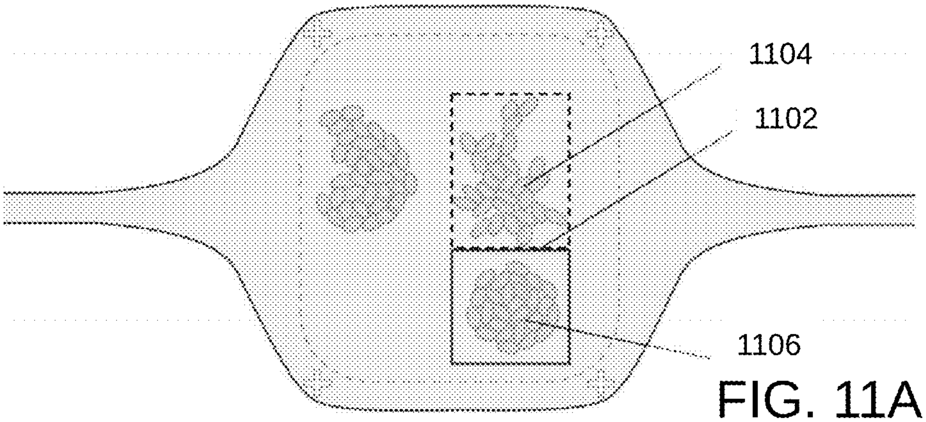
FIGS. 11A-C are diagrams illustrating removal of a cell colony during an iPSC reprogramming process in accordance with various implementations.
Figure 11B:
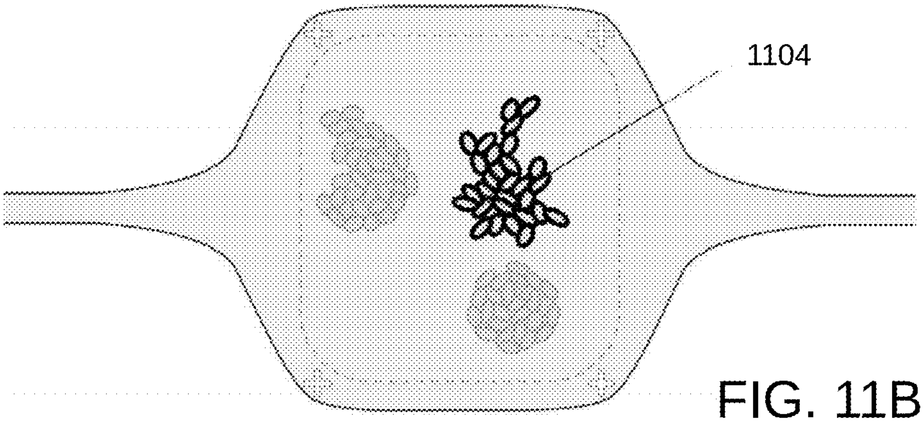
Figure 11C:
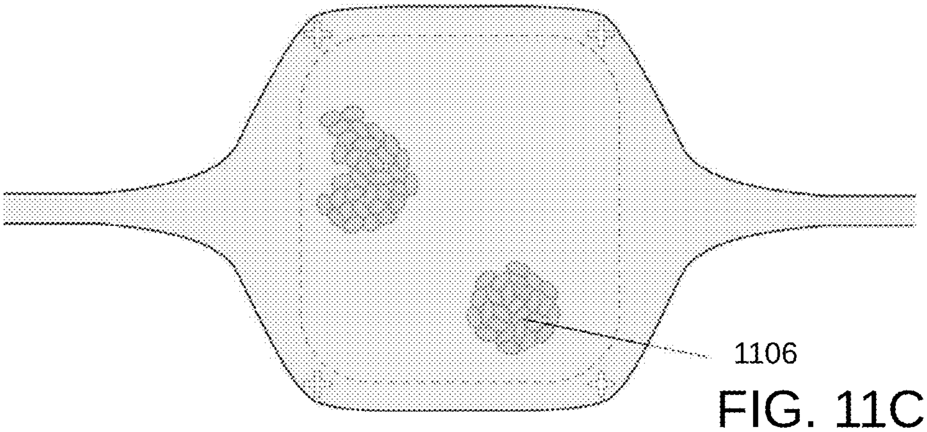

FIGS. 11A-C are diagrams illustrating removal of a cell colony during an iPSC reprogramming process in accordance with various implementations. Cell colonies may be removed when, for example, two clonal colonies of different clonal origin are in danger of colliding and cross-contaminating. The cell culture system disclosed herein has the advantage that through continuous imaging, tracking, and isolation of clonal colonies, it can allow multiple clonal colonies to co-exist in a cell culture container without the possibility of cross-contamination of clones (i.e., creation of non-clonal colonies). As a result, the behavior of each colony is more uniform due to its clonal origin, and ultimately no post-reprogramming clone process is required to ensure valid quality control results. Clone behavior can be tracked over time, and when a clone is determined to be poor, or when two clones are in danger of colliding in the container, one clone may be selected for removal.

FIG. 11A shows two clonal colonies 1104 and 1106 that have been determined to be in danger of colliding within the next imaging/editing period, as indicated by the border 1102. In this example, the clone 1106 has been determined to have a higher probability of yielding a good iPSC clone. These determinations may be made by a computing subsystem (e.g., computing subsystem 110) in coordination with a cell imaging subsystem (e.g., imaging subsystem 112), or may be determined by manual observation and selection, or a combination of automation and manual observation/selection. As a result, as shown in FIG. 11B, the colliding but (by prediction) inferior clone 1104 is selected for removal. After removal, as shown in FIG. 11C, the selected clone 1106 is now in no danger of collision or cross-clone contamination.

Figure 12A:
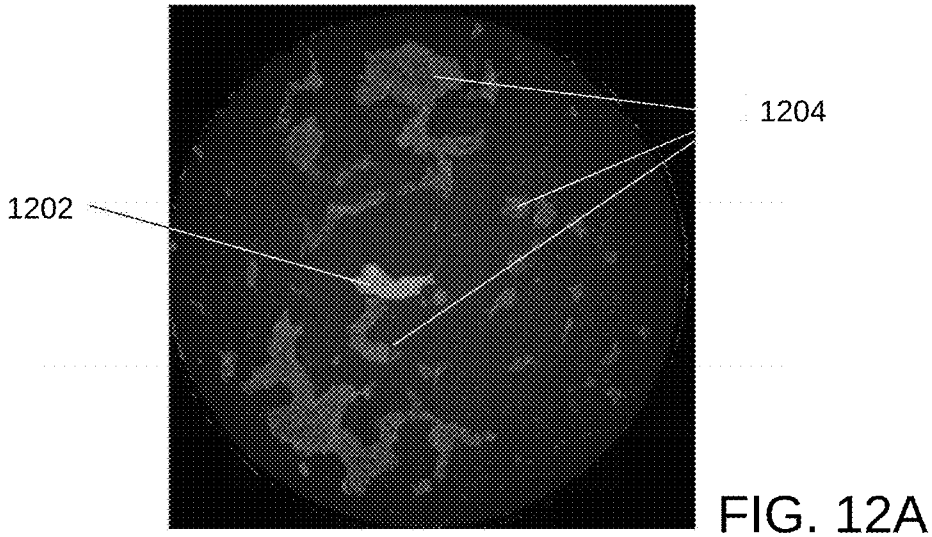
FIGS. 12A-B are images illustrating removal of a cell colony during an iPSC reprogramming process in accordance with various implementations.
Figure 12B:
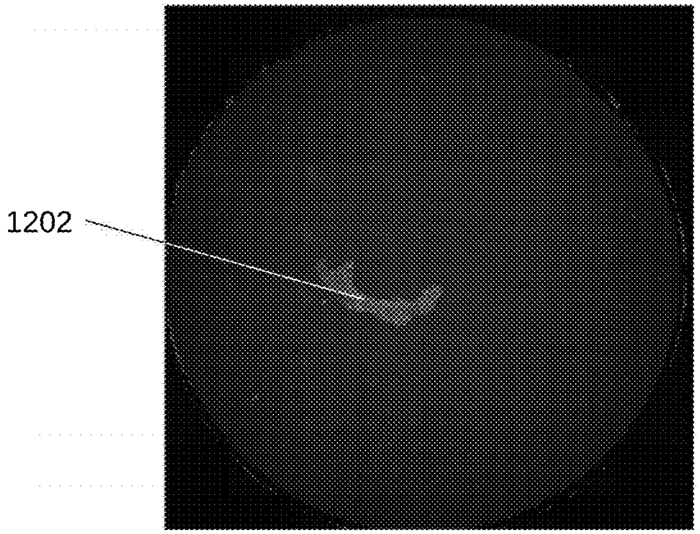

FIGS. 12A-B are images illustrating removal of a cell colony during an iPSC reprogramming process in accordance with various implementations. In the example shown in FIGS. 12A-B, a terminal decision may be made in which a single clone//colony is selected to make a single clonal sample in the cell culture container. In FIG. 12A, a desired colony 1202 is selected by manual or automatic means (e.g., by a computing subsystem). A number of other (non-selected) colonies 1204 are present in the cell culture container. In this example, the images shown are brightfield microscopy images of a single well on a 96-well microplate. The brighter (colony) regions are in fact an array of points plotted over the image that represent the extract (x, y) coordinates of each cell, as predicted by a deep learning algorithm that effectively converts brightfield images into cell nuclear coordinates. A polygon image of the desired colony 1202 represents a selection of those cells that is selected to remain in the container. The inverse of this cell selection is used to guide removal). FIG. 12B shows an image acquired 24 hours after cell removal by pulsed laser, in which the selected colony 1202 is the sole remaining colony (and has proliferated). The other colonies have been removed so that the microplate well is open for the selected colony 1202 alone to proliferate and expand.

Figure 13A:
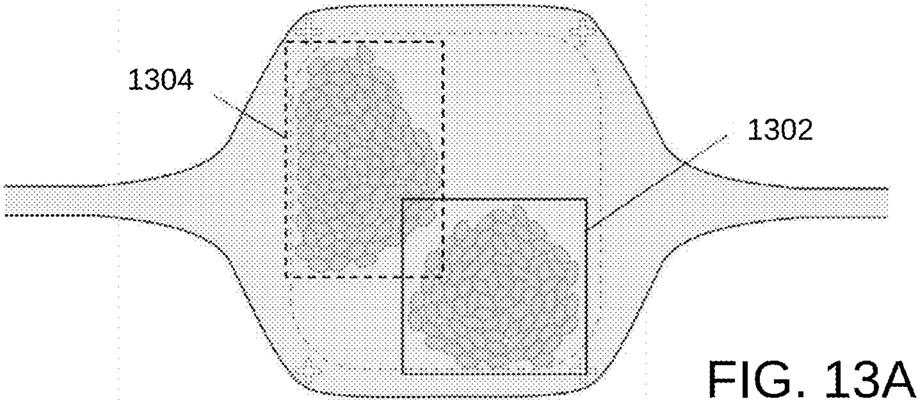
FIGS. 13A-C are diagrams illustrating selection of a cell colony during an iPSC reprogramming process in accordance with various implementations.
Figure 13B:
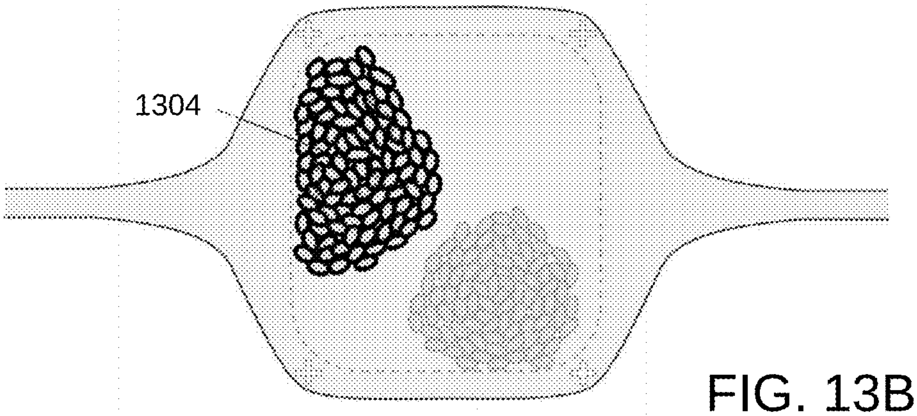
Figure 13C:
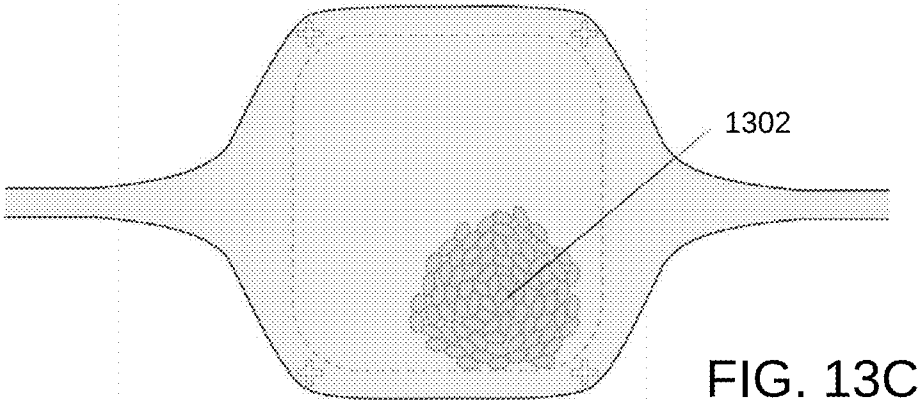

FIGS. 13A-C are diagrams illustrating selection of a cell colony during an iPSC reprogramming process in accordance with various implementations. This illustrates the ultimate selection of a single clonal colony to create the output iPS cell product. A cell removal mechanism (e.g., cell editing subsystem 114) is used to remove any other cells or colonies not stemming from the selected clone. In FIG. 13A, a selected colony 1302 is retained while any other colonies 1304 are marked for removal and removed by the cell removal mechanism as shown in FIG. 13B. Ultimately only the selected colony 1302 remains in the container, as shown in FIG. 13C. The non-presence of any other cells in the well may be checked by one or more subsequent imaging runs, and any remaining cells removed using the cell removal mechanism (and appropriate washing) until it is verified that only the desired clonal colony 1302 is present.

Figure 14A:
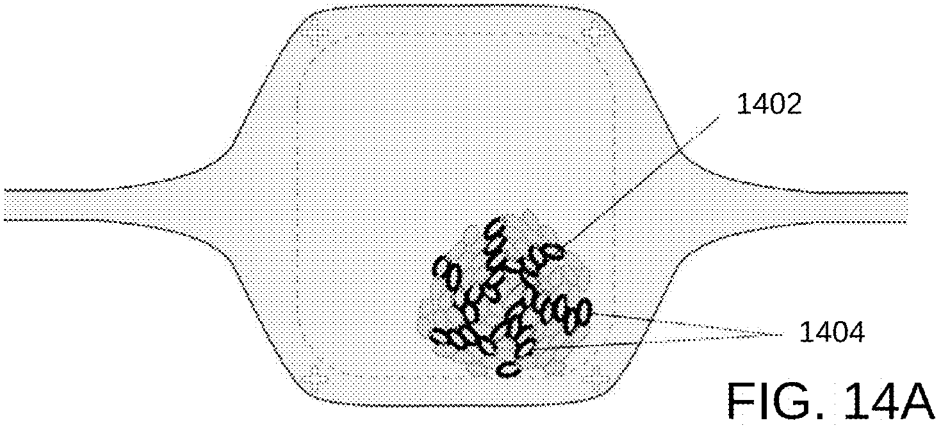
FIGS. 14A-C are diagrams illustrating spreading of a cell colony in a cell culture chamber during an iPSC reprogramming process in accordance with various implementations.
Figure 14B:
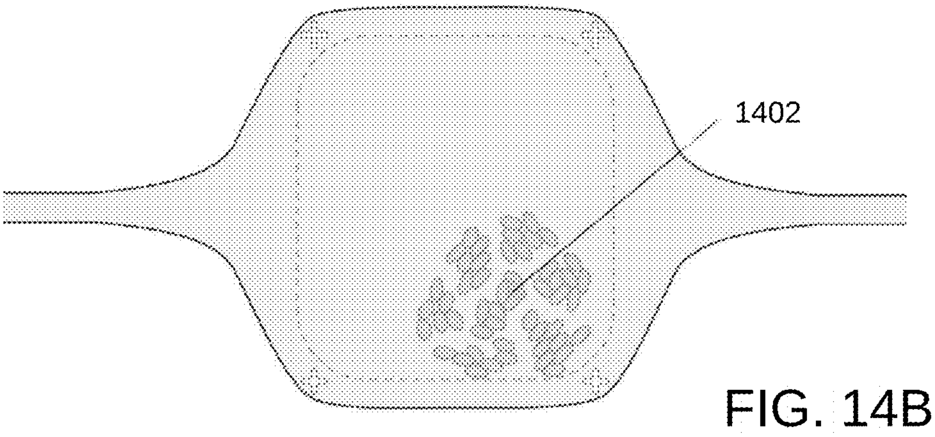
Figure 14C:
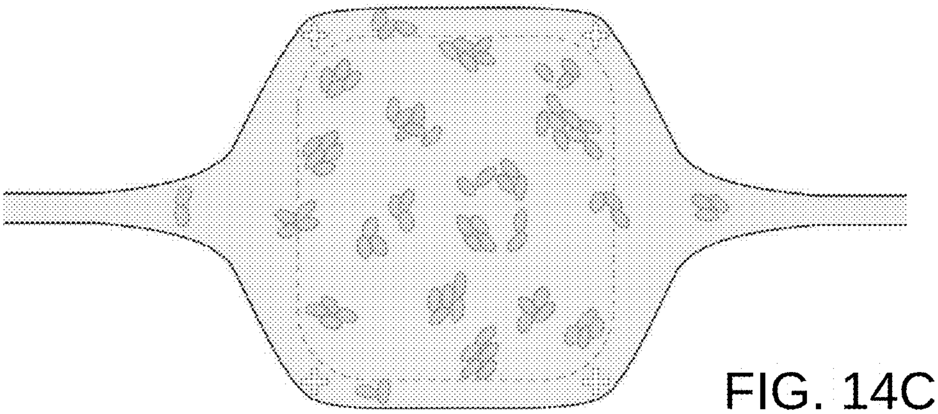
Figure 14D:
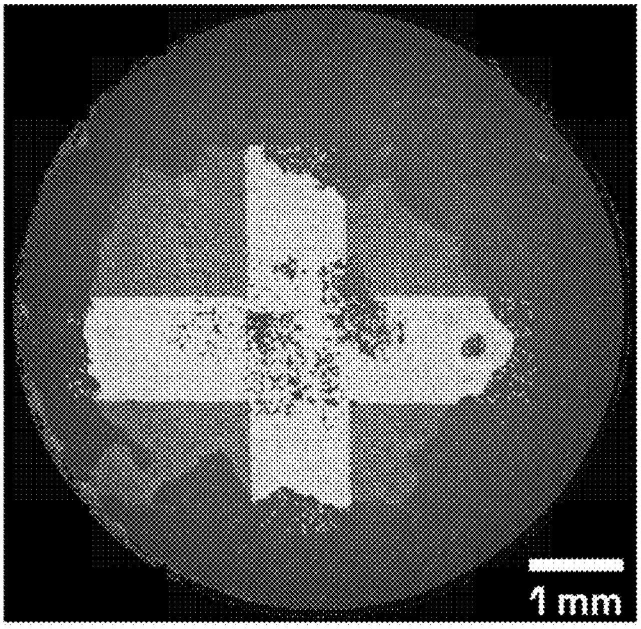
FIGS. 14D-14E show an initial colony controlled for density that spread over a growth chamber in accordance with various implementations.
Figure 14E:
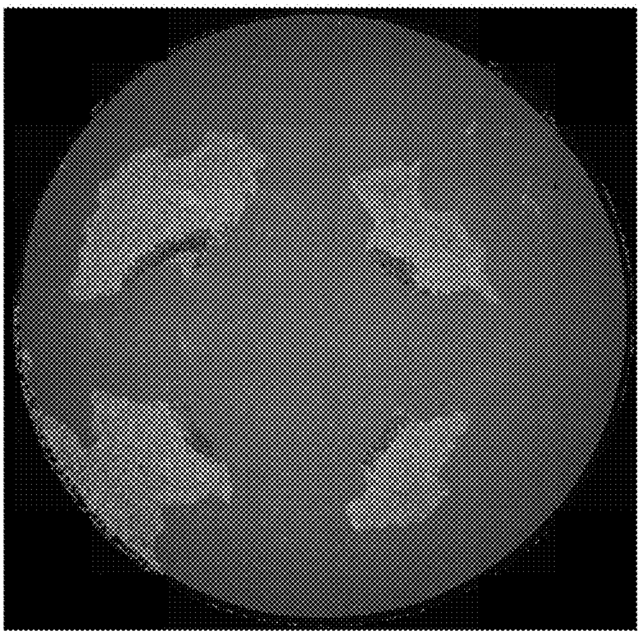

FIGS. 14A-C are diagrams illustrating spreading of a cell colony in a cell culture chamber during an iPSC reprogramming process in accordance with various implementations. Specifically, a cell removal mechanism (e.g., cell editing subsystem 114) may be used to break apart one or more cell colonies derived from a common cell (i.e., a monoclonal colony), followed by detachment of the fragments of the colony/colonies, and distribution over the cell culture container so as to provide maximum space for expansion of the clone. In the example shown in FIGS. 14A-C, a clonal colony is sectioned into pieces, then gently lifted off the cell culture surface, and then distributed across the cell culture chamber in order to seed a uniform expansion of the clone. In FIG. 14A, a clonal colony 1402 is treated with a selective cell removal mechanism acting on a subset of cells 1404, which are then removed from the cell culture container. After removal of the subset of cells 1404 as shown in FIG. 14B, the clonal colony 1402 has been fragmented. The individual colony fragments are easier to lift off the cell growth surface using trypsinization or any similar process. The pieces, once in suspension, may then be redistributed around the container as shown in FIG. 14C. FIGS. 14D-E show an initial colony controlled for density that spread over a growth chamber. As shown in FIG. 14D, a single colony is divided into four pieces with laser processing. Next, as shown in FIG. 14E, the divided pieces of the colony continue to grow, with some preference to outward direction, after washing and continued cell culture.

Figure 15A:
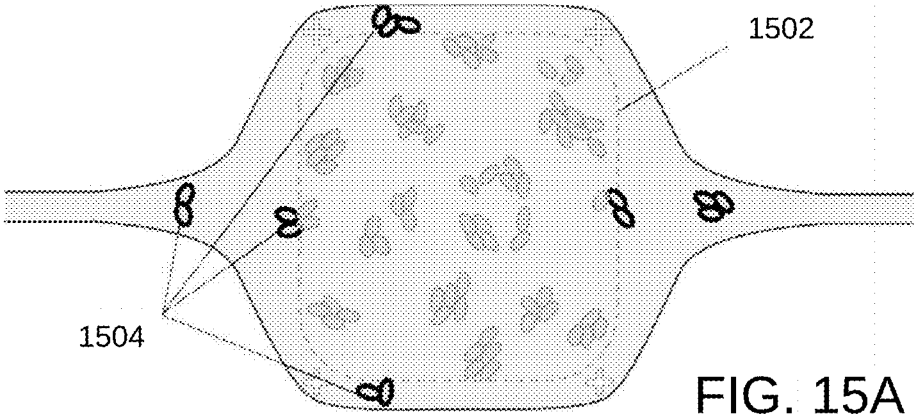
FIGS. 15A-B are diagrams illustrating removal of cells outside of designated regions during an iPSC reprogramming process in accordance with various implementations.
Figure 15B:
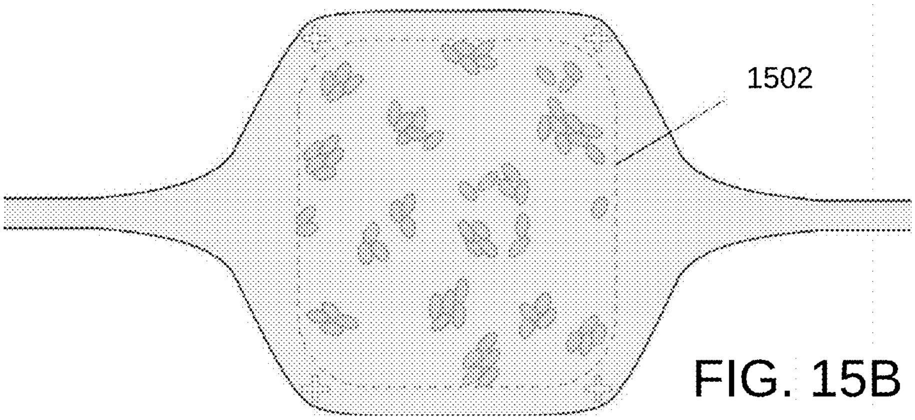

FIGS. 15A-B are diagrams illustrating removal of cells outside of designated regions during an iPSC reprogramming process in accordance with various implementations. Cells growing outside of designated regions of the cell culture chamber may be removed to prevent cell growth in border regions of the cell culture container where media conditions, chemical gradients, temperature, flow rate/shear, convection may be less uniform or consistent. FIG. 15A depicts a number of cells 1504 that are outside of a designated region 1502 of the cell culture chamber. The cells 1504 may be identified and removed using a cell removal mechanism (e.g., cell editing subsystem 114), such that afterwards all cells in the cell culture chamber are growing within the designated region 1502.

Figure 16A:
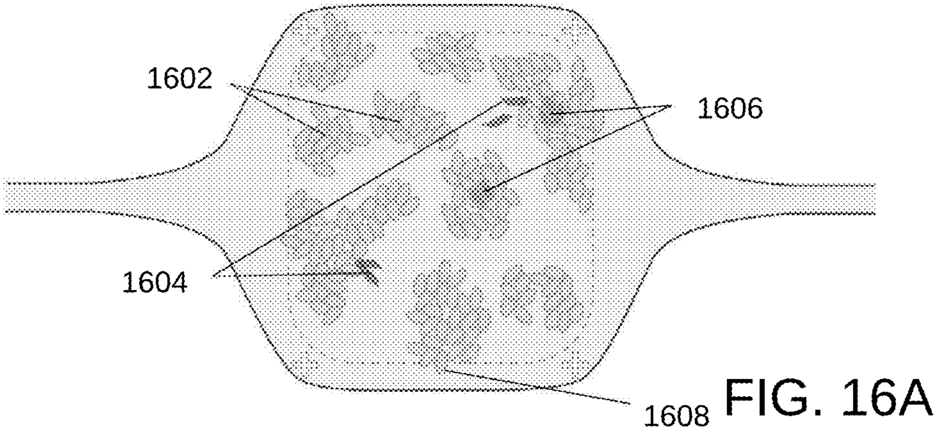
FIGS. 16A-C are images illustrating removal of various cells during an iPSC reprogramming process in accordance with various implementations.
Figure 16B:
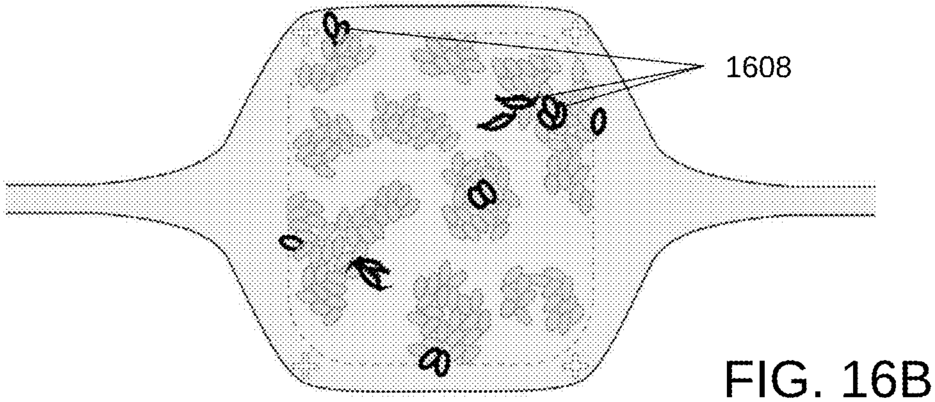
Figure 16C:
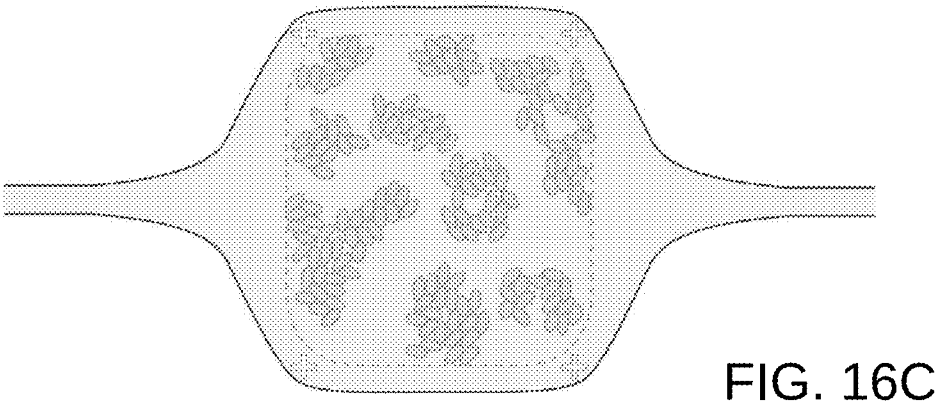

FIGS. 16A-C are images illustrating removal of various cells during an iPSC reprogramming process in accordance with various implementations. Cells may be removed during the cell culture process for a number of reasons, including cells that (a) proliferate outside the designated growth area, (b) grow to excessive density within colonies, or (c) spontaneously differentiate. FIG. 16A depicts a cell culture chamber containing a variety of cells, including iPSCs 1602 that are at desirable density and without spontaneously differentiating cells, spontaneously differentiated cells 1604, regions of iPSC colonies 1606 that are too high a density due to internal colony proliferation, and cells 1608 pushing over the established boundary for cell growth. It is desirable to control the internal density of iPSC colonies such that all cells remain observable in label-free imaging, all cells remain removable by a cell removal mechanism (e.g., cell editing subsystem 114), and cells do not grow to a density at which they spontaneously differentiate or form 3D structures that tend to differentiate. As depicted in FIG. 16B, the spontaneously differentiated cells 1604, high density colonies 1606, and boundary cells 1608 are all designated as contaminant cells targeted for removal 1610 via imaging (e.g., imaging subsystem 112) and downstream computation (e.g., computing subsystem 110). The cell culture system may determine the coordinates of the targeted cells 1610 and then remove them using the cell removal mechanism. The resulting cell culture is free of these potential impairments to a high-quality clonal iPSC culture, as shown in FIG. 16C.

Figure 17A:
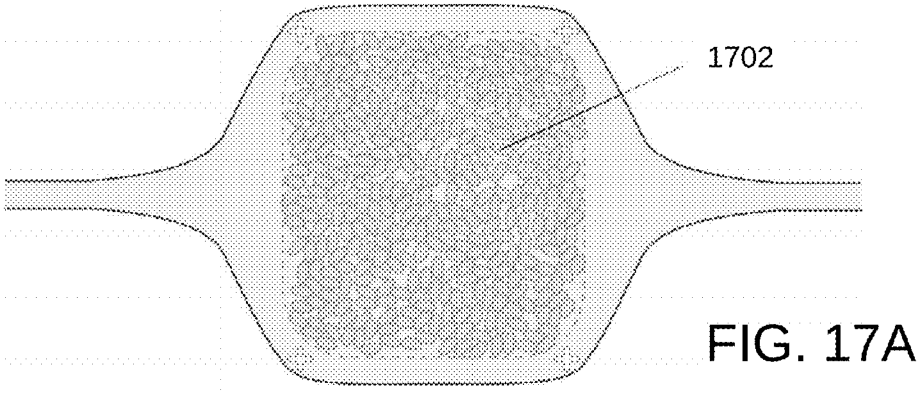
FIGS. 17A-C are diagrams illustrating fragmenting of a cell colony in a cell culture chamber during an iPSC reprogramming process in accordance with various implementations.
Figure 17B:
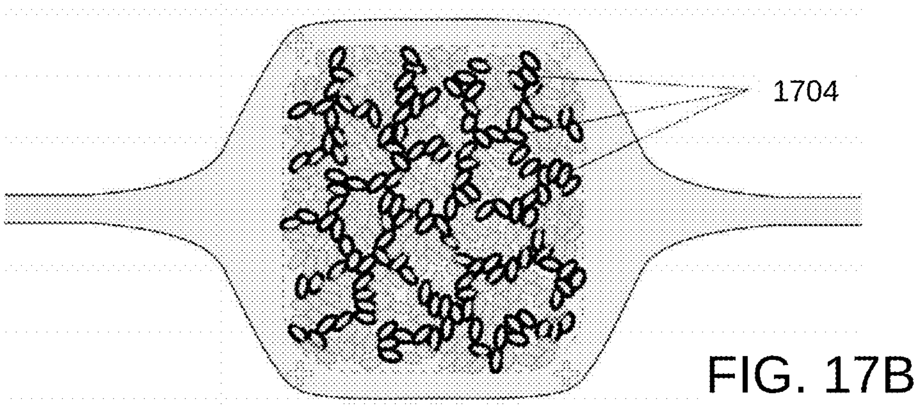
Figure 17C:
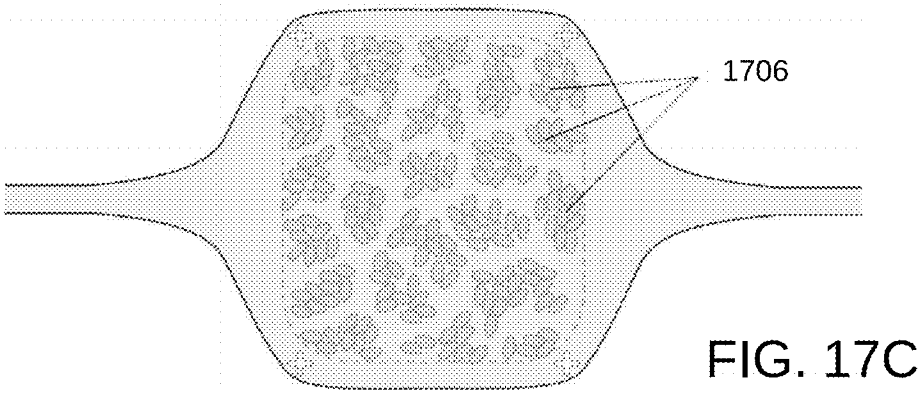

FIGS. 17A-C are diagrams illustrating fragmenting of a cell colony in a cell culture chamber during an iPSC reprogramming process in accordance with various implementations. Once a clonal cell colony reaches a maximum confluency (e.g., it grows to fill the entirety of the designated growth region of a cell culture chamber), a cell removal mechanism (e.g., cell editing subsystem 114) may repeatedly remove some of the cells to allow for multiple divisions of iPS cells (conventionally known as "passages," but as implemented herein does not require removal of the clonal iPS cells from the cell growth surface or cell culture container). This may, for example, enable clearance of a reprogramming vector including, but not limited to, episomal vectors, Sendai virus, or self-replicating mRNA. In this example, the cell count is reduced and growth areas are opened using the cell removal mechanism, but cells are removed in a biologically-relevant manner that leaves iPS cells in contact with clusters neighboring cells.

A clonal iPSC cell culture 1702 approaching high or full confluency is depicted in FIG. 17A. FIG. 17B shows a method of reducing cell count to allow cell division without overcrowding, and therefore vector clearing. Namely, a cell removal pattern 1704 is calculated based on cell imaging that leaves iPSC structures with sufficient iPSC numbers and neighbor contacts that maintain iPSC health. This is akin to clumped passaging of iPS cells in conventional container-to-container passaging, but allows the process to be conducted in a single container, which significantly simplifies the process, reduces consumable usage, lowers stress on the remaining cells, and allows the process to be performed inside of a closed, sterile container, isolated from other patient samples and potential contaminants. A computing subsystem (e.g., computing subsystem 110) may determine the cell removal pattern 1704 from images obtained from a cell imaging subsystem (e.g., imaging subsystem 112). FIG. 17C shows the remaining cell colony 1706 after the cell removal mechanism has removed the cell removal pattern 1704. The cell colony 1706 may now undergo further cell division into the resulting gaps, while keeping sufficient connection between cells to maintain cell health and chemical and mechanical signaling, which is often lost during conventional passaging. It should be noted that a number of patterns that meet these criteria are possible, for example an "island positive" pattern such as the one shown here (where on average convex islands of cell remain, surrounded by a network of cleared areas), or "island negative" where cells form a network around cleared convex areas.

Figure 18A:
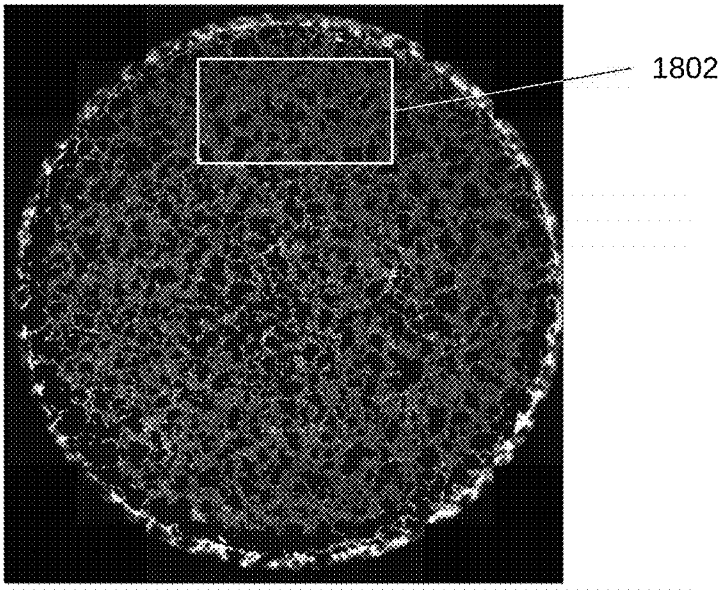
FIGS. 18A-B are images illustrating fragmenting of a cell colony in a cell culture chamber during an iPSC reprogramming process in accordance with various implementations.
Figure 18B:
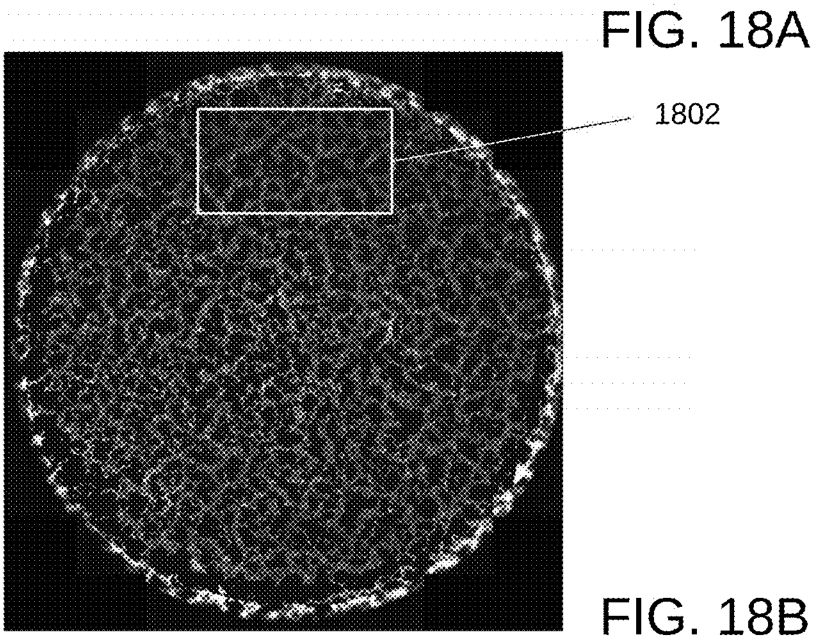
Figure 18C:
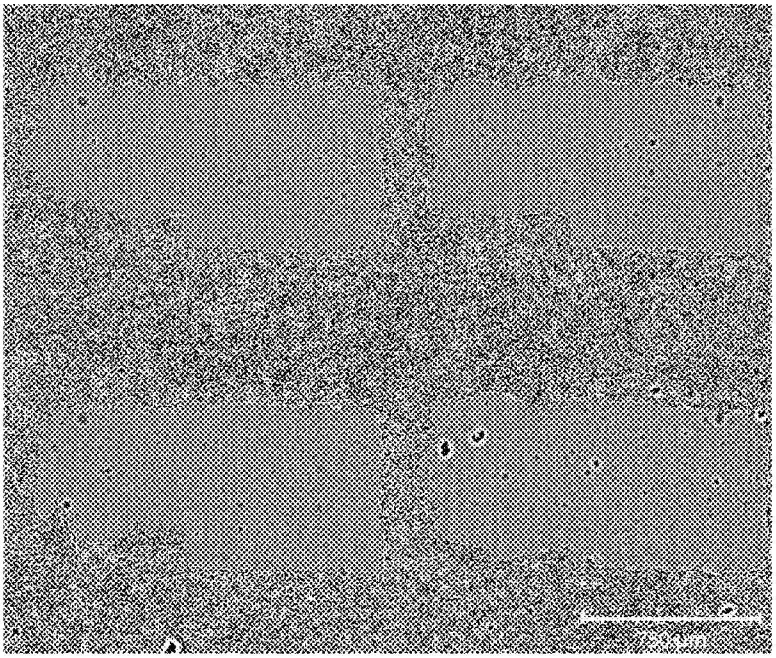
FIG. 18C shows a dense hiPSC cell culture removed using laser microbubble lysing and washing in accordance with various implementations.
Figure 18D:
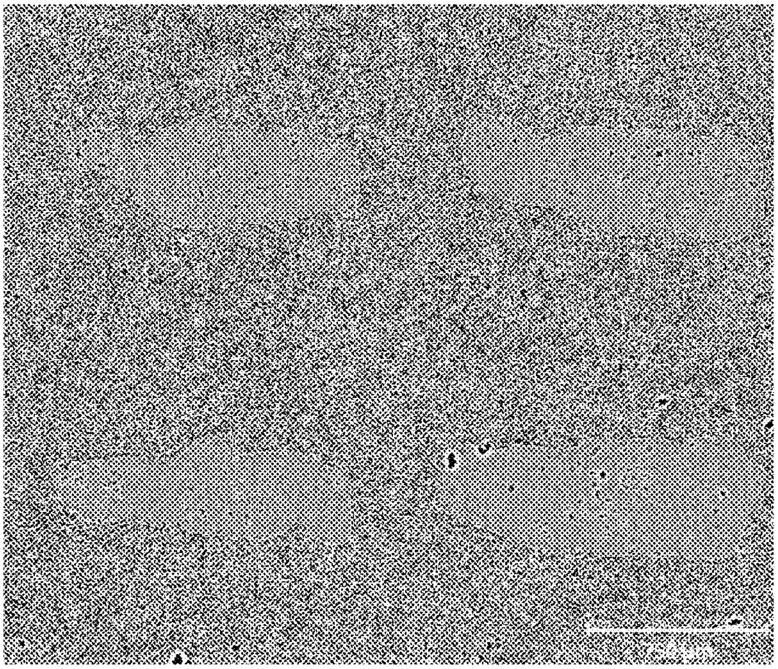
FIG. 18D shows regrowth of the hiPSC cell culture after 24 hours in accordance with various implementations.

FIGS. 18A-B are images illustrating fragmenting of a cell colony in a cell culture chamber during an iPSC reprogramming process in accordance with various implementations. FIGS. 18A-B are images illustrating the operation described with reference to FIGS. 17A-C on actual cells. FIG. 18A shows a cell culture container (e.g., a single well within a 96-well plate) with iPS cells that have been Calcein AM (live cell stain) labelled. Near the top of the well, the iPS cells have reached high density in region 1802. The cells were imaged in label-free brightfield (not shown) imaging, and a deep learning network was used to extract (x, y) coordinate positions of all cells. The cell positions were used to calculate local density. Where density was higher than desirable as in the region 1802, a pattern of cell removals that left intact contiguous networks of iPSCs was calculated. As can be observed from the difference between images in FIG. 18A (prior to selection and removal) and FIG. 18B (after selective removal of cells), the region 1802 has had density decreased significantly, while leaving a viable network of iPSCs (as indicated by the Calcein AM cell viability stain) for further proliferation. This process may be repeated to clear reprogramming vectors from the iPSCs. Another example of cell removal and subsequent regrowth is illustrated in FIGS. 18C-D. FIG. 18C shows a dense hiPSC cell culture removed using laser microbubble lysing and washing. FIG. 18D shows regrowth of the hiPSC cell culture after 24 hours.

Figure 19A:
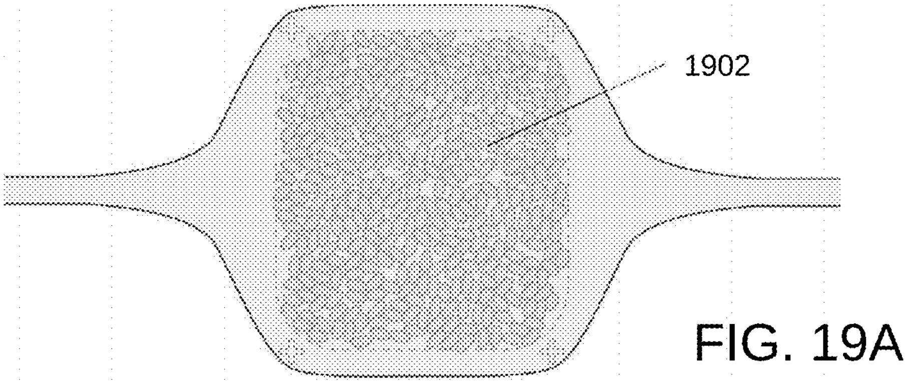
FIGS. 19A-C are diagrams illustrating harvesting of cells in a cell culture chamber during an iPSC reprogramming process in accordance with various implementations.
Figure 19B:
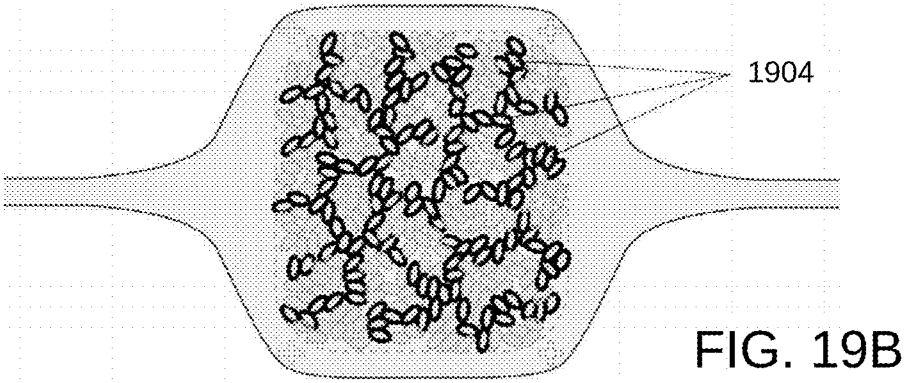
Figure 19C:
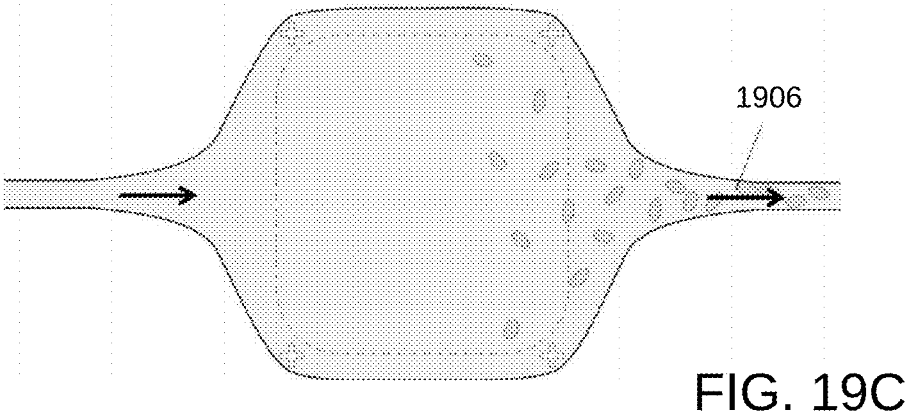

FIGS. 19A-C are diagrams illustrating harvesting of cells in a cell culture chamber during an iPSC reprogramming process in accordance with various implementations. In this example, a cell removal mechanism (e.g., cell editing subsystem 114) is used to prime the cell culture by opening up gaps between small islands of cells, making the subsequent removal with an agent such as Trypsin gentler (e.g., requiring less exposure time), before removal of the clonal iPS cells in suspension. FIG. 19A depicts a clonal cell colony 1902 produced with the systems and methods disclosed herein, approaching full confluency. The cell population may be directly treated with trypsin for liftoff and harvest. However, in this example, a selective cell removal mechanism may be used, as shown in FIG. 19B, to selectively remove a sparse set of cells 1904 that cuts the clonal cell colony 1902 into smaller islands prior to lift-off into suspension. Finally, as shown in FIG. 19C, clonal cells 1906 from the clonal cell colony 1902 may be harvested in suspension from the cell culture container.

The operations described with respect to FIGS. 3A-19C may be conducted by a cell culture system as disclosed herein (e.g., cell culture system 100). The cell culture system may provide a closed system for cell culture growth (e.g., a closed cassette system), as well as provide automated imaging, cell editing, cell harvesting, cell monitoring and prediction, and other cell culture functions. In some implementations, the cell culture system may operate in a fully automated fashion with user oversight of cell culture processes through user interfaces. In some implementations, the cell culture system may also operate in a semi-automated fashion, in which users may manually conduct one or more of the cell culture steps. For example, a user may manually observe the cell culture and identify cells and cell colonies that should be kept or removed, and the cell culture system may use automated cell editing functions to remove the unwanted cells and cell colonies. Thus, the cell culture system disclosed herein may be configured to produce monoclonal cell output products, such as monoclonal iPSCs, in a closed system using the operations described with respect to FIGS. 3A-19C. The use of automated cell imaging and editing may help keep cell cultures clonal during cell growth and proliferation. Because the output cell products are to be used in various cell therapies and other medical applications, ensuring monoclonality is important for a variety of reasons such as patient safety, differentiation/treatment efficacy, and adhering to applicable statutes, regulations, and standards concerning cell therapies utilizing the output cell products.

Cell Culture Density Mapping, Statistics and Management

In some implementations, the imaging subsystem disclosed herein is used to generate a map of cell density across at least a portion of the cell culture container. This density can be recorded over time as a time series of cell density maps. The density map may be generated from label-free images using a number of methods including but not limited to: (1) prediction of individual cell or nuclear locations via a machine learning model such as a pre-trained convolutional neural network, and then aggregation of these locations into a local density map; (2) direct prediction of local density from label-free images via a machine learning model such as a pre-trained convolutional neural network; and/or (3) prediction of local density from label-free images via a set of conventional image processing operations, for example, bandpass filters on multiple z slices, thresholding, and summation and then scaling to estimate the number of nuclei or cells in a local region. As previously described, the label-free images may include, but are not limited to: brightfield images, darkfield images, phase images, quantitative phase images, DIC images, and other image types, optionally wherein each of these images include multiple Z slices (focal planes).

Density maps may be generated at multiple scales, meaning the span of the local area over which density is estimated. For example, the resolution of the incoming brightfield image may be 0.65 microns and have 3 Z planes, and a density mapping model may be trained using ground truth densities with a span (two times the sigma used in Gaussian filtering) of 20 microns, and the resulting map output has a resolution of 10 microns to capture the map with this span. Further density maps at lower resolution may be produced, or the density map may be processed via image processing operators such as bandpass filters in order to bring out specific features in cell cultures such as colonies of a certain size, colony margins, or individual cells.

For example, in an iPSC cell culture, the density map may be used to track both confluence and local density as cells expand in a container. A range of healthy cell densities may be established, for example a maximum local density of 750,000 cells/$cm^2$ may be established. Then a cell deletion mechanism such as laser-activated explosive microbubbles may be used to remove (1) regions over a certain size (e.g., a threshold surface area of adherent cells) exhibiting this density or (2) regions that are predicted to reach that density within a set time-frame, for example, over the next 24 hours, in a process where the cell culture is imaged and laser-scanned regularly (e.g., daily or more frequently). The cell removal maps may be processed in such a manner as to leave biologically relevant structures, for example, leaving intact clusters of cells in iPSC cultures in order to preserve good cell health.

Using this local density mapping and management technique, a cell culture such as an iPSC culture may be maintained with healthy local densities while maintaining or achieving a range of global densities. This is opposed to conventional processes where cells grow uncontrolled, and rule-of-thumb "confluence" (rough area covered by cells) measures are used to decide when to transfer cells into a new container. Using the present method, a relatively high local density may be maintained in a globally sparse container (for example where islands of cells reach a sufficiently high density to commence a reprogramming or differentiation process), or a maximum healthy local density may be maintained while pushing the global cell culture much closer to 100% confluence than conventional cell culture processes allow (due to local pileup of cells beyond healthy densities, which may cause spontaneous formation of unwanted 3D structures, cell death or quiescence, or spontaneous cell differentiation). For example, if confluence is defined as the percentage of the desired cell container growth area covered by cells (which may be in some cases defined as, for example, 10% of the maximum desirable local cell density (for example 75,000 cells/$cm^2$ for iPSCs)), and local cell density is measured only inside these covered areas, the present disclosure allows combinations of confluence and local cell density measures to be achieved and maintained that have desirable outcomes, such as differentiation efficiency or cell process yield, but that are not generally achievable by passive cell culture. For example, for the purpose of expanding cells with maximum efficiency in a single container, cell confluence of >75%, >80%, >85%, >90% or even >95% may be achieved with the present disclosure while maintaining local cell density measures such that the 90th percentile local density as measured over a roughly 250 micron diameter region still remains under the desired maximum, which may be in the ranges of 400,000-500,000 cells/cm$^2$, 500,000-600,000 cells/cm$^2$, 600,000-700,000 cells/cm$^2$, 700,000-800,000 cells/cm$^2$, or 800,000-900,000 cells/cm$^2$. These maximum desirable densities may vary by cell type and cell culture condition. Conversely, the present disclosure may be used to maintain a narrow distribution of local cell densities while keeping an overall low cell confluence, for example during a cell differentiation process. For example, local density may be maintained with a CV of <50%, <40%, <30%, <25%, <20%, <15% or even <10% as measured in a 250 micron diameter region, while maintaining confluence levels of <50%.

Cell Division, Proliferation and Motility Measurements

The systems and methods disclosed herein can use cell density map time series with two or more measurements to generate maps of cell culture dynamics, including but not limited to, local cell division rate, cell colony proliferation over adjacent regions or into regions that have been cleared by cell deletion processes, or cell motility across adjacent regions.

A computing subsystem (e.g., computing subsystem 110) may calculate the approximate local cell division rate by generating density maps at a first timepoint and at a later second timepoint, and dividing the density at the second timepoint by the density at the first timepoint, taking the log base 2 of this ratio, inverting the result and multiplying by the time elapsed between the first and second timepoints. A typical division rate for low-density iPSCs may be in the 16-18 hour range, for example, whereas cells that have committed to a lineage (i.e., are differentiating) have a cell cycle (division rate) in the range of 24-32 hours. iPSCs that are at high density (over 500,000 cells/cm$^2$, for example) may also exhibit a lower cell division rate. Importantly, cell division rate, adjusted for these density effects, is a significant marker for spontaneous differentiation and also for some karyotypic abnormalities that occur during iPSC reprogramming, and some DNA damage that may occur during reprogramming or be inherent to the somatic source cells.

As a result, the present disclosure allows the mapping of density and cell division rates, and then the selection, by use of matrix operations in a computing subsystem, regions of cells where the division rate and density are out of a normal or desired range. In some cases, for process development, ranges outside of the "normal" may be selected. In many cases, including during production of clinical cell doses, a known good range of densities and division rates will be known, and cell regions that fall outside of this range may be marked for deletion, and deleted using a cell editing subsystem such as a pulsed laser and laser-activated film that cause explosive microbubbling. In this manner, by managing both cell density and division rate, it is possible to restrict the range of cell division rates in a sample to a narrower distribution than occurs naturally in an unmanaged cell sample (e.g., an iPSC cell sample or any other cell type disclosed herein including differentiating or differentiated cells). For example, the resulting cell division rate (which may be adjusted for cell density effects by a curve that relates normal cell division rate to local cell density) may be limited to a standard deviation that is less than 25%, 20%, 15%, 10%, 7.5%, 5%, 2.5%, or 1% of the mean division rate (i.e., the coefficient of variation, or CV). This narrowing of the distribution using a combination of an imaging subsystem to image the cell culture repeatedly (potentially using fiducial markings to ensure alignment as described above), a computing subsystem to compute cell density maps and division rates, and a cell culture editing (i.e., cell deletion) subsystem to remove regions of cells falling outside of a certain band of density and division rate, may be used to improve yield of the resulting cells by providing more uniform and therefore predictable properties, by resulting in more pluripotent cells, or by removing populations that have abnormal karyotype or other DNA abnormalities. In some implementations, the same concept may be applied during cell differentiation processes to remove undifferentiated cells, cells that are improperly differentiated, or cells that have sustained some sort of karyotypic, DNA, or epigenetic damage.

In other applications, it is important to achieve a certain number of cell divisions during the course of a process. For example, for some iPSC reprogramming processes, reprogramming vectors (including but not limited to Sendai virus and episomal vectors) must be cleared from a cell population prior to quality control assays measuring pluripotency and other characteristics. The clearance of these vectors typically occurs as a byproduct of cell division, where the vector DNA is not replicated at the same rate as the cellular DNA. For example, for some episomal vectors the loss rate per cell division is roughly 5%. Conventional cell culture processes use "passages" (transfers from one container to another) as a rough timing tool to estimate when vector would be sufficiently cleared. However, there is no tracking of actual number of cell divisions: even the average across the entire population would be difficult to calculate accurately since only "confluence" (visually estimated coverage of the container by cells) is recorded prior to passaging. Tracking of subpopulation division rates or number of total divisions is impossible since cells are completely remixed during each passaging step. For example, some cell culture processes include approximately 20 passages ("late-passage" processes). One passage typically lasts 3-4 days, so a 20-passage cell culture process may span 60-80 days. Nominal population doubling time (PDT) is approximately 18 hours but in practice might be a bit higher because of density effects, so 20 passages might result 70-90 population doublings over the course of the cell culture process.

The systems and methods disclosed herein, with a passage-free process that is enabled using density mapping and laser or other density control, allows the calculation of local cell division rate, and therefore also the integrated number of divisions over time. The removal of regions of cells that are dividing too slowly or too quickly, as described herein, can equalize the number of divisions and therefore the expected vector clearing time. In addition to narrowing the range of cell division rates, the present disclosure may be used to remove regions that are calculated to have had too few cumulative cell divisions over a time period. For example, regions that differ from the mean number of divisions by more than 20%, or more than 10%, or more than 5%, may be ablated. This also removes regions of cells that have divided significantly more than the minimum number of divisions needed for vector clearance, and may be doing so remove some additional mutations that accumulate with excess cell divisions. This local cell division monitoring and management method may be used in multiple types of cell processes where a certain number of cell divisions are required to achieve a stable end population.

Cell Colony Density Mapping, Statistics and Management

Cell colonies may be imaged, located, and tracked over time using the imaging subsystem and computing subsystem. Methods for such location and tracking may include the use of the cell culture density mapping as described herein. The computing subsystem may further measure features of each colony including but not limited to area, perimeter, cell count, circularity, fine scale circularity, fractal dimension, cell morphology, density, variation of density over the area of the colony, prevalence of debris and/or dead cells, and prevalence of differentiated cells. In addition, the evolution of these features over time may in turn be used as features (for example, area growth rate, density change rate, cell division rate, etc.).

These features may be presented to an operator during the selection of a cell colony from a plurality of cell colonies located in a cell culture container. In other cases, the computing subsystem may rank or score cell colonies by these features based on a database of previous operator selections and features. In other cases, the computing subsystem may rank or score cell colonies by these features based on a database of previous assay results on selected cell colonies.

Ultimately the cell colony features and selection may be used to preserve and preferentially expand one cell colony, which may be a clonal cell colony, while removing other cell colonies from the cell culture container, which may be done using a laser and laser-activated film cell ablation system.

Aseptic Transfers and Expansion

The cell processes described here may be performed aseptically inside of a single chamber that is configured to allow imaging and selective removal of cells. In other cases, portions of the process are performed in different chambers, and cells transferred aseptically from one chamber to another using one-time use fluid connectors or aseptic tube welding operations. The output population of these imaging/laser-based chamber processes may be >5 million cells, >10 million cells, >15M cells, >50M cells, or >100M cells. In other cases, cells may be transferred aseptically from a chamber to a larger bioreactor system for expansion of the population of cells. For example, aseptic cell culture systems or various stirred-tank bioreactors (with microcarriers) may be used to expand the cell population, full aseptically, to >100M, >500M, or >1B cells. At each aseptic transfer point, a sample may also be pulled (aseptically) from the system for intermediate assays to assess the cell population.

iPSC Quality Assessment

The systems and methods disclosed herein enable the production of high quality cell products. The resulting cell products can be characterized as having a relatively higher degree of quality compared to conventionally produced cell products. In particular, iPSC production is characterized by challenges to maintaining sterility and maximizing the functionality of the resulting iPSC colony when reprogramming and expanding the cell culture. For example, iPSCs can vary with respect to pluripotency and self-renewal over time as the cells accumulate genetic abnormalities while undergoing multiple cycles of division. These defects can impair the ability of iPSCs to maintain their stem-like qualities as well as increase the risk of tumorigenesis when used in cell therapy. However, the present systems and methods provide for the automated or semi-automated manufacture of high quality iPSCs, including clonal iPSCs in a sterile environment. For example, the cell culture density mapping, cell division, proliferation, and motility measurements, and cell colony density mapping, and aspetic transfers/expansion described herein may improve the quality of the resulting iPSC cell product.

The quality of iPSC cell products (e.g., clonally expanded iPSC population) may be assessed by various assays and analytical methods disclosed throughout the present disclosure. In some implementations, molecular analyses are performed to verify the improved qualities of the iPSC product. Non-limiting examples of such molecular analyses are described in MacArthur et al., "Generation and comprehensive characterization of induced pluripotent stem cells for translational research," Regen. Med. (2019) 14(6), 505-524, which is hereby incorporated by reference in its entirety. For example, MacArthur et al. describes molecular assays for evaluating pluripotency, genomic stability, and safety, including: (1) using a computational pluripotency model to evaluate microarray-based global transcriptome data (e.g., PluriTest); (2) evaluation of real-time qPCR data for a biomarker panel of select genes to provide a quantitative assessment of pluripotency and trilineage differentiation (e.g., TaqMan hPSC Scorecard); (3) using whole genome array-based assay (e.g., KaryoStat Assay or KaryoStat HD Assay) to determine gross chromosomal copy number gain/loss or genetic mosaicism; (4) identification of variants associated with cancer-causing hotspot mutations including Tp53 using next generation sequencing-based assay (e.g., oncomine comprehensive assay v3-OCAv3); and (5) authentication of the parental and resulting reprogrammed iPSC lines using microsatellite short tandem repeat (STR) analysis (e.g., AmpFLSTR Identifiler Direct PCR Amplification Kit).

In some implementations, a cell product (e.g., iPSC or cells differentiated from the iPSCs) generated according to a system or method disclosed herein is evaluated for one or more categories of cell quality or cell culture quality. Examples of such categories include safety, identity, cell health, and pluripotency. These categories may correspond to clonal quality (cell health) or clonal functionality (e.g., pluripotency).

The safety category can include tests for contamination such as assays for *mycoplasma*, bacteria or fungi, and endotoxin. The systems and methods disclosed herein can provide an overall percentage reduction in the likelihood of contamination by one or more of *mycoplasma*, bacteria, fungi, or endotoxin of at least 10%, 20%, 30%, 40%, 50%, 60%, 70%, 80%, 90%, 95%, or 99%, compared to a conventional protocol for generating and expanding iPSCs. The systems and methods disclosed herein can provide an overall percentage of contamination by one or more of *mycoplasma*, bacteria, fungi, or endotoxin within a random selection of cell products of no more than 0.5%, 1%, 2%, 3%, 4%, 5%, 6%, 7%, 8%, 9%, 10%, 15%, 20%, or 25%. The selection of cell products used to determine contamination rate can include at least 10, 20, 30, 40, 50, 60, 70, 80, 90, 100, 200, or 400 cell products. For example, the detection of *mycoplasma* contamination in 1 of a random selection of 20 iPSC cell products generated using the systems and methods disclosed herein indicates a 5% contamination rate. Testing for *mycoplasma*, bacteria, fungi, and endotoxins can be evaluated using various commercially available assays. In some implementations, *mycoplasma*, bacteria, and fungi assays provide positive/negative identification of contamination, while endotoxin testing determines whether the cell product exceeds a threshold endotoxin concentration (e.g., 0.25 EU/mL).

The safety category can include evaluation for the presence of residual vector used for iPSC reprogramming. Through the control and monitoring of cell divisions using the systems and methods disclosed herein, any vector used for reprogramming can be confirmed to have been cleared within the cell culture (e.g., a clonal iPSC colony) by qPCR testing (e.g., <0.01 copies/cell). The safety category can include genetic tests such as assays for chromosomal integrity (e.g., g-band karyotyping, KaryoStat, whole genome sequencing) and oncogene integrity (e.g., RNA sequencing or whole genome sequencing). For example, chromosomal integrity can be evaluated to confirm the cell product's karyotype is normal (diploid and identical to donor). The systems and methods disclosed herein enable colony measurement & selection (e.g., removal of abnormal karyotypes associated with abnormal colonies), selection for regions with normal division rates (e.g., abnormal karyotypes associated with abnormal growth rates are removed via cell culture editing), and minimization of overall variation in cell divisions (e.g., some karyotype abnormalities result from excess divisions). In some implementations, the cell product (e.g., iPSC clonal colony) has a population of at least 10,000 cells, 50,000 cells, 100,000 cells, 200,000 cells, 500,000 cells, 1 million cells, 5 million cells, or 10 million cells, wherein a random selection of at least 10, 20, 30, 40, 50, 60, 70, 80, 90, 100, or 200 cells within the population are determined to have an abnormal karyotype percentage (e.g., according to any of the methods disclosed herein or known in the field) of no more than 1%, 2%, 3%, 4%, 5%, 6%, 7%, 8%, 9%, 10%, 15%, 20%, or 25%.

Oncogene integrity can be evaluated to confirm the iPSC cell product is genetically identical to the donor with respect to oncogenes or other markers of tumorigenicity (e.g., oncogene duplication, deletion of tumor suppressor genes, and other de novo mutations can occur during reprogramming and/or cell culture division/expansion). The systems and methods disclosed herein can enable colony measurement and selection as well as selection for regions with normal division rates, which may be associated with oncogene integrity. Therefore, this selection process can produce an iPSC product without requiring any invasive imaging (e.g., immunostaining) that has improved oncogene integrity. In some implementations, the cell product has a population of at least 10,000 cells, 50,000 cells, 100,000 cells, 200,000 cells, 500,000 cells, 1 million cells, 5 million cells, or 10 million cells, wherein a random selection of at least 10, 20, 30, 40, 50, 60, 70, 80, 90, 100, or 200 cells within the population are determined to lack oncogene integrity at a percentage of no more than 5%, 10%, 15%, 20%, or 25%.

The category of identity can be evaluated using an assay for short tandem repeats (STR) to determine donor identity. The systems and methods disclosed herein can enable an aseptic process with fewer or minimal transfers compared to conventional iPSC reprogramming and culturing, which reduces the risk of cross-contamination. In some implementations, the cell product has a population of at least 10,000 cells, 50,000 cells, 100,000 cells, 200,000 cells, 500,000 cells, 1 million cells, 5 million cells, or 10 million cells, wherein a random selection of at least 10, 20, 30, 40, 50, 60, 70, 80, 90, 100, or 200 cells within the population are determined to have a 100% match with the donor.

The category of cell health can be evaluated using viability and proliferation assays and analyses. The systems and methods disclosed herein can provide colony measurement and selection over time to remove unwanted/undesirable cells or clones using imaging features determined to be associated with cell quality. For example, cells can be evaluated and selected for an optimal division rate, which can result in improved viability and downstream differentiation. The cell product may be frozen for storage and/or transportation before differentiation or some other manipulation for cell therapy (e.g., autologous cell therapy). In these cases, it is important to maximize cell viability upon thawing. In some implementations, a dye exclusion assay is used determine cell viability. In some implementations, the thawed cell product has a population of at least 10,000 cells, 50,000 cells, 100,000 cells, 200,000 cells, 500,000 cells, 1 million cells, 5 million cells, or 10 million cells, wherein a random selection of at least 10, 20, 30, 40, 50, 60, 70, 80, 90, 100, or 200 cells within the population are determined to be viable using dye exclusion assay at a percentage of at least 60%, 70%, 80%, 90%, or 95%. In some implementations, the thawed cell product has a population of at least 10,000 cells, 50,000 cells, 100,000 cells, 200,000 cells, 500,000 cells, 1 million cells, 5 million cells, or 10 million cells, wherein the population has an average viability using dye exclusion assay of at least 60%, 70%, 80%, 90%, or 95%. The thawing may be performed at least 1 day, 2 days, 3 days, 4 days, 5 days, 6 days, 7 days, 2 weeks, 3 weeks, 4 weeks, 5 weeks, 6 weeks, 7 weeks, or 8 weeks post-freezing.

Cell proliferation can be evaluated using cell culture and imaging. The systems and methods disclosed herein can enable colony measurement and selection, and the selection for regions with normal or optimal division rates, which may be a reflection of cell fitness. Growth or division rates can be measured using a proliferation assay or by monitoring the growing colony via imaging analysis (e.g., machine learning identification of the number of cells within a certain area of the cell culture for images collected over time). In some implementations, the cell product has a population of at least 10,000 cells, 50,000 cells, 100,000 cells, 200,000 cells, 500,000 cells, 1 million cells, 5 million cells, or 10 million cells, wherein a random selection of at least 10, 20, 30, 40, 50, 60, 70, 80, 90, 100, or 200 cells within the population are determined to fall within a target or optimal average division rate at a percentage of at least 50%, 60%, 70%, 80%, 90%, or 95%. In some implementations, the thawed cell product has a population of at least 10,000 cells, 50,000 cells, 100,000 cells, 200,000 cells, 500,000 cells, 1 million cells, 5 million cells, or 10 million cells, wherein a random selection of at least 10, 20, 30, 40, 50, 60, 70, 80, 90, 100, or 200 cells within the population are determined to have an average division rate with a coefficient of variation of no more than 0.05, 0.1, 0.2, 0.3, 0.4, 0.5. In some implementations, the thawed cell product has a population of at least 10,000 cells, 50,000 cells, 100,000 cells, 200,000 cells, 500,000 cells, 1 million cells, 5 million cells, or 10 million cells, wherein a random selection of at least 10, 20, 30, 40, 50, 60, 70, 80, 90, 100, or 200 cells within the population are determined to have an average division rate with a standard deviation of no more than 0.5 hours, 1 hour, 1.5 hours, 2 hours, 2.5 hours, 3 hours, 3.5 hours, or 4 hours. In some cases, the division rate is 10 hours to 20 hours. In some cases, the average division rate is 10 hours to 12 hours, 10 hours to 14 hours, 10 hours to 16 hours, 10 hours to 18 hours, 10 hours to 20 hours, 12 hours to 14 hours, 12 hours to 16 hours, 12 hours to 18 hours, 12 hours to 20 hours, 14 hours to 16 hours, 14 hours to 18 hours, 14 hours to 20 hours, 16 hours to 18 hours, 16 hours to 20 hours, or 18 hours to 20 hours. In some cases, the average division rate is 10 hours, 12 hours, 14 hours, 16 hours, 18 hours, or 20 hours. In some cases, the average division rate is at least 10 hours, 12 hours, 14 hours, 16 hours, or 18 hours. In some cases, the average division rate is at most 12 hours, 14 hours, 16 hours, 18 hours, or 20 hours.

The category of pluripotency can be evaluated using a variety of methods, including but not limited to, assays for iPSC gene expression (e.g., via immunostaining or RNA expression analysis), trilineage differentiation, and other differentiation assays. Immunostaining such as flow cytometry or other imaging can be performed to evaluate iPSC gene expression. In some implementations, at least 70%, 80%, 90%, 95%, or 99% of a random selection of cells from an iPSC product expresses at least one intracellular pluripotency marker (OCT4, NANOG) and one extracellular/membrane (SSEA4+, TRA-1-60, TRA-1-81) marker. In some implementations, a random selection of cells from an iPSC product expresses at least 2%, 4%, 6%, 8%, 10%, 15%, or 20% higher levels of at least one intracellular pluripotency marker (OCT4, NANOG) and/or one extracellular/membrane (SSEA4+, TRA-1-60, TRA-1-81) marker, when compared to an iPSC product generated using a conventional protocol.

Evaluating the pluripotency of an iPSC cell product through RNA expression analysis can be performed, for example, using commercially available assays providing microarray or RNAseq analysis (e.g., PluriTest). As an illustrative and non-limiting example, the PluriTest assay utilizes expression data to determine a Pluripotency Score and a Novelty Score. The Pluripotency Score is an indicator of how strongly a model-based pluripotency signature is expressed in the analyzed sample, while the Novelty Score indicates the general model fit for a given sample (a low Novelty Score shows the sample is well represented in the current data model). In some implementations, the cell product (e.g., iPSC clonal colony) has a population of at least 10,000 cells, 50,000 cells, 100,000 cells, 200,000 cells, 500,000 cells, 1 million cells, 5 million cells, or 10 million cells, and a statistically representative selection of the population has a Pluripotency Score of at least 25, 30, 35, 40, 41, 42, 43, 44, 45, 46, 47, 48, 49, or 50, and a Novelty Score of no more than 0.8, 0.9, 1.0, 1.1, 1.2, 1.3, 1.4, or 1.5. The Pluripotency Score and/or the Novelty Score can be average values calculated using a sample size of at least 5, 10, 15, 20, 30, 40, or 50 samples. In some implementations, the cell product (e.g., iPSC clonal colony) has a population of at least 10,000 cells, 50,000 cells, 100,000 cells, 200,000 cells, 500,000 cells, 1 million cells, 5 million cells, or 10 million cells, and a statistically representative selection of the population has a Pluripotency Score that is at least 1, 2, 3, 4, or 5 higher than the cell product generated using a conventional protocol, and a Novelty Score that is at least 0.01, 0.02, 0.03, 0.04, 0.05, 0.06, 0.07, 0.08, 0.09, or 0.1 smaller than the cell product generated using a conventional protocol.

The iPSC cell product can be evaluated for differentiation into a target lineage using various assays including differentiation, immunostaining, and functional assays. In some implementations, the cell product has a population of at least 10,000 cells, 50,000 cells, 100,000 cells, 200,000 cells, 500,000 cells, 1 million cells, 5 million cells, or 10 million cells, wherein the population is determined to have a differentiation efficiency that is at least 10%, 15%, 20%, 25%, 30%, 40%, 50%, 60%, 70%, 80%, 90%, or 100% more efficient than an iPSC cell product generated using a conventional protocol. In some implementations, the cell product has a population of at least 10,000 cells, 50,000 cells, 100,000 cells, 200,000 cells, 500,000 cells, 1 million cells, 5 million cells, or 10 million cells, wherein the population is determined to have a coefficient of variation that is reduced by at least 10%, 15%, 20%, 25%, 30%, 40%, 50%, 60%, 70%, or 75% compared to an iPSC cell product generated using a conventional protocol.

The iPSC cell product can be evaluated for trilineage differentiation using various assays, for example, qPCR (e.g., TaqMan hPSC Scorecard). Trilineage differentiation can be used to evaluate for iPSC differentiation into ectoderm, mesoderm, and endoderm. Endoderm markers can include SOX17, FOXA2, CXCR4, and GATA4. Mesoderm markers can include NCAM1 and TBXT. Ecoterm markers can include NES (nestin) and PAX6. Other markers can include but are not limited to the markers disclosed in the TaqMan hPSC Scorecard, as described in Fergus et al., "Characterizing Pluripotent Stem Cells Using the TaqMan® hPSC Scorecard™ Panel." Methods Mol Biol. 2016; 1307: 25-37, which is hereby incorporated by reference in its entirety. In some implementations, the iPSC cell product has a population of at least 10,000 cells, 50,000 cells, 100,000 cells, 200,000 cells, 500,000 cells, 1 million cells, 5 million cells, or 10 million cells, wherein the population is determined to have a score or indicator of trilineage differentiation that is statistically improved or higher than an iPSC cell product generated using a conventional protocol. In some implementations, the process of generating an iPSC cell product according to the systems and methods disclosed herein produces, on average, a failure rate (e.g., failure to undergo trilineage differentiation) that is at least 20%, 30%, 40%, 50%, 60%, 70%, 80%, or 90% lower or reduced compared to a conventional protocol for generating an iPSC cell product, optionally wherein the iPSC cell product has a population of at least 10,000 cells, 50,000 cells, 100,000 cells, 200,000 cells, 500,000 cells, 1 million cells, 5 million cells, or 10 million cells.

As used herein, a conventional protocol for generating an iPSC product refers to the same reprogramming methodology used according to the systems and methods disclosed herein and known in the art, but using a manual process for cell selection and culturing, including manual passaging. For example, the conventional protocol would not include ongoing imaging, analysis, and cell editing based on cell or colony measurements and/or observed division rates, as described herein.

Methods for Controlling Cell Culture Systems

Current cell culture processes rely either on timed processes without observation or, in some 2D cell culture processes, occasional imaging and largely human observation of the cell culture in order to monitor progress, assess quality, and/or make "editing" decisions which are largely carried out manually. Examples of how cell cultures may be edited include passaging cells when a certain density is reached, removing cells that are differentiating, or transferring colonies that have the "correct" morphology as seen by a human observer.

There is a strong desire in the industry to automate cell culture processes, and accordingly there has been development in image processing techniques to attempt to replicate expert observations of cell cultures. For example, a number of image processing systems have been demonstrated that assess iPSC colonies based on their overall morphology, in order to guide decisions on colony selection. These systems essentially replicate current human observations, which may be done at a single point in time or at multiple timepoints but without correlating information between images. Decisions may be based on the overall image (pixel data) of a cell colony, corresponding roughly to shape and density. These systems generally do not incorporate cell-level data or statistics, nor do they incorporate time series data or statistics.

There are few, if any, models that relate cell-level and time-series statistics to outcome data for cell culture processes (e.g., reprogramming, differentiation, gene editing expansion). As a result, the ability to predict and control cell cultures is extremely limited using current image analysis techniques, even if appropriate feedback control measures are put into plate (for example, editing the cell culture with a mechanism capable of removing cells, or transferring cells or colonies). Even if large scale times-series data could be collected, the volume of data that may be generated would make data storage and analysis difficult. Large-scale automated biological manufacturing must address these issues to be economically viable.

Figure 20A:
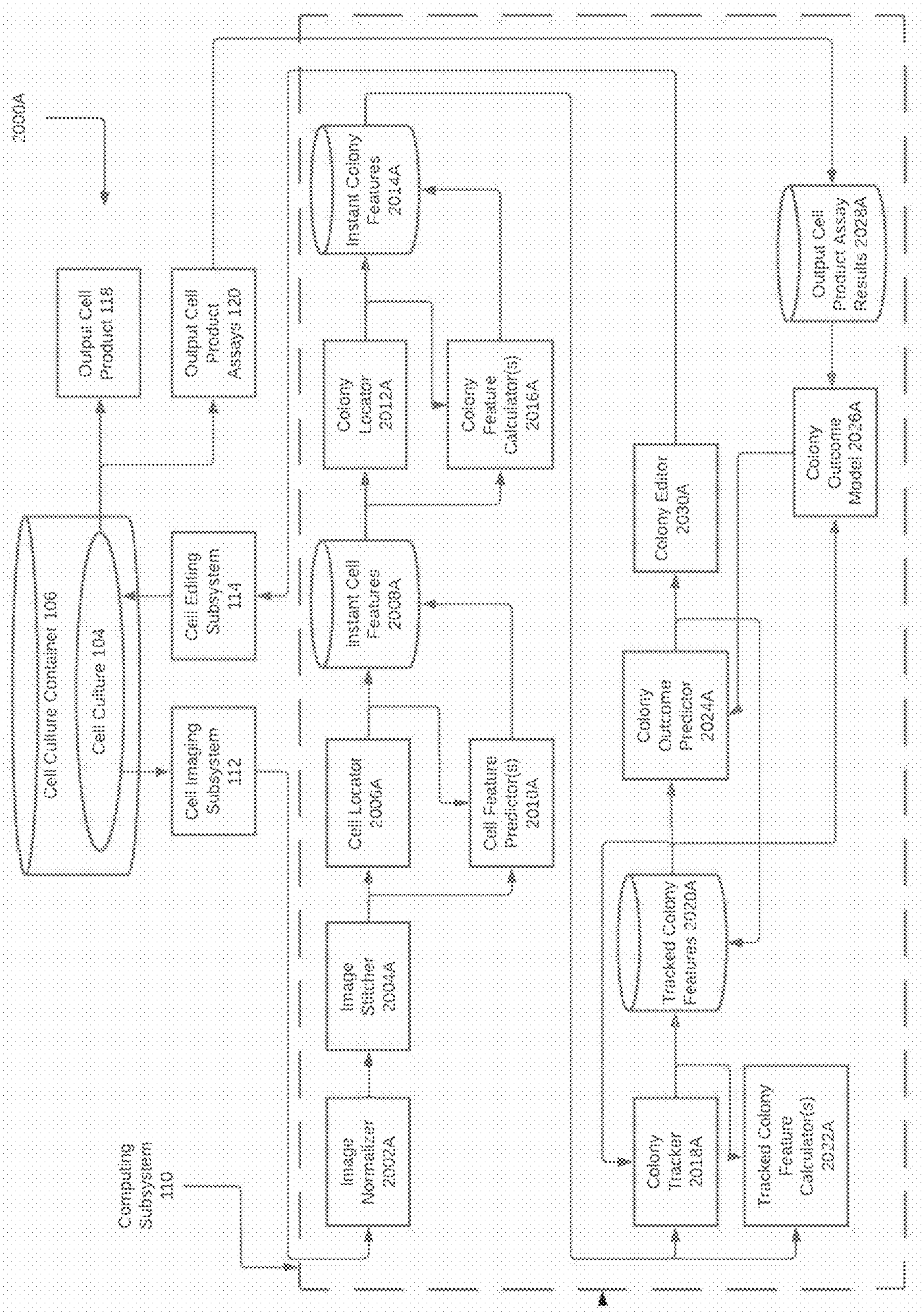
FIG. 20A is a block diagram of a computing subsystem in a cell culture system in accordance with various implementations.

The various implementations disclosed herein include systems and methods for efficiently collecting and analyzing data from a cell culture and utilizing the data to automate cell editing decisions on the cell culture. These systems and methods solve the shortcomings of the prior art and allow for dynamic, automated, easily expandable cell monitoring and editing. FIG. 20A is a block diagram of a computing subsystem in a cell culture system 2000A in accordance with various implementations. The cell culture system 2000A may be similar to the cell culture system 100 described with reference to FIG. 1. For example, the cell culture system 2000A may include a cell culture 104 in a cell culture container 106 that undergoes a cell culture process to produce output cell products 118. The cell culture system 2000A may also include computing subsystem 110, cell imaging subsystem 112, and cell editing subsystem 114 that collectively monitor and controls the cell culture process. Output cell product assays 120 may be performed on the output cell products 118.

The cell culture container 106 may be configured to enable label-free imaging access to the cell culture 104 held within it. In an example implementation, the cell culture container 106 may include a 96-well microplate with an imaging-compatible coverslip (glass, or optical-quality polymer) that is used to contain a cell culture 104 of somatic cells being reprogrammed to iPSCs through the use of episomal vectors expressing the Yamanaka factors.

Figure 21B:
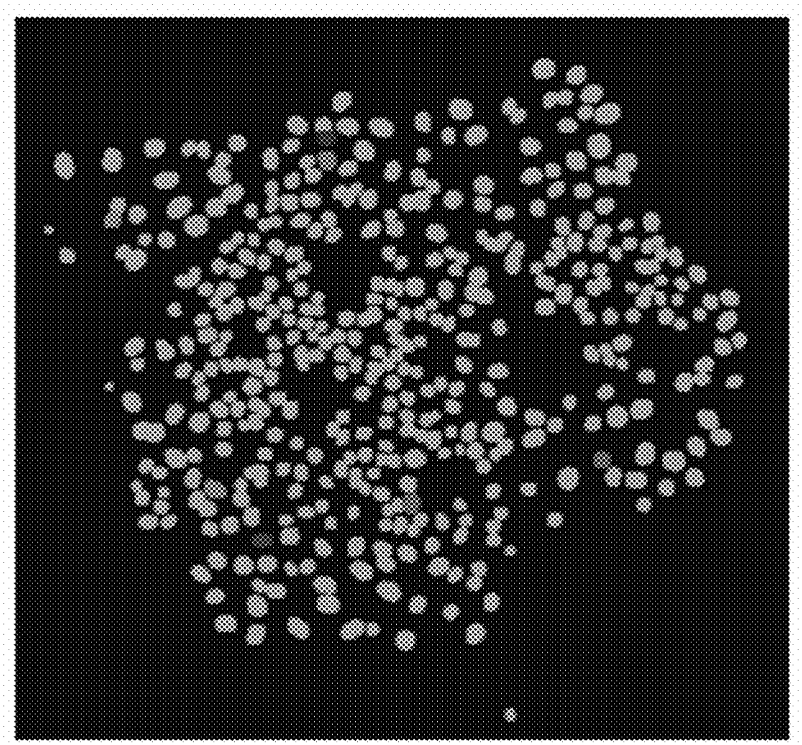
FIG. 21B shows an exemplary output of a deep learning neural network that has been trained to predict nuclear stains from brightfield z-stacks, after thresholding in accordance with various implementations.
Figure 21A:
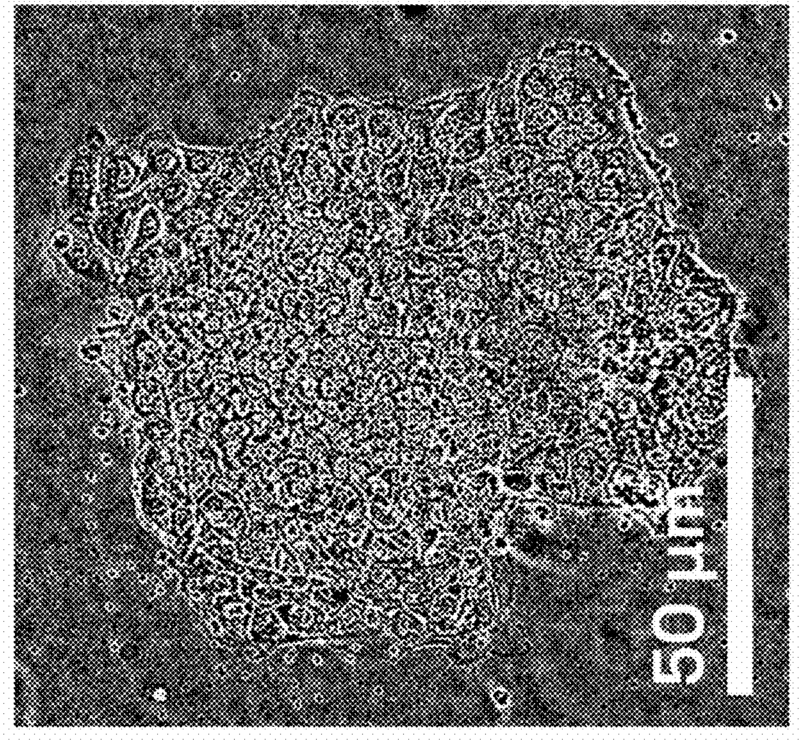
FIG. 21A shows an exemplary normalized brightfield z-stack image of a hiPSC colony in accordance with various implementations.

The cell imaging subsystem 112 may be configured to acquire label-free images of the cell culture 104 over time (for example, every 24 hours, or in another example, at a rate equal to more than two times the cell doubling rate). The cell imaging subsystem 112 may employ imaging modes including but not limited to brightfield imaging, darkfield imaging, phase contrast imaging, differential interference contrast imaging, quantitative phase imaging, Fourier Ptychographic imaging, or combinations thereof. The cell imaging subsystem 112 may acquire multiple images over the cell culture, with those images subsequently merged into a single larger image. In some implementations, the cell imaging subsystem 112 may acquire a Z stack of images, with the Z stack subsequently used to better determine cell locations and cell data. An example of a normalized brightfield z-stack image of a hiPSC cell culture is shown in FIG. 21A. In some implementations, the cell imaging subsystem 112 may use programmable illumination to provide illumination at multiple modes, angles, and/or colors. The cell imaging subsystem 112 may employ CMOS, CCD, or other image sensors to capture images. The sensors may be area sensors or line sensors.

An example implementation of cell imaging subsystem 112 may include a broadband LED-based brightfield illuminator that is configured to illuminate the cell culture 2004A in the cell culture container 106. The brightfield illuminator may have a 10× microscope objective (NA=0.3) that is mounted on a Z translation stage and a 5-megapixel 12-bit monochrome CMOS camera that is used to capture images of the cell culture at 3 Z levels near optimal focus for the cell culture 104 (in this example, at Z=−5 microns, Z=0, and Z=+5 microns).

The images acquired by the cell imaging subsystem 112 are generally of a resolution that at least allows the resolution of individual cells or nuclei within the cell culture. For example, for a 2D adherent cell culture, images may be acquired at a resolution equal to at least several times lower than the mean cell nuclear diameter, or the mean nuclear spacing, whichever is smaller. In an example implementation, when monitoring iPSC reprogramming from blood cells the nuclear diameters average around 9 microns, and mean nuclear spacing may become as low as 5 microns in very dense iPSC colonies. In this example, an imaging resolution of approximately 2 microns or lower is desirable in order to subsequently identify cell nuclei. In some implementations, the imaging resolution used to identify cells or cell components (e.g., organelles) is no more than about 10 microns, about 9 microns, about 8 microns, about 7 microns, about 6 microns, about 5 microns, about 4 microns, about 3 microns, about 2 microns, about 1 micron, or lower. In some implementations, the imaging resolution used to identify cell colonies is no more than about 25 microns, about 20 microns, about 15 microns, about 14 microns, about 13 microns, about 12 microns, about 11 microns, about 10 microns, about 9 microns, about 8 microns, about 7 microns, about 6 microns, about 5 microns, about 4 microns, about 3 microns, about 2 microns, about 1 micron, or lower.

The cell imaging subsystem 112 may transmit the resulting image data to the computing subsystem 110 via electronic or optical methods, which may be wired or wireless. The computing subsystem 110 may include a number of software and/or hardware modules that perform the image analysis and cell editing determinations. For example, all of the components in the computing subsystem 110 as illustrated in FIG. 20A may be implemented as software applications or routines. In another example, some of the components may be implemented in software while others may be implemented in hardware or a combination of software and hardware.

The computing subsystem 110 may include an image normalizer 2002A that is configured to normalize all the received cell culture images. Normalization may include removal of local image artifacts or lighting conditions. For example, in the case of non-uniformity in illumination over a single image field, the image normalizer 2002A may remove this non-uniformity by means of bandpass filtering, local mean subtraction or division, or division by/reduction by a pre-measured image field. In another example, each image may be low-pass filtered to produce an image of the local lighting, in which the cutoff frequency for this low-pass is chosen to remove most or all cell-related features. Subsequently, in this example the original image is divided by the low-pass result, producing an image that has been normalized to remove effects from local illumination or light capture conditions.

An image stitcher 2004A may receive the normalized images and is configured to produce a contiguous image from multiple images of the cell culture 2004A. For example, a single well of a microwell plate may require around 50 image frames to capture all areas of the cell culture with sufficient resolution. The image stitcher 2004A re-assembles these tiles into a single contiguous image for storage and subsequent processing. The resulting contiguous image may have dimensions beyond 2-dimensional axes. Examples of other axes may include but are not limited to Z axis (from multiple Z slice images), illumination or capture color channel, illumination or capture angle and combinations to make 3- or higher-dimensional data volumes.

An important consideration is the sheer data volume that may be generated at the point. In a relatively simple example in which a single well of a 96-well microplate is imaged at 5 Z positions, with imaging performed at 1 micron resolution and with an output format of 16 bits, the resulting data volume for a single imaging pass is roughly 50 Megabytes. This results in almost 5 Gigabytes of data for a single pass over the plate. Cell culture processes performed herein may last upwards of 30 days, with images captured daily or more, so data volumes of hundreds of Gigabytes are possible. This amount of data would be extremely difficult to analyze or model directly against the biological results of the cell culture process. As a result, most current approaches have used only snapshots of image data for this purpose. However, this sampling or single-timepoint approach loses a vast portion of the potentially relevant data in the cell culture. The computing subsystem 110 includes a number of modules designed to distill this data into a much smaller amount of information that nonetheless captures all the critical features of the cell culture 104.

For example, the computing subsystem 110 may include a cell locator 2006A that performs the first step towards transforming large volumes of imaging data into a much more compact representation of the cell culture 104. The cell locator 2006A may be configured to receive the stitched image of the cell culture 104 and to first segment the images to identify cells or nuclei, and then to extract their center coordinates and potentially nuclear envelopes from the segmented image. The cell locator 2006A may utilize conventional image processing and/or neural network-type processing to perform these functions. In an example, image information from five or more Z slices may first be combined into three images. These three images are then input, in tile form, into a convolutional neural network that has been pre-trained with sets of label-free images and corresponding fluorescent nuclear-stained images. An example of a convolutional network architecture used for this task is U-Net. The network produces a single image corresponding to the predicted corresponding nuclear fluorescence image. This image is subsequently thresholded, and watershed morphological image processing is used to determine the centroid of each nucleus, as well as the corresponding nuclear envelope. As an example, FIG. 21B shows an output of a deep learning neural network that has been trained to predict nuclear stains from brightfield z-stacks.

The cell location data generated by the cell locator 2006A may be stored in an instant cell features database 2008A. "Instant" in this case means location data from a single imaging timepoint. The data stored in the instant cell features database 2008A may include, for each cell, the coordinates of the cell in the observed portion of the cell culture 104 and the time at which the data was obtained. It may also include other data such as cell or nuclear envelope information, which may either be a polygon representing the envelope or a feature description of the shape.

Additional cell features may be extracted and added to the instant cell features database 2008A by one or more cell feature predictors 2010A. The cell feature predictors 2010A may make further predictions at the cell or regional level based on prior training. For example, the cell feature predictors 2010A may be trained with a series of brightfield images together with corresponding fluorescently-labeled images staining for cell pluripotency, the images received from the image stitcher 2004A. The cell feature predictors 2010A may then produce an image of this predicted fluorescence, and use the previously-extracted XY coordinates for each cell to calculate the local mean "virtual" fluorescence, and add the resulting feature to the cell record in the instant cell feature database 2008A. Other cell features may be calculated directly from the instant cell feature database 2008A and added to the cell records for convenience (for example, a calculation of the local cell density at various scales).

The cell locator 2006A and cell feature predictor 2008A may utilize a range of processing algorithms including, but not limited to: predictive models for semantic segmentation trained with supervised, unsupervised, and semi-supervised methods based on learned representations derived from morphological features by the application of deep learning models (e.g., multilayer perceptrons and convolutional neural networks, including fully-connected networks, such as Mask R-CNN, networks with expansive-path/contractive-path architectures (such as U-Net), with and without residual connections, trained with a multiplicity of objective functions (such as focal loss, cross-entropy loss, and mean square error loss)), using various optimizers in sequence and/or in combination (such as stochastic gradient descent with and without momentum, RMSProp, Adagrad, and Adam) with various learning rate schedules, and ensembles of models trained with the foregoing methods, together with image-processing algorithms for the generation of training examples for the supervised and semi-supervised training regimes, as well as image-based post-processing and refinement of the semantic segmentation masks derived from the deep-learning models.

A colony locator 2012A may be configured to use the instant cell locations stored in the instant cell feature database 2008A to calculate the bounds of colonies within the cell culture 104. A colony of cells may include any subset, cluster, or region of the cell culture 104. This process may be performed using local density calculations and may also use additional features extracted by cell feature predictors 2010A (for example, a prediction of pluripotency). The colony locator 2012A establishes the bounds of each colony, typically in the form of a polygon.

Each colony record is then stored in an instant colony features database 2014A. Additional colony properties may be calculated using colony feature calculator(s) 2016A. For example, various statistics regarding the cells contained in the colony may be determined or estimated, including count, density, mean virtual fluorescence predictions, and other measures. In addition, geometric features of the colony may be calculated from the cell locations and/or outline polygon.

As a time series of images is collected, a colony tracker 2018A associates successive instant colonies with one another, in order to produce persistent records of colonies, which are stored in a tracked colony features database 2022A. For example, the colony tracker 2018A may determine that a cell colony that is at roughly the same location between two time-series images is the same colony. The colony may then be assigned a number or some other indicator, and information about the colony at each point in time may be associated with each other and stored together. The tracked colony features of a colony may include a series of instant colonies in the instant colony features database 2014A, such that a time-series of instant colony feature may be reconstructed. However, it may be desirable to precompute and store a range of features for tracked colonies, including centroid trajectory, cell count history, area history, shape factor history, etc. These features, together with cell statistic features, may be calculated using one or more tracked colony feature calculators 2022A, and added to the appropriate tracked colony record in the tracked colony features database 2022A. FIGS. 21C-H provide an illustrative example of brightfield image z-stack slices of a hiPSC colony proliferating over about 65 hours and the corresponding image with calculated polygons delineating determined colony areas.

The databases in the computing subsystem 110 (e.g., the instant cell features database 2008A, the instant colony features database 2014A, and the tracked colony features database 2022A) may be relational in a manner that allows features to be traced back to their origin. In other words, tracked colonies are related to the instant colonies that make them up, which are related to the instant cell features that compose them, which can be traced back to specific regions of pixels in the image data.

At this point the vast volume of image time series data has been reduced to a small set of features per tracked colony. This allows a colony outcome predictor 2024A to operate efficiently, and importantly to be trained with a reasonably small dataset. The colony outcome predictor 2024A is configured to use the tracked colony features in the tracked colony features database 2022A to predict outcomes for the colony in terms of phenotype, functionality, genotype, pluripotency, purity, proliferation rate or other product characteristics. The colony outcome predictor 2024A may calculate a score for each colony, the score representing the likelihood that the colony is or will produce high quality cell output products 2018A. The colony outcome predictor 2024A may be driven by a statistical cell outcome model 2026A that has been optimized with a set of tracked colony features from the tracked colony features database 2022A and corresponding output cell product assay results 120, which are in turn generated for each output cell product 118 using output cell product assays 120. The colony outcome predictor 2024A and statistical outcome model 2026A may use one of a number of machine learning methods including, but not limited to, logistic and multinomial regression, ordinal logistic regression, support vector machines, classification and regression trees, random forests, boosted trees, principal components analysis, independent components analysis, k-means, hierarchical, density-based, and neighborhood-based clustering, autoregressive models, gaussian process fitting, hierarchical Bayesian models, probabilistic graphical models, methods from topological data analysis such as persistent homology, deep learning models, including multilayer perceptron models and recursive neural networks, reinforcement-based models such as genetic algorithm models and virtual ant colony methods, as well as ensembles and cascades of these methods together with heuristics and rules-based methods to predict quantitative and qualitative colony outcomes based on the extracted features stored in the tracked colony database 2022A and output cell product assay results 2028A.

In the case where colonies or regions of cells should be removed from the cell culture 104 in order to make space for cells/regions with higher predicted scores and/or to ensure clonality of the product, a colony editor 2030A may be configured to select regions or colonies to be removed from the cell culture 104. The colony editor 2030A may drive the editing subsystem 114 that is capable of removing cells, colonies, or regions of cells. The colony editor 2030A may also terminate a cell culture in order to dispose of it or to harvest output cell products 118. In some implementations, the colony editor 2030A may also control various actuators or other controls (e.g., controls 116) to manipulate other environmental parameters within the cell culture container 106. For example, the colony editor 2030A may control functions such as shifting reagents or changing parameters such as temperature, pH, O2, nutrients, and media feed rate. The result of this editing operation should be that the net predicted score for the cell culture 104 is raised, and/or space in the cell culture container 2006A is opened for the remaining (predicted) higher-scoring cells.

Figure 20B:
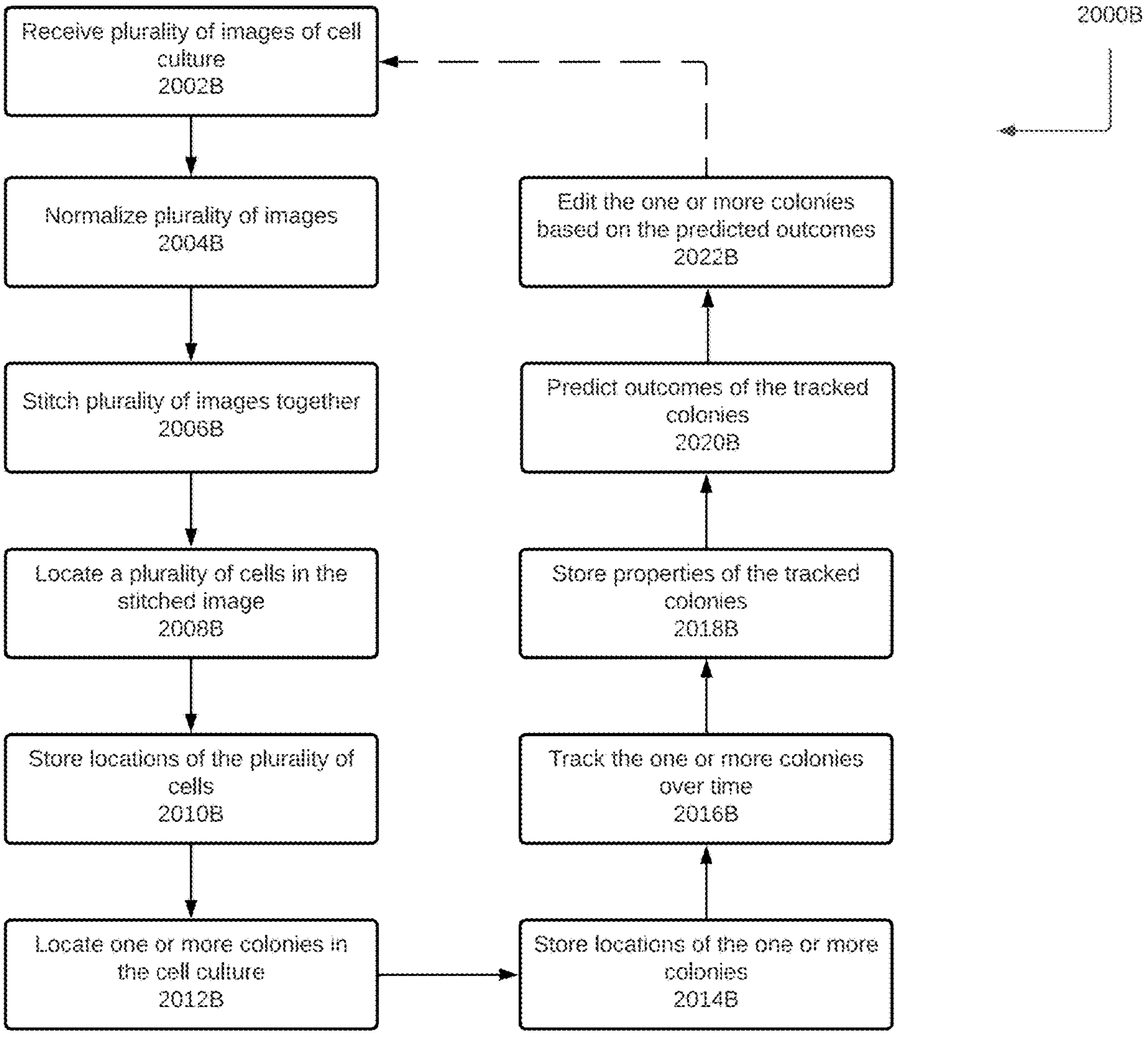
FIG. 20B is a flow chart of a method of controlling a cell culture in accordance with various implementations.

FIG. 20B is a flow chart of a method 2000B of controlling a cell culture in accordance with various implementations. The method 2000B may be performed by a computing subsystem of a cell culture system (e.g., computing subsystem 110 in cell culture system 100). The method 2000B may also the cell culture system to automatically monitor and edit the cell culture during a cell culture process.

In block 2002B, the computing subsystem may receive a plurality of images of the cell culture in a cell culture container. The images may be received from a cell imaging subsystem (e.g., cell imaging subsystem 112) that collects the plurality of images. The plurality of images may collectively image the cell culture. The cell imaging subsystem may utilize one of a variety of imaging methods to capture the images, including brightfield imaging, phase imaging, darkfield imaging, transmission imaging, reflection imaging, quantitative phase imaging, holographic imaging, two-photon imaging, autofluorescence imaging, Fourier ptychographic imaging, defocus imaging or any other implementations known to persons of ordinary skill in the art. Before image analysis of the plurality of images, the computing subsystem may perform a number of preprocessing steps, as described with reference to blocks 2004B-2006B.

In block 2004B, the computing subsystem may normalize the plurality of images. Normalization may include removal of local image artifacts or other irrelevant lighting effects or conditions from the images in order to obtain clear images of the cell culture.

In block 2006B, the computing subsystem may stitch together the plurality of images in order to form a single image of the cell culture. The stitched image may be 2D image of the cell culture, or may include 3-dimensional aspects as well. Each of the plurality of images may be associated with location data that may be used to stitch the images together properly.

In block 2008B, the computing subsystem may locate a plurality of cells in the stitched image. The stitched image may represent the state of the cell culture at a specific point in time. A variety of image processing and/or neural network-type processing may be used to locate the plurality of cells. The location of a cell may be represented as coordinates of the nucleus or center of the cell, and may also include nuclear envelope information as well. A cell feature predictor may be utilized, which uses prior imaging data as well as training set data that allows the computing subsystem to distinguish individual cells from other cells and background images, and to determine a coordinate representing the location of the cell. The cell feature predictor may improve over time as more data is analyzed so that the predictor becomes more accurate.

In block 2010B, the location of the plurality of cells may be stored. For example, the location data may be stored in an instant cell feature database which records the location of each cell at each instant of time at which the plurality of images (and the resulting stitched image) are collected.

In block 2012B, the computing subsystem may identify one or more cell colonies or cell clusters in the stitched image. A cell colony or cluster may be any grouping, subset, or region of the cell culture. A colony feature calculator may be utilized to distinguish cell colonies from each other and from background images. The colony feature calculator may utilize cell location data, prior imaging data as well as training set data to accurately identify distinct cell colonies within the stitched image. A cell colony may be defined by shape and location data, as well as other data conveying information about the cell colony.

In block 2014B, information about each cell colony may be stored. For example, the cell colony data may be stored in an instant colony features database which records the location and properties of each cell colony at each instant of time at which the plurality of images (and the resulting stitched image) are collected.

In block 2016B, the computing subsystem may track the one or more colonies over time. This may include iterating the steps in blocks 2002B-2014B at a number of points in time in order to collect time-series cell colony data. The computing subsystem may utilize a tracked colony feature calculator to determine the cell colonies in the images over time. All data associated with the same cell colonies may be associated with each other in order to produce time-series data about the growth and changes of the cells and cell colonies over time. The tracked colony feature calculator may utilize instant colony feature data, prior imaging data, and training set data to accurately identify the same colonies over time.

In block 2018B, the times-series data about each tracked colony may be stored in a database. For example, the tracked cell colony data may be stored in a tracked colony features database which records the location and properties of each cell colony over time.

In block 2020B, the computing subsystem may predict outcomes of each tracked colony in the cell culture. For example, the computing subsystem may generate an outcome score based on the time-series tracked cell colony data. The outcome score may represent the likelihood that a particular cell colony may successfully produce the desired output cell product at a future time. A cell outcome model may be utilized to generate the outcome score. The outcome score may be based on a number of data sources, including the time-series tracked colony data of the current cell culture, tracked colony data from prior cell culture processes of the same type, output cell product assay data, and training set data.

In block 2022B, the computing subsystem may edit one or more of the tracked colonies based on the predicted outcome for the tracked colonies. For example, if an outcome score of a cell colony indicates that it is a low quality colony unlikely to produce the desired output cell product, the computing subsystem may instruct a cell editing subsystem (e.g., cell editing subsystem 114) to remove the low quality colony. In another example, the computing subsystem may determine that two cell colonies will soon overlap and instruct the cell editing subsystem to remove the cell colony with a lower outcome score in order to provide more space for the remaining cell colony to grow. Editing may encompass other functions that effect cell colony growth, such as transferring cargo into and out of cells, or changing environmental parameters of the cell culture container.

The method 2000B may repeat itself iteratively throughout the cell culture process until the output cell product is completely harvested, or the cell culture is disposed of in its entirety. In this manner, the method 2000B provides automated and dynamic tracking, prediction, and control of the cell culture process. This eliminates the need for manual human intervention and lessens the potential for contamination from these interventions, and also increases the speed at which cell cultures are processed. Finally, by reducing high density imaging data into low density cell colony data, the method 2000B reduces the need to store, transfer, and analyze large quantities of data.

Figure 21C:
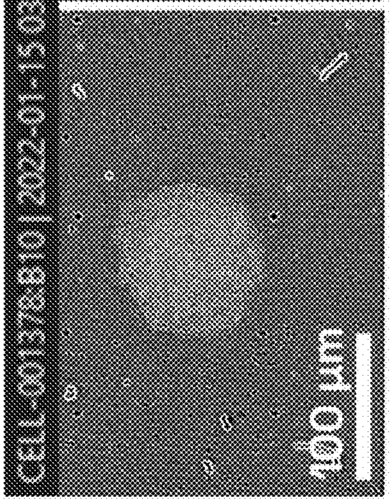
FIG. 21C shows a first exemplary brightfield image z-stack slice of a hiPSC colony proliferating over about 65 hours in accordance with various implementations.
Figure 21D:
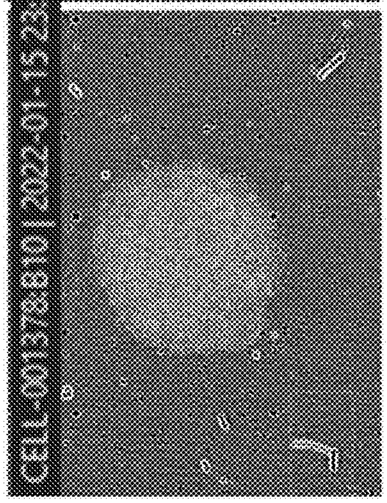
FIG. 21D shows the image of FIG. 21A with polygons delineating determined colony areas in accordance with various implementations.
Figure 21E:
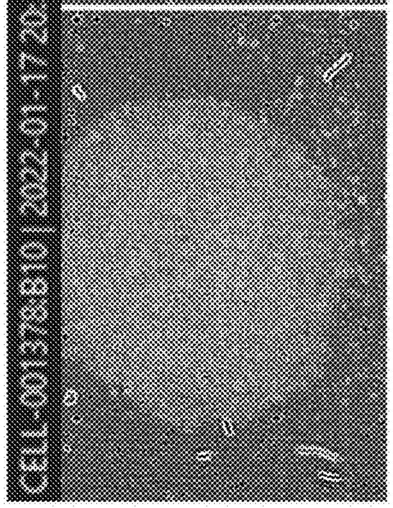
FIG. 21E shows a second exemplary brightfield image z-stack slice of a hiPSC colony proliferating over about 65 hours in accordance with various implementations.
Figure 21F:
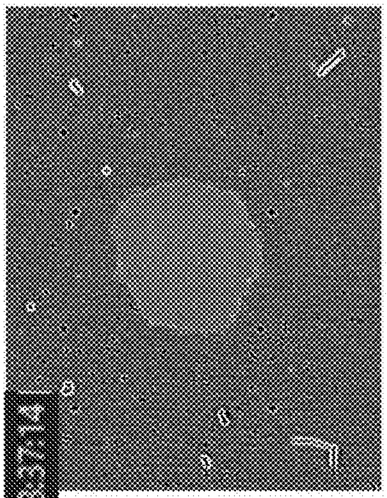
FIG. 21F shows the image of FIG. 21C with polygons delineating determined colony areas in accordance with various implementations.
Figure 21G:
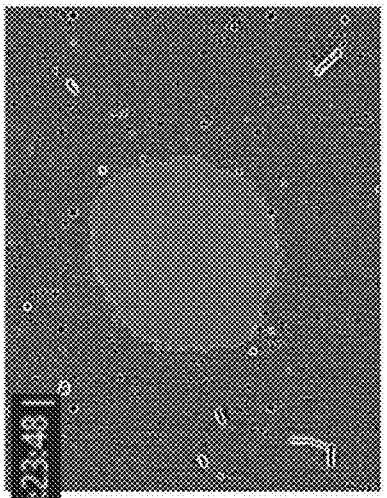
FIG. 21G shows a third exemplary brightfield image z-stack slice of a hiPSC colony proliferating over about 65 hours in accordance with various implementations.
Figure 21H:
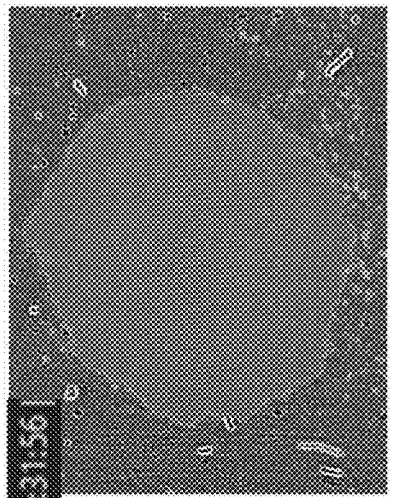
FIG. 21H shows the image of FIG. 58E with polygons delineating determined colony areas in accordance with various implementations.

The computing system shown in FIG. 20A may be used to implement the method shown in FIG. 20B in order to generate images such as those shown in FIGS. 21A-21H. FIG. 21A shows an exemplary normalized brightfield z-stack image of a hiPSC. FIG. 21B shows an exemplary output of a deep learning neural network that has been trained to predict nuclear stains from brightfield z-stacks, after thresholding. FIG. 21C shows a first exemplary brightfield image z-stack slice of a hiPSC colony proliferating over about 65 hours. FIG. 21D shows the image of FIG. 21A with polygons delineating determined colony areas. FIG. 21E shows a second exemplary brightfield image z-stack slice of a hiPSC colony proliferating over about 65 hours. FIG. 21F shows the image of FIG. 21C with polygons delineating determined colony areas. FIG. 21G shows a third exemplary brightfield image z-stack slice of a hiPSC colony proliferating over about 65 hours. FIG. 21H shows the image of FIG. 21E with polygons delineating determined colony areas.

Closed Cassette Systems

There is currently no bioreactor or other system in the art for clinical-grade manufacturing of cells that (1) allows 100% non-contact measurement of cells in culture to monitor and control the biomanufacturing process, and (2) is sealed in a manner that allows parallel manufacture in a non-sterile facility, and further, in some cases, allows editing of cell cultures based on image-derived characteristics (e.g., in a cell culture system).

Such a system would enable a wide range of cell biomanufacturing processes at a scale, consistency, yield, and cost that are not currently achievable. This capability is particularly important to translate emerging patient-specific therapies from the laboratory to clinical trials and ultimately to larger patient populations.

The systems and methods disclosed herein include a cell culture container that includes a closed media path and at least one culture chamber suitable for aseptic cell manufacturing in a non-sterile facility. The at least one cell culture chamber has at least one growth surface for cells that is optically accessible for label-free imaging by transmission and/or reflection illumination. The cell culture chamber may be liquid-filled and substantially free of any gas layer, and the growth surface may be is inverted for at least part of the cell culture process in order to gravitationally separate debris and/or non-adherent cells from the culture surface. The cell culture container may provide a sterile-sealed closed loop liquid system to support cell cultures grown in the cell culture container.

In some implementations, the liquid system disclosed herein can be referred to as a liquid handler. A liquid handler can be coupled to the one or more cell culture chambers, and configured to (i) provide input fluid media to the one or more cell culture chambers; (ii) receive output fluid media from the one or more cell culture chambers; and (iii) mix a circulated fluid within the one or more cell culture chambers, wherein the circulated fluid comprises the input fluid media, the output fluid media, or both.

In some implementations, the cell culture container may include a mechanism for selectively removing cells from the cell culture surface without opening the media path, with the removed cells or cell fragments separated at least in part by using the inverted configuration. In some implementations, time-series imaging of the cells on the cell culture surface and image processing of the resulting images may be used to predict the outcome of a cell culture process. This prediction may be used to manage the manufacturing process by discarding the cell cultures with poor predictions, and/or starting back-up cultures, selectively remove cells within the cell culture chamber in order to improve the predicted outcome, and manage the media inside the closed system, for example the addition of fresh media, in order to improve or maintain the predicted outcome. In some implementations, the cell culture container may include a mechanism for agitating liquid in the cell culture chamber without opening the media path in order to dislodge debris or cells from the growth surface.

The various implementations disclosed herein may be used for scaling out 2D cell culture processes in a manner compatible with good manufacturing practice (GMP) requirements for cells and tissue to be used in patients. Furthermore, the disclosed implementations allow long-term processes to be run, observed, and controlled in a sealed system, in order to allow dozens or hundreds of patient samples to be processed in parallel in a single facility, without the risk of cross-contamination. The disclosed implementations may be used for reprogramming of somatic cells into induced pluripotent stem cells (iPSCs), for differentiation of stem cells into cells and/or tissue for screening or transplantation, for expansion of cells, for gene modification of cells, and other applications requiring multi-day processes where cells are maintained with nutrients, factors, vectors to be delivered, etc.

Figure 22:
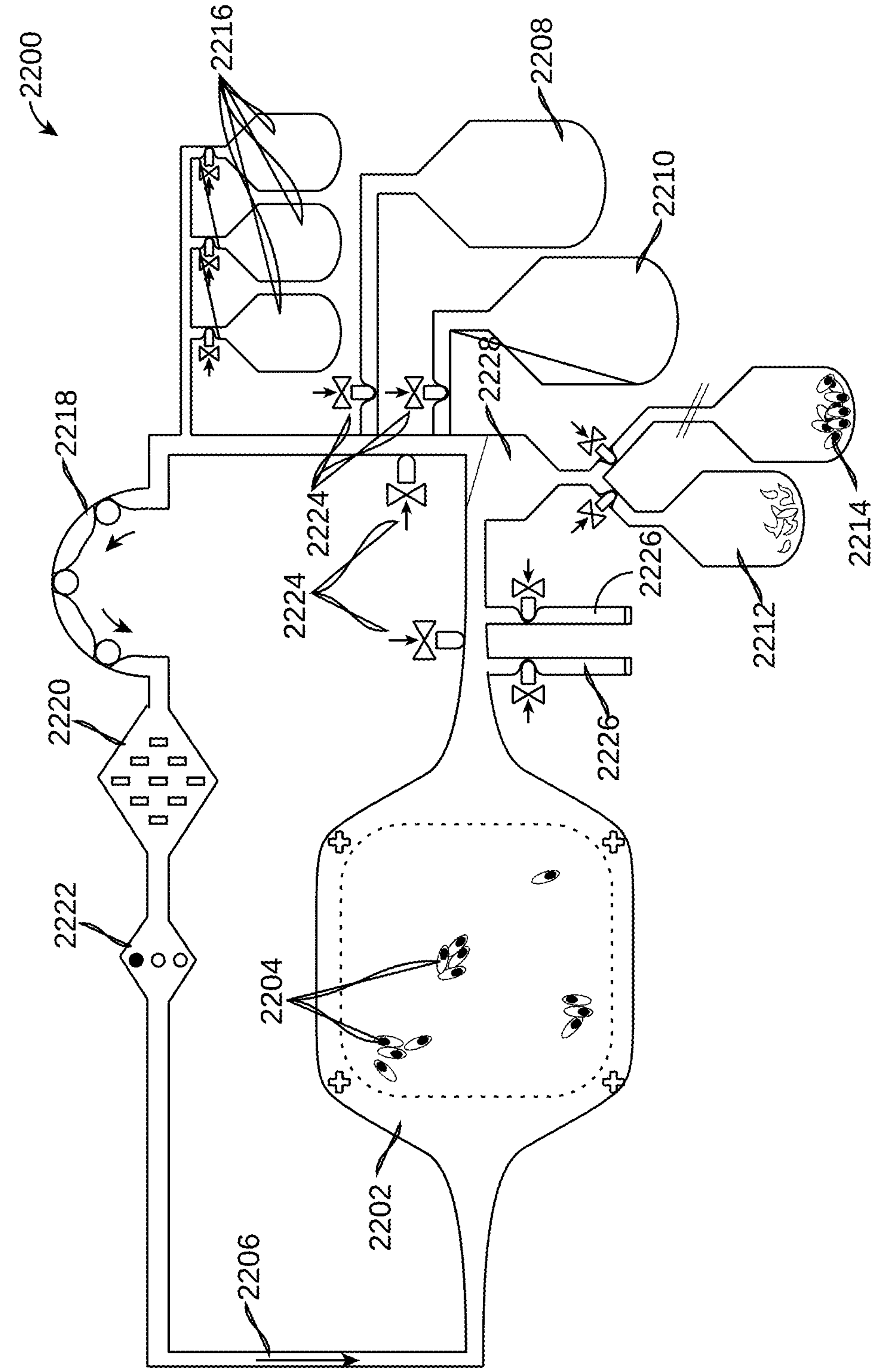
FIG. 22 is a diagram of a closed cassette system for use in a cell culture system in accordance with various implementations.

FIG. 22 is a diagram of a closed cassette system 2200 for use in a cell culture system in accordance with various implementations. The closed cassette system 2200 may be an implementation of the cell culture container 106 shown in FIG. 1. The closed cassette system 2200 may include a cell culture chamber 2202 supporting the growth of an adherent cell culture 2204. In some implementations, the closed cassette system 2200 may include more than one cell culture chamber 2202. A closed liquid loop 2206 provides the cell culture chamber 2202 with fluid media and allows for media and reagent exchange. The closed liquid loop 2206 may be an aseptically-sealed liquid system (also referred to as a fluidic system), built for example using planar microfluidic channels and/or sterile tubing that may be sterile-welded and pre-sterilized using gamma and/or UV radiation. The closed liquid loop 2206 enables the growth and maintenance of the cell culture 2204 over an extended period of time for the purpose of reprogramming, differentiating, gene-editing and/or expanding the cells.

The closed liquid loop 2206 may include a plurality of reservoirs, typically sterile bags that may deflate or inflate over the course of the cell culture process. The reservoirs may include a fresh media reservoir 2208 which supplies cell culture nutrients, vitamins, and other factors, and a waste reservoir 2210 into which spent media is pumped during complete or partial media exchanges. Additional reagents or buffers (for example for pH control) are shown as reservoirs 2216. There may also be a debris collection reservoir 2212 and cell collection reservoir 2214. Debris and/or cells are cleared from the cell culture chamber 2202 and moved to the debris collection reservoir 2212 to remove them from the media loop through the use of a filtration feature 2228. Debris are typically discarded, while the cells captured in the cell collection reservoir 2214 are the output cell product (e.g., output cell product 118 in FIG. 1) of the cell culture process.

A pump 2218 circulates liquid through the closed liquid loop 2206. The pump 2212 shown in FIG. 22 is a peristaltic-type pump, but in general the closed cassette system 2200 may use other configurations compatible with a closed system. In the case of a peristaltic pump, it may act upon tubing or a channel in a planar microfluidic system. The pump 2218 may run forwards as well in reverse. Reverse pumping may be used to clear the cell filtration unit and pump the filtered solids (debris and/or cells) into the debris collection reservoir 2212 or cell collection reservoir 2214. The closed liquid loop 2206 may additionally be pumped in reverse to ensure even distribution of media within the cell culture chamber 2202. The pump 2218, in conjunction with actuated valves 2224 (only some of which may be shown in FIG. 22), controls all the liquid protocols on the closed cassette system 2200.

The closed cassette system 2200 may also include a mixing and exchange section 2220, which is shown schematically in FIG. 22. The mixing and exchange section 2220 may perform two functions. First, it serves to promote mixing in the circulated liquid to ensure homogeneity once it reaches the cell culture chamber 2202. For example, if a small amount of fresh media has been added, the mixing and exchange section 2220 serves to mix it with the existing media. The mixing and exchange section 2220 may have a liquid feedback mechanism to provide a greater mixing factor.

A second function of the mixing and exchange section 2220 may be gas exchange. For example, the dissolved oxygen level in the fluid media may be an important factor in certain bioprocess. When outfitted with gas exchange surfaces//mechanisms, the mixing and exchange section 2220 may be used to control the dissolved oxygen and other gas concentrations in the circulated media. In cases in which pH is controlled indirectly (rather than by addition of liquid), the mixing and exchange section 2220 may be used to control dissolved $CO_2$. In cases in which cavitation mechanisms (e.g., laser, ultrasound, or other) are used to edit cell cultures 2204 within the cell culture chamber 2202, the mixing and exchange section 2220 may be used to control overall dissolved gas concentration, potentially with an inert gas that has no other effect on cell culture, for the purpose of maintaining a stable threshold and predictable energy transfer for cavitation.

Temperature may be separately controlled for the mixing and exchange section 2220, or even within different parts of the mixing and exchange section 2220, to control gas solubility for the purpose of facilitating gas exchange. Additionally, external gas pressure may be controlled in one or more parts to facilitate gas exchange. For example, in a first portion of the mixing and exchange section 2220 the media temperature may be raised and external gas pressure is at below atmospheric pressure, in order to maximize outgassing (for example, to remove $CO_2$, which is a product of the live cell culture). In a second section of the mixing and exchange section 2220 temperature is lowered and external gas pressure is at above atmospheric pressure to maximize transfer of $O_2$ or other gases into dissolved form in the liquid media to support cell culture. One or more bubble-trapping and removal stages (not shown) may be integrated into the closed liquid loop 2206 to trap and remove, via a gas-permeable membrane and reduced external gas pressure, any gas that comes out of solution so it does not interfere with the cell culture or liquid loop functions.

The closed cassette system 2200 may also include a sensing section 2222, which is shown schematically in FIG. 22. The sensing section 2222 may be used to monitor media conditions in a non-invasive manner. In the example shown in FIG. 22, the sensing section 2222 includes two colorimetric patches (top and bottom circles) inside the closed liquid loop 2206. The optical characteristics of the patches may vary with pH and dissolved oxygen, respectively, and may be read using an external light source and detector. Other media property and components may be monitored with similar patches.

In the center of the sensing section 2222, a circular outline is shown that represents a clear optical path for transmission, reflection, or scattering measurements performed without the aid of inserted materials. For example, spectroscopic transmission measurements in the ultraviolet (UV), visible, near infrared (NIR), mid-wave infrared (MWIR) or long-wave infrared (LWIR) may be performed to assess media contents, including but not limited to nutrients, waste products, vitamins, and bioprocess byproducts. Alternatively, Raman spectroscopic measurement may be made of the media and its contents. In addition, scattering measurements at one or more wavelengths and scattering angles may be made to assess media contents. The measurements made in the sensing section 2222 may be used in a closed-loop control of the closed cassette system 2200. For example, data from the sensing section 2222 may be used to make decisions about adding fresh media, adding liquid to control pH, or changing gas exchange rates or composition. In addition, these measurements, in conjunction with imaging-based measurements, may be used to track the cell culture bioprocess and predict outcomes using statistical models (or to train these statistical models, based on endpoint results).

The closed cassette system 2200 may also include a plurality of ports 2226, positioned at various points along the closed liquid loop 2206. These may be single-use ports (e.g., for filling or inoculating the cell culture chamber 2202 or entire closed cassette system 2200, or for harvesting output cell product) that are sterile welded after use. Such ports may also be fitted with one-time sterile connectors.

In typical usage of the closed cassette system 2200, incremental exchange of media is performed over time, either on a fixed time schedule, or more preferably based on some combination of time and observed cell culture characteristics (total cell count, etc.). Media exchange may be monitored by a computing subsystem (e.g., computing subsystem 110) of a cell culture system that utilizes the closed cassette system 2200. Such incremental exchange may be performed by closing the valve in the flow loop situated between the waste outlet (e.g., outlet leading to the waste reservoir 2210) and fresh media inlet (e.g., inlet from the fresh media reservoir 2208), opening the waste inlet, opening the fresh media inlet, and then activating the pump 2218 in the forward direction for a given duration. In this manner, any amount from a small fraction up to the entirety of the media in the closed cassette system 2200 may be replaced, depending on the pumping duration and speed. The closed cassette system 2200 may include other components not shown in FIG. 22, such as additional pumps, valves, reservoirs, and sensors.

Figure 23A:
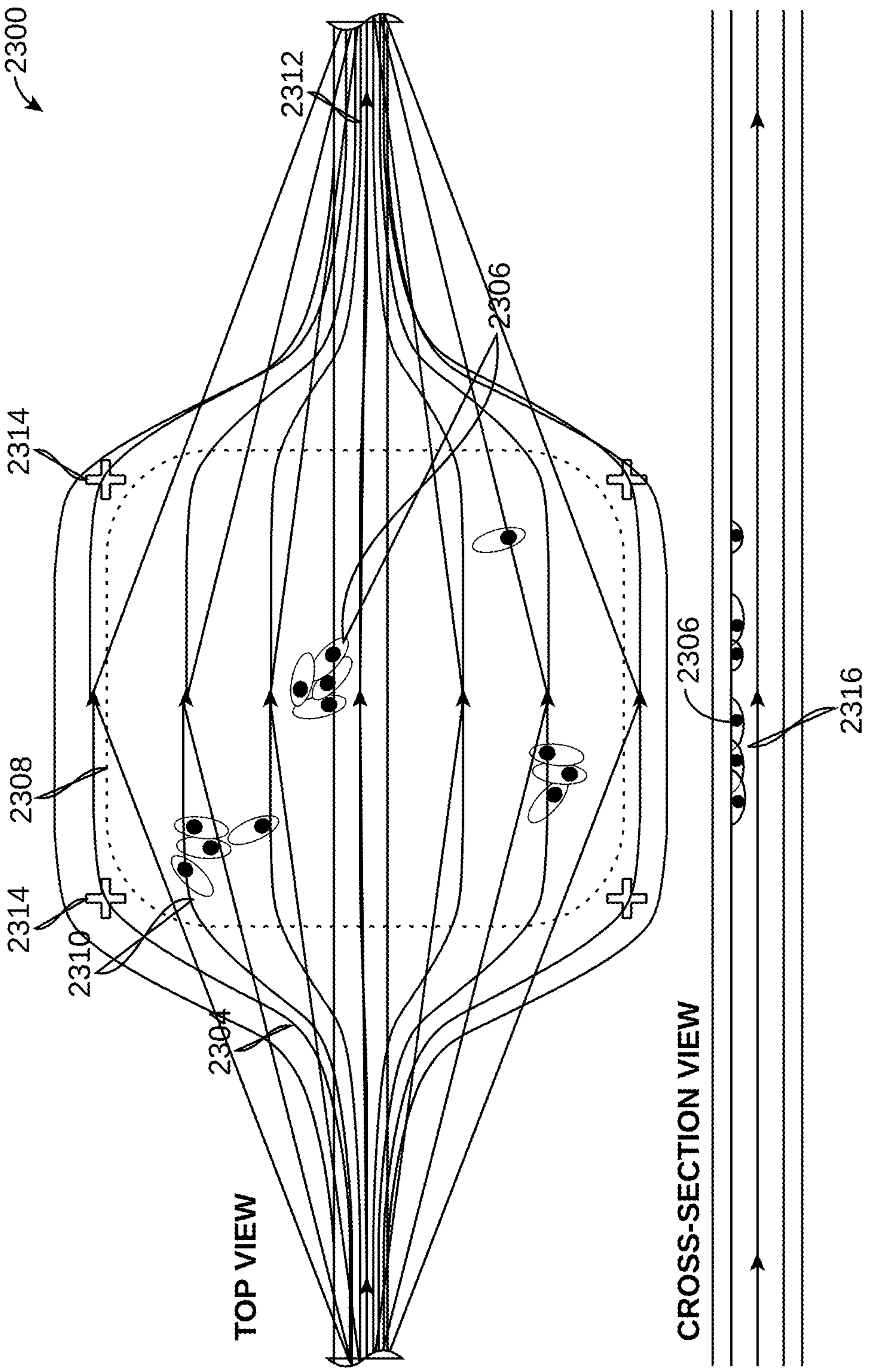
FIG. 23A is a diagram of a cell culture chamber in a closed cassette system in accordance with various implementations.

FIG. 23A is a diagram of a cell culture chamber 2300 in a closed cassette system in accordance with various implementations. The cell culture chamber 2300 may be similar to cell culture chamber 2202 in FIG. 22. FIG. 23A shows both a top view and a cross-section view of the cell culture chamber 2300. The cell culture chamber 2300 includes at least one inlet channel 2302 that is used to deliver media into the cell culture chamber 2300. This media may come from a closed liquid loop of the closed cassette system. The media may include fresh media and/or reagents are incrementally added and mixed into the fluid flow of the closed liquid loop. The fluid flow, which is typically slow and laminar, is expanded gradually through an expansion section 2304 into the cell culture chamber 2300. Additional features may be added to make the overall flow profile uniform. The target is to establish a uniform, very low velocity flow in the target cell growth region 2308. In many cases, the goal is to minimize continuous and/or directional shear stress on the cells in culture, preferably keeping it to <5 dyne/cm$^2$, and preferably <1 dyne/cm$^2$. In some implementations, the shear stress exerted on the cells in culture is less than about 10 dyne/cm$^2$, 9 dyne/cm$^2$, 8 dyne/cm$^2$, 7 dyne/cm$^2$, 6 dyne/cm$^2$, 5 dyne/cm$^2$, 4 dyne/cm$^2$, 3 dyne/cm$^2$, 2 dyne/cm$^2$, or 1 dyne/cm$^2$. Media is removed from the cell culture chamber 2300 via outlet channel 2310. It should be noted that for portions of the cell culture process, the flow direction may be reversed (i.e., media enters from the outlet channel 2310 and exits from the inlet channel 2302).

Cells 2306 are cultured within the cell culture chamber 2300, potentially confined via surface treatment and/or an editing system to target cell growth region 2308. Within this region, the cells are observable via a label-free imaging system (e.g., cell imaging subsystem 112). The imaging may operate in one or more known modalities, including but not limited to transmission imaging, reflection imaging, brightfield, darkfield, phase, differential interference contrast (DIC), quantitative phase imaging (QPI), Fourier ptychographic imaging in transmission or reflection, holographic imaging, or combinations of these. All the cells 2306 may be imaged over time to monitor the progression of the cell culture and make predictions with respect to quality and yield. For this purpose, registration marks 2312 visible to the cell imaging subsystem may be provided to provide stable spatial references over time and accurately monitor cell behavior at a colony or even cell level.

The cells 2306 may be an adherent cell culture adhered to the top surface of the cell culture chamber 2300, as shown in the cross-section view of FIG. 23A. The cells 2306 may be adhered to a laser film on the top surface that enables light-based imaging and cell editing operations without breaking the seal on the cell culture chamber 2300. The cells 2306 may initially be cultured on the bottom surface of the cell culture chamber 2300 until they adhere to the surface, and then the cell culture chamber 2300 may be inverted so that the cells 2306 reside on the now-top surface as shown in the cross-section view. Inversion, enabled by a growth chamber that is completely filled with media, may be utilized to separate non-adherent cells, cell debris, and other debris or particles of density greater than the cell media from the adherent cell culture. For example, when reprogramming suspension somatic cells into iPSCs (which are adherent), inversion of the cell culture chamber 2300 may gently separate somatic cells that are not successfully reprogrammed from the reprogrammed iPSCs using gravity. The somatic cells that fall to the bottom surface may then be washed out of the cell culture chamber 2300. In the reverse case, in which stem cells are differentiated into suspension cells, successfully differentiated cells may be gently separated by inverting the cell culture chamber 2300.

In another example, the cell culture chamber 2300 may be used to grow adherent cells that are genetically reprogrammed or have episomal vectors delivered to them for non-integrating expression, in which the programming includes an antibiotic resistance. The antibiotic may subsequently be used to kill the undelivered cells. The debris from these cells may then fall away from the top growth surface of the cell culture chamber rather than potentially contaminating the remaining successfully delivered (hence antibiotic-resistant) cells. In another example, an editing mechanism (e.g., a laser) may be used to lyse or damage specific cells on the growth surface by means of mechanical force, heat, ultrasound, electrical fields or photodamage in a manner compatible with a closed cassette, and the damaged/destroyed cell debris is gravitationally separated from the untouched live cells, such that it does not settle on the live cells. In another example, a matrix or coating is used under the cells that may be selectively altered//removed to release the attached cells. This alteration being performed in a manner that is compatible with a closed container. The separation mechanisms described herein may be used to remove unwanted cells, or to remove wanted (product) cells, or to remove select cells for analysis.

Figure 23B:
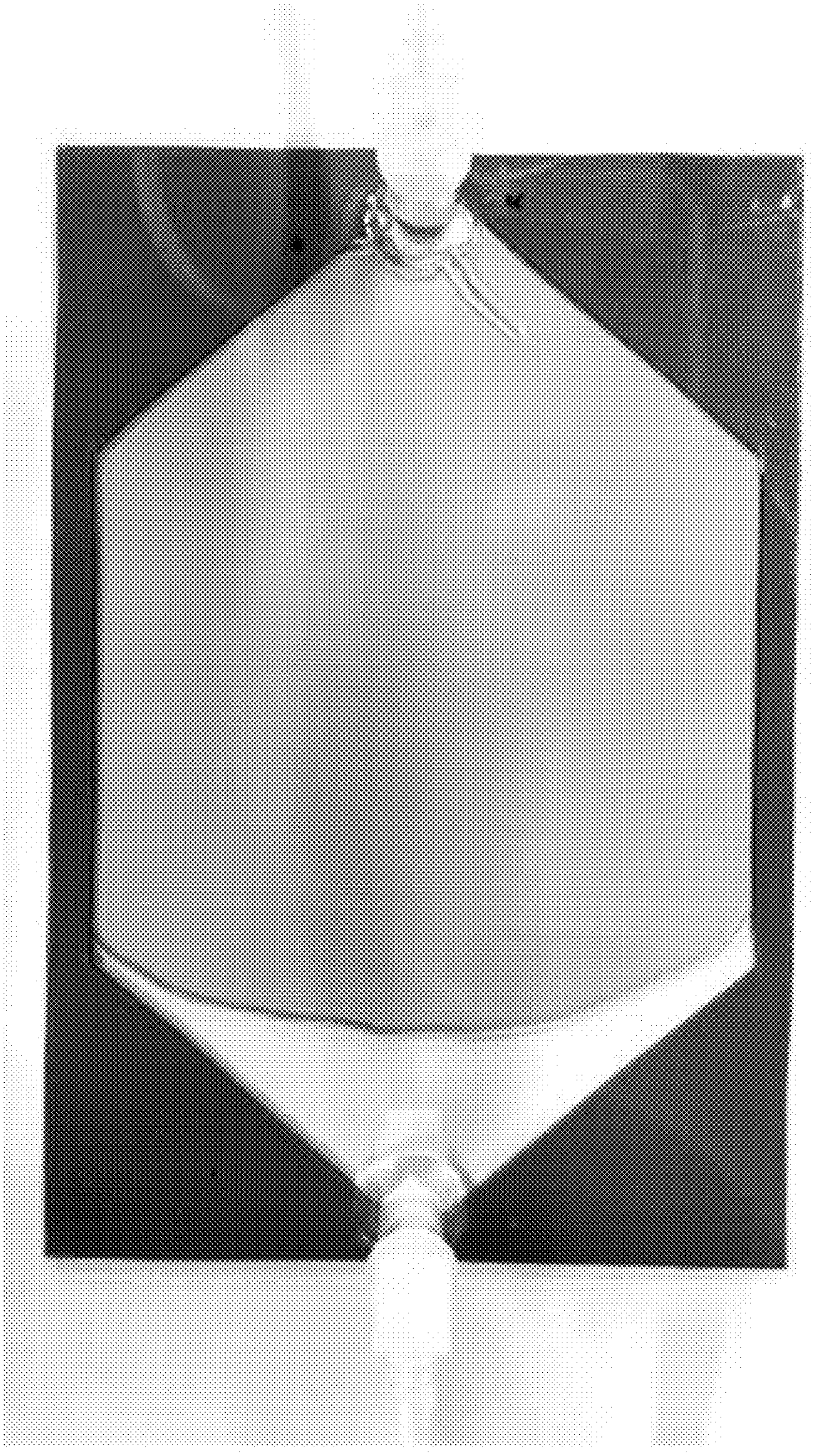
FIG. 23B is an image of an exemplary cell culture chamber in accordance with various implementations.
Figure 23C:
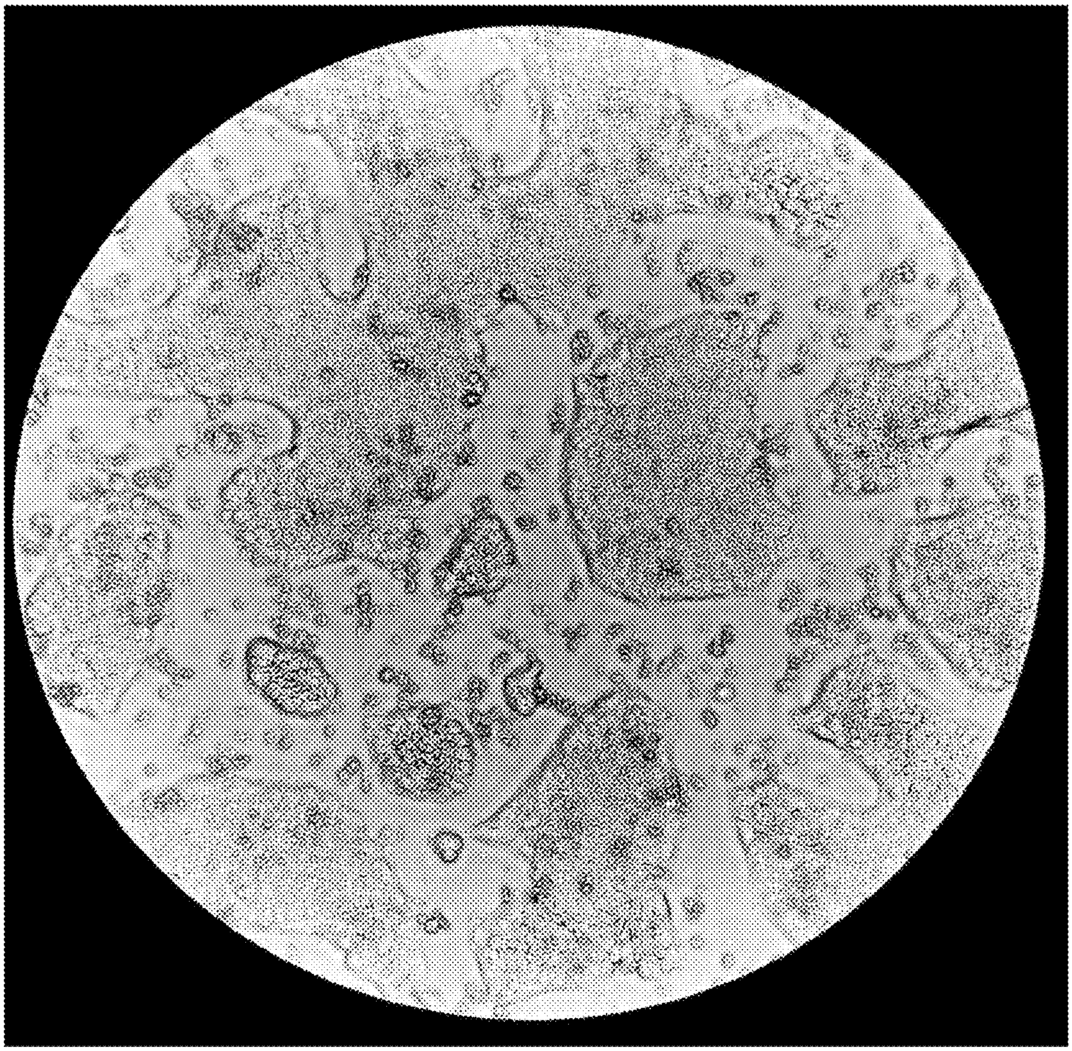
FIG. 23C shows an exemplary hiPSCs grown under continuous media flow in a liquid-filled chamber with a height of less than about 1 mm height in accordance with various implementations.

As an illustrative and non-limiting example, a prototype adherent cell growth chamber as shown in FIG. 23A supports over 50 $cm^2$ of cell culture area on a single surface, and has liquid filled height of approximately 0.5 mm, with a total volume of approximately 3 ml for very high efficiency cell culture. This prototype chamber can be modified for highest-uniformity liquid flow (elimination of angled corners in particular). The chamber in this particular example includes two pieces of 110×74 mm 0.17 mm thick borosilicate glass coverslips, one with two liquid ports cut through it, separated by an 0.5 mm thick silicone gasket with adhesive surfaces that has been cut to define the chamber. Tubing connectors are attached to the liquid ports. FIG. 23B is an image of an exemplary cell culture chamber. This chamber supports over 50 $cm^2$ of cell culture area on a single surface, and has liquid filled height of approximately 0.5 mm, with a total volume of approximately 3 ml for very high efficiency cell culture. This chamber has not yet been modified for highest-uniformity liquid flow (elimination of angled corners in particular). The chamber consists of two pieces of 110 mm×74 mm 0.17 mm thick borosilicate glass coverslips, one with two liquid ports cut through it, separated by an 0.5 mm thick silicone gasket with adhesive surfaces that has been cut to define the chamber. Tubing connectors are attached to the liquid ports. FIG. 23C shows an exemplary hiPSCs grown under continuous media flow in a liquid-filled chamber with a height of less than about 1 mm height.

Figure 24:
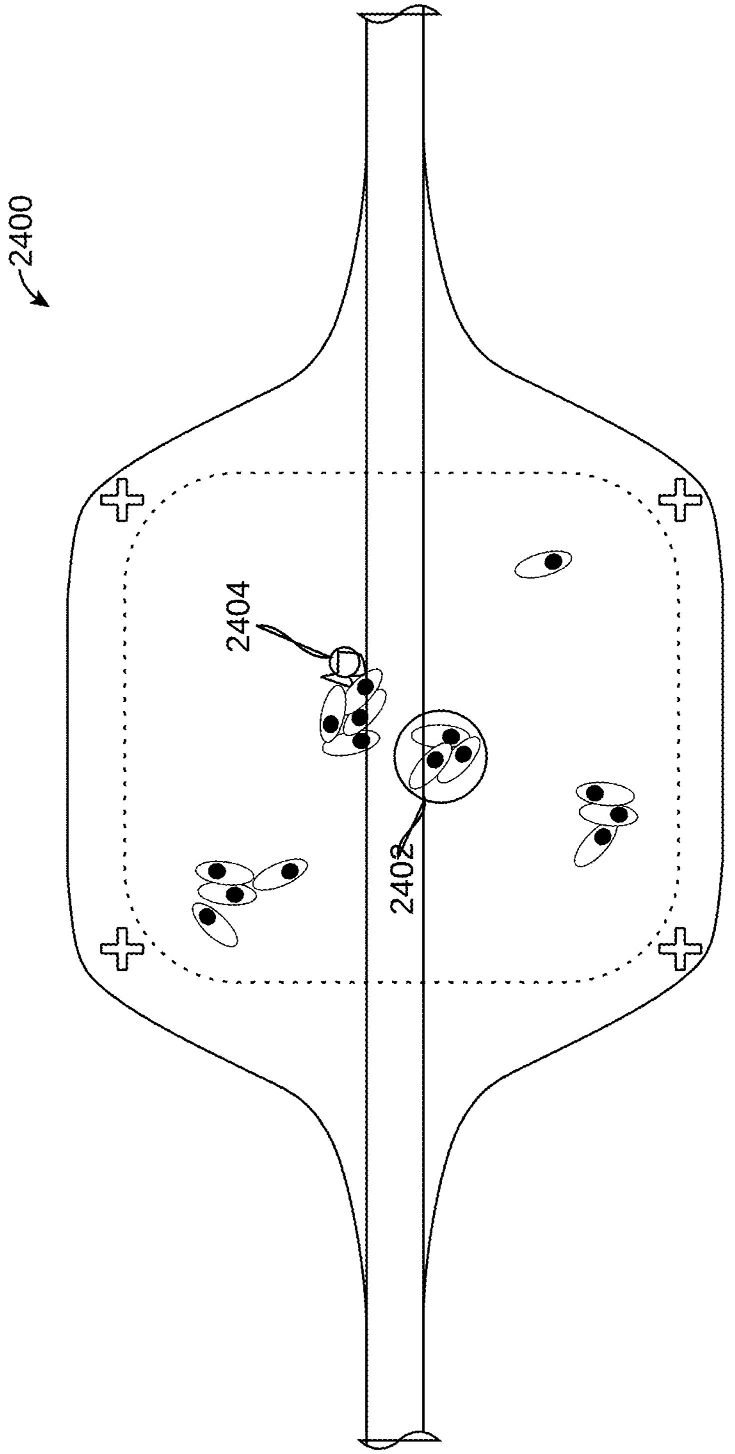
FIG. 24 is a diagram illustrating removal of cells from a cell culture chamber in a closed cassette system in accordance with various implementations.

FIG. 24 is a diagram illustrating removal of cells from a cell culture chamber 2400 in a closed cassette system in accordance with various implementations. The cell culture chamber 2400 may be similar to cell culture chamber 2202 in FIG. 22. Cell colonies 2402 or individual cells 2404 may be selectively lysed via a steered pulsed. For example, in an iPSC reprogramming process colonies may be kept separated to ensure clonality. A cell imaging subsystem (e.g., cell imaging subsystem 112) may collect images of the cell culture chamber 2400 and a computing subsystem (e.g., computing subsystem 110) may utilize various machine learning processes to determine whether one or more of the cell colonies 2402 may be in danger of merging. The computing subsystem may then control a cell editing subsystem (e.g., cell editing subsystem 112) to remove at least one of the cell colonies 2402. Additionally, individual cells or groups of cells may be determined by a human viewer or a computer algorithm to be spontaneously differentiating, in which case they may be removed via the cell editing subsystem as shown herein.

Figure 25:
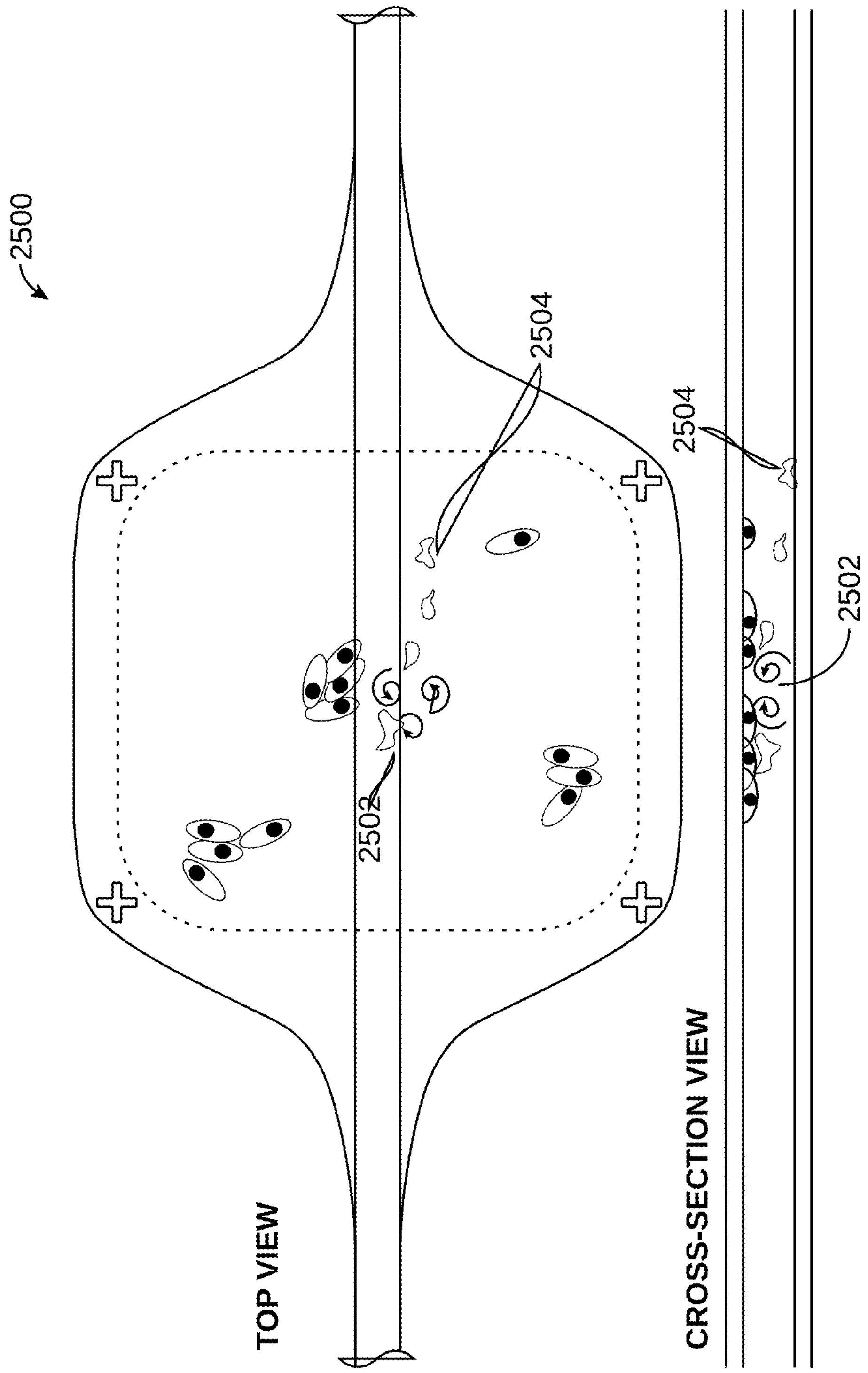
FIG. 25 is a diagram illustrating agitation of cells from a cell culture chamber in a closed cassette system in accordance with various implementations.

FIG. 25 is a diagram illustrating agitation of cells from a cell culture chamber 2500 in a closed cassette system in accordance with various implementations. The cell culture chamber 2500 may be similar to cell culture chamber 2202 in FIG. 22. FIG. 25 shows both a top view and a cross-section view of the cell culture chamber 2500. The systems and methods disclosed herein may allow for agitating or mixing of liquid within the cell culture chamber 2500 without opening the closed cassette system. In this case, the agitation mechanism may be used to detach cell debris from the culture growth surface so that the debris then settles on the opposite surface of the cell culture chamber 2500 (e.g., the bottom surface). The turbulent mixing effect of the mechanism is indicated in the top view and cross-section view by arrows 2502.

The agitation mechanism may include a number of physical modes, including but not limited to: magnetic mixing in which one or more magnets are resident inside the cell culture chamber 2500, and an external magnetic actuator is used to translate and/or rotate these magnets to achieve local mixing and agitation; mechanical actuators acting on the upper and/or lower surfaces of the cell culture chamber, potentially in conjunction with liquid flows or stoppage; laser-based techniques where a pulsed laser is used to induce cavitation inside the cell culture chamber 2500 in order to produce local mechanical forces and mixing (the focus of this laser may be on the surface opposite the cell culture, for example); or ultrasound transmission into the cell culture chamber 2500 that may be uniformly distributed or focused on specific regions where debris needs to be dislodged. As a result of the agitation, the detached cells and/or cell debris 2504 settles on the lower surface. From there the cell debris 2504 may be removed by one or more mechanisms including the above, but also liquid flow and gravitational techniques (e.g., tilting).

Figure 26:
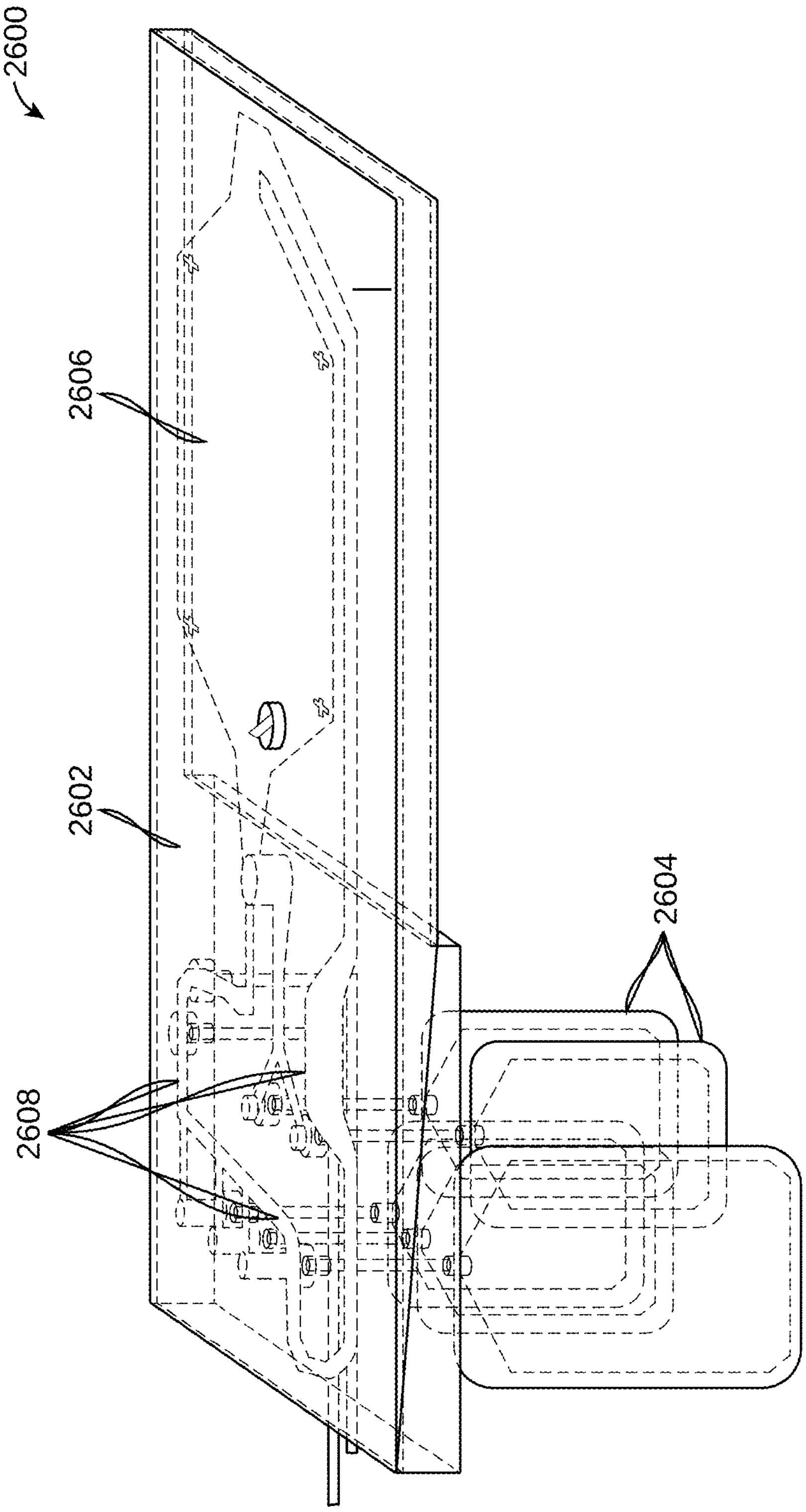
FIG. 26 is a diagram of a single-use portion of a closed cassette system for use in a cell culture system in accordance with various implementations.

FIG. 26 is a diagram of a single-use portion 2600 of a closed cassette system for use in a cell culture system in accordance with various implementations. The single-use portion 2600 may be configured to support a single cell culture process before being discarded. The single-use portion 2600 may include a chamber, fluidics, and supply and waste bags and associated tubing, similar to those shown in FIG. 22. All of the components of the single-use portion 2600 may be sterilized, filled under aseptic conditions, and then used in a cell culture process. After use, the bags containing the output cell product are removed using a sterile weld, and the remainder of the single-use portion 2600 may be disposed of properly.

The single-use portion 2600 may include a body 2602 housing fluidic system 2608 as well as cell culture chamber 2606. The body 2602 may be transparent or semi-transparent to allow for visual or automated imaging of the fluidic components and channels, for example to verify that there is no contamination, blockage, bubbles, etc. Bags 2604 are attached to the single-use portion 2600. The bags 2604 may contain media reagents as well as waste products and cellular products. The fluidic system 2608 in the single-use portion 2600 may include channels for circulating liquid, valve sections, pump sections, gas concentration control fluidics, non-invasive sensing patches, etc.

Figure 27:
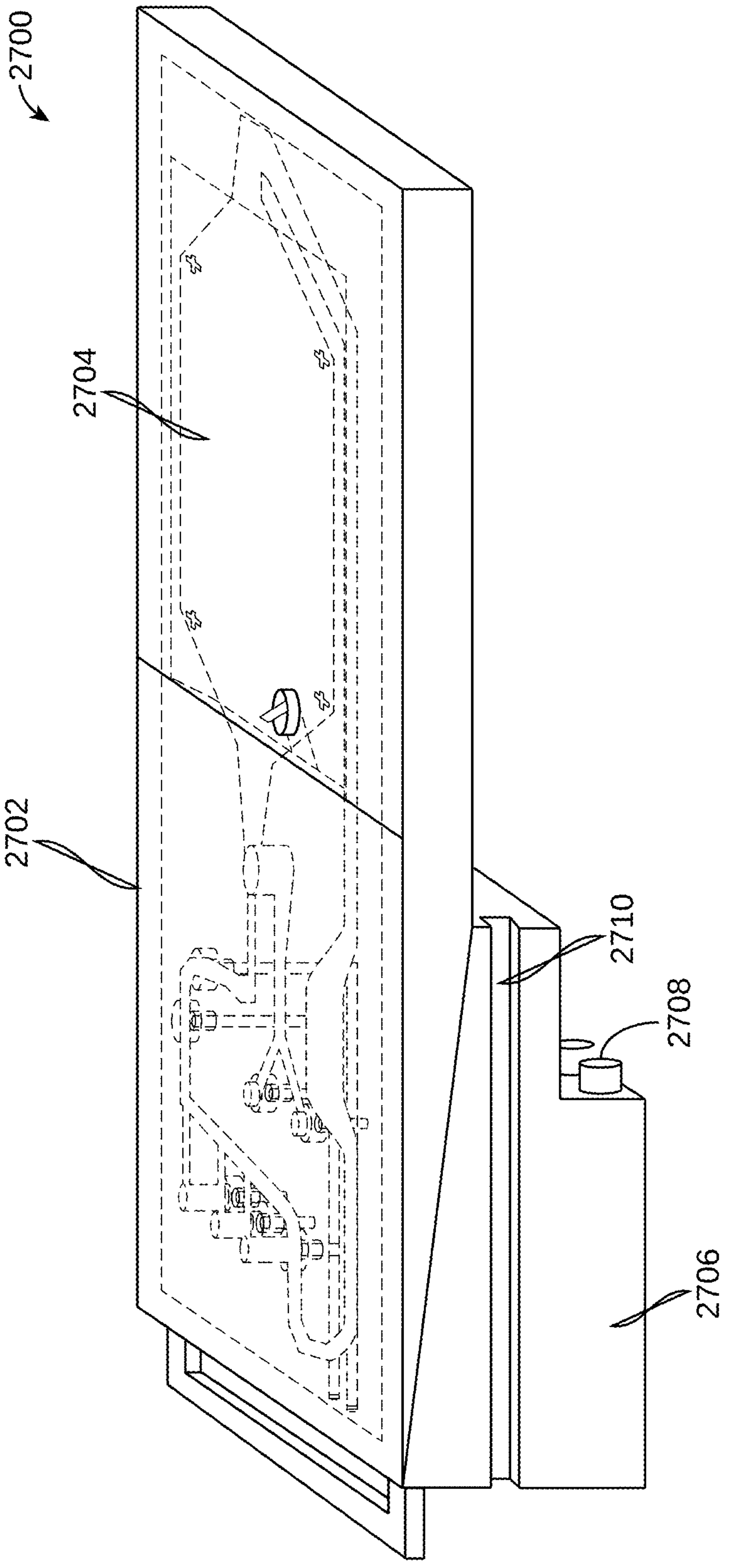
FIG. 27 is a diagram of a permanent portion of a closed cassette system for use in a cell culture system in accordance with various implementations.

FIG. 27 is a diagram of a permanent portion 2700 of a closed cassette system for use in a cell culture system in accordance with various implementations. The permanent portion 2700 may include a reusable housing 2702 that encloses the single-use portion of the closed cassette system (e.g., single-use portion 2600). The combination of the permanent and single-use portions may form a complete closed cassette system (e.g., closed cassette system 2200). The permanent portion 2700 may also include at least one clear window 2704 to allow complete imaging of the cell culture chamber located in the single-use portion. In some implementations, the window 2704 may be on both sides of the cell culture chamber in order to allow transmission imaging. In other implementations, the window 2704 may only be located on one side of the cell culture chamber when reflective imaging is sufficient (i.e., light source and sensor on same side of chamber).

A compartment 2706 houses the supply, waste and product bags of the single-use portion and may provide one or more temperature-controlled chambers for long-term storage (for example, cellular products may be held at 37° C., while some reagents are held at 4° C. until use). In some implementations, the permanent portion 2700 may also include actuators for actuating valves and pumps on the single-use portion of the closed cassette system. For example, spring-loaded solenoids may apply pressure to the tubing on the disposable fluidics to keep valves closed in their unactuated state, and when an electrical current is provided, the solenoid opens the valve by releasing pressure. Similarly, pumps may be driven by electromechanical systems within the permanent portion, for example by driving a series of cylindrical rollers in a semicircle along the path of tubing on the single-use portion to initiate peristaltic pumping.

A mechanical rail 2710 may integrated in the permanent portion 2700 to provide alignment within one or more pieces of equipment. For example, the closed cassette system may reside in equipment that also includes imaging systems, power systems, central computing systems, heating and cooling systems, cassette movement systems, and other components to support parallel cell culture processing on multiple closed cassette systems. In one implementation, such equipment may include a server rack, and the mechanical rail 2710 may allow the closed cassette system to slide in and out of the server rack. The permanent portion 2700 may also include pluggable connectors 2708 that interface with connectors on the equipment (e.g., server rack). The pluggable connectors 2708 may include, but are not limited to, electrical connectors to power on-board electronics and actuators, data connectors to collect sensor and status information centrally, liquid connectors for circulating liquid for temperature control, and gas connectors to supply gas for maintaining gas concentrations in the cell culture media.

Figure 28:
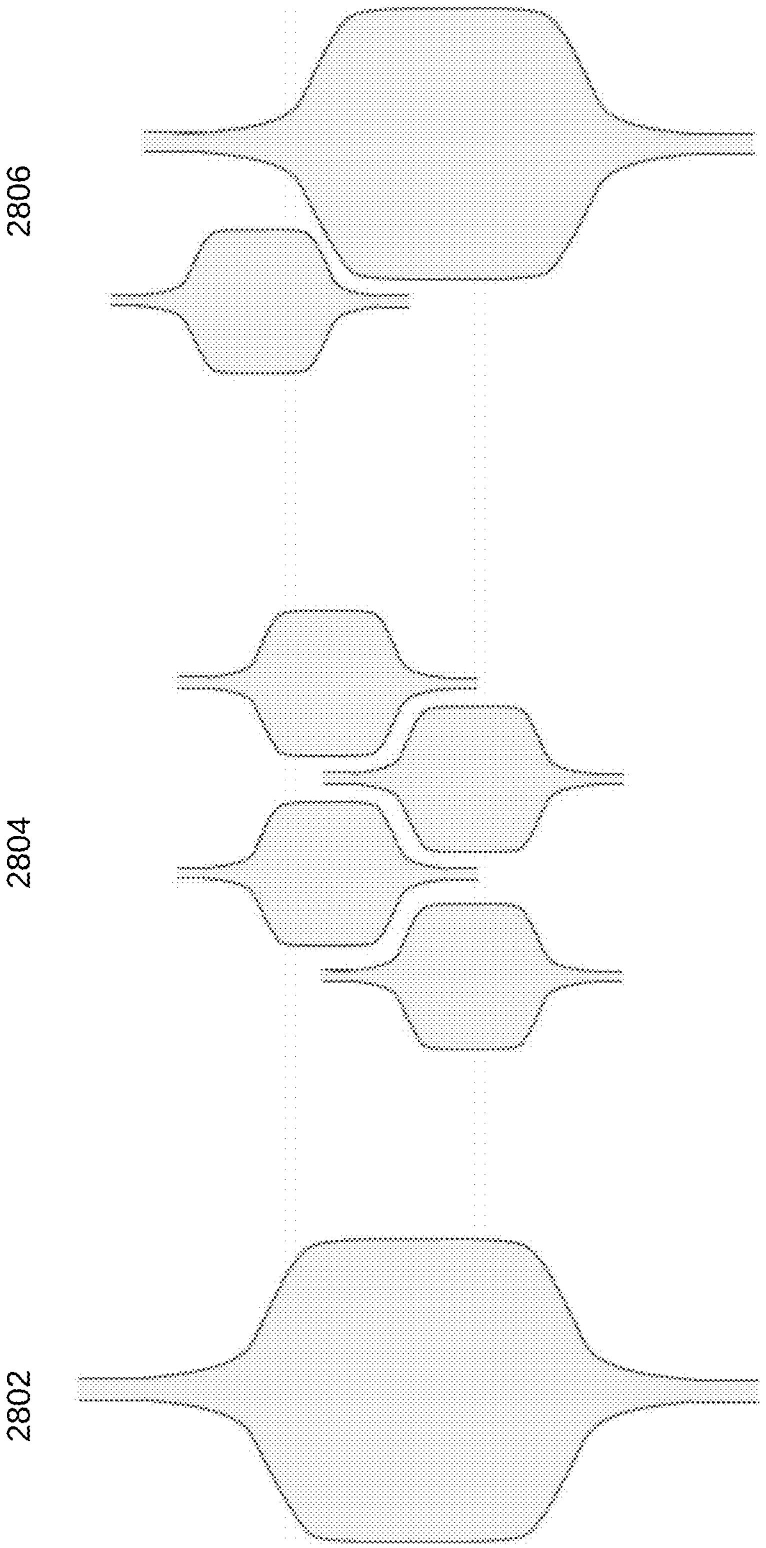
FIG. 28 illustrates various cell culture chamber configurations in a closed cassette system for use in a cell culture system in accordance with various implementations.

FIG. 28 illustrates various cell culture chamber configurations in a closed cassette system for use in a cell culture system in accordance with various implementations. These configurations may include a single large chamber configuration 2802, a multiple small chamber configuration 2804, a small and large chamber configuration 2806, and other configurations not shown in FIG. 28 but known to persons of skill in the art. The single large chamber configuration 2802 may be used for cell expansion, for example. The multiple small chamber configuration 2804 may be used in cases in which multiple clonal populations are desired in order to have a diversity of product, for example. The small and large chamber configuration 2806 may be used to first prime cells in a small chamber using relatively little reagent (this may include delivery of compounds into the cells), followed by reprogramming or differentiation and expansion in the larger chamber. In all of these configurations, it is possible using appropriate valving and/or filtration to keep cells from inadvertently moving from one chamber to another. However, as in the last example, the fluidics may be configured to explicitly allow movement from one chamber to another through valving filtration and pumping operations.

Modular Bioprocessing System

Bioprocessing is the process of using living cells or their components to obtain a desired output. Current bioprocessing equipment is available largely in two types. The first type are large-scale bioreactors derived originally from the chemical industry and repurposed for cell-based processes such as protein or viral production. These bioreactors typically using large steel tanks, but more recently have been fitted with one-time-use bags or scaled down to glass-based stirred bioreactors. These systems are usually surrounded with bespoke, sealed tubing and other modifications to make the bioreactors suitable for handling biological materials. The second type of bioprocessing equipment are small-scale systems derived from manual R&D laboratory instruments, typically including benchtop instrumentation and utilizing microwell plates or small flasks. In some cases, small scale systems have been scaled up to larger containers, and custom systems have been developed in order to transport, fill, and handle stacks of plastic containers containing cell cultures.

In the case of large scale bioreactor systems, the amount of data collected during the bioprocess is often minimal. There has been a largely stalled push to get more measurement and control in tank bioreactor-style systems. However, the proposed measurements, even if implemented, would be minimal representations of the state of the bioreaction, typically measurements of nutrients, waste products, cell mass/density, pH, $O_2$, temperature, and a few other factors that allow for better control of the process. Some additional sampling-based measurements allow for more detailed, but less frequent, measurement of the cell mixture. However, the physical volumes of these systems are large, and the data volume is quite low.

Recent autologous cell and gene therapy processes, such as CAR-T therapies, have taken a similar approach, simply miniaturized. It has become increasingly clear that the absence of higher-bandwidth measurement, monitoring, and feedback control are a challenge in these therapies, where patient-to-patient variations can lead to poor consistency and yield. On-time delivery of therapies is crucial, and these drawbacks may lead to significant delays. Some bioprocessing equipment suppliers have sought to build automated, modular units to address these issues, but although these provide the ability to perform cell processes in non-sterile facilities, they still keep to the convention of separating biological equipment from the data infrastructure, and are built with only human operators in mind.

On the other hand, in the small scale system model, derived from R&D laboratory equipment, there is at least the potential to gather more data on the actual cell culture conditions by use of imaging, because many formats were developed specifically to allow microscopy and other optical measurements. However, imaging measurements of cell culture are done almost only as "spot checks" rather than to quantitatively assess the cells or guide process parameters. High content imaging has largely remained in the domain of R&D or is used in quality control assays at the end of a cell culture process. For example, immunofluorescent-labelled imaging may be used on a small sample that seeks to reflect the whole product.

Bioprocessing systems should ideally collect detailed, fine-grained information about the progression of the process, the state of cells and cell colonies, and potential problems with purity or yield far in advance of final quality control assays. This fine-grained data, together with appropriate control algorithms, may be used to control and optimize both process parameters (such as nutrient flow, product harvest, vitamin or gas concentrations, temperature, pH, etc.) and to actively guide the cell cultures by use of selecting cell removal or editing based on imaging results. In addition, other optical techniques such as spectroscopy may be employed in such formats to extract data related to biochemical constituents within the cell media or cell mass.

With such expanded use of online imaging and spectroscopic techniques, the amount of data generated per biological sample in process explodes. Take for example the equivalent of a T-225 flask (225 $cm^2$ growth area) used in a process for differentiating cells from induced pluripotent stem cells (iPSCs). Using brightfield imaging with a 5-layer Z stack, at a cycle time matching the rough cell division (18 h), a resolution of 1 micron, and a standard 16 bits per pixel, the daily raw data stream of imaging alone is 150 Gigabytes. This imaging data must be collected, processed, interpreted, and made into actionable information relevant to bioprocess prediction and control. Scale up to a facility in which hundreds of patient samples are processed in parallel, and the scale and reach of the data infrastructure alongside the bioprocessing infrastructure becomes clear: many terabytes per day flow through the biomanufacturing environment. Small scale data storage means are no longer useful. An infrastructure in which biology and data coexist and work together is required.

Another issue in bioprocessing is the ability to automate processes efficiently. The current approach includes setting instruments on benches (similarly to how they would be situated in a manual R&D laboratory), placing one or more robots between the instruments, and then training the robots to very precisely find the correct locations to place or pick consumables to/from the various instruments. Any movement (swap-out for repair, etc.) of an instrument requires retraining. Almost every instrument has a slightly different mechanical interface, usually designed primarily with manual R&D lab operations in mind, with mechanical interfaces to robotic systems as an afterthought. As a result, building an automated system with even just a few instruments becomes a major undertaking for which specialized contractors are hired, custom benches are fabricated, and the reach of a central robot arm must be carefully calculated. Once built, the setup offers limited expandability. As a result, the up-front investment in time, dollars, and real estate footprint for incremental capacity can be very significant.

Some companies have attempted to remedy the expandability issues with large-scale transport system for microplates and extensive custom automation hardware. Others have built more linear robotics that move along shelving constructed specifically for each piece of equipment, with appropriate widths, heights, etc., for shelves. However, these systems rely on specific positioning of instrumentation to properly interface with the robotics, and where the robotics are required to be highly flexible, with multiple degrees of freedom, and therefore quite expensive.

Additionally, because of the format of these systems and the constraints of the type of robotics and automation that is required the systems end up having a large, planar footprint. The result resembles a warehouse where bulk goods of various shapes and sizes are simply placed on shelving of varying proportions. When faced with these analogous issues, large warehouse operators have tried to standardize shelving and storage, and then try to automate the storage and retrieval process and adopt a vertical format for space and transport logistical efficiency. Similarly, in order to scale up biology, and in particular bioprocessing and biomanufacturing, a more modular, standardized, expandable, and data-integrated system that minimizes footprint and transport complexity is needed.

The systems and methods disclosed herein utilizes industry standard data and communications infrastructure and equipment to serve as the basis and backbone for a highly modular bioprocessing system. The bioprocessing modules used in these systems may be closed cassettes that are fully imageable for monitoring and control purposes, including the ability to actively edit cell cultures by removing cells or cell colonies during the course of the process. The present implementations may utilize such cassette-based systems, but may also utilize existing microwell plate, flask, and larger (closed) container formats.

The bioprocessing modules may be sized to fit within standard server rack units, with heights measured in standardized units of U (1 U, 2 U, 4 U, etc.) and widths the same as computing, storage, and communications equipment. The modular bioproces sing system also includes common modules that may be shared between multiple bioprocessing modules on the same rack, such as data storage modules, computing modules, power supplies, communications modules, environmental control modules, laser modules, liquid handler modules, and imaging modules. This not only allows for a highly modular, incrementally expandable format for bioprocessing facilities, but also allows for very tight integration between bioinstrumentation and data processing to address the high volumes of data and communication in fully-monitored, closed-loop bioprocessing. Other advantages of such a system include fast setup and delivery, easier automation, incremental expansion, use of existing modular units for power, environmental management, and direct integration with data infrastructure and modules.

The modular bioprocessing systems may have standardized dimensions, such as 19 inch width enclosures, various depths including but not limited to 24", 36" and 48", and various heights up to the industry-standard 42 U (in which 1 U=1.75"). All instrumentation and equipment in the various implementations may mount into these racks and have heights in 1 U increments, so positioning may be calculated purely from rack position index. The front-facing panel of the instrumentation modules may have a loading area to load/unload the micro plate, flask, cell culture vessel, or cell culture cassette for which the system is designed. The modular bioprocessing system may also include vertical transport mechanisms to move cell culture containers (e.g., microwell plates) in and out of bioprocessing modules and onto/off of horizontal transport mechanisms designed to move cell culture containers between modular bioprocessing systems and other locations. These mechanisms may be automated in order to form a fully automated bioprocessing facility, but may also allow for easy human interaction with the system.

The systems and methods disclosed herein include a modular bioprocessing system that includes a rack, one or more bioproces sing modules configured to fit within the rack, the one or more bioprocessing modules configured to accept one or more cell culture containers, and a plurality of common modules configured to fit within the rack, the plurality of common modules shared by the one or more bioprocessing modules. This system has many advantages over current bioprocessing designs, which may include, but are not limited to, easy setup, alteration, and expansion in capacity, and easy integration with data, communication, and power systems.

Figure 29:
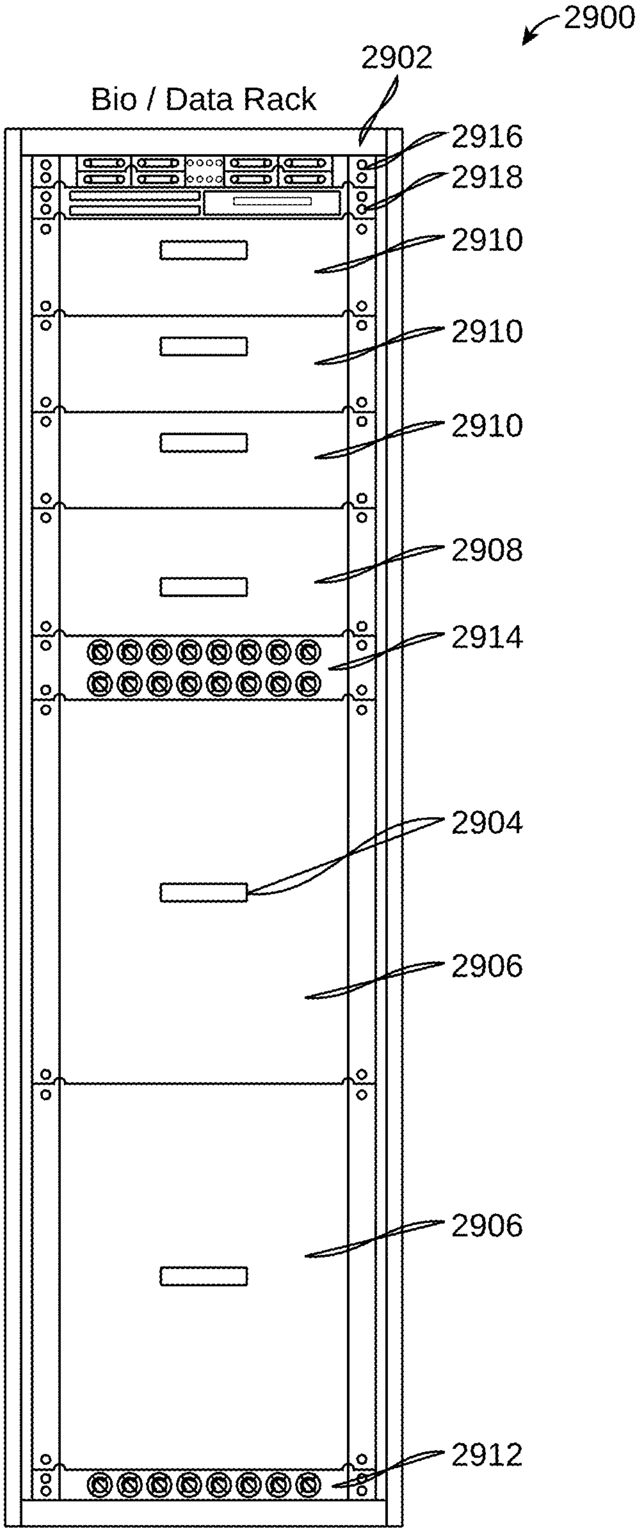
FIG. 29 is a diagram of a modular bioprocessing system in accordance with various implementations.

FIG. 29 illustrates a modular bioprocessing system 2900 in accordance with various implementations. The modular bioprocessing system may be an implementation of a cell culture system (e.g., cell culture system 100), or may be part of a larger cell culture system that includes one or more modular bioproces sing systems. The modular bioprocessing system 2900 may include a rack 2902 for holding all the modular elements in the modular bioprocessing system 2900, including both data processing and communications modules, as well as bioproces sing modules. The rack 2902 may have standardized server rack sizes. For example, server rack height may be measured in units of U (1 U=1.75 inches). For example, a rack with a size of 42 U has a usable height of 73.5 inches. The rack 7402 may also have standard depth and width dimensions. This allows for a number of standard-shaped modular elements to be placed in the rack 2902, rather than requiring custom-sized components.

The modular bioprocessing system 2900 may also include one or more container interfaces 2904 for accepting and holding cell culture containers. These cell culture containers may include, but are not limited to, standard microwell plates (for example 6-, 12-, 24-, 48-, 96-, 384- . . . well plates), cell culture flasks, microfluidic chambers, or custom cassettes for cell cultures. In FIG. 29, an implementation that uses standard microwell plates is shown. In this case, the container interface 2904 include a plate holder that extends from the front of each bioprocessing module for loading/unloading microwell plates. The microwell plates are then retracted into each bioproces sing module for processing or storage.

The modular bioprocessing system 2900 may also include one or more bioprocessing modules 2906. Each bioprocessing module 2906 may be a closed container (i.e., the internal components are not exposed to external components that may contaminate the container) that includes a cell culture container holding a biological sample to be processed (e.g., differentiated cells that are processed into iPSCs or vice versa) and components that support the growth, editing, cleaning, imaging, sensing, and other functions for processing the biological samples. The bioprocessing modules 2906 may include, but are not limited to, closed cassettes that are fully imageable for monitoring and control purposes, microwell plates, flasks, and other closed container formats. Each bioproces sing module 2906 may maintain independent environmental conditions corresponding to different cell processes or cell process stages or states. For example, the temperature for each module may be set differently, pH may be controlled, or the dissolved oxygen level may be set differently in each module in order to maintain a hypoxic environment for some cell culture processes or stages of processes.

The modular bioprocessing system 2900 may also include one or more liquid handler modules 2908 that is configured to change media in the bioprocessing modules 2906. Appropriate tubing and containers for media and waste may be connected to the rear (utility) side of the liquid handler module 2908 and connected to the bioprocessing modules 2906. A single liquid handler module 2908 may support one or more bioproces sing modules 2906. For example, bioproces sing modules 2906 that contain the same biological samples undergoing the same process may share a liquid handler module 2908. In other implementations, there may be a one-to-one correspondence between bioprocessing modules 2906 and liquid handler modules 2908. The liquid handler modules 2908 may include relatively simple media exchange modules, which withdraw waste media from cell culture containers, and refill with fresh media. Such media exchange functionality may further include centrifugation in the case of suspension cell cultures. Other modular liquid handling implementations may include the ability to add multiple reagents to wells within microplates in various combinations, for the purpose of drug screening or high-throughput cell process development. Other modular liquid handling implementations may include the ability to simultaneously load multiple cell culture containers and affect transfers between these containers, for example to distribute cell samples among multiple wells for subsequent quantitative polymerase chain reaction (qPCR analysis), which may also be implemented in the present application via a modular unit.

The modular bioprocessing system 2900 may also include one or more imaging modules 2910 that are configured to capture time series images of biological samples cultured in the bioprocessing modules 2906. Different imaging modules 2910 may have different capabilities. For example, two label-free (brightfield, phase, quantitative phase, transmissive or reflective darkfield, etc.) modules may be used to capture label-free time series images of cell cultures over days, and a single fluorescent imaging module may be used to capture high-content multi-channel fluorescently-labelled cell culture images at an endpoint. In some implementations, one imaging module 2910 may be configured to capture multiple types of images. The imaging modules 2910 may be configured to automatically capture images based on a schedule, the schedule set by a control module within the modular bioproces sing system 2900 or by an external controller that controls multiple modular bioproces sing systems.

One of the advantages of the modular bioproces sing system 2900 is that modules may share resources, similar to how resources may be shared in data server rack configurations. For example, the modular bioprocessing system 2900 may include a power supply module 2912 provides power (for example, 24V DC) to all modules in the system, with redundancy. Similarly, the modular bioproces sing system 2900 may also include an environmental control module 2914 that is configured to provide heating and cooling capacity via liquid to all modules in the system. For example, the environmental control module 2914 may maintain cell cultures at 37° C., reagents to be maintained at 4° C., and data/computing modules to be cooled to appropriate operating temperatures even under high loads. The modular bioprocessing system 2900 may utilize standardized liquid connectors and distribution manifolds used in cooling CPU/GPU server racks because of the standardized setup of the rack 2902 and other modules. Similarly, an imaging module 2910 may be shared between multiple bioprocessing modules 2906.

The modular bioprocessing system 2900 may also include one or more data storage modules 2916 and computing modules 2918. The data storage module(s) 2916 may be configured to store images collected by the one or more imaging modules 2910, sensor data collected by various sensors in the modular bioprocessing system 2900, and data and applications used by the computing modules 2918. The computing module(s) 2918 may be configured to perform various data processing and analysis functions related to bioprocessing the cell cultures in the bioprocessing modules 2906. For example, the computing module(s) 2918 may perform image pre-processing, registration, normalization, and stitching functions for the imaging modules 2910, reducing or eliminating the need for dedicated processors or computing modules for each imaging module 2910, and potentially significantly distilling or compressing imaging data before it is transferred to a centralized location (either on-premises, in another location including cloud resources, or both in a hybrid architecture). The computing module(s) 2918 may also perform other data processing, input/output, and communications functions for the modular bioprocessing system 2900.

The modular bioprocessing system 2900 may be communicatively connected to a central controller, such as a central server that controls one or more modular bioprocessing systems 2900. For example, there may be multiple modular bioprocessing systems 2900 located in a room, and there may be wired and/or wirelessly connected to a central server that controls the operation of each modular bioproces sing system 2900. The central server may also collect data from each modular bioprocessing system 2900, and may also provide a user interface for a person to view data (e.g., imaging data) collected from any modular bioprocessing system 2900, monitor the status of any bioprocessing module, and control any of the modules in any modular bioprocessing system 2900. The central server may implement many functions, including scheduling automated processing schedules of cell cultures, alerting users of emergency conditions in any modular bioprocessing system 2900, and presenting real-time operational data for any modular bio-processing system 2900.

The modular bioprocessing system 2900 shown in FIG. 29 is a full-height rack. However, it should be clear from the modular nature of the system that smaller systems are feasible. For example, a minimal system for continuous cell culture measurement may include one bioprocessing module 2906, one liquid handler module 2908, one imaging module 2910, plus shared systems. The system may fit into a very compact rack suitable for even the densest environments such as university laboratories. The modular bioproces sing system 2900 may include other components not illustrated in FIG. 29, and may include variations known to persons of ordinary skill in the art.

Figure 30:
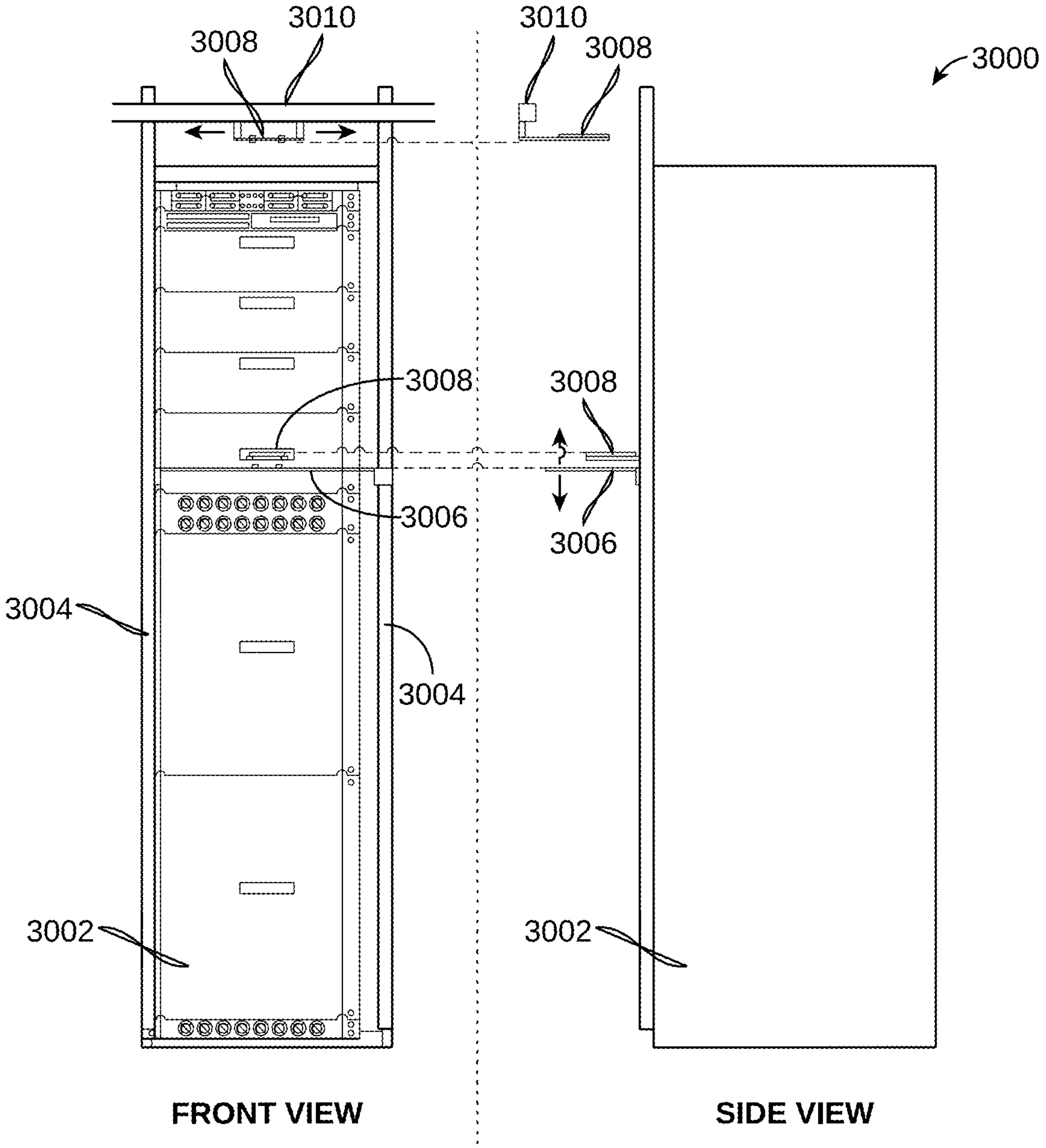
FIG. 30 illustrates container transportation functionality in a modular bioprocessing system in accordance with various implementations.

FIG. 30 illustrates container transportation functionality in a modular bioprocessing system 3000 in accordance with various implementations. Because of the modular nature and vertical format of the various implementations, a highly simplified cell culture container transport mechanism is possible. Moreover, the transport is compatible with side-by-side work with human operators, unlike robotic transport systems where a potentially hazardous robot arm sits in the center of a cluster of bioinstruments. The standardized modular format disclosed herein dramatically simplifies the requirements for such an automated transport system, since it defines discrete vertical rack locations for container pickup/drop-off, and a fixed horizontal position, allowing a single-axis, low-precision actuator (track system) to be utilized, with low-cost sensors to confirm container pick-up and drop-off at individual modules or on an overhead transport system.

The modular bioprocessing system 3000 may be similar to the modular bioprocessing system 2900 shown in FIG. 29. The modular bioprocessing system 3000 may include one or more bioprocessing modules 3002 that host cell culture containers. The example shown in FIG. 30 uses microwell plates 3008 as cell culture containers, but any suitable cell culture container is compatible with the described implementation, such as closed cassettes. A set of rails 3004 may be mounted on the rack front, allowing vertical motion control of a vertical transporter 3006 mounted on the rails 3004. A bioprocessing module 3002 may eject a microwell plate 3008 from the front of the module onto an extended container interface (e.g., container interface 2904). The vertical transporter 3006 may approach the container interface from the bottom to retrieve the microwell plate 3008 from a bioproces sing module 3002 presenting the microwell plate 3008. The vertical transporter 3006 may then transport the microwell plate 3008 to another location along the vertical axis of the rack and/or allow a person to collect the microwell plate 3008. Alternatively, the vertical transporter 3006 may approach an extended container interface from the top when it is delivering a microwell plate 3008 to a bioprocessing module 3002, and the microwell plate 3008 remains on the extended container interface as it passes. The container interface may then retract the microwell plate 3008 into the associated bioprocessing module.

For single-rack installations, or multi-rack installations where the racks are independent, this vertical transport is sufficient to completely automate the bioproces sing system, again with an extremely compact footprint compared to existing bio-automation configurations. In the case of multi-rack systems where automated microplate exchange is desired between racks, or between individual racks and a fill//harvest or other central location, a horizontal track-based transporter 3010 is provided. The horizontal transporter may transport cell culture containers in a horizontal axis of the rack. The horizontal transporter 3010 provides a mechanical interface similar or identical to the container interfaces, in order to hold the microplate wells 3008 for transport. The vertical transporter 3006 may load microwell plates 3008 onto the horizontal transporter 3010 by approaching from the top, or picks up a plate from the horizontal transporter 3010 by approaching from the bottom. Neither the vertical nor horizontal transport system interfere with human operator access to the front (or back) of the modules, so plates may be manually retrieved or added by human operators in concert with automated transport. Moreover, the automated transport works with minimal footprint, and may use low mechanical force to increase safety.

Figure 31A:
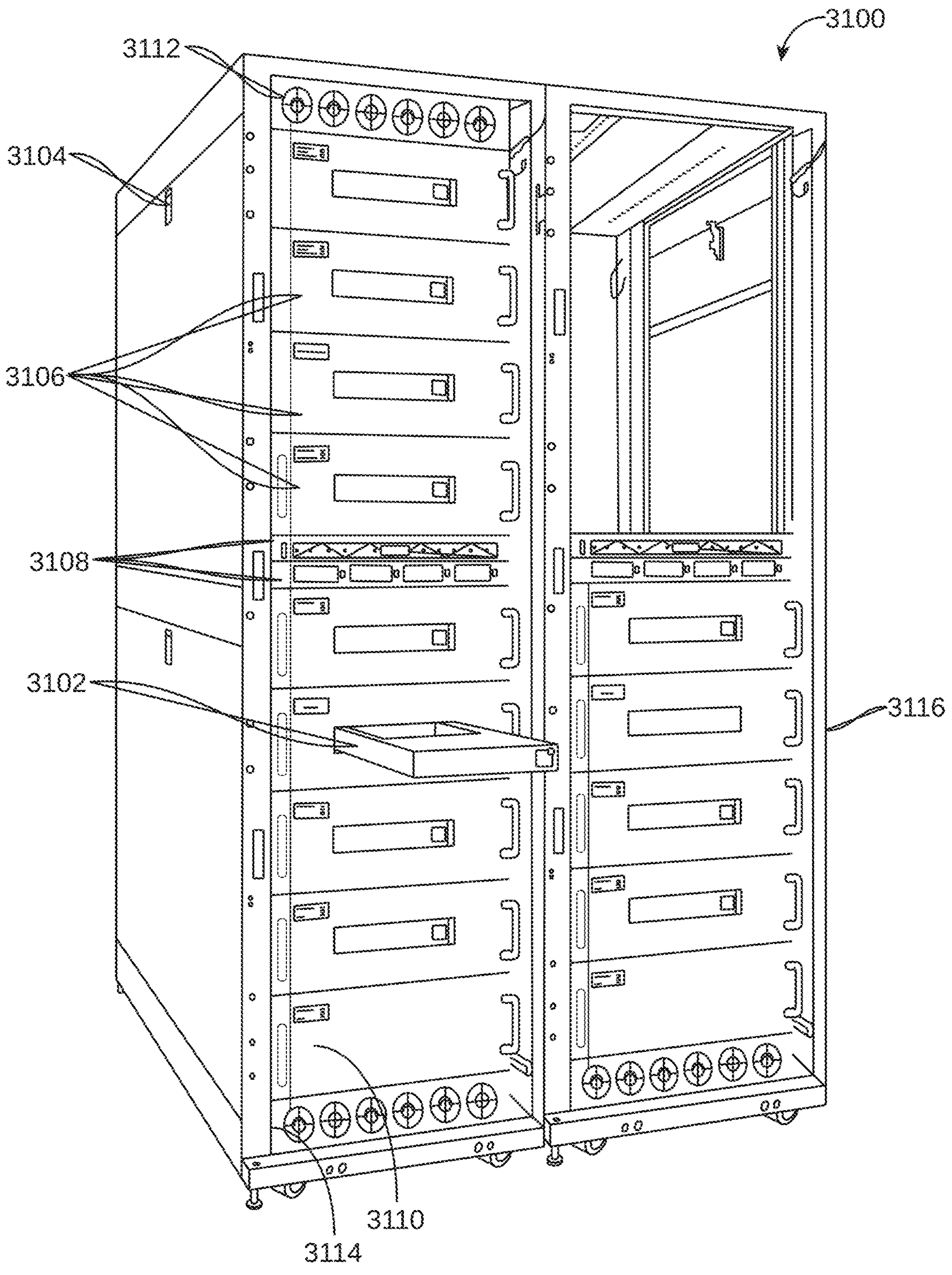
FIG. 31A is another diagram of a modular bioprocessing system in accordance with various implementations.

FIG. 31A is another diagram of a modular bioprocessing system 3100 in accordance with various implementations. In this implementation, the cell culture container is implemented as a cassette 3102 that may be used for various cell culture processes, including but not limited to cell reprogramming, cell differentiation, cell gene editing, and/or cell-based bioproduction. The cassette 3102 is sealed in order to allow sterile processing of multiple samples in the same environment, for a high degree of control and consistency, and potentially for good manufacturing practice (GMP) compliance for therapeutic (patient-bound) products. An example of the application of this implementation is the production of patient-specific human induced pluripotent stem cells (hiPSCs), and subsequent differentiation of hiPSCs into replacement cells for cell therapies. In such an application, complete isolation of patient samples from one another is required, and accomplished using a cassette-based system where required media and reagents, as well as waste reservoirs, are contained within a sealed liquid system on the cassette 3102. In this example, the cassette 3102 may include a cell culture chamber that is fully imageable, and the cell culture chamber is configured to allow selective laser ablation of cells from the cell culture, with subsequent removal of resulting debris by on-board liquid handling subsystems. Using this combination of elements, a high degree of control and therefore predictability and yield is possible to achieve in a sealed cell culture.

The cassettes 3102 may be inserted into bioprocessing modules 3106 mounted in a rack 3104, which may have standard server rack dimensions. The cassette hosts 3106 may provide a number of functions, such as (a) incubating the cells in the cassette inserted into the host; (b) actuating on-cassette liquid handling systems for media replenishment, reagent additions, waste removal; (c) monitoring media conditions in the cassette, for example dissolved oxygen and pH, and making adjustments as necessary; (d) providing gas exchange with the on-cassette circulated media to adjust oxygen and other dissolved gas levels; (e) imaging the cells within the cassette; (f) selectively destroying and ablate cells within the growth chamber using a laser system; and (g) editing cells (e.g., inserting cargo into a cell or removing cargo from a cell) within the growth chamber using a laser system. In this manner, a single bioprocessing module 3106 may monitor and control a long-duration cell culture process without removal or transport of the cassette 3102, reducing the potential sources of variability in the process. The bioproces sing modules 3106 in a rack operate independently but may share a number of resources, as described below.

Shared computing, storage, and communications modules 3108 may be used to process imagery acquired by each bioprocessing module 3106 for normalization, registration, stitching, and other functions. The resulting images/data may be further processed using a machine learning system that is located either locally or remotely (e.g., elsewhere on the premises or in the cloud). Algorithmic choices or predictions may then be computed internally or transmitted back to this computing infrastructure to drive selective laser removal of cells within each bioproces sing modules 3106 and associated cassette 3102. For example, a shared pulsed laser module 3110 may provide laser energy to multiple bioprocessing modules 3106 via standard fiber optic connectors located on the rear of the rack 3104. The energy may be split among the bioprocessing modules 3106 via a tree of static fiber optic splitters or switched from unit to unit via an optical switch, or via some other method. In some implementations, there may be more than one laser module in the modular bioprocessing system 3100. In some implementations, a single laser module may be used for modules in multiple racks within the modular bioprocessing system 3100.

A shared environmental control module 3112 may be used to provide cell culture temperature control (usually 37° C.), reagent cooling (often 4° C.), laser cooling, and cooling for the data storage and computing modules, especially in the case where local central processing units (CPUs) or graphics processing units (GPUs) perform large workloads for image processing or machine learning operations. A shared power supply 3114, in some implementations a power supply with built-in redundancy, may be used to provide reliable DC current to the bioprocessing modules 3106, laser module 3110, and potentially the data storge and computing modules, so that there is no need for individual power supplies.

The various implementations allow for small system configurations, as shown by the half-height setup 3116 with very small footprint and setup time, and incremental addition of bioprocessing modules 3106 for additional capacity as demand requires. The modular configuration also enables a high degree of redundancy and reliability because spare modules may be added or brought online very quickly to compensate for any failures. In the example shown in FIG. 31A, a small modular system, even in a half-height rack, may take the place of several high-grade cleanrooms (often located in expensive urban spaces) for GMP cell culture, and negate the need for extensive suiting-up for personnel for daily cell culture observation and manual modification// transfer steps.

The modular bioprocessing system 3100 illustrated in FIG. 31A may be fitted with a transport system similar to the one described with reference to FIG. 30, with simple, human operator-compatible vertical as well as horizontal transport for large multi-rack facilities. The modular bioprocessing system 3100 may include other components not illustrated in FIG. 31A, and may include variations known to persons of ordinary skill in the art.

Figure 31B:
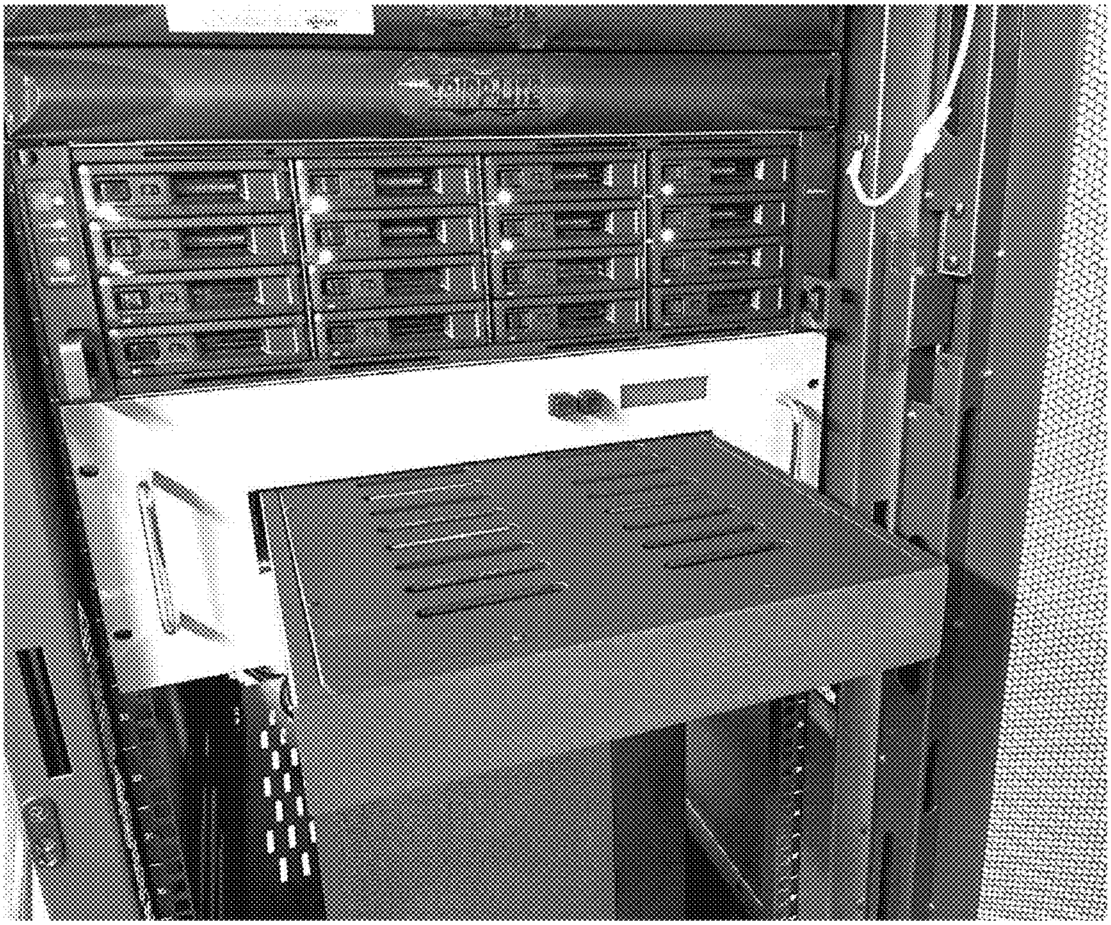
FIG. 31B shows an exemplary prototype process module (lower, with handles) and partially inserted cell culture cassette, which is shown co-located with RAID storage array (with 16 drive bays visible) and backup power module (above, marked Tripp Lite), in accordance with various implementations.

FIG. 31B shows an exemplary prototype process module (lower, with handles) and partially inserted cell culture cassette, which is shown co-located with RAID storage array (with 16 drive bays visible) and backup power module (above, marked Tripp Lite).

Hot-Swap Redundant Cell Culture Systems

Many cell culture processes, including gene editing, reprogramming (for example, reprogramming cells into iPSCs), expansion, differentiation, and bioproduction, may require lengthy, complex processes. Cell culture systems that run these processes may be complex and have many different subsystems, such as environmental sensors and controls, media/waste and reagent transfer subsystems (pumps, valves, sensors), imaging subsystems, and cell editing and/or manipulation subsystems (including directed-energy systems for intracellular delivery or selective cell destruction or removal, cell culture washing systems, etc.). This complexity makes these systems prone to failures due to the failure of a single component, subsystem, or software. In current systems, this usually results in the loss of the cell culture, which may be extremely expensive and also have a large impact on patients awaiting the cell product.

Implementations disclosed herein, for example in FIGS. 29-31, describe the use of a distributed, modular system, in which cell cultures are processed simultaneously in multiple modules that each encompass a range of functionality. These implementations reduce the chance of mass failures due to shared equipment (for example, robotic arms, imaging systems, liquid handling systems, and cell editing systems). These implementations also prevent bottlenecks, for example if a transport robot that is used to move cell cultures around the system fails or becomes misaligned, or a central shared imaging subsystem fails due to a software issue. However, even modular systems may fail, and though this failure impacts only a single cell culture in process, it would be highly desirable that the failure of a cell culture module does not result in the failure, destruction, or denaturing of the cell culture being handled by the module.

In some cases, cell culture processes may require a diversity of processes that cannot practically be accomplished within a single cell culture system. Current systems require at least tubing and other reconfigurations, if not cell material transfers, to achieve such change-overs, resulting in more complex processes, more manual steps, higher probabilities of damage to the cell culture, or contamination.

The systems and methods disclosed herein include a cell culture system in which components may easily be switched out and replaced so that the cell culture system may easily be adapted for different cell culture processes and also to allow for easy repairs. The cell culture system may include a cell culture container (e.g., a closed cassette system) that includes at least one cell culture chamber and supporting components. All fluidic paths, including the cell culture chamber(s), may be sealed for at least a portion of the cell culture process to ensure sterility and prevent cross-contamination. The cell culture container may also include on-board media, reagents, buffers, product, and/or waste reservoirs and tubing components. The cell culture chamber(s) may be configured to allow imaging of the cell culture and allow directed-energy editing (e.g., intracellular delivery or lysis) of the cell culture.

The cell culture container (which may be a closed cell culture cassette in some implementations, as described with reference to FIGS. 22-28) may be quickly connected and disconnected to external components through connection plugs so that the cell culture container may be plugged into, or removed from, a modular bioprocessing system which manages the cell culture container and cell culture conditions. These connections may include electronic connections (e.g., for power, sensor readouts, valve or pump actuation), communication connections (e.g., for processor-to-processor communication), and liquid or gas connections (e.g., for temperature control of the cell culture and/or media, reagent, buffer, waste, product containers on board the cell culture container, or dissolved gas control). The liquid path inside the cell culture container may be self-contained and non-accessible to preserve a closed loop and keep the cell culture container sterile.

The cell culture system may also include process module (s) that receive one or more cell culture containers and provide cell culture support functions. The process modules may be configured so that the cell culture containers may hot-plug into the process module using the connectors to provide monitoring and support to the cell culture containers. The process module and cell culture containers may be designed so that if the process module fails or malfunctions, the cell culture containers may be removed from the process module via a simple mechanism, for example a mechanical unlock and subsequent pull.

In some implementations, the process module disclosed herein can be referred to as a cell culture process module, a cell culture process system/subsystem, a cell culture process mechanism, or a docking station. The cell culture process modules include physical devices that are configured to provide cell culture support functions such as, for example, media monitoring and replenishment, and gas monitoring, mixing, and replenishment. A cell culture process module may be configured to receive one or more cell culture containers (e.g., cell culture cassettes). The cell culture process module configured to receive one or more cell culture containers may be referred to as a docking station. For example, a cassette may be received by the cell culture process module such that it "docks" with a receiving space of the cell culture process module hosting the cassette. The cell culture process module may operate in combination with the cell culture cassette to handle one or more cell culture support functions. For example, the cell culture cassette may include a fresh media reservoir, and the cell culture process module may fluidically connect with the cell culture chamber and the media reservoir of the cell culture cassette and then transfer fresh media into the cell culture chamber.

The cell culture system may also include a computing and communication system that monitors and tracks the status of each cell culture container as it undergoes a cell culture process recipe. The system may essentially maintain a "digital twin" of the cell culture container (e.g., a dynamic digital profile of the cell culture) that may be stored on the cell culture container, and/or on a remote server. This allows a cell culture container to be removed from one process module and inserted into another without any data entry, and allows the receiving process module to quickly resume the cell culture process with appropriate conditions (temperature, media exchange, reagent or buffer additions, dissolved gas control, flow rate/liquid shear control, washing or agitation, etc.). For example, the cell culture container may contain non-volatile memory such as FLASH memory that contains a record of the cell culture process recipe, as well a history of what steps have been performed, and conditions on the cell culture container. Thus, if the cell culture container is removed from one process module and inserted into another, the process module may read this memory and proceed with the current or next steps of the cell culture protocol under the correct conditions. In some implementations, the cell culture container includes a barcode or an electronic tag (which could include nonvolatile memory on board) that presents a container ID to the process module, and the process module retrieves a process recipe and history from a server when the container is inserted, so that it may immediately resume the process.

Figure 32:
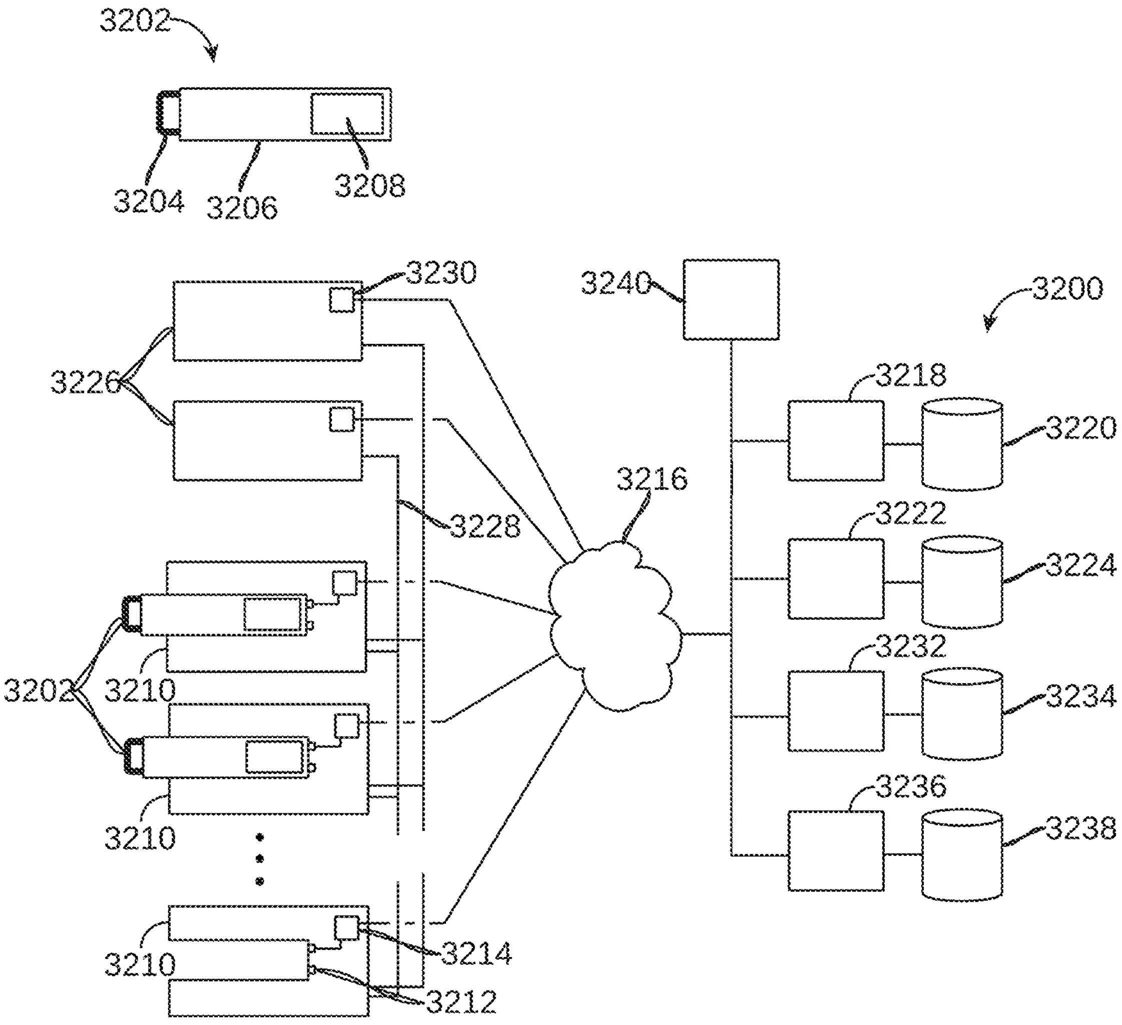
FIG. 32 is a diagram of a modular cell culture system in accordance with various implementations.

FIG. 32 is a diagram of a modular cell culture system 3200 in accordance with various implementations. The modular cell culture system 3200 may support a number of cell culture containers, which may be formatted as a closed cell culture cassette 3202 (e.g., closed cassette system 2700). The cassette 3202 may have a housing that includes a handle 3204. The housing encloses one or more compartments 3206 for carrying cell culture media, reagents, waste, cell products, etc., as well as a liquid handling system to circulate media, waste, debris, cell products, etc., into and out of a one or more cell culture chambers 3208. The cell culture chambers 3208 may be suited for culturing of suspension and/or adherent cells. The cell culture chambers 3208 may further be configured for imaging of the cell culture (e.g., label-free imaging through a transparent surface of the cell culture chambers 3208) and directed energy editing of the cell culture (e.g., using cell editing subsystem 114).

The modular cell culture system 3200 may include a series of cell culture process module 3210, each of which are configured to receive the cassettes 3202. Each process module 3210 may be configured to manage the cell culture functions on the cassette 3202 docked in that particular process controller 3210. These functions include, but are not limited to, temperature controls (e.g., for cell cultures, and for media, reagents, products, and waste, which may each be controlled independently or in groups), cell media and/or reagent addition and circulation, cell culture washing or harvest, control of dissolved gas concentrations, control of pH, imaging of the cell culture, and directed energy editing of the cell culture (e.g., laser editing).

The process module 3210 interfaces to the cassette 3202 via plug sockets 3212 for electrical, communications, gas, temperature control and other connections. These plug sockets 3212 may be configured such that a cassette 3202 may be quickly loaded or unloaded from the process module 3210 without manual connection or disconnection of wires or tubes, or in some cases even without execution of software programs and associated functions in the containing cell culture module, so a "hot swap" may be performed to move cassettes 3202 from one process module 3210 to another. An on-board computer 3214 in the process module 3210 may connect electronically with an on-board computer or memory of the cassette 3202, or read a barcode on the cassette to ascertain the identity and retrieve the current operating state of the cassette 3202.

The process module 3210 communicates via a communications network 3216 to a cassette data monitoring system 3218 which maintains a cassette state database 3220. The cassette state database 3220 stores a "digital twin" for each cassette 3202 in the modular cell culture system 3200, the digital twin reflecting the current cassette status and intended cell culture process. Thus, if a cassette 3202 is pulled from one process module 3210 and inserted into another, the receiving process module 3210 can immediately resume the desired cell culture program for the cassette 3202. This allows a cassette 3202 to be moved quickly in case of a malfunction in a process module 3210 or supporting infrastructure, or moved around a facility depending on the stage of a cell process. The process modules 3210 may also communicate with a module monitoring system 3222 which maintains a process module "digital twin" database 3224 to monitor critical module functions and detect any deviations. Additionally, the module monitoring system 3222 may be used when a process module 3210 is moved from one process cluster or facility to another, or from one set of supporting systems to another.

The modular cell culture system 3200 may include supporting subsystems 3226 that are shared by multiple process modules 3210. Supporting subsystems 3226 may include, but are not limited to, environmental control systems (e.g., for providing warming for cell cultures and/or cooling for media, reagents, products, and computing or optical subsystems), laser systems for directed-energy editing of cell cultures, cell culture imaging, autofocus or registration functions, and/or spectral sensing of media or cell cultures, power supply systems (e.g., an internally redundant 24 VDC power supply), and computing systems for computing or storage associated with imaging, spectral sensing, cell culture editing, etc. (which may also have internal redundancies). The supporting subsystems 3226 are connected to the process modules 3210 via pluggable or quick connectors 3228 to facilitate easy connection or disconnection of the process modules 3210 from a local cluster, for example a cluster of process modules 3210 on a server rack along with supporting subsystems 3226. The supporting subsystems 3226 typically have embedded computers or sensing/computing modules 3230 to monitor and/or control these subsystems.

One or more supporting subsystem monitoring services 3232 may monitor the supporting subsystems 3226 and tracks performance in a supporting subsystem database 3234, again establishing a "digital twin" for each supporting subsystem 3234 for redundancy and quick-resume functions. If a supporting subsystem 3226 indicates a problem it may be quickly replaced and cell processes continued, or the affected cassettes 3202 may be moved to process modules 3210 on another set of functioning supporting subsystems 3226, and/or one or more process modules 3210 may be moved to a new set of functioning supporting subsystems 3226.

The modular cell culture system may also include a cell culture monitoring system 3236 configured to tracking the cell culture state in each cassette 3202 (and in turn the cell culture chambers in each cassette) and maintains a cell culture database 3238 that stores a "digital twin" of each cell culture (which may include time series images, cell or colony feature databases, sensor data streams, etc.). Finally, an overall monitoring and control system 3240 may be configured to monitor the overall modular cell culture system 3200, by communicating with the monitoring systems 3218, 3222, 3232 and 3236, and coordinates responses to failures or states requiring attention, for example transfer of cassettes 3202 from one process area to another. The modular cell culture system 3200 may include other components not illustrated in FIG. 32.

The process modules 3210 may have different configurations corresponding to different cell culture processes, or stages of these processes. Thus, the ability to pull cassettes 3202 from one process module 3210 and place them in another while maintaining continuity in cassette conditions, environmental parameters, and cell culture data and processes enables very efficient, failure-free multi-stage cell culture processes. In addition, the modular cell culture system 3200 is very flexible as it can accommodate different cell culture processes performed in parallel, which increases throughput while minimizing delays in equipment failures or other issues.

Figure 33:
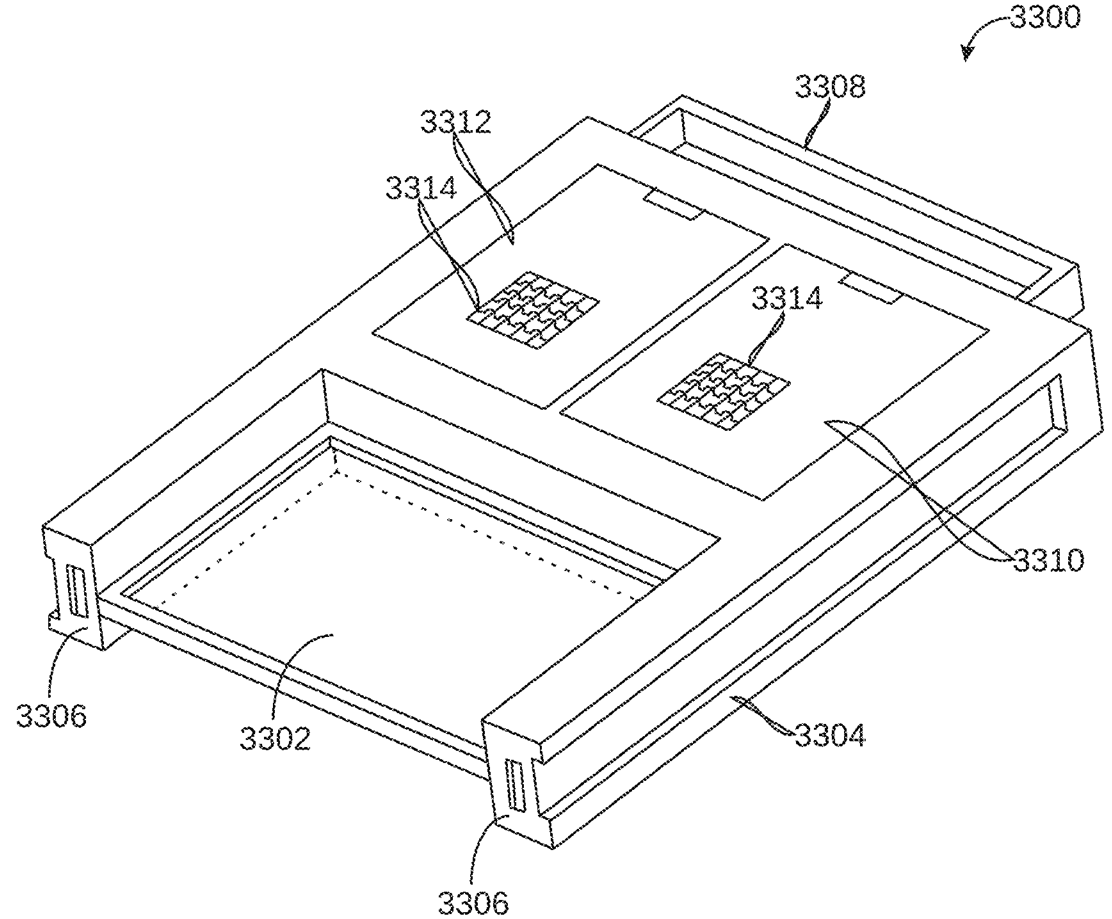
FIG. 33 is a diagram of a cell culture cassette compatible with a modular cell culture system in accordance with various implementations.

FIG. 33 is a diagram of a cell culture cassette 3300 compatible with a modular cell culture system in accordance with various implementations. The cell culture cassette 3300 is an example implementation of a cell culture container (e.g., cell culture container 106) in a cell culture system. The cassette 3300 may be primarily designed for 2D adherent cell cultures. The cassette 3300 may include a 2D liquid cell culture chamber 3302 with transparent upper and lower surfaces, which may be used for imaging and directed-energy editing of the cell culture. Mechanical guide rails 3304 serve to align the cassette 3300 to the process module as it is inserted. As it is inserted, connectors 3306 plug into complementary connectors on the process module. These connectors carry electrical signals, including but not limited to any required power, communications, signals from sensors aboard the cassette, and controls signals to actuators aboard the cassette. The connectors 3306 may also include non-mechanical elements such as gas or liquid ports. For example, cooling or warming liquids may flow in a loop through the connectors 3306, or gases for maintaining proper dissolved gas concentrations may flow in a loop through the connectors 3306. In these cases, quick-connect fittings may be used to seal the connections upon disconnection of the cassette 3300, and open them when the cassette 3300 is inserted.

The connectors 3306 may be disengaged mechanically through a locking mechanism accessible from the front of the cassette 3300 or process module (possibly on or near handle 3308), or electromechanically by the process module. The cassette 3300 may be removable from the process module regardless of software, electrical, or other failures in the process module, so the cassette 3300 may be quickly withdrawn using handle 3308 and placed in another process module. In the example shown in FIG. 33, the cassette 3300 may include two independent storage compartments for maintaining liquids associated with the cell culture, including but not limited to cell media, reagents, buffers, cell products, and waste, which may be stored in sealed bags or other containers. For example, one compartment 3310 may store media and reagents at 4° C., while another compartment 3312 may store cell products at 37° C. Temperature control ports 3314, which are sealed when the cassette 3300 is not in a process module, may be pushed open by the insertion of the cassette 3300 into the process module. This allows the process module to push temperature-controlled air through the compartments 3310, 3312 perpendicular to the plane of the cassette 3300. Thus, each compartment 3310, 3312 may be precisely temperature-controlled in a closed-loop fashion while in the process module, but when the cassette 3300 is pulled from the process module the ports 3314 may close automatically, such that temperature within compartments 3310, 3312 may maintained passively while the cassette 3300 is in transit or awaiting transfer to another process module.

In some implementations, the cassette 3300 may be designed to allow an optical system to access the cell culture chamber 3302 for the purpose of imaging the cell culture (e.g., cell imaging subsystem 112) and/or editing the cell culture through a cell editing mechanism such as using directed energy (e.g., cell editing subsystem 114). The directed energy editing may take the form of laser light, ultrasound, magnetic tools inside the cell culture chamber 3302 that are directed by external magnetic actuators, or other methods. The cell imaging and cell editing subsystems may interact with the cassette 3300 without physical entanglement such that it may be manually withdrawn from the process module without damage to the cassette 3300 or process module when any subsystem fails. The cell imaging and cell editing subsystems may also be configured to return to an "off" mode in case of a software, power, or mechanical failure in the process module, for example cutting off laser illumination, cutting off imaging illumination, and retracting magnetic actuators though a "active-on" solenoid or compressed-air mechanism.

In the case that a failure is detected in the process module, an "eject" sequence may be activated which unlocks the cassette 3300 and pushes it partially out of the process module. The partial ejection may include disengaging all ports and connectors 3306, to close all valves on board the cassette 3300, to stop pumping on board the cassette 3300, and to seal all temperature control ports 3314 (liquid or gas). This may be achieved, for example, by solenoid and spring actuators that are retracted electromagnetically when the process module is active and running properly and a cassette 3300 is inserted, but when there is a failure detected in the process module, or power is lost, spring back to eject the cassette 3300 into retraction position. In this position, the cell culture is effectively in a "safe" mode where liquid is not flowing and temperatures are maintained passively until it may be moved to an active process module.

Figure 34:
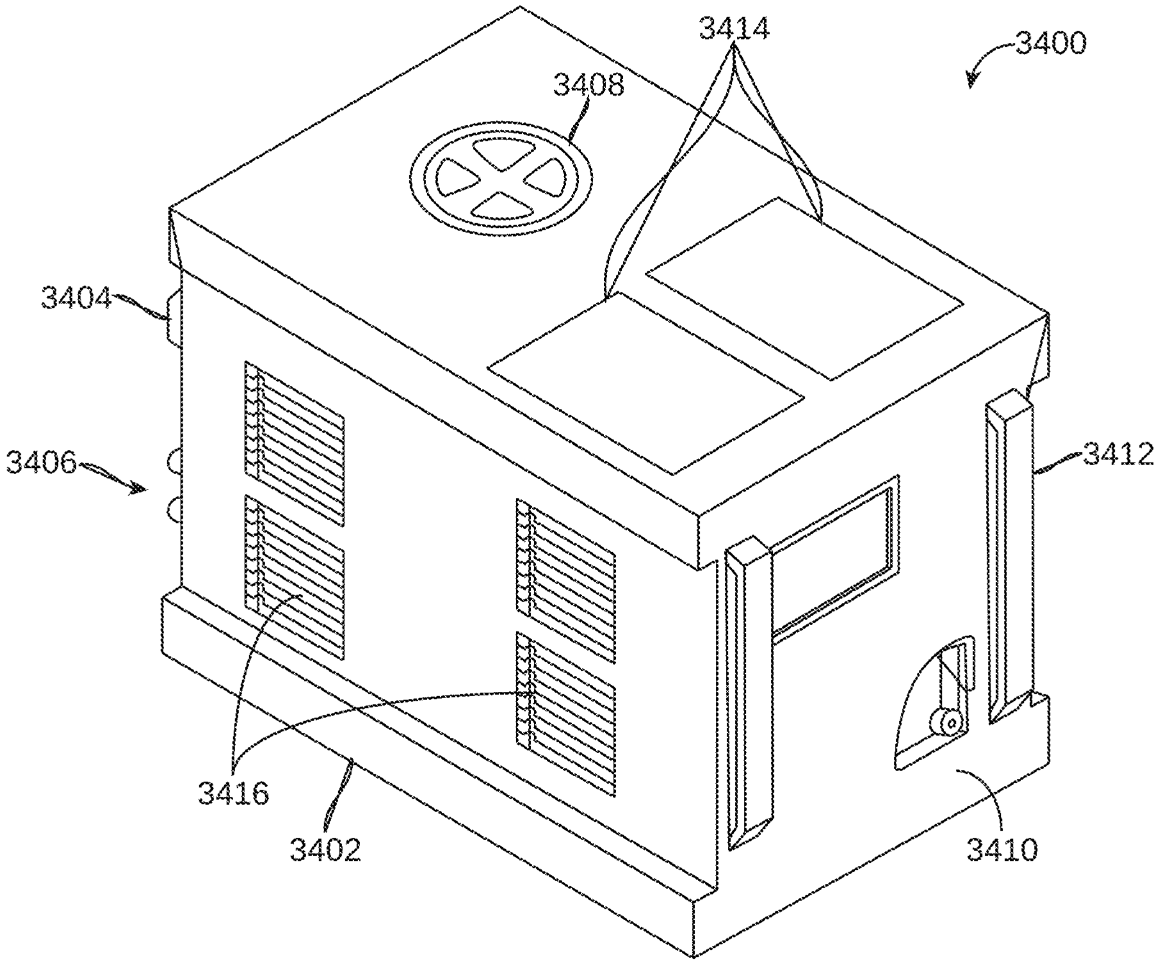
FIG. 34 is another diagram of a cell culture cassette compatible with a modular cell culture system in accordance with various implementations.

FIG. 34 is a diagram of a cell culture cassette 3400 compatible with a modular cell culture system in accordance with various implementations. The cell culture cassette 3400 is an example implementation of a cell culture container (e.g., cell culture container 106) in a cell culture system. The cassette 3400 may be primarily designed for suspension cell cultures held in a miniature stirred tank bioreactor, with a sterile tubing set connecting it to cell media, buffers, reagents, and waste and cell product bags that are all stored on-board. Guide rails 3402 allow the cassette 3400 to be inserted into a corresponding process module and assure mechanical alignment of plug connector ports including electrical/communications connectors 3404 and gas/liquid quick-connectors 3406. In some implementations, when inserted, a magnetic actuator on the process module aligns with a follower magnetic component 3408 which is connected to the stirrer in the cell culture vessel. However, in general any number of non-contact methods of stirring the interior of the cell culture vessel may be implemented in the cassette 3400. For example, other implementations may include magnetic couplings to actuate valves on the cassette 3400, operate peristaltic pumps on the cassette 3400, or move actuators within the sealed cell culture vessel for the purpose of washing cell cultures, circulating media, or removing cells or debris from surfaces.

A latch 3410 may be used to lock the cassette 3400 in place in the process module, and may be mechanically coupled to a number of components to open/close them appropriately, including but not limited to the gas/liquid ports 3406. The latch 3410 may be opened prior to retrieving the cassette 3400, assisted by handles 3412. A display on the cassette 3400 may display the current status of the cassette 3400 and cell process, and may include touchscreen functions.

In the implementation shown in FIG. 34, two compartments 3414 are configured to carry media, reagents, buffers, cell sources, and waste, cell products, etc. However, in general there may be any number of compartments 3414. The compartments 3414 may be temperature controlled via air ports 3416 on the side of the cassette 3400. For example, the air ports 3416 may be used for entry (top) and exit (bottom) of temperature-controlled air from the process module to keep the left-side compartment to 4° C. temperature. The air ports 3416 may be configured to close when the cassette 3400 is not fully-docked to the process module, to maintain the internal temperature of the compartments 3414 as long as possible. Similarly, the air ports 3416 corresponding to the bioreactor may be used in either in top-to-bottom or side-to-side configuration to move air through the bioreactor enclosure and maintain its temperature, typically at 37° C.

Figure 35:
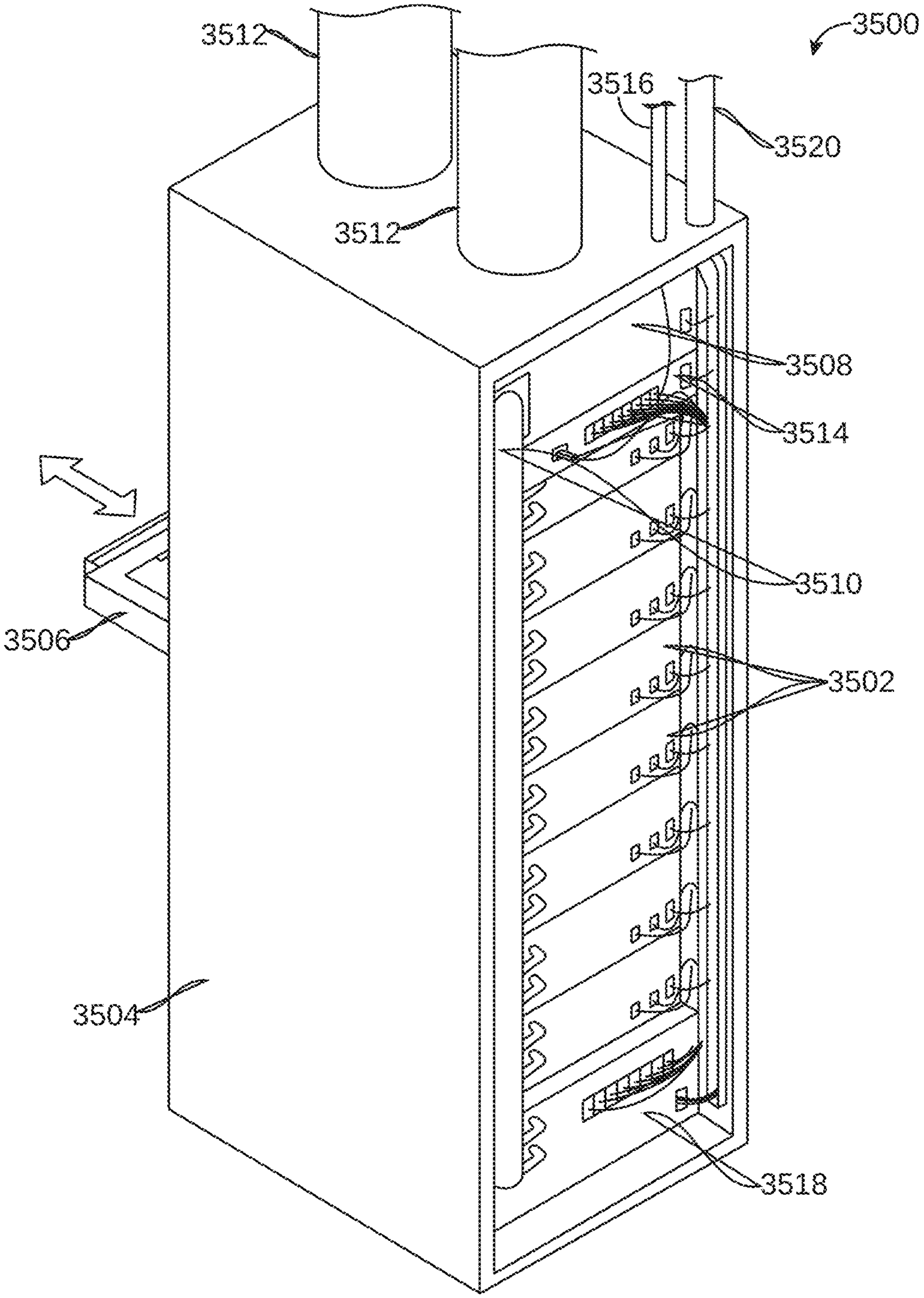
FIG. 35 is a diagram of a rack-style modular cell culture system in accordance with various implementations.

FIG. 35 is a diagram of a rack-style modular cell culture system 3500 in accordance with various implementations. The modular cell culture system 3500 may include any number of cell culture process modules 3502 (eight shown in FIG. 35) and several supporting modules mounted in a server-style rack 3504. The process modules 3502 may be configured to receive a cell culture cassette 3506 (shown in insertion/retraction position in FIG. 35), which may be similar to cassette 3300 in FIG. 33 for 2D adherent cell cultures.

The modular cell culture system 3500 may include a shared environmental control module 3508. In an example implementation, the shared environmental control module 3508 may circulate refrigerant and two temperatures, for example 0° C. and 40° C., along liquid manifolds contained in an environmental control column 3510. The environmental control column 3510 provides process modules 3502 with thermal "rails" to maintain temperatures for cell culture and various media, reagent, waste, or cell product compartments. It also provides components that generate significant heat (for example, computing modules, if present, or shared laser modules) with cooling, while maintaining a compact footprint (as opposed to air-cooling each one). The environmental control module 3510 may exchange heat between the return streams, and may also include high-flow air circulating through it for heat exchange purposes, through ducts 3512.

The modular cell culture system 3500 may also include a computing and communications module 3514 that provides local computing, storage and network communications (e.g., computing subsystem 110). In an example implementation, multimode fiber and optical transceivers may be used to provide communication between the computing and communications module 3514 and individual process modules 3502, ensuring high bandwidth during cell culture imaging. The computing and communications module 3514 may also provide local processing and storage of the images, and potentially computing of cell culture editing functions. The computing and communications module 3514 may also be connected to external networks via fiber optics or other communications links that pass through a duct 3516. External networks may store "digital twins" of process modules 3502, cassettes 3506, and supporting modules 3508, 3514, 3518 in the modular cell culture system 3500. These digital twins may aid in monitoring and tracking cell culture, cassette, and process module status and performance versus nominal, and provide hot-swap capability in the case of failure of a process module or any supporting system.

The modular cell culture system 3500 may also include a cell editing subsystem, such as a shared pulsed laser system 3518. Pulsed laser light from the pulsed laser system 3518 may be transmitted via optical fiber to each process module 3502. For example, the pulsed laser system 3518 may include a nanosecond pulsed laser with 532 nm or 1064 nm emission. The laser light may be split into eight equal power beams (may be achieved using free-space optics, or fiber optic couplers), and coupled into polarization-maintaining single-mode fiber. These fibers are routed to respective process modules 3502. Each process module 3502 may be configured to synchronize to the pulse timing (for example, 500 kHz) and then apply modulation (for example, with an acousto-optic modulator) and beam steering for the purpose of directed-energy cell culture editing. In other implementations, laser sources may be shared for other purposes, such as illumination for fluorescent, auto-fluorescent, two-photon imaging, Raman spectroscopy, or other sensing modalities within the cell culture modules. The modular cell culture system 3500 may also include a shared DC voltage power rail to provide power to the entire rack 3504 and supported equipment, fed by power duct 3520. In alternate implementations, DC power supplies may be mounted on the rack 3504 itself as rack-mounted equipment (potentially with connections for cooling).

Selective Material Extraction and Analysis

During a cell culture process, it may be beneficial to selectively collect and sample cells in the cell culture to determine its characteristics. The characteristics may be used in different applications. For example, a computing subsystem (e.g., computing subsystem 100) may associate characteristics of the sampled cells with the cell regions or colonies that the cells came from. It may also be important to image live cells at multiple timepoints to enable the measurement of trends at the subcellular, cellular, cell neighborhood, or colony level. Another application of selective cell sampling and characterizing is to monitor the cell culture state, for example during a cell-based process or in a bio production system, and doing so in a selective manner in order to obtain a representative sample of cell material. This may allow a cell culture system to determine whether the cell culture process should be continued, altered, or stopped based on the attributes of the harvested cells. The information may also be used in machine learning models to improve future cell culture processes.

The characteristics of the cells that may be observed or measured from label-free images may include, but are not limited to, morphology, presence/count/size of subcellular components, density, refractive index, absorption or absorption spectrum, polarization-dependent absorption or refractive index, degree of attachment to substrate or surrounding cells, proliferation rate, velocity, projection of cell outgrowths such as neurites, interaction with other cells, and spectroscopic characteristics including but not limited to Raman spectra, infrared spectra, autofluorescence, etc. The measured or observed characteristics may also include parameters measurable by fluorescent labelling, such as surface markers or other components known to the industry. The measured or observed characteristics may also include phenotypic, genomic, epigenetic, transcriptomic, proteomic characteristics of those cells.

The selective cell extraction and analysis should be done in situ on live or recently live cell cultures in a cell culture vessel suitable for long-term cell processes, and observation should be conducted via imaging. The cell extraction process should be minimally invasive so that the remaining cells can remain in culture and continue the cell process. In addition, it should be compatible with a closed or semi-closed cell culture system such as a flask or microfluidic cell culture chamber, or other 2D cell culture vessel that does not allow manual access to the cell culture region. The selective cell extraction and analysis should also be compatible with existing analysis techniques, including but not limited to qPCR, RNA sequencing, DNA sequencing, karyotyping, DNA methylation sequencing, chromatin accessibility measurements such as ATACseq/MNase-seq/DNase-seq, and proteomic measurements including but not limited to microarrays, liquid chromatography, and mass spectroscopy.

There are several current approaches in the art for sampling cells during a cell culture process. One example is laser microdissection. This is a well-established technique by which samples are "cut out" of cell or tissue sheets and retrieved for analysis. Often the technique is used on preserved intact tissues, or when cells have been secured to a foil for extraction. The disadvantages of this technique are that it is generally relevant to continuous tissues only, not where there are individual cells, and requires mechanical extraction of the cut-out cell sheets, which is performed in a number of ways, all of which are generally incompatible with a long-term cell culture system, particularly one that is semi-closed (like a tissue culture flask) or entirely closed (like a microfluidic cell culture vessel).

Another approach is foil-based, in which tissue is attached to a foil which absorbs laser radiation and may be cut, allowing sections to be cut and then retrieved mechanically. Another approach is membrane retrieval, in which after cutting of the tissue section of interest, a "stamp" that contains a textured membrane is lowered onto the tissue surface to make contact with the section of interest and retrieve it. There is also ejection/gravity, in which a section of tissue is suspended (on a foil) in air, and sections that are laser-cut drop off into a collection chamber. Another method is called fluorescent in-situ hybridization (FISH), including both DNA-FISH and RNA-FISH. This technique allows a number of pre-determined DNA sequences or RNA sequences to be labelled and imaged in situ. However, cells must be fixed prior to hybridization and labelling, the number of sequences that can be examined is generally limited, and high-resolution fluorescence microscopy is required to image the fluorophores. Yet another approach is micropipette-based extraction of cells, or cellular components. These techniques are able to target individual cells, or small groups of cells, and are able to work on live cell cultures.

There are also spatial transcriptomic techniques for cell sampling. These techniques rely on a specialized surfaces that has been pre-coded with DNA sequences to allow tracing of the spatial origin of RNA molecules. To date these techniques have been developed primarily for tissue sections that have been preserved in a thin slice, for use in pathology or ex-vivo studies. The drawbacks of this approach are that they do not apply to in situ measurement of live cell cultures, and that they are currently restricted to RNA sequencing.

In short, while existing methods address situations where preserved tissue samples are used, or may act on recently-live cells but with expensive instruments and consumables, there are few viable options for using standard analytical methods in conjunction with dynamic live cell imaging. Particularly, no current approach is suitable for performing such measurements inside of closed or semi-closed cell culture vessels, and potentially within the course of a cell process (without damaging the remaining live cells). Thus, what is needed in the art are methods of extracting and sampling cells during a cell culture process in a closed, automated cell culture system while not disturbing the cell growth process.

The systems and methods disclosed herein include a system for selective cell extraction and sampling which is compatible with a cell culture system (e.g., cell culture system 100). The system may include a cell culture chamber suitable for long-term cell culture and imaging, a coating on the cell culture chamber for laser absorption (but transmits imaging light), an imaging subsystem configured to image cells resident on the coated surface, a computing subsystem for selecting one or more cells for analysis, and a cell editing subsystem that utilizes laser pulses that strike the coating, causing an explosive microbubble and cavitation. The cells are de-adhered from the coated surface as a result of the microbubbles and are harvested via liquid extraction, and/or cells are lysed by the microbubbles and their components are harvested via liquid extraction. The cells and/or cell components may then be analyzed via a range of analytical techniques. In some implementations, the analyzed cells may be selected by their image characteristics, including time series image characteristics and/or analysis thereof. In some implementations, a series of laser processes and liquid removal processes may be used to sample multiple subpopulations.

Additional methods of targeted cell extraction or cell lysis are contemplated in this disclosure. For example, cells may be extracted using magnetic tools operable in a live cell culture container, including a closed fluidic chamber or cassette. The magnetic tool may be controlled by an external component actuating the in-chamber component, the external component guided by a computing subsystem based on imaging data. In an alternate example, focused ultrasound operable in a live cell culture container, including a closed fluidic chamber or cassette, may be used to extract cells. An external transducer transmitting focused sound waves through the container wall may be used to focus on cells of interest and loosen them from the cell culture surface. The transducer may be controlled by a computing subsystem based on imaging data.

Cell lysis may take place in situ, and resulting debris are removed from the container with the surrounding liquid. If cell lysis is done in situ, the cell culture fluid media may be replaced with an "extraction and measurement" media prior to lysis. This extraction media may be free of potential contaminants, components that will interfere with the downstream measurements, or sample-degrading components such as RNAse. In some implementations when cell lysis takes place in situ, the cells may be fixed prior to the process, and reverse transcription of RNA to cDNA may be performed in situ. This "freezes" the state of the cell culture, preserves mRNA information, and allows for a multi-part selective harvest of material over a longer period if needed.

Cells may be selectively harvested intact through this selective method, with lysis done prior to analysis, enabling single-cell measurements. Once cells or cell debris have been selectively separated from the cell culture, harvest may be done in a number of ways, including but not limited to, pipetting (including automated pipetting systems) for open cell culture containers such as microwell plates, and liquid replacement and outflow in closed fluidic chambers, in which the liquid exiting chamber flushes the extracted cells with it.

There may be several approaches for selecting cells for extraction. For example, one approach is random sampling of cells from a cell culture. This may include random area selection for cells or cell components in a high-confluency cell culture (e.g., choosing random 2D patches to act upon with transducer and then harvesting the material) or random area selection from within cell-bearing areas, based on an image of the cell culture. Using such an image, regions of different local densities may be randomly sampled to obtain a representative sample. In another approach, the sampling may be guided by manual annotation of images of the cell culture, with humans observing the cell culture image and selecting regions of interest, and the cell editing subsystem acting upon these areas prior to sample extraction.

In another approach, the sampling may be guided by image characteristics as measured by a computing subsystem (e.g., computing subsystem 100). The relevant image characteristics may include (1) outputs of image processing subsystems that measure local density, morphology, order, orientation, etc.; (2) outputs of machine learning models whose input is the images of the cell culture and whose output is a spatial map classifying the cell culture at the cell, neighborhood, region, colony or other level (the machine learning model may be, for example, a supervised model that has been trained with labelled data or an unsupervised model that classifies spatial regions into a series of clusters based on image data alone); (3) outputs of a computing subsystem that locates each cell in the cell culture and computes local characteristics such as cell morphology, density, colony membership, etc.; and (4) outputs of a computing subsystem that locates each colony and computes colony characteristics, including time series characteristics.

Figure 36D:
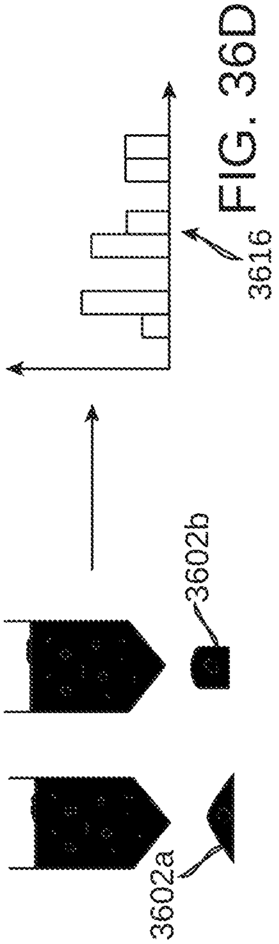
FIGS. 36A-36E are diagrams illustrating selective cell extraction and analysis of adherent cells in accordance with various implementations.
Figure 36E:
Figure 36A:
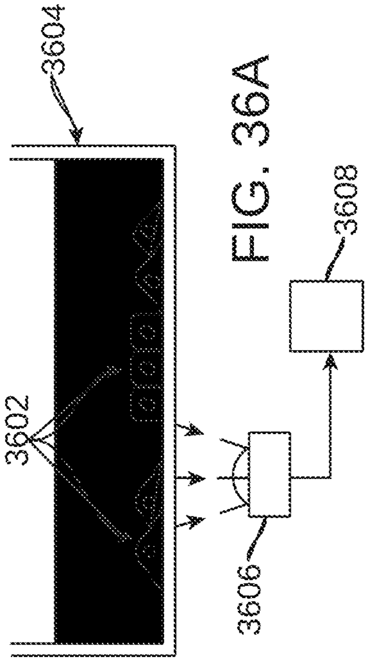

FIGS. 36A-E are diagrams illustrating selective cell extraction and analysis of adherent cells in accordance with various implementations. In FIG. 36A, cells 3602 undergo a cell culture process in a cell culture container 3604. The cells 3602 may be adhered to a surface of the cell culture container 3604, the surface configured to allow imaging (e.g., a transparent surface). The cells are imaged using an imaging subsystem 3606 (e.g., cell imaging subsystem 112), which transmits data to a computing subsystem 3608 (e.g., computing subsystem 110). In one example, the computing subsystem 3608 may classify the regions of cells using an unsupervised clustering model which classifies cell regions by texture, morphological characteristics, and time series characteristics (e.g., changes of properties over time, optical flow measurements). Similarly, the computing subsystem 3608 may identify individual colonies, and categorize cells by colony membership.

Figure 36B:
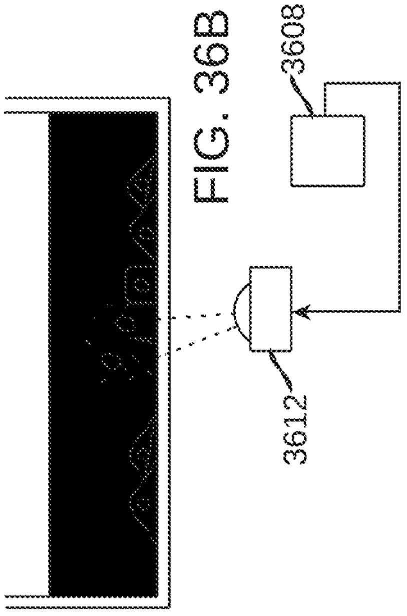

In FIG. 36B, the computing subsystem 3608 may select a first group of cells for lysing using any of the methods described herein (e.g., unsupervised clustering models). The computing subsystem 3608 may control a cell editing subsystem 3612 (e.g., cell editing subsystem 114) to lyse the selected cells using a non-contact lysis method. For example, the cell editing subsystem 3612 may be a steered pulsed laser system that interacts with a coating on the internal surface of the cell culture container 3604 to form explosive microbubbles and lyse the targeted cells. Prior to this lysing process, the cell media in the cell culture container 3604 may be exchanged for a specialized, temporary lysis and material harvest buffer that is RNAse free and/or may contain compounds to accelerate cell dissociation upon lysis.

Figure 36C:
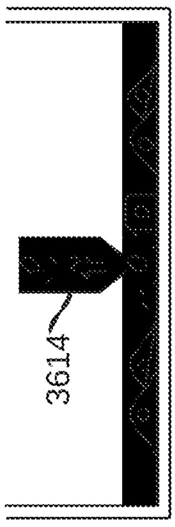

In FIG. 36C, liquid is withdrawn from the cell culture container 3604. The liquid contains the components of the cells that were targeted and lysed by the cell editing subsystem 3612. In the example shown in FIG. 36C, an automated pipetting system 3614 is used to withdraw the liquid from the cell culture container 3604. The automated pipetting system 3614 may optionally position the pipette to draw liquid from the specific region where cells were lysed, and withdraw only a portion of the total liquid in the cell culture container 3604, in order to maximize the concentration of the cellular constituents within the harvested liquid. The automated pipetting system 3614 is only one possible method of liquid extraction. In general, multiple liquid extraction methods may also be utilized to withdraw liquid containing the lysed cell components. The lysing and extraction process illustrated in FIGS. 36B-C may be repeated multiple times for each distinct cell population that has been identified.

In FIG. 36D, extracted cell samples may be processed for analysis according to one or more pre-existing analysis techniques. For example, two cell samples 3602*a* and 3602*b* may have been extracted. In one example, each sample 3602*a*, 3602*b* is analyzed by qPCR, and levels of expression for a series of target genes, along with housekeeping genes that normalize for cell quantity, are measured and compared to each other as well as reference readings. The data analysis is represented in FIG. 36D by chart 3616. This approach may allow analysis of multiple cell phenotypes that are linked to image or image timeseries characteristics. This information may be used in future predictive model and process optimization operations by a cell culture system. For example, a cell culture system may selectively lyse cells and remove them from the cell culture container for analysis. The cell culture system may utilize the resulting information to monitor progression and success of similar cell cultures with imaging alone and the use of a machine learning model (now trained with the qPCR data and other information), and may also use the information to optimize the cell culture process given certain output cell target attributes.

Various cellular components obtained through the extraction techniques disclosed herein can be used as biomarkers suitable for downstream analysis. Examples of cellular components include cell surface proteins (particularly surface biomarkers), cytoplasmic proteins, cytoplasmic RNA, nuclear proteins, mitochondrial DNA/RNA, nuclear DNA/RNA, and extracellular vesicles (EVs) and their associated materials (endosome, exosome, and their associated contents). RNA could include total RNA, run-on RNA transcripts, enhancer RNAs, general non-coding RNAs (including but not limited to lncRNAs, lincRNAs, snoRNAs, miRNAs, and similar), mRNAs, or any combination thereof.

Various capture technologies can be used to obtain the target cellular component(s). Bead capture can be used to capture cellular components after laser cell lysis. In some cases, the primary capture method uses magnetic beads targeting a given cellular component. Examples include DNAs/RNAs capture using SPRI paramagnetic beads (such as AmpureXP), and antibody-conjugated protein capture superparamagnetic beads (such as protein A/G dynabeads pre-conjugated to an antibody targeting a protein of interest). Alternative bead/slurry methods can also be utilized when appropriate, such as coated agarose-based bead capture for isolation of targeted molecules. Capture may also be achieved through collection of total lysed material in an appropriate buffer for further downstream analysis, followed by gradient ultracentrifugation to isolate the components of interest (in the case of EVs, for example).

The captured cellular component(s) can be analyzed according to various available analytical methods. For RNAs, suitable methods include all forms of applicable NGS, including but not limited to total RNAseq, mRNAseq, scRNAseq, enhancer RNAseq, and exome capture sequencing approaches. More targeted qPCR-based evaluations and/or arrays may be used to evaluate isolated RNAs on a smaller scale as well. For DNAs, suitable methods include all forms of applicable NGS, including but not limited to ATACseq, ChIPseq, scATACseq, whole exome sequencing, whole genome sequencing, or targeted DNA region or portion sequencing. More targeted qPCR-based evaluations and/or arrays may be used to evaluate isolated DNA on a smaller scale as well.

For proteins, analysis may be performed using an extremely wide and diverse array of downstream applications depending on the quantity and purity that can be isolated. Mass-spectrometry analysis based or antibody probe based methods can be used to evaluate, for example, the identity and/or quantity of select protein biomarkers. Alternatively, any of a vast number of other protein analytics methods could be applied as necessary (e.g., Western Blot, ELISA, immunostaining, etc.).

Following the selective extraction of cell material, the cell culture process may continue in the cell culture container 3604, as shown in FIG. 36E. Thus, the implementations disclosed allows harvest of cell material (often a very small fraction of the overall growth) from a live cell culture and therefore allows the remaining cells to progress to an endpoint of the cell culture process without interruption. In some implementations, the selective harvest and analysis may be performed at multiple points during the cell culture process. The methods disclosed herein may be used for cell processes including, but not limited to, stem cell reprogramming (e.g., iPSCs), stem cell differentiation, trans-differentiation, cell maturation, cell gene editing, clonal growth and selection, etc. The methods disclosed herein may be used for the purpose of training image-based models for predicting cell process outcomes, or may be used directly to select optimal regions, colonies, clones, cell cultures for further processing.

Figure 37A:
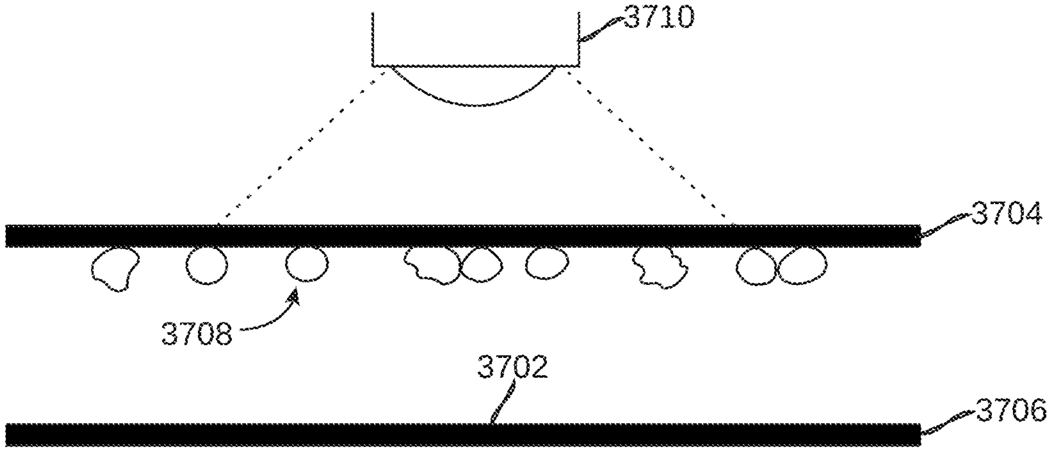
FIGS. 37A-37C are diagrams illustrating selective cell extraction and analysis of semi-adherent cells in accordance with various implementations.
Figure 37B:
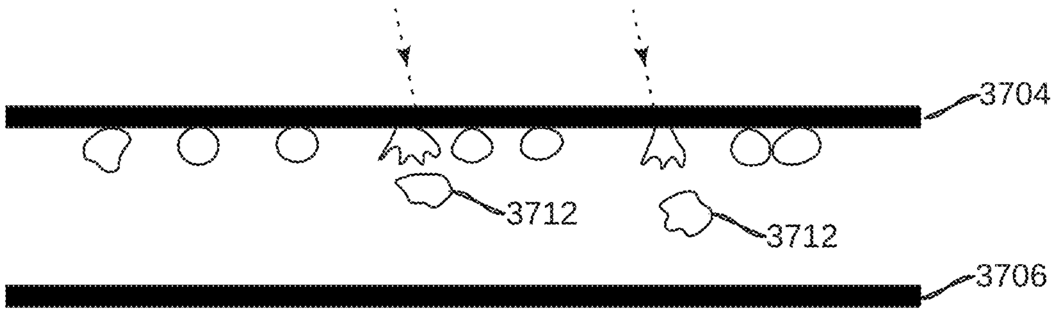
Figure 37C:
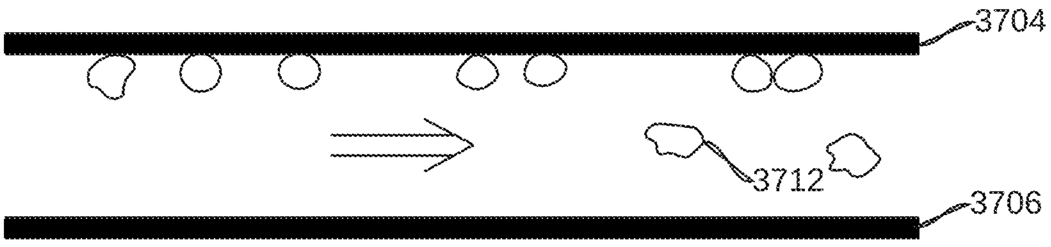

FIGS. 37A-C are diagrams illustrating selective cell extraction and analysis of semi-adherent cells in accordance with various implementations. The semi-adherent cells may be grown in a cell culture container having a closed liquid chamber, and the cells may be selected for extraction based on imaging or imaging time series characteristics. In FIG. 37A, a closed liquid chamber may include a volume of liquid media 3702 bounded by an upper surface 3704 and a lower surface 3706. The upper and lower surfaces may be transparent so that cells within the closed liquid chamber may be imaged using transmitted-light imaging (e.g., brightfield imaging, Zernike phase imaging, darkfield imaging, differential interference contrast imaging, quantitative phase imaging, etc.).

In the example shown in FIG. 37A, cells 3708 have been introduced into the closed liquid chamber when it was inverted (i.e., the upper surface 3704 is below the lower surface 3706), and due to their semi-adherence, attach weakly to the upper surface 3704 when the chamber is inverted back to the orientation shown in FIG. 37A. When the closed liquid chamber is inverted to the orientation shown in FIG. 37A, any cells or debris that are not adhered to the upper surface 3704 drop towards the lower surface 3706 and may be washed out of the closed liquid chamber by pumping liquid through it.

An imaging subsystem 3710 (e.g., cell imaging subsystem 112) may image the cells 3708 that are attached to the upper surface 3704 at one or more timepoints. A computing subsystem (e.g., computing subsystem 110) may calculate characteristics of individual cells based on size, morphology, intracellular components, polarization dependence, refractive index, phase, cell division, or other characteristics captured by the images. In some implementations, fluorescent labels may be applied as well to indicate presence of specific surface markers. In some implementations, time series trends of one or more of the measured characteristics are used. As a result of these observations, cells are grouped by classifications. The cells may be grouped automatically by the computing subsystem or manually by a human operator who can look at the distribution of these characteristics (e.g., one or more scatter plots) and select one or more clusters of cells of interest.

A non-invasive selective cell harvesting system (e.g., cell editing subsystem 114) may be used to dislodge selected cells 3712 with a specific classification from the upper surface 3704, as shown in FIG. 37B. For example, the cell harvesting system may be a pulsed laser system which creates microbubbles when it strikes an absorbing film on the upper surface 3704. The microbubbles detach the selected cells 3712 from the upper surface 3704, causing them to fall away from the upper surface 3704 into the liquid media 3702 contained within the cell chamber.

The selected cells 3712 are then harvested from the closed liquid chamber by exchanging the liquid media 3702 in the chamber as shown in FIG. 37C. The media exchange may be done as part of a regular media change. The selected cells 3712 are then collected for analysis. Because the selected cells 3712 are intact when extracted, both bulk analysis techniques as well as single-cell techniques such as single-cell RNAseq may be used on the harvested cells.

Figure 38A:
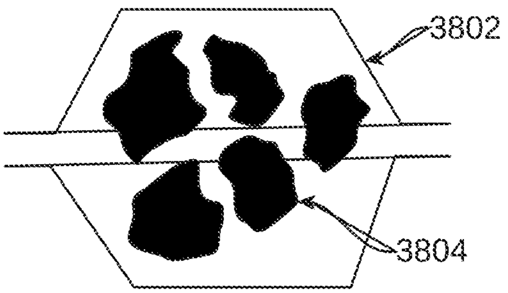
FIGS. 38A-38C are diagrams illustrating a cell culture process with selective cell extraction and analysis in accordance with various implementations.
Figure 38B:
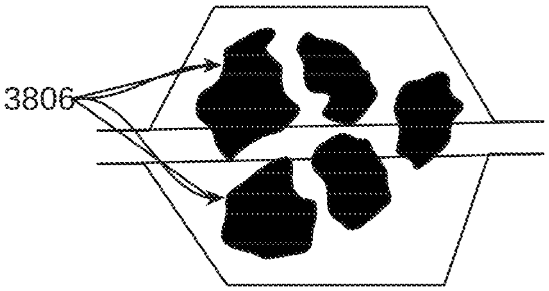
Figure 38C:
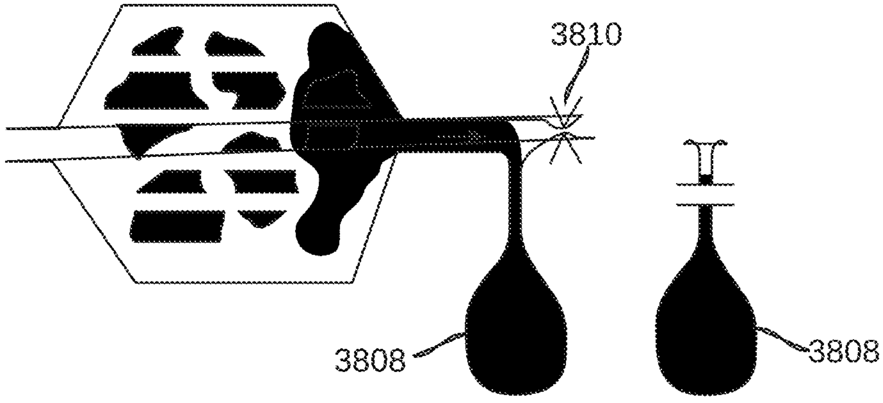

FIGS. 38A-C are diagrams illustrating a cell culture process with selective cell extraction and analysis in accordance with various implementations. FIG. 38A illustrates a perfused cell culture chamber 3802 in which a cell culture 3804 is growing. For example, the cell culture 3804 may be an adherent cell culture in a continuous perfusion 2D reactor and may be approaching maximum specified cell confluency. The cell culture 3804 may be imaged periodically to assess confluency, and optionally to locate cells/colonies for treatment. The number of cells may be periodically reduced via a non-invasive cell editing method (for example, using the laser, ultrasonic or magnetic tool techniques described herein) to prevent overgrowth of cells. This may be useful for certain cell culture processes, for example during clearing of episomal or viral vectors from cells, in which each cell division reduces the load of vectors in the cell population.

In FIG. 38B, a subset of the cells 3806 in the cell culture may be targeted for lysis. The selected subset of cells 3806 is shown as dark bands as shown in FIG. 38B. The cells may be selected in a pre-set pattern as shown in FIG. 38B, or may be based on the configuration of cells in the cell culture 3804. For example, cells may be selected from regions of the cell culture 3804 that are most dense, or regions that are approaching the bounds of the cell culture chamber 3802 (where conditions are more variable), or some combination of these or other factors.

The selected subset of cells 3806 may be lysed, as shown in FIG. 38C, and the lysed cells are suspended in the fluid media in the cell culture chamber 3802. The fluid media may be exchanged or flushed, and at least a portion of the spent fluid media containing the lysed cell debris may be collected by a sampling bag 3808 or some other collection mechanism. In the case of collection via the sampling bag 3808, a pinch valve 3810 in the primary fluid path may be closed to direct the fluid media into the sampling bag 3808. The sampling bag 3808 may be subsequently detached with a sterile tube welder, which enables sterile detachment of the sample bag 3808 from the cell culture system. The contents of the sampling bag 3808 may then be sent to analysis. In alternate implementations, an analysis system may be directly connected to the cell culture system to allow online measurements of the resulting cellular matter without detachment of a sample bag or container. Such an online system may perform further fractionization/homogenization of the cell debris, filtration, preparation steps and then analysis of the cell contents.

Using the example of iPSC reprogramming in which a reprogramming vector is cleared over time, the measurement enabled by the system may include, for example, a qPCR measurement of the contents of the sampling bag 3808 to measure RNA expression levels of: (1) one or more housekeeping genes (e.g., GAPDH) in order to normalize for the cell count; (2) one or more components of the reprogramming vector, for example OCT4 if the episomal reprogramming vector contained it, in order to monitor clearance of the vector; and (3) one or more non-vector gene expressions to measure pluripotency markers of the cells, for example SSEA4 if not included in the vector. The vector-specific measurement could assess progress in clearing the vector from the cells (a necessary condition for completion of the process). The endogenous gene expression is used to verify that the cell culture remains highly pluripotent and is not differentiating. Optionally, regions that are potentially differentiating may be selectively harvested in a separated iteration from regions that are thought to be pluripotent, and this may be confirmed by analysis of the cell lysis product.

Figure 39:
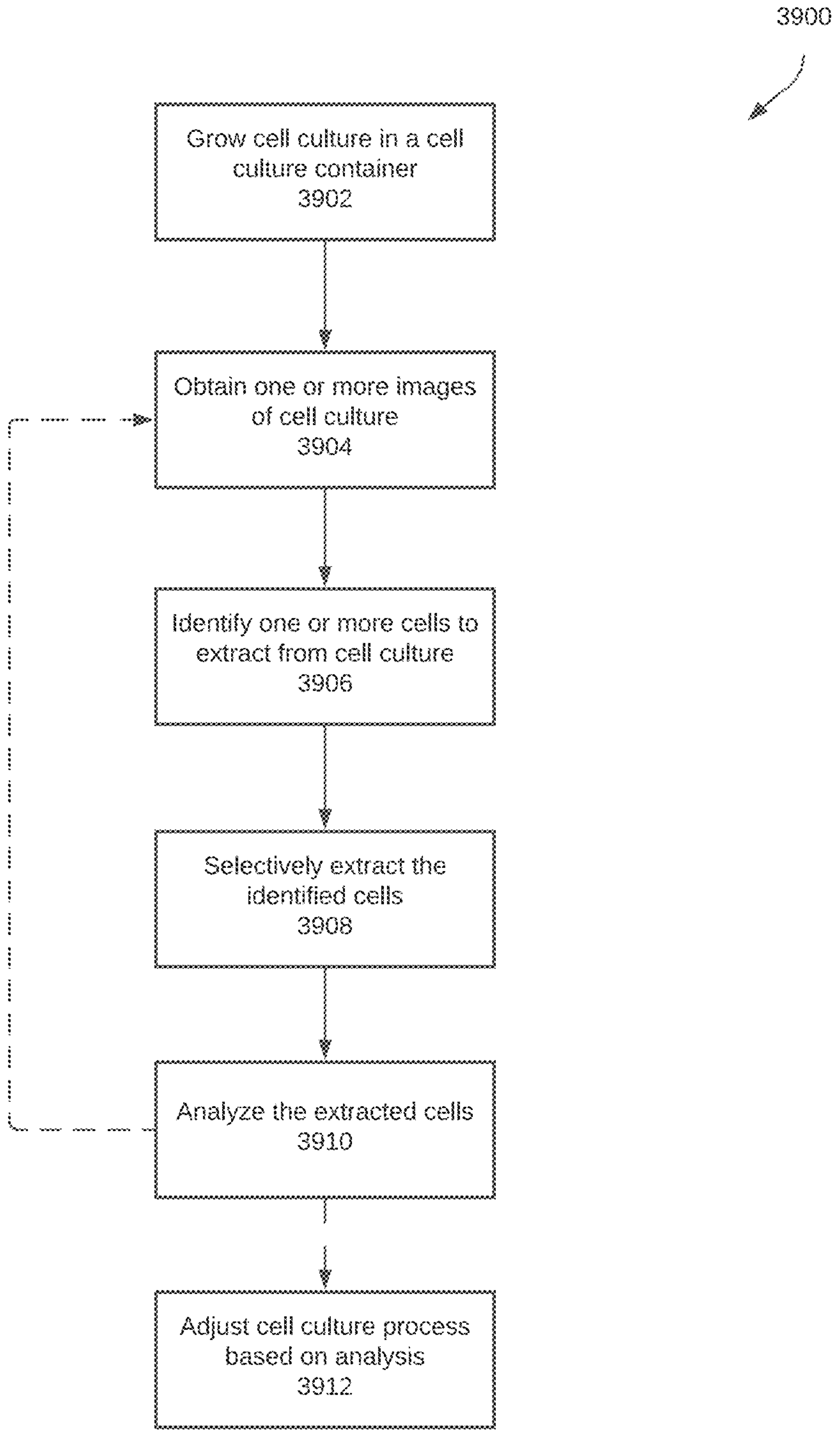
FIG. 39 is a flow chart illustrating a method of cell extraction and analysis in accordance with various implementations.

FIG. 39 is a flow chart illustrating a method 3900 of cell extraction and analysis in accordance with various implementations. The method 3900 may be performed by a cell culture system (e.g., cell culture system 100 in FIG. 1). In some implementations, the method 3900 may be performed by a mix of an automated cell culture system and manual effort by humans.

In block 3902, a cell culture may be grown in a cell culture container (e.g., cell culture container 106). The cell culture may be adherent or semi-adherent cells adhered to a cell growth surface of the cell culture chamber in the cell culture container. The cell growth surface may be transparent to enable imaging of the cell culture. The cell culture container may be a closed system, such as a closed cassette.

In block 3904, the cell culture system may obtain one or more images of the cell culture. For example, the cell culture system may include a cell imaging subsystem (e.g., cell imaging subsystem 112) that is configured to take one or more images of the cell cultures. In some implementations, the images may be a time-series of images of the cell culture.

In block 3906, the cell culture system may identify one or more cells to extract from the cell culture. For example, a computing subsystem (e.g., computing subsystem 110) may identify and select one or more cells to extract based on the collected images. The computing subsystem may utilize one or more characteristics derived from the cell images to determine which cells to extract. The characteristics may include direct measurements or observations from the images as well as the output of various machine learning models or other algorithms that process the image. For example, the computing subsystem may classify the regions of cells using an unsupervised clustering model which classifies cell regions by texture, morphological characteristics, and time series characteristics (e.g., changes of properties over time, optical flow measurements). Similarly, the computing subsystem may identify individual colonies and group cells by colony membership. The computing subsystem may then select one or more cells from each cell region or colony so that cells having different characteristics may be extracted and sampled. In some implementations, the identification of cells may be done manually by a person rather than by the cell culture system.

In block 3908, the cell culture system may selectively extract the identified cells. For example, a cell editing subsystem (e.g., cell editing subsystem 114) may be used to lyse or otherwise dislodge the identified cells from the cell growth surface of the cell culture chamber. The cell editing subsystem may utilize, for example, lasers, ultrasound, or magnetic tools among other approaches, to dislodge the identified cells without destroying them. Before extraction, the fluid media in the cell culture chamber may be changed to a specialized, fluid that accelerates cell dissociation upon lysis. The dislodged cells may then be extracted from the cell culture chamber using a fluid media exchange/flush, automated pipetting system, or other means.

In block 3910, the cell culture system may analyze the extracted cells. For example, qPCR assays and other tests/assays/measurements may be conducted to determine various properties and characteristics of the extracted cells. The cell culture system may periodically repeat the steps shown in blocks 3904-3910 to extract and sample cells at different points in the cell culture process.

In block 3912, the cell culture system may adjust the cell culture process based on the analysis of the extracted cells. For example, the cell culture system may determine that a sampled cell from a particular cell colony is outside the preferred cell growth parameters and thus the cell colony should be destroyed. In another example, the cell culture system may determine that a sampled cell from a particular cell colony may need additional nutrients and may initiate a fluid media exchange to freshen the media in the cell culture chamber. In general, the cell culture system may change a number of environmental or growth parameters, destroy certain cells, or take other actions based on the results of the analysis. The cell culture system may also incorporate the data into a machine learning model to improve future cell culture processes. In this manner, the method 3900 provides a way for selective extraction and analysis as to benefit the operation of a cell culture system and to provide dynamic cell growth feedback.

Wavelength-Selective Films for Cell Culture Imaging and Control

With the industrialization of cell-based processes such as bioprocessing and cell therapies, the need for tools to manipulate cells within a cell culture has grown rapidly. High variability in cell culture processes has driven the need for tools that can be responsive to real-time cell culture conditions, not only at the vessel level but also at the local level. Information about cell culture conditions may be useful for making various cell culture process decisions, such as the addition of media, reagents, buffers, or other compounds to the cell culture as a whole, or decisions to terminate a cell culture, either positively for harvest or negatively for disposal.

One preferred method for monitoring cell cultures at a local level, whether it be a region, colony, local cluster of cells, or at the single cell level is by imaging. The imaging may be conducted either by fluorescently-labeled imaging or using label-free imaging such as brightfield, phase contrast, darkfield or other transmission/scattering based techniques. These techniques, in particular the label-free techniques, require cell culture vessels and/or inserts into these vessels that by their construction enable high-fidelity imaging, meaning that they transmit light with high efficiency, and without imparting diffraction or other spatial artifacts that would interfere with the contained imaging cell cultures.

At the same time, a range of tools for active cell culture manipulation have been developed, intended to replace mostly open-loop cell culture control (in which only vessel-level changes are applied in bulk to the contained cells), or manual processes such as pipette scratching of cells, or manual transfer of cell colonies from one vessel to another. These tools include tools for selective cell removal, as well as tools for selective intracellular delivery of compounds to cells in a cell culture. A wide range of such tools used to manipulate cells are described in Stewart, Martin P. et. al., "Intracellular Delivery by Membrane Disruption: Mechanisms, Strategies, and Concepts," Chem. Rev. 118, 16, 7409-7531 (2018), which is hereby incorporated by reference in its entirety.

One known method for selective cell manipulation is using optical energy. For example, optical cell trapping may be used to individually move cells, and optoporation may be used to focus light on individual cell membranes to porate them for the purpose of compound delivery, cell content extraction, or cell destruction. However, cells are highly transmissive over a wide range of wavelengths from the ultraviolet (UV) to the near infrared (NIR), meaning extremely high power and energy densities are required to accomplish these operations. The devices that generate this optical energy may include lasers with very high pulse energies (and often associated low pulse rates) and/or focusing objectives with high numerical apertures (and therefore very limited fields of view), resulting in very low throughputs. This has made direct optical manipulation of cells suitable mostly for research only, and not for large-scale application in bioprocessing, gene or cell therapies, or high-throughput drug discovery or screening.

As a result, many efforts have been made to enhance optical energy absorption in the proximity of target cells within cell cultures. Some approaches include optoporation, UV killing (selective cell killing in a cell culture using UV lasers), photothermal and/or photochemical (photoacid), photomechanical, photomechanical or photothermal with gold nanoparticles mixed into cells, photomechanical with gold pyramids, and photomechanical with a metal film. However, each of these approaches comes with drawbacks that make them ineffective for incorporating into an efficient, automated, closed cell culture system. For example, optoporation requires large power and time requirements and is not scalable; UV killing is likely to genetically alter or damage cells. Photothermal and/or photochemical (photoacid) approaches may result in chemical leaching from the film layer, high collateral damage, and slow cell death. Photomechanical approaches may cause cell death and have very high energy and area requirements. Photomechanical or photothermal approaches with gold nanoparticles mixed into the cells may cause variable effects across the cell culture, may alter cell health/behavior and introduce contaminants, and may necessitate repeated dosing of nanoparticles because cells may grow away from the nanoparticles. Photomechanical approaches with gold pyramids hinder imaging and may alter cell culture growth and differentiation. Photomechanical approaches with continuous metal films introduces significant optical loss and as a result amplifies any film defects in the cell culture images. Therefore, none of these approaches satisfy the requirements for a satisfactory imaging-compatible, high-throughput optical energy transfer system that does not leave exogenous compounds or particles in the resulting cell culture. Thus, there is a need for supporting components that make cell imaging and editing efficient and effective without comprising the underlying cell culture.

A supporting component for cell imaging and editing in cell culture systems should ideally have several attributes and capabilities for efficient, automated cell culture imaging and editing. For example, a cell culture system should be capable of delivering localized optical energy to a cell culture for the purpose of imparting energy to cells (for example, by causing rapid heating of cell media to form explosive microbubbles and cavitation, or causing highly localized heating of cells) for the purpose of destroying specific cells, or for intracellular delivery or extraction of compounds into/from cells. The cell culture system should have a high efficiency of conversion from optical energy to local thermal and/or mechanical energy, such that a significant amount of energy is transferred within a small volume. This allows the use of lower-energy optical sources and/or allows very high throughput (e.g., area and number of cells processed per unit time).

The supporting component should also be capable of imparting optical energy without the addition or leaching/escape of exogenous compounds or particles into the cell culture, which may alter the behavior of the cell culture, be deleterious to the health of the cells, or leave residual compounds in cells to be used in downstream applications.

In addition, the supporting component should use materials that are known to be biocompatible and non-toxic, and have a surface that in its base configuration is free of mechanical features that could perturb cell growth or differentiation.

The supporting component should also achieve energy absorption and conversion using an absorbing layer that, while meeting the criteria above, allows high-fidelity imaging of the cell culture through this supporting component, meaning that it imparts low optical extinction (absorption and/or scattering) at desired imaging wavelengths and does not result in image artifacts at the desired imaging resolution. The supporting component should also be configured to enable energy absorption in cell culture chambers ("consumables") that are constructed with materials typically used for cell culture and/or high-throughput cell screening or high-content cell imaging, such as polymers or glass.

The systems and methods disclosed herein include a supporting component as described above embodied as a unique optically-resonant film that is permanently attached to a cell culture chamber, or component within a cell culture chamber. This means that the optically-resonant film remains on the surface of the cell culture chamber during cell editing operations, such as light-based removal of cells adhered to the optically-resonant film. The resonant optical film may be designed and configured to simultaneously achieve high-efficiency coupling of optical energy into the local cell environment at wavelengths that are not directly harmful to cells, and allow high-fidelity transmission and fluorescence imaging of the contained cell cultures, while obviating the need for addition of exogenous dyes, particles, or other constructs to the cell culture to achieve energy delivery. The optically-resonant film does not detach from the cell culture chamber surface when exposed to this optical energy (e.g., from a laser), either for imaging or for cell editing/removal.

The resonant optical film may be located on one surface of the cell culture chamber or may be on the surface of an insert that is placed into the cell culture chamber. The resonant optical film may be configured to preferentially absorb light at one wavelength range (absorption range) while maintaining high transmission at another wavelength range (imaging range) using a resonant optical film design that is resonant at the laser absorption range. The resonant optical film may be configured to remain on the surface of the cell culture chamber when illuminated by light in both the imaging wavelength range (in which it transmits light) and the cell editing/removal wavelength range (in which it absorbs light). In some implementations, the resonant optical film may be flat, without any protruding structures.

In some implementations, the resonant optical film may absorb more than 5%, 10%, 15%, 20%, or 30% of light at a cell processing optical wavelength, while absorbing less than 5%, 10%, 15% or 20% of light at a cell imaging optical wavelength. In some implementations, the resonant optical film may not have inherent features with median dimensions larger than 10%, 20%, or 50% of the cell imaging optical wavelength, with the exception of fiducial markings imparted on it. In some implementations, the resonant optical film may be located on a wall of a cell culture chamber, or may be situated on a foil in the cell culture chamber. In some implementations, the foil may be a membrane with pores.

In some implementations, the resonant optical film may be configured to have a resonant absorption at 532 nm and/or 1064 nm. In some implementations, the resonant optical film may be configured to withstand laser pulses of less than 25 ns of 0.05, 0.1, 0.2, or 0.4 J/cm$^2$ energy with less than a certain percentage of change in optical transmission at the cell imaging wavelength. In some implementations, the resonant optical film may include gold nano-islands with mean diameter less than 20, 30, 40, or 50 nm as measured along at least one axis. The nano-islands may be permanently attached to an optically transparent material, which may include glass, cyclic olefin copolymer, polystyrene, polycarbonate, polyethylene terephthalate or other materials suitable for cell culture.

Figure 40:
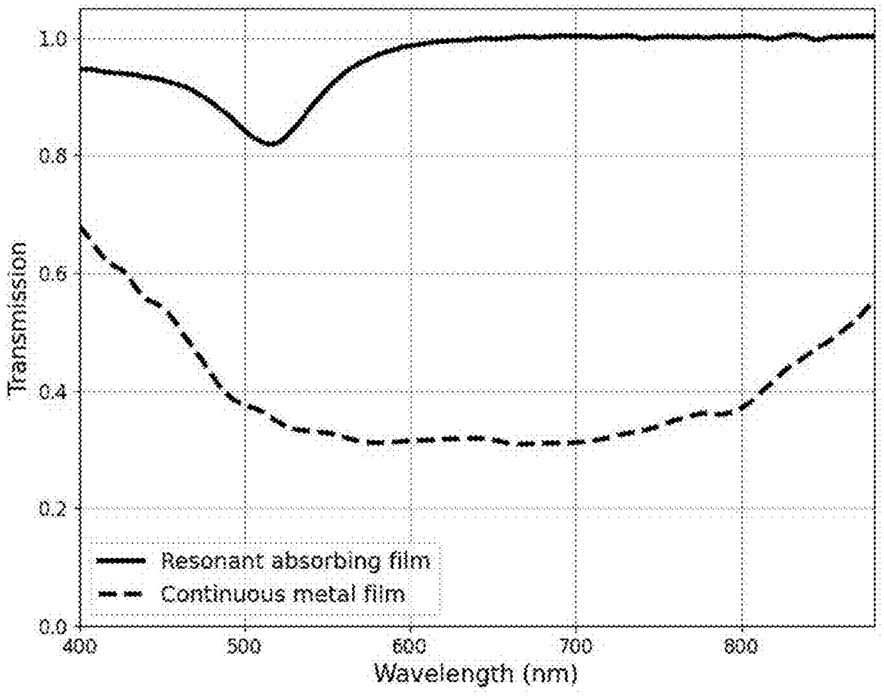
FIG. 40 is a graph illustrating the absorption/transmission behavior at different wavelengths of a resonant optical firm in accordance with various implementations.

FIG. 40 is a graph 4000 illustrating the absorption/transmission behavior at different wavelengths of a resonant optical firm in accordance with various implementations. The graph 4000 shows data from two different laser-absorbing semi-transparent films developed for the purpose of transferring laser energy to a cell culture for both cell imaging and cell editing purposes. The dashed line shows the optical transmission of an optical film on a cell culture chamber, namely a previously disclosed 20 nm Titanium film. This film provided some transmission across the entire VIS/NIR band, allowing imaging of a live cell culture. However, the optical transmission of the film was only 30-35%, resulting in low transmission efficiency, therefore requiring longer exposure times and/or more intense illumination. For epifluorescent imaging, there were 65-70% losses on both the excitation and emission paths to and from the sample, meaning a compound efficiency of only 9-12%, again requiring long exposure times and/or more intense illumination. The titanium optical film absorbed 532 nm nanosecond pulsed laser light and transferred energy to targeted cells via explosive bubble formation and collapse. A fluence of approximately 250 mJ/cm$^2$ was required to lyse and remove cells.

The solid line in the graph 4000 shows a transmission spectrum of a resonant optical film on the cell culture chamber surface in accordance with various implementations. In this instance, the resonant optical film is a 4 nm layer of gold on a 170 micron thick borosilicate coverslip sufficiently large to form the cell culture surface of a 96-well SBS microwell plate, and then annealed in order to consolidate the material into small islands that exhibit plasmonic resonance at roughly 520-540 nm. The resulting extinction can be seen by the dip at this wavelength, at which the film absorbs light from a 532 nm pulsed laser. The resonant optical film achieves cell lysis at similar laser fluences (~250 mJ/cm$^2$) as the titanium film. However, the transmission through the resonant optical film, and therefore the imaging efficiency, are superior, with virtually 100% transmission at wavelengths longer than 625 nm, meaning over 3 times as much light transmission for transmission-type imaging, and a roughly 10× improvement in round-trip efficiency for epifluorescent imaging. This efficient transmission is beneficial for long-term imaging of cell cultures, as the lower illumination power or shorter illumination/exposure times that are enabled reduce exposure of cells to light and minimize any effects on cell metabolism or health. In addition, the low reflectivity of the coating (near zero at imaging wavelengths) prevents a double-pass of light through the cell culture, further reducing any of these effects. This near-full transparency at imaging wavelengths also means that alterations to the optical film do not cause changes in the images observed, assuming a band-limited light source (or image sensor) is used to capture a transmission image of the sample.

Figure 41:
FIG. 41 is an image of a microwell plate with a resonant optical film on the cell-bearing surface in accordance with various implementations.

FIG. 41 is an image of a microwell plate 4100 with a resonant optical film on the cell-bearing surface in accordance with various implementations. The microwell plate 4100 depicted in FIG. 41 is a 96-well SBS-standard format microwell plate fitted with a resonant optical absorbing film on the cell-facing surface. As may be seen in the bottom left wells, the coverslip and film are highly transmissive over most wavelengths, allowing high-quality imaging. The film may have a pinkish hue due to the enhanced absorption in the green wavelength range.

The microwell plate 4100 is an example implementation of a cell culture chamber, but in general many cell culture chambers known in the art may be used. For example, microwell plate 4100 is not limited to 96 wells, but may include single-well plates to 6, 12, 24, 96, 384, 1536 and other numbers of wells on the microwell plate, as well as well plates with microwells within each well for the purpose of isolating cells or cell clusters. In addition, the cell culture chamber may include well plate inserts such as transwell membranes constructed with a permeable polymer membrane and coated with the resonant optical firm to allow cells to be cultured on a permeable membrane between two layers of media (often with different contents), and to be manipulated using optical radiation that is absorbed by the resonant optical film for the purpose of lysis or compound delivery.

In alternate implementations, the cell culture chamber may include petri dishes, flasks, or other large cell culture chambers with resonant absorbing films to allow for larger-format cell cultures. In such cases, the coating may be applied directly to the chamber wall(s), or it may be inserted into the cell culture chamber using a coating-bearing sheet made of thin glass or polymer that is attached to a chamber wall. Alternate implementations of cell culture chambers may also encompass closed fluidic chambers in which media flows through the chamber, such as microfluidic or macro-scale fluidic flow chambers that allow automated media perfusion of cell cultures.

Figure 42A:
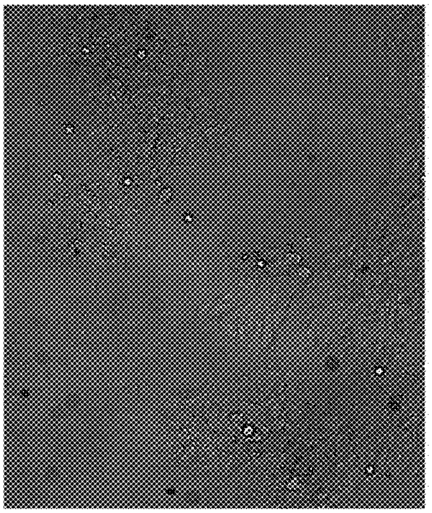
FIGS. 42A-42C are images of cells undergoing cell editing and washing in a cell culture chamber having a resonant optical film in accordance with various implementations.
Figure 42B:
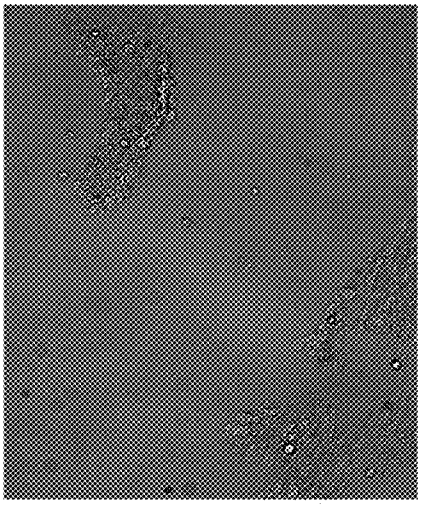
Figure 42C:
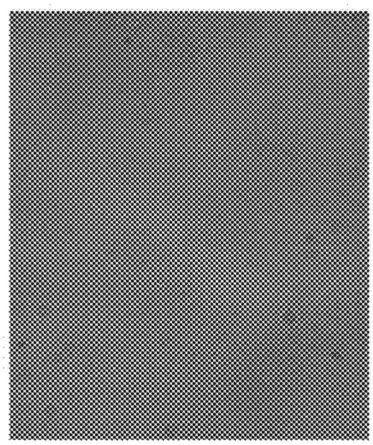

FIGS. 42A-C are images of cells undergoing cell editing and washing in a cell culture chamber having a resonant optical film in accordance with various implementations. FIG. 42A shows human induced pluripotent stem cells (hiPSCs) grown in a region of a cell culture chamber, with a laser-absorbing resonant optical film on the cell culture chamber surface. Imaging, performed with a 10× objective, shows a high level of detail in the cell culture. FIG. 42B shows the same region of cells immediately following pulsed laser illumination with ~40 nJ pulses, 15 nsec pulse width at 532 nm, in which pulses were applied in a grid of 4×4 microns over the field of view. Cell lysis is evident from detachment of some cells, and extensive blebbing observable along the periphery of the cell clusters. FIG. 42C shows the same area following washing of cell debris from the cell culture chamber. Cells within the field of view have been removed completely, without marking evident on the resonant optical film. Some cells at the edges of the scanned area are visible, where they remain attached to intact regions outside of the scanned area. Despite spots from out-of-focus dust, the surface displays a feature-free quality that is important for highly-repeatable imaging of cell cultures, especially when these images are used for image processing routines and ultimately for automated management of the cell culture in a cell culture system (e.g., cell culture system 100). The resonant optical film is compatible with a pulsed laser system as the cell editing subsystem. In addition to the use of pulsed laser systems to produce microbubbles for cell lysis or intracellular delivery, continuous-wave sources (whether lasers or other sources) may be used to impart thermal energy selectively to a cell culture using the resonant optical film.

Figure 43:
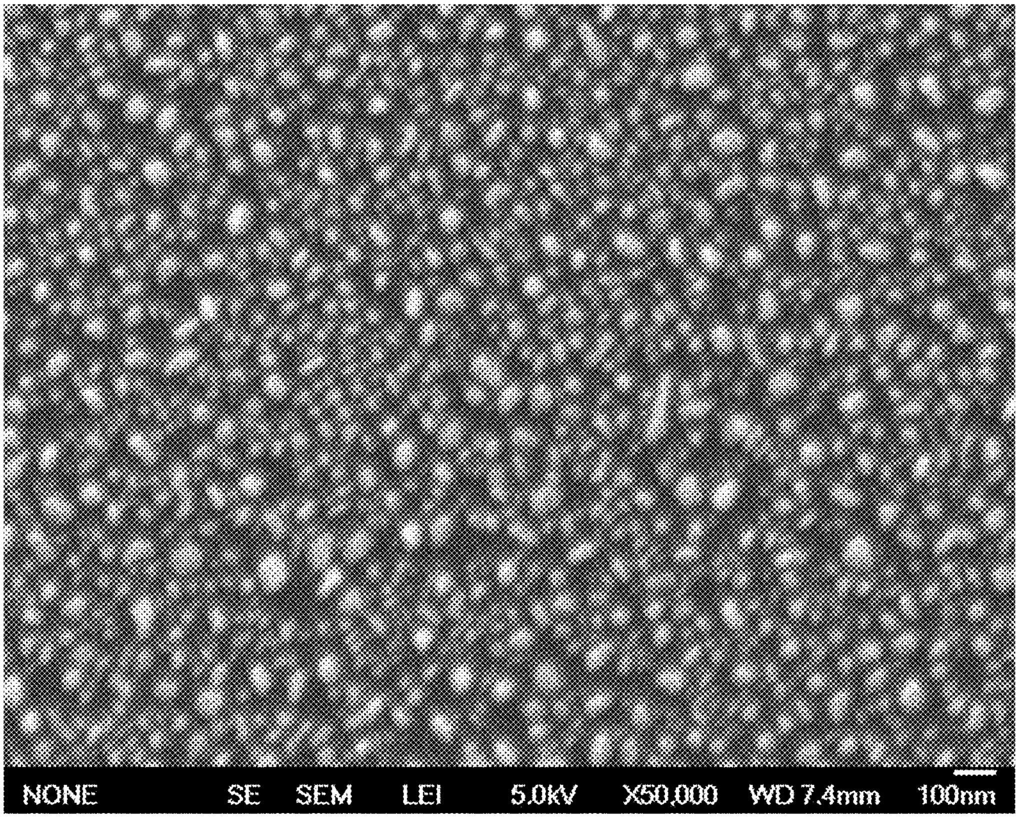
FIG. 43 is an image of a resonant optical film surface in accordance with various implementations.

FIG. 43 is an image of a resonant optical film surface 4300 in accordance with various implementations, taken by a scanning electron microscope (SEM). The resonant optical film surface 4300 was fabricated using gold deposition and subsequent film annealing at approximately 500° C. to form islands that exhibit plasmonic resonance at around 520-540 nm. As can be seen from the image, the maximum feature size is around 100 nm, with the median feature size closer to 25 nm. As a result, the film has very low scattering or absorption at the desired imaging wavelengths (roughly ≥600 nm) and with no visible features at 10× magnification.

The resonant optical film described herein may be fabricated using several approaches. The first is using thin semiconductor films. Thin semiconductor films may work near the edge of the bandgap, where film thickness is tuned such that one optical resonance is at the laser wavelength (where the material absorption is relatively high) and at least one other optical resonance point at a wavelength where the inherent absorption is lower (the point at which imaging will be performed). For example, multiple forms of silicon have absorption coefficients that drop rapidly over the visible wavelength range. Deposition of thin layers of silicon onto a substrate material such as glass or plastic therefore results in a transmission spectrum with peaks and valleys in the visible and NIR wavelength range where there are optical resonances. These resonances may then be used to preferentially absorb optical radiation for manipulation of cells (at shorter wavelengths) and transmit optical radiation for imaging cells (at longer wavelengths).

An example of such a resonant film may be found in Zhou, Jaiping et al., "Si surface passivation by SiOx: H films deposited by a low-frequency ICP for solar cell applications," Journal of Physics D Applied Physics 45(30):395401 (2012), which is hereby incorporated by reference in its entirety. The Zhou reference discloses a transmission spectrum of a hydrogenated amorphous silicon layer with transmission maxima at ~520 nm and ~600 nm. The optical film disclosed in Zhou may be modified for use in the present implementations, for example by using a slightly thicker layer to achieve a resonance at the 532 nm frequency-doubled Er:YAG laser line, and another resonance at just over 600 nm, where high power density LED illuminators are readily available for transmission imaging.

Figure 44:
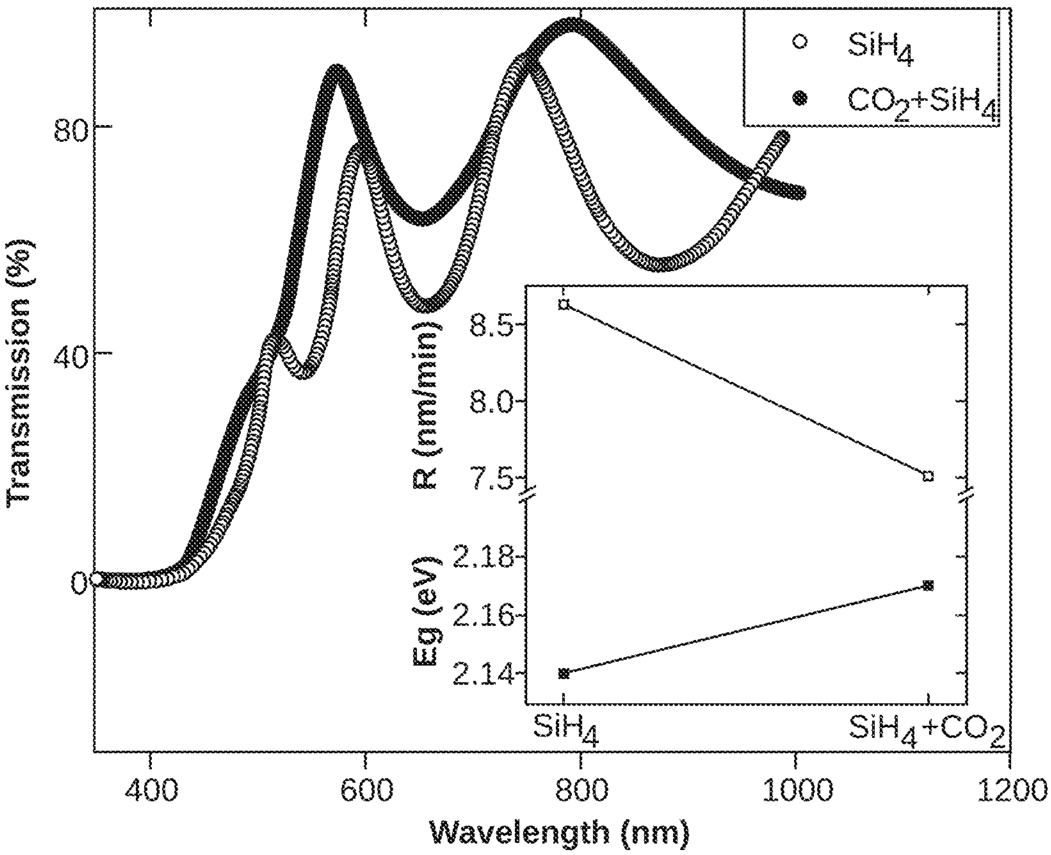
FIG. 44 is a graph showing the transmission spectrum of an optical film which has resonances at specific wavelengths.

FIG. 44 is a graph 4400 showing the transmission spectrum of the film disclosed in the Zhou reference, which has resonances at specific wavelengths and progressively higher absorption at short wavelengths. Such a resonant, partially-absorbing layer may be deposited directly on a coverslip material (borosilicate glass or polymer). It may then be capped with a dielectric layer such as silicon dioxide or silicon nitride to form a consistent index difference interface at high contrasts (to enhance reflection) and prevent deterioration or modification of the semiconductor layer by cell media components. In an example implementation, a layer of amorphous silicon is deposited by plasma-enhanced chemical vapor deposition (PECVD) onto an optical-grade sheet of cyclic olefin copolymer (COC) to form a layer of approximately 400 nm. This layer is then recrystallized using a Xenon flash lamp to convert the amorphous Silicon into microcrystalline silicon, which exhibits a lower optical absorption at over 500 nm and has a higher thermal conductivity. The deposition layer thickness is tuned such that it results in a half-wave multiple of 532 nm (the laser wavelength) after annealing. Finally, the silicon layer is capped with a thin (10-20 nm) layer of silicon dioxide to protect the silicon and provide a biocompatible surface. The resultant resonant optical film will have a resonance at 532 nm where the material has sufficient absorbance to capture laser light and transmit this energy in the form of heat to the cell media above it. Additionally, it has other resonant transmission peaks where the transmission is 75% or higher at longer wavelengths, for example 620-650 nm, which is suitable for transmission microscopy of cell cultures.

Another approach for fabricating optical films as disclosed herein may include plasmonic resonant absorbing films. One class of these films useful in the present implementations is patterned conductive structures on a transparent substrate (coverslip or insert into a cell culture chamber). Metal structures with appropriate (usually high) conductivity, dimensions, and spacing can have plasmonic resonances that may couple with specific wavelengths. Films that are useful in the present implementations should (a) have high uniformity and consistency in the distribution of absorption; (b) have no residual particles or materials in cell culture products; and (c) prevent aggregation of materials such as nanoparticles that could become visible in cell culture imaging. Films with resonant structures that are inherently and uniformly attached to a surface in the cell culture chamber may satisfy these qualities. For example, gold nanostructures with dimensions on the order of tens of nanometers have resonances in the visible spectrum from roughly 520 nm upwards, and can be used to absorb laser wavelengths while transmitting wavelengths for imaging.

Patterned films for use in the present implementations may be formed in a number of ways. One set of fabrication techniques include pre-defined patterning. One example of pre-defined patterning is photolithographic patterning, in which a lift-off process is used in which photoresist is applied onto the substrate, exposed using a photomask, developed, and removed from selected areas. Metal such as gold is then deposited onto the substrate (where exposed) or photoresist using deposition techniques including, but not limited to, evaporation or sputtering. The remaining photoresist is then removed from the substrate, along with any gold that was deposited on top of it. A variation of photolithographic patterning is optical interference based photolithography, in which instead of a mask being used to expose photoresist, an interference pattern is used to produce a periodic pattern.

Another example of pre-defined patterning is nano-imprinting, in which a template is used to pattern photoresist on the substrate, and then the photoresist is processed as in the photolithography approach. A representative technique for such patterning is given in Lopatynskyi, Andrii M. et al., "Au nanostructure arrays for plasmonic applications: annealed island films versus nanoimprint lithography," Nanoscale Research Letters 10:99 (2015), which is hereby incorporated by reference in its entirety. Further examples of pre-defined patterning include: e-beam lithography, in which the plasmonic features are patterned by electron beam writing in photoresist (described in Chen, Yifeng, "Nanofabrication by electron beam lithography and its applications: A review," Microelectronic Engineering Vol. 135, pp. 57-72 (2015)); ion beam lithography (described in Wat, F., et al., "Ion Beam Lithography and Nanofabrication: A Review, Int. J. Nanoscience, Vol. 4, No. 3, pp. 269-286 (2005)); colloidal mask deposition, in which self-organizing particles such as microspheres are layered onto the substrate and temporarily attached (for example, spheres that form a hex-packed layer on the substrate surface), and metal is then deposited onto the substrate only where there are gaps in these spheres (described in Sanchez-Esquivel, Hector et al., "Spectral dependence of Nonlinear Absorption in Ordered Silver Metallic Nanoprism Arrays," Scientific Reports 7(1) (2017)); and self-assembled polymers or other layers (described in Segalman, Rachel A., "Patterning with block copolymer thin films," Materials Science and Engineering R 38, 191-226 (2005)), which may be used to pattern metallic films into plasmonic resonant structures either by applying such a structure to the substrate, depositing metal, and then removing the structure (acting as a mask for deposition, or "lift-off" mask) to yield metal structures, or by applying such a structure to a substrate with an existing metal film, using the structure as a mask for etching the metal film, and then removing the structure to yield a structured metal film. Each reference listed above are incorporated by reference in their entirety.

Another set of fabrication techniques for patterned films include self-forming patterned metal films. In this technique, a film of metal is first deposited on the substrate (for example, a layer of gold onto a borosilicate glass), and then annealed to form semi-random islands based on surface energy alone. While the islands are random, the distribution of island sizes and spacing is controllable and repeatable, and as a result the optical properties of the films are consistent from spot to spot and from sample to sample. Metal is deposited by mechanisms including but not limited to evaporation, e-beam evaporation, and sputtering, and then annealed to form islands by one or more methods. The annealing methods may include oven annealing (in which the substrate and film are placed in an oven, for example a nominal 3 nm gold film annealed for 8 hours at 500° C., in a nitrogen environment) and optical annealing (in which the substrate and as-deposited film are exposed to intense light, for example laser light or intense flash lamps, in order to heat the film and cause it to form plasmonic islands). For example, using optical annealing a 532 nm laser may be used to anneal the film with repeated pulses. Such optical annealing may be done in a gas environment, or in a liquid environment for the purpose of dissipating heat and removing any particulates that form, and generally reflect the ultimate operating environment of the plasmonic film during this pre-treatment. In alternate implementations, the islands may be created via direct deposition of metal onto a substrate under appropriate conditions, for example sputtering gold onto a borosilicate glass at elevated temperature. This may allow the film to re-form into islands as it is deposited, which may directly yield a plasmonic resonant film. An example is described in Tvarozek, V. et al., "Plasmonic behaviour of sputtered Au nanoisland arrays," Applied Surface Science Vol. 395, pp. 241-247 (2017), which is hereby incorporated by reference in its entirety. In some implementations, high-conductivity metals such as gold, which form the plasmonic structures, may be co-deposited with other materials such as titanium to promote adhesion to the substrate material.

Another set of fabrication techniques for patterned films include deposition of metallic nanoparticles and then permanent attachment to an optically clear substrate. In this approach, pre-formed nanoparticles in a liquid are applied and attached to the substrate material, for example as described in Ahmed, Syed Rahin et al., "In situ self-assembly of gold nanoparticles on hydrophilic and hydrophobic substrates for influenza virus-sensing platform," Scientific Reports 7, 44495 (2017), which is hereby incorporated by reference in its entirety. For cell manipulation applications (as opposed to sensing applications such as the one described in Ahmed), the resonant optical film is configured to absorb a significant amount of energy, and may need to operate over a period of days or weeks without detachment of constituent materials. For that reason, both chemical and thermal methods may be used to create a strong attachment between the nanoparticles and surface. For example, the deposition of metallic nanoparticles and permanent attachment may be followed by a thermal annealing process in which the nanoparticles re-shape and increase contact area with an underlying glass or polymer substrate.

It should be understood that the disclosed implementations of resonant optical films and methods of constructing them is not exhaustive, and that the present implementations are not dependent on a specific implementation. Rather, in general the present implementations utilize a combination of resonant optical films within a cell culture chamber that achieves the goal of efficient cell culture imaging and editing within a cell culture system, particularly one that is automated. The properties of the resonant optical film should be conductive to accurate and easy imaging.

Surface Enhanced Raman Spectroscopy of Cell Cultures

Chemometric monitoring of bioprocessing systems, such as bioreactors, is a growing field because it allows for closed-loop monitoring and control of biological processes to increase yields. Label-free methods that can monitor media components, cells or cell components, or cell products, are particularly useful because they may be applied to bioprocessing systems non-invasively and without perturbing the cell culture.

Vibrational spectroscopy, and in particular Raman spectroscopy, have made inroads in bioprocessing and automated cell culture control because they are able to measure media constituents and cells/cell products without exogenous labels, and in situ without breaking system sterility (e.g., through a clear surface, or fiber optic probe). However, conventional Raman spectral signals are very weak due to the very low probability of inelastic scattering within a sample such as cell media. This can limit the constituents or concentrations that such systems can measure, and usually require high excitation laser powers, high-NA objectives and related corrections, very high sensitivity spectrometer systems, and/or long integration times and extensive baselining procedures.

The systems and methods disclosed herein include the use of surface-enhanced Raman Spectroscopy (SERS) in bioprocessing systems, for example in automated or semi-automated cell culture systems. The cell culture system may include a cell culture container enclosing cells undergoing a cell culture process. The cell culture system may also include an imaging subsystem for imaging cells in the cell culture container, a computing subsystem for analyzing cell images and other information to monitor the progress of the cell culture process, and a cell editing subsystem for manipulating and removing the cells in the cell culture container (e.g., using pulsed lasers).

The cell culture container may include a semi-transparent, resonant plasmonic film that allows imaging of the cell culture by the cell imaging subsystem at one or more select wavelengths. The cell editing subsystem may use a pulsed laser focused on the resonant film and at roughly the resonant absorption wavelength of the film to create transient microbubbles for the purpose of achieving mechanical effects on cells, including cell lysis or removal and cell membrane poration.

In the systems and methods disclosed herein, the film of the cell culture container may also be used to enhance Raman scattering signals, particularly SERS signals. Particularly, when the cell editing subsystem focuses an excitation laser onto the film, the film may scatter the light at wavelengths shifted from the laser wavelength. The magnitude of the scattered light at these shifted wavelengths is indicative of the chemical composition of the cell media, biofilm, cellular matrix, cell membrane or other substances in the immediate proximity of the film.

In some implementations, the cell editing subsystem may also be used to clean the film surface prior to or during SERS measurements using the film. For example, a laser may remove biofouling or other materials from the surface of the film prior to measuring the local media environment using SERS. In another example, SERS may be used to measure prior to and after laser clearing to get a measurement of biofilms accumulated on the film.

In some implementations, the cell editing subsystem may use pulsed lasers to create explosive microbubbles that locally mix media to ensure good sampling of media by subsequent SERS measurements. In some implementations, the cell editing subsystem may use the microbubbles formed by the lasers to lyse or temporarily porate cell membranes of nearby cells prior to SERS measurement to measure cell contents. This microbubble poration may be combined with the laser clearing operation, or the SERS measurement may be alternated with ramped pulsed laser energy to clear the film, measure a baseline, and then measure cell contents. In some implementations, the laser in the cell editing subsystem may have multiple uses, such as for biofouling clearing and Raman excitation.

In some implementations, the cell culture system may use SERS to monitor media components, including but not limited to nutrients, metabolic and waste products, and vitamins. In some implementations, the cell culture system may use SERS-derived cell media data together with cell culture imaging-derived data in a model that predicts cell culture state. In some implementations, the cell culture system may use SERS-derived data from cell regions in conjunction with transcription data in models to predict transcriptomes from SERS data.

The use of SERS in the systems and methods disclosed herein can address the issue of low signal levels with conventional spectroscopy. SERS uses an arrangement of conductive particles to enhance local field strengths when illuminated by the excitation source (typically a laser), and as a result can produce Raman scattering signals that are many orders of magnitude larger than conventional Raman. An overview of SERS techniques applied to biological systems is given in Kogler, Martin, et al., "Comparison of time-gated surface-enhanced Raman spectroscopy (TG-SERS) and classical SERS based monitoring of Escherichia coli cultivation samples," Biotechnology Progress 34(6): 1533-1542 (November 2018), which is hereby incorporated by reference in its entirety. As a result, SERS is used extensively for one-time measurements of samples that are placed onto a SERS substrate, and sometimes allowed to dry or settle onto the substrate.

However, when SERS is applied to time series monitoring of biological systems, the settling or attachment of material to the SERS surface can have both positive and negative effects on the desired measurements. For example, materials such as live cells, dead cells, debris, media components, cell excretions (such as extracellular matrices or other proteins), exosomes, and the like may accumulate on the SERS surface. If the SERS system is used to monitor media constituents (nutrients, waste products, vitamins, growth factors, proteins, etc.) this accumulation ("biofouling") on the SERS surface may dominate the spectral signal and obscure the desired measurement. Conversely, the accumulation of biological material on the SERS substrate may allow analysis via spectroscopy of this material, which may be indicative of the state of the biological system. For example, the excretion of proteins or exosomes by cells that accumulate on the surface may be measured. However, continued accumulation past a certain point reduces accurate time series analysis of secretions and therefore reduces the ability to monitor the status of the biological system over time.

Accordingly, there is a need in the art to clean biofouling from the SERS surface when SERS is used in biological systems so that media measurements remain accurate, and also a need to directly measure the accumulation of biological material on the surface over time, with a series of timepoints or intervals. Further, it would be desirable to couple such a SERS system with imaging systems so that the SERS surface and any cells growing on it, or debris residing on it, may be imaged.

An electrically-based system for performing such cleaning has been proposed, in which a conductive layer is used on conjunction with the SERS substrate. See Meier, T.-A., et al., "Fast electrically assisted regeneration of on-chip SERS substrates," Lab on a Chip 15, 2923 (2015), which is hereby incorporated by reference in its entirety. However, this electrical means require feed-throughs into the biological chamber, which may compromise integrity or sterility, and requires additional materials in the biological chamber, which may introduce cytotoxic effects. Finally, the required voltages are on the order of 100V for even a small chip, which makes the approach impractical for most applications, and the resulting electrical fields may cause other biological or biochemical side-effects (electrophoretic or cell electroporation included). Instead, it is desirable to achieve the aforementioned solution without the need for additional feedthroughs into the biological container, and without the need for additional materials.

Accordingly, implementations of the systems and methods disclosed herein provide mechanisms for removal and/or reduction of biofouling that enables accurate measurements over time without compromising cell culture sterility. In some implementations, the systems and methods disclosed herein include an editing subsystem that allows for measurement of the accumulation of biological material and/or cell culture media components.

Figure 45:
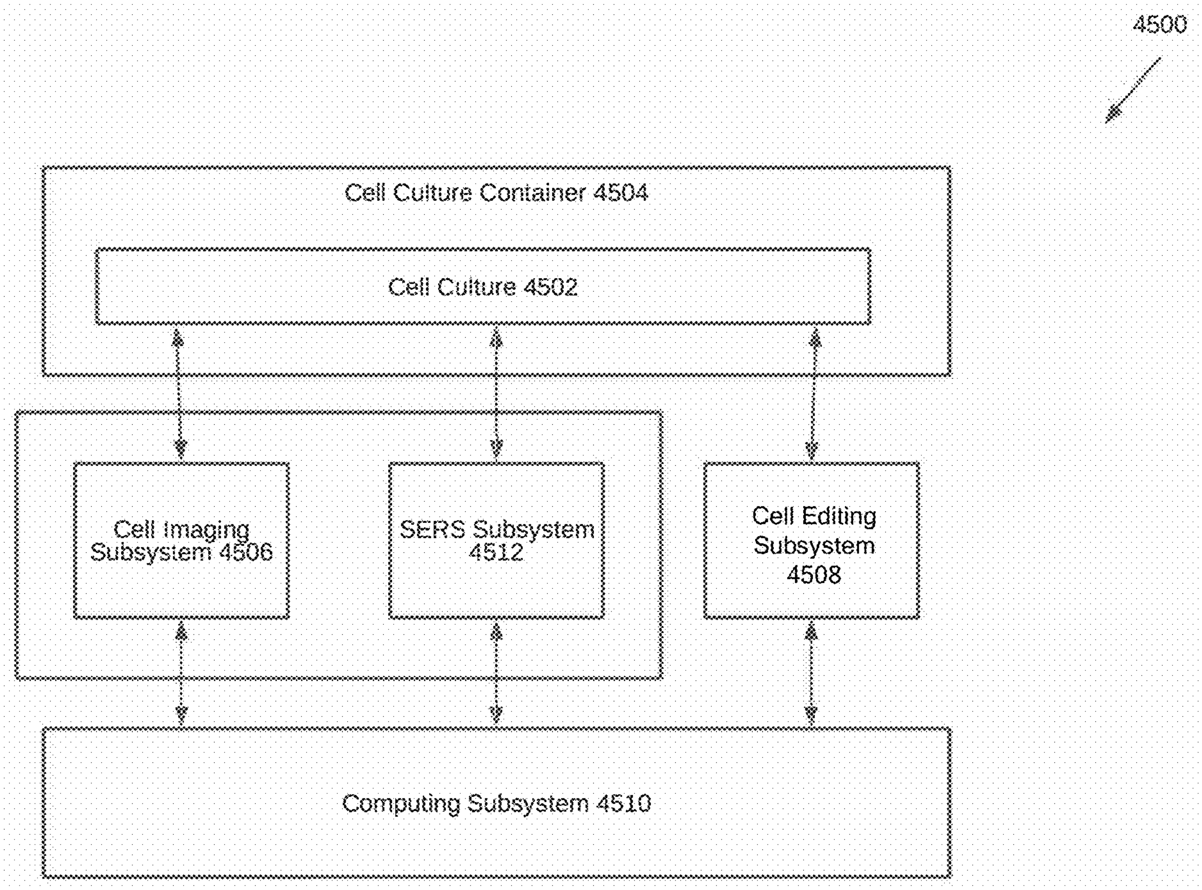
FIG. 45 is a block diagram of a cell culture system in accordance with various implementations.

The systems and methods disclosed herein contemplate the use of SERS in bioprocessing systems, for example in automated or semi-automated cell culture systems. FIG. 45 is a block diagram of a simplified cell culture system 4500 in accordance with various implementations. The cell culture system 4500 includes one or more cell culture containers 4504, each cell culture container 4504 supporting a cell culture 4502. The cell culture 4502 may start as source cells that undergo a cell culture process to produce an output cell product. The cell culture 4502 may be used for a number of cell culture processes performed and monitored by the cell culture system 4500, including but not limited to: cell reprogramming (into pluripotent or multipotent forms), cell differentiation, cell trans-differentiation, cell expansion, cell sorting, clonal isolation, cell gene editing, cell-based protein production, cell-based viral production, combinations thereof, or any other implementations known to persons of ordinary skill in the art.

The cell culture container 4504 may include one or more cell culture chambers to hold the cell cultures, and may take the form of microwell plates, flasks, stackable cell culture containers, closed cassette systems, microfluidic chambers, purpose-built bioreactor vessels, or any other implementations known to persons of ordinary skill in the art. The cell culture container 4504 may be in a format that allows for observation of the cell culture 4502 at regular intervals using an imaging subsystem 4506. For example, the cell culture container 4504 may include a closed cassette system having a transparent or semi-transparent surface that allows for light or laser-based imaging and editing. The cell culture container 4504 may include a semi-transparent, resonant plasmonic film that allows imaging of the cell culture by the cell imaging subsystem at one or more select wavelengths. This film may also be used to enable SERS measurements of the contents within the cell culture container.

The imaging subsystem 4506 may be configured to provide label-free imaging suitable for long-term cell culture observation, although some implementations may include fluorescent imaging capability for immunofluorescent or other labeled images. Label-free modalities employed by the imaging subsystem 4506 may include, but are not limited to, brightfield imaging, phase imaging, darkfield imaging, transmission imaging, reflection imaging, quantitative phase imaging, holographic imaging, two-photon imaging, autofluorescence imaging, Fourier ptychographic imaging, defocus imaging or any other implementations known to persons of ordinary skill in the art.

The cell culture system 4500 further includes a cell editing subsystem 4508 for editing the cell culture 4502. The cell editing subsystem 4508 may edit the cell culture 4502 at a regional, colony-specific, and/or cell-specific level. Editing, in this context, may include selective destruction and/or removal of cells or cell regions, and non-destructive operations on cells (including intracellular delivery of compounds into cells or extraction of compounds from cells). The mechanism by which the cell editing subsystem 4508 acts upon cells in the cell culture may include, but not be limited to, mechanical mechanisms, ultrasound mechanisms, electric field mechanisms, optical mechanisms, combinations thereof, or any other implementations known to persons of ordinary skill in the art.

Optical mechanisms for cell editing may include, but are not limited to, optical systems that deposit energy directly into cells or surrounding media in the cell culture, optical systems that deposit energy into particles or dyes that are added to the cell culture media (including but not limited to particles functionalized in a manner to attach to specific cells, or that are taken up by cells), or optical systems that deposit energy into particles or films that are on surfaces proximate to portions of the cell culture, or any other implementations known to persons of ordinary skill in the art. For example, one optical mechanism is a pulsed laser that can impart energy to the contents of the cell culture container 4504. Optical mechanisms may operate on the cell culture by a number of means including, but not limited to, elevating the local temperature to a point where cells are destroyed due to heat damage, elevating local temperature to cause boiling and/or bubble formation to cause portions of the cell culture to detach from a surface, or elevating local temperature rapidly in order to cause rapid bubble formation and then subsequent collapse to affect mechanical forces on the local cell membranes, or combinations thereof.

The computing subsystem 4510 of the cell culture system 4500 may be configured to control the other components of the cell culture system 4500 to perform the specified cell culture process on the cell culture 4502. The computing subsystem 4510 may be configured to gather data from a range of sources, organizes the data in a manner that allows it to make predictions of success/quality/functionality of the cell culture 4502, and in many cases do so on a cell-by-cell, colony-by-colony, or region-by-region basis. For example, the computing subsystem 4510 may be configured to predict which regions of cells are most likely to yield superior cell products, and which regions are less likely to yield good product. In another example, the computing subsystem 4510 may use cell data derived from imaging in conjunction with sensor data and assay data to pre-emptively adjust cell culture conditions. Similarly, the computing subsystem 4510 may use cell data obtained from imaging, potentially in conjunction with cell media sensor data, to determine when the cell culture 4504 is ready for harvest.

The computing subsystem 4510 may control the cell editing subsystem 4508 to make edits to the cell culture 4502 according to cell management algorithms (for example, to maintain a certain cell density, to maintain certain exclusion areas within the cell culture container), in a timed manner (for example, delivering gene-activating or gene-editing compounds to cells at a specific interval), and/or as a result of predictions made by the computing subsystem 4510 (for example, removal of cells predicted not to yield the desired phenotype or optimal level of function). "Editing" includes a variety of individual functions such as destruction of cells and/or colonies (including inducing apoptosis, lysing, physically removing) as well as selective delivery of compounds into cells and/or regions of cells via intracellular delivery mechanisms, or selective extraction of compounds from the cells via intracellular delivery mechanisms.

The cell culture system 4500 may also include a SERS subsystem 4512 configured to perform SERS measurements of the cell culture container 4504. Information derived from SERS measurements may be used to monitor media components in the cell culture container 4504, including but not limited to nutrients, metabolic and waste products, and vitamins. In some implementations, the cell culture system 4500 may use SERS-derived cell media data together with cell culture image data from the imaging subsystem 4506 in a model that predicts cell culture state. In some implementations, the cell culture system 4500 may use SERS-derived data from cell regions in conjunction with transcription data in models to predict transcriptomes from SERS data. In some implementations, components and/or functionality of the SERS subsystem 4512 may be combined with the cell imaging subsystem 4506 in a single subsystem. The cell culture system 4500 may have additional functionality and components not shown in FIG. 45.

Figure 46A:
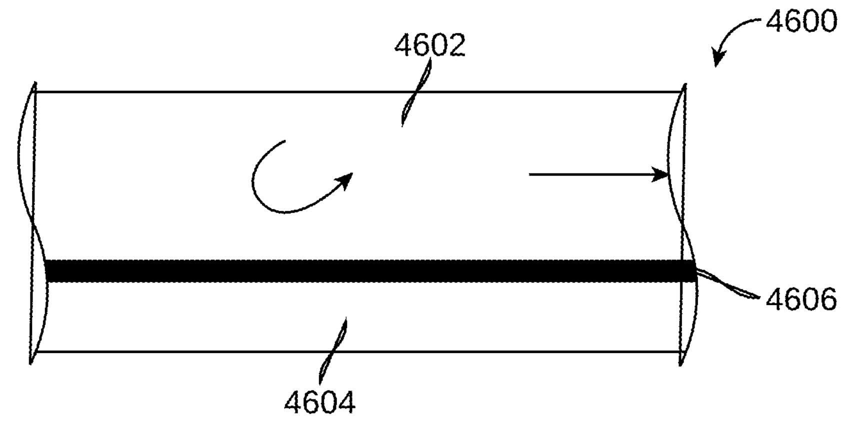
FIGS. 46A-D are diagrams depicting use of SERS to measure contents in a cell culture container in accordance with various implementations.

FIGS. 46A-D are diagrams depicting use of a SERS subsystem (e.g., SERS subsystem 4512) to measure contents in a cell culture container 4600 in accordance with various implementations. In FIG. 46A, the cell culture container 4600 includes a fluid media 4602 enclosed by walls (only a lower wall 4604 is shown in FIG. 46A). The lower wall 4604 may be transparent to allow for imaging of the contents of the cell culture container 4600. The fluid media 4602 may be circulated and periodically refreshed. A film or layer 4606 is in contact with the fluid media 4602 and is designed to enhance Raman scattering for SERS or resonant SERS (in which the Raman excitation wavelength matches a resonant wavelength of the film 4606). The film 4606 may reside on one of the walls of the cell culture container 4600, for example the bottom of a microwell plate container or the window of a bioreactor. Alternatively, the film 4606 may reside on a standalone substrate that is inserted into the cell culture container 4600, located such that it may still be interrogated by cell editing and imaging subsystems. The film 4606 may also be semi-transparent to allow for imaging of the contents of the cell culture container 4600. The film 4606 may be flat. The film 4606 may be configured to remain on the one or more walls of the cell culture container 4600 when exposed to optical energy (e.g., from a laser) for imaging or cell editing purposes.

Figure 46B:
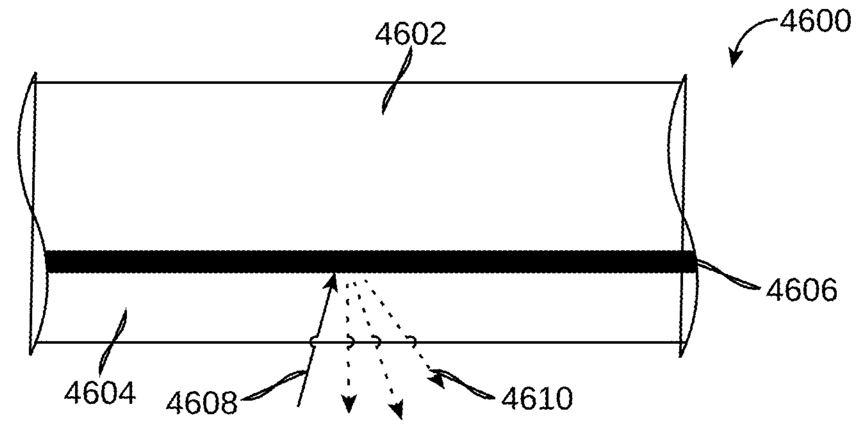

FIG. 46B illustrates an example operation of a SERS subsystem to measure biochemical constituents in the fluid media 4602 of the cell culture container 4600. An excitation source 4608 (e.g., a laser) is focused through the clear wall 4604 and strikes the film 4606, causing light scattering including inelastic light scattering 4610. The scattered light 4610 may be captured and measured spectroscopically. The light measurement component of the SERS subsystem may block the wavelength of the excitation source 4608 so as to measure only light that has been scattered inelastically (i.e., at wavelengths other than the incoming excitation wavelength).

Figure 46C:
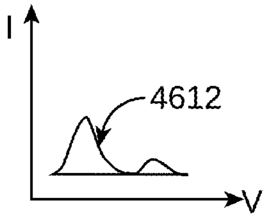

FIG. 46C is a chart showing an intensity spectrum 4612 of scattered light collected by a SERS subsystem after reflection from the film 4606. The spectrum 4612 is shown with a frequency shift (typically given in wavenumbers υ, in units of $cm^{-1}$) on the X-axis and intensity I on the Y-axis, and peaks correspond to characteristic vibrational modes of the molecules sensed by the SERS subsystem.

Figure 46D:
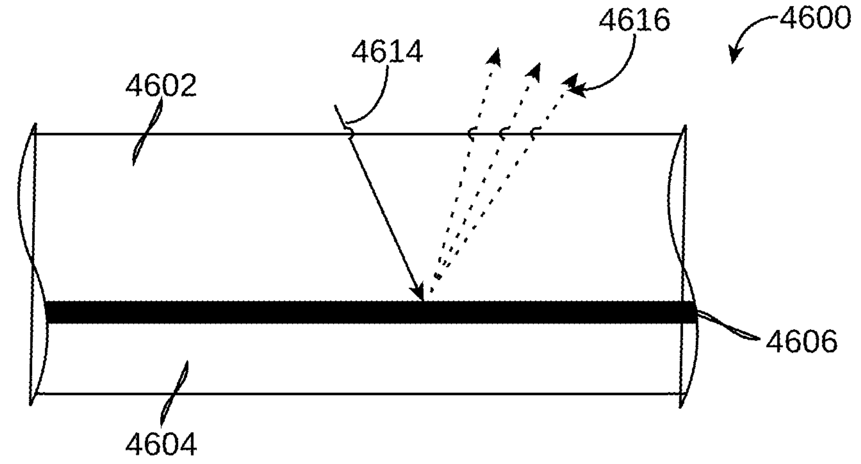

FIG. 46D illustrates an alternative implementation of the SERS subsystem in which an excitation source 4614 is incident on the film 4606 on the opposite side as opposed to the configuration illustrated in FIG. 46B (i.e., after traveling through the fluid media 4602 rather than through the lower wall 4604). The inelastically scattered light 4616 also travels through the fluid media 4602 before it is captured by the light measurement component of the SERS subsystem.

Figure 47A:
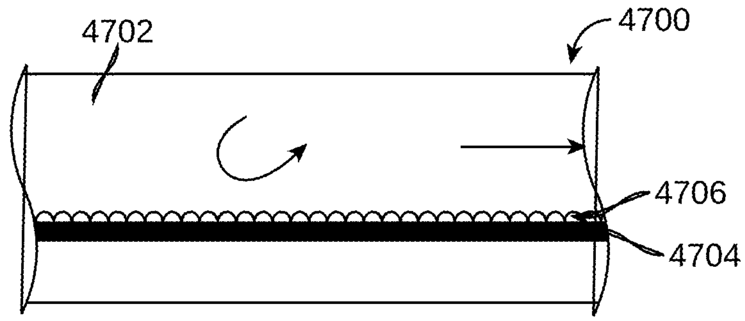
FIGS. 47A-F are diagrams depicting laser clearing of a cell culture container film during SERS measurement in accordance with various implementations.

FIGS. 47A-F are diagrams depicting laser clearing of a cell culture container film during SERS measurement in accordance with various implementations. FIG. 47A depicts a cell culture container 4700 containing fluid media 4702. The fluid media 4702 may be circulated and periodically refreshed. The cell culture container 4700 includes a film 4704 designed to enhance Raman scattering for SERS or resonant SERS. The film 4704 may reside on one of the walls of the cell culture container 4700, for example the bottom of a microwell plate container or the window of a bioreactor. Alternatively, the film 4704 may reside on a standalone substrate that is inserted into the cell culture container 4700. The film 4704 may also be semi-transparent to allow for imaging of the contents of the cell culture container 4700. The film 4704 may be flat. The film 4706 may be configured to remain on the one or more walls of the cell culture container 4700 when exposed to optical energy (e.g., from a laser) for imaging or cell editing purposes. During a cell culture process, the film 4704 may adsorb molecules or analytes, and/or be covered with cell debris, extracellular matrix, or cell growth byproducts. These materials (termed "biofouling") form a layer 4706 on the film 4704.

Figure 47B:
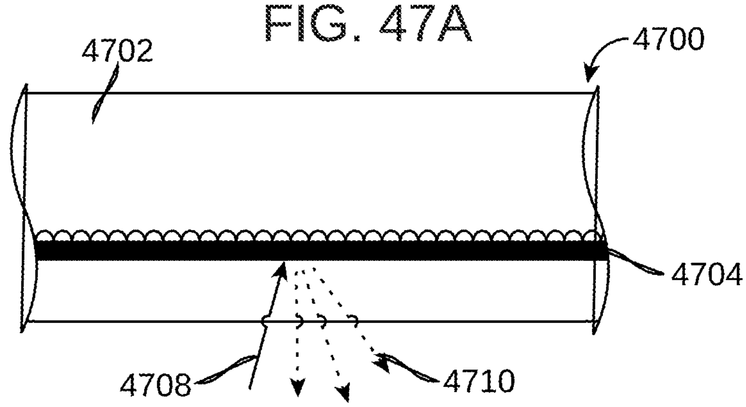

FIG. 47B illustrates a SERS measurement on the cell culture container 4700. A SERS subsystem emits excitation light 4708 that impinges on the film 4704, which results in inelastic scattered light 4710 that is collected and spectrally measured to ascertain the chemical composition of material proximate to the film 4704. In this scenario, the signal from the scattered light 4710 may represent information that is a combination of the biofouling layer 4706 and components of the liquid media 4702.

Figure 47C:
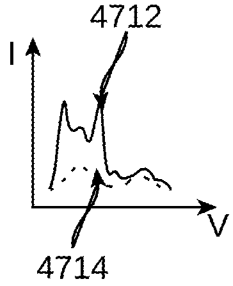

FIG. 47C is a chart showing an intensity spectrum 4712 of the scattered light 4710 collected by a SERS subsystem after reflection from the film 4704, with intensity on the Y-axis and wavenumber on the X-axis. The intensity spectrum 4712 may be a combination of the signal from the liquid media components (shown as media spectrum 4714) and the biofouling layer 4706 components. Thus, the compound intensity spectrum 4712 cannot be used to accurately determine characteristics of the liquid media components.

Figure 47D:
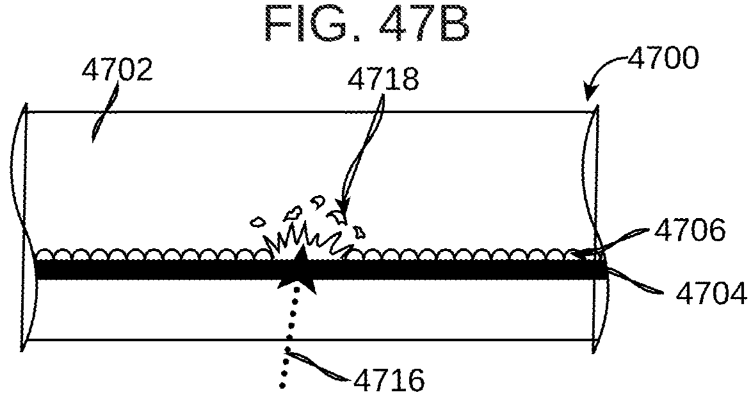

FIG. 47D illustrates optical clearing of the biofouling layer 4706 in the cell culture container 4700 in accordance with various implementations. One or more laser pulses 4716 are directed at the film 4704. These laser pulses 4716 are at a wavelength and duration configured to be absorbed by the film 4704 and create sufficient local energy to cause explosive microbubbles 4718 to form at the film surface. The explosive expansion and subsequent collapse of the microbubbles 4718 ablates a portion of the biofouling layer 4706 from the surface of the film 4704.

Figure 47E:
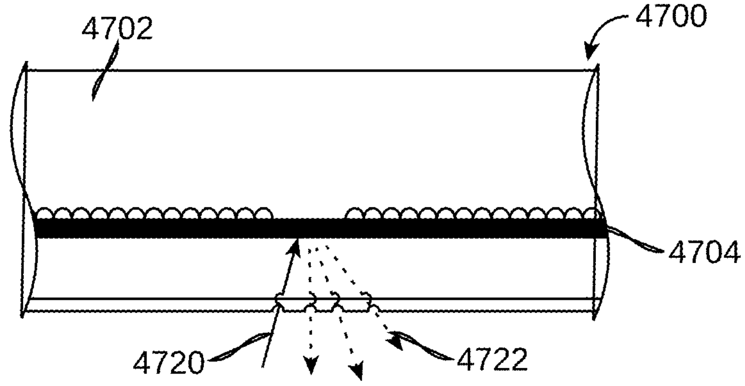

FIG. 47E illustrates a SERS measurement on the cell culture container 4700 after the optical clearing operation on the biofouling layer 4706. The SERS subsystem emits excitation light 4720 that impinges on the film 4704 at the spot where it was optically cleared, and the resultant scattered light 4722 is collected and spectrally measured to ascertain the chemical composition of material proximate to the film 4704.

Figure 47F:
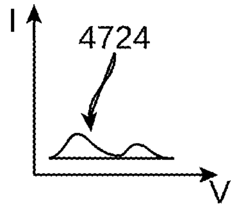

FIG. 47F is a chart showing an intensity spectrum 4724 of the scattered light 4722 collected by a SERS subsystem after reflection from the film 4704 after optical clearing. The intensity spectrum 4724 is now representative of the surrounding cell media, without the biofouling molecular signals that previously dominated. Thus, an accurate representation of the cell media state can be measured, for example for measuring levels of nutrients, waste, vitamins, proteins, cell products, etc. Moreover, by using the intensity spectrum 4712 prior to clearing as well as the intensity spectrum 4724 post-clearing, the differential spectrum resulting from the biofouling may be calculated. The biofouling or biolayer signal may be indicative of longer-term biological state or cell culture state, as it represents the accumulation of material over time. In such a manner even molecular species that are at low concentration but that tend to accumulate on the surface of the film 4704 over time may be measured with high sensitivity. The rate of accumulation/adsorption may also be measured by repeated accumulation, measurement, clearing, measurement, accumulation, etc.

Figure 48A:
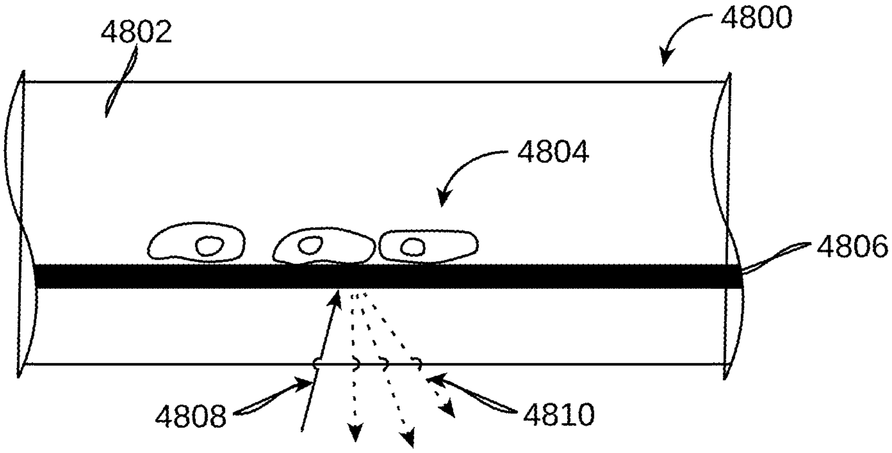
FIGS. 48A-C are diagrams depicting poration of cells in a cell culture container during SERS measurement in accordance with various implementations.
Figure 48B:
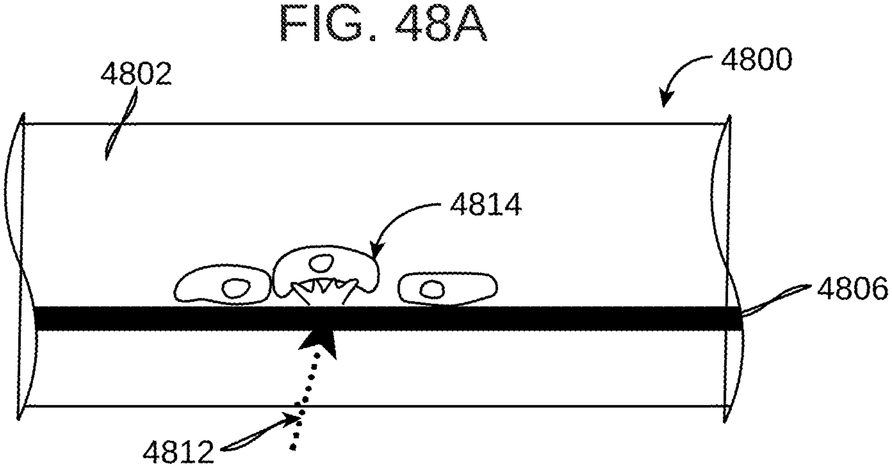
Figure 48C:
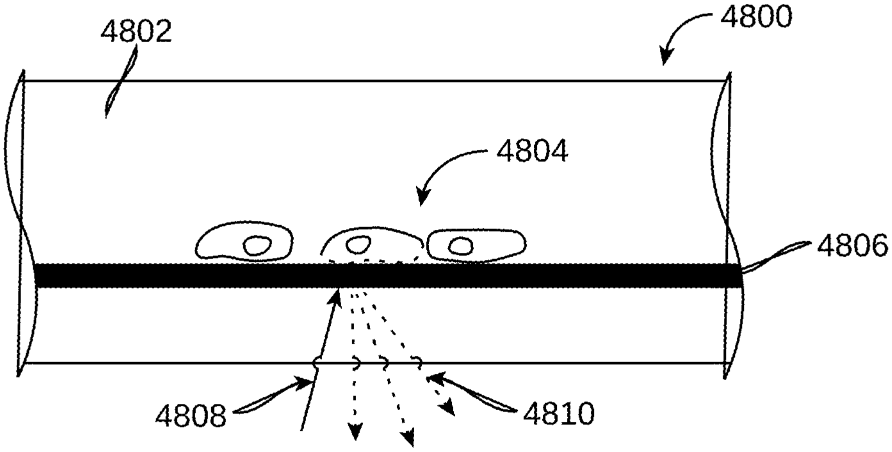

FIGS. 48A-C are diagrams depicting poration of cells in a cell culture container 4800 during SERS measurement in accordance with various implementations. FIG. 48A illustrates the cell culture container 4800 containing fluid media 4802 and cells 4804 resting or adherent on a film 4806. The cells 4804 may be adherent cells that adhere to the surface of the film 4806, or suspension cells that are resting on the film 4806. A SERS measurement (with excitation light 4808 and captured scattered light 4810) may be made, which measures the local chemical environment under one or more of the cells 4804. However, since SERS measures chemical composition in a manner extremely local to the resonant structure, it will not measure cellular composition. Rather, what is measured is the conditions of the fluid media 4802 as it is affected by cell condition and metabolism, and perhaps components of the cell membrane that are in direct contact with the film 4806. These measurements may in many cases be sufficient to characterize a cell or clusters of cells. However, in other cases it may be desirable to measure cellular contents.

FIG. 48B illustrates the use of a pulsed laser mechanism 4812, together with the film 4806, to create an explosive microbubble 4814 under a target cell or cells. The same laser pulses 4812 may clear any biofouling from the film 4806, as previously described. The expansion and collapse of the microbubble 4814 generates energy that causes the membranes of nearby cells to partially porate, making it easier for biological materials to enter and exit the cells. In some cases, the pulsed laser mechanism 4812 may emit sufficient intensity to cause destructive lysing of cells via the microbubble 4814, meaning that all the contents of the cell are released into the fluid media 4802.

FIG. 48C illustrates SERS measurement of cells in the cell culture container 4800 after partial poration. When a cell membrane is partially porated, some cell contents escape into the surrounding fluid media. A SERS measurement (with excitation light 4808 and captured scattered light 4810) is then able to capture information about the cell contents, and thus the internal contents of cells can be released and measured on demand. Such functionality may be used to manage cell cultures, in which SERS measurements may be used to profile cells or regions of cells and the cell editing subsystem may be used to selectively lyse or remove certain cells based on these measurements. The SERS measurements may be combined with label-free imaging to make predictions/assessments of which cells to retain and which cells to lyse or remove. In combined imaging and SERS implementations, the film 4806 may be transmissive for label-free imaging such as by brightfield, phase, darkfield, differential interference contrast, differential phase contrast, phase-from-defocus, Fourier Ptychographic imaging, or other imaging techniques including but not limited to various quantitative phase imaging techniques.

Figure 49:
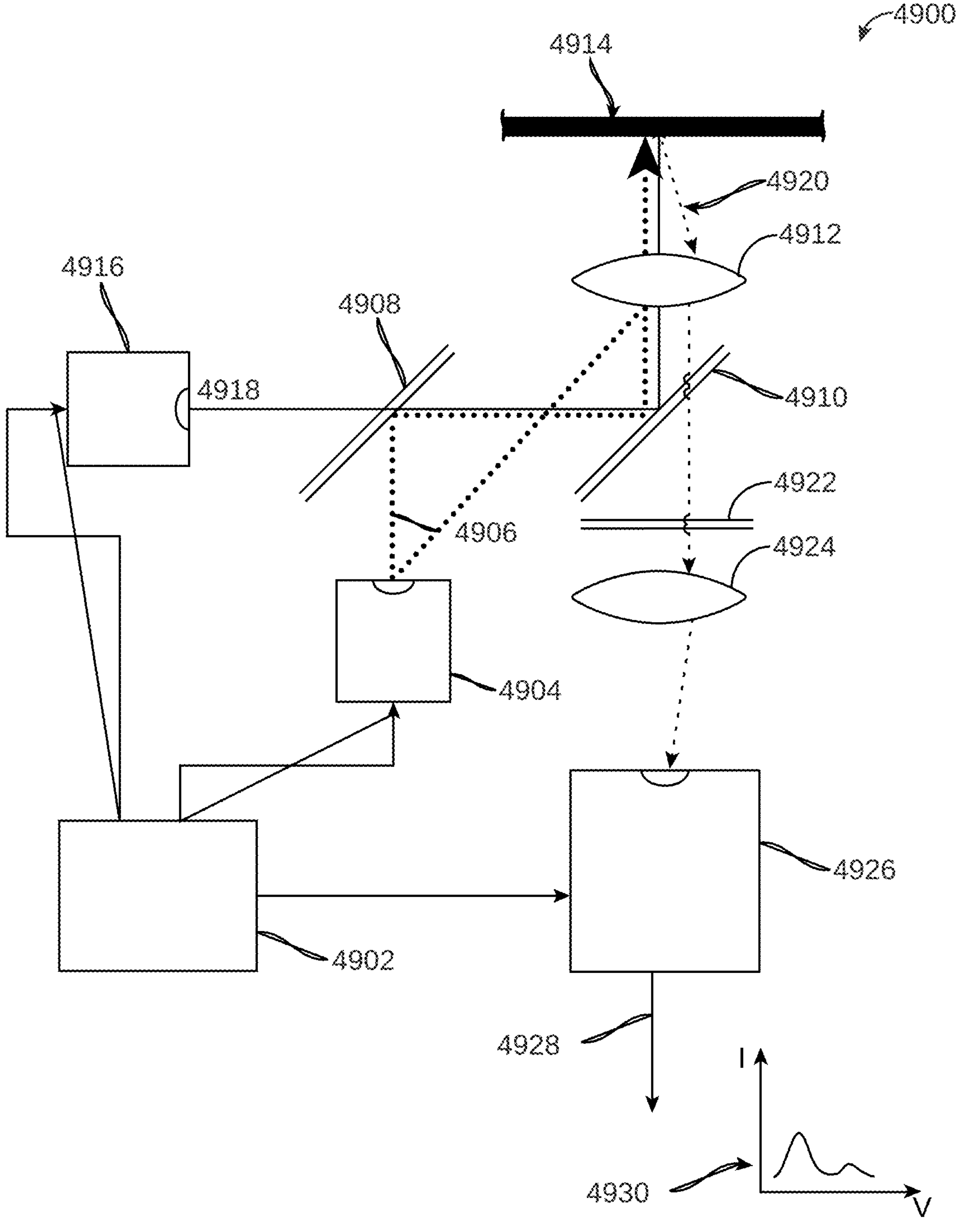
FIG. 49 is a block diagram of an example SERS subsystem for use in a cell culture system in accordance with various implementations.

FIG. 49 is a block diagram of an example SERS subsystem 4900 for use in a cell culture system (e.g., cell culture system 4500) in accordance with various implementations. The SERS subsystem 4900 may include a controller 4902 (e.g., computer or microprocessor) that controls a laser 4904 that produces pulsed light 4906 for the purpose of clearing a SERS substrate, such as a resonant plasmonic film in a cell culture container. The pulsed light 4906 is redirected by optical component 4908, which may either be a dichroic filter (when the clearing light wavelength is different from the SERS excitation wavelength) or polarization beam combiner (when the clearing wavelength is same or similar to excitation wavelength, but differently polarized for the purpose of combining the two beams). The pulsed light 4906 is then redirected again by a Raman filter 4910, which reflects excitation and clearing wavelengths, but passes through inelastically scattered light (higher wavelength than the excitation wavelength).

The pulsed light 4906 is focused by an objective 4912 onto film 4914, which is located in the cell culture container. The pulsed light 4906 may clear biofouling from the film 4914 in conjunction with SERS measurements. In addition, the pulsed light 4906 may be used to porate or lyse cells that are on or near the surface of the film 4914. Before and/or after this clearing and porating/lysing action, the controller 4902 activates an excitation source 4916, which is typically a laser source. The excitation source 4916 emits excitation light 4918 which passes through the optical component 4908, is reflected by the Raman filter 4910, and is focused onto the film 4914 via the objective lens 4912. The excitation light 4918 may be aligned with the clearing pulsed light 4906 so that that they target the same region. The relative beam sizes of the clearing pulsed light 4906 and the excitation light 4918 may be configured such that the spot size of the excitation light 4918 is smaller than the spot size of the clearing pulsed light 4906 on the film 4914 to ensure the excitation light 4918 samples only regions that have been cleared by the clearing pulsed light 4906.

Some inelastically scattered light 4920 results from the excitation light 4918 interaction with the film 4914 and surrounding molecules. Some of the scattered light 4920 is captured by the objective 4912 and passes through the Raman filter 4910. An additional laser line (rejecting) filter 4922 may be used to remove any residual excitation or clearing laser light from the signal of the scattered light 4920. A lens 4924 then focuses the scattered light 4920 to the entrance of a spectrometer 4926. The acquisition of the spectrum of the scattered light 4920 is controlled by the controller 4902. This may include triggering to coincide with excitation illumination, including systems where very short exposure time is used to generate time-resolved Raman spectra to distinguish Raman spectral signals (which are ultra-short duration) from autofluorescent signals (which have a longer overall duration). Such a time-resolved setup may be particularly useful when shorter excitation wavelengths (such as 532 nm) are employed: these produce strong Raman spectra, but also excite autofluorescence in many materials. The spectrometer 4926 may generate an output spectra 4928 from the scattered light 4920, which may be supplied to a downstream computing system for analysis (e.g., computing subsystem 110, 4500), usually as an array of intensities versus wavelengths or wavenumbers as depicted schematically by graph 4930.

Figure 50:
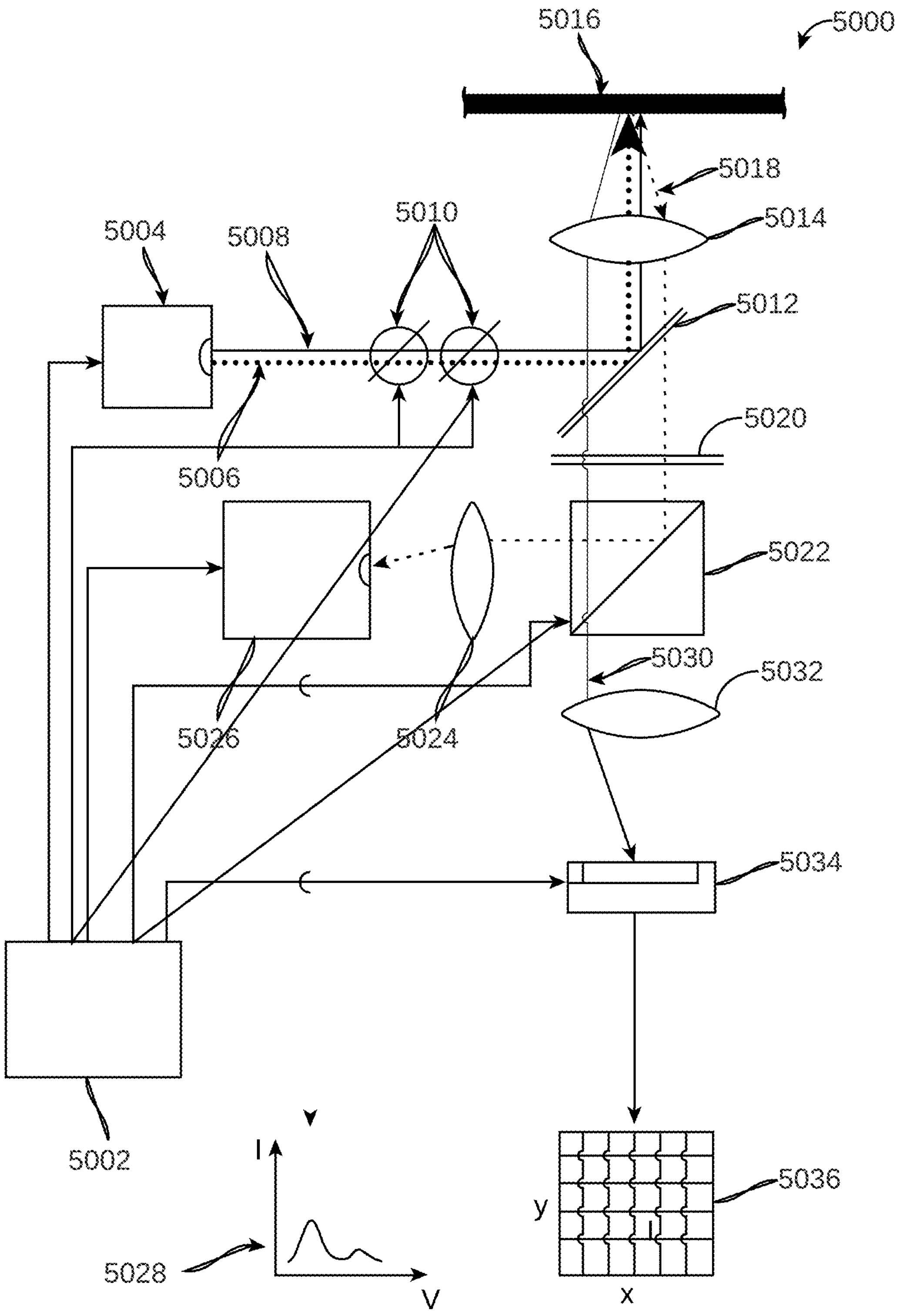
FIG. 50 is a block diagram of another example SERS subsystem for use in a cell culture system in accordance with various implementations.

FIG. 50 is a block diagram of another example SERS subsystem 5000 for use in a cell culture system (e.g., cell culture system 4500) in accordance with various implementations. In this implementation, a single laser source may be used for both film clearing and SERS measurement operations, and images of the biological sample may be captured alongside a spatially-resolved SERS spectrum. In addition, the multi-use laser may also be configured to porate or remove cells proximate to the film.

The SERS subsystem 5000 includes a controller 5002 (e.g., computer or microprocessor) that controls a laser source 5004 used for both film clearing and Raman excitation operations. The laser source 5004 may generate clearing pulses 5006 generally being of higher peak energy than Raman excitation light 5008. Both the clearing pulses 5006 and the excitation light 5008 are steered in two axes by steering mechanisms 5010 so that they impinge a film 5016 within the field of view of an objective 5014 after being reflected by a Raman filter 5012. The film 5016 may be located in a cell culture container containing fluid media and a cell culture. Cells and/or biofouling may be resting on the film 5016.

Scattered light 5018 from the film 5016 is collected by the objective 5014, and the inelastically scattered portion (shifted wavelength) of the scattered light 5018 passes through the Raman filter 5012. In some implementations, the scattered light 5018 may pass through an optional filter 5020 to remove any remaining laser light from the beam. In alternate implementations, this functionality may be part of the next component in the beam path, optical switch 5022. The optical switch 5022 allows light to be diverted either to a spectroscopy path (leftward direction in FIG. 50) or an imaging path (downward direction in FIG. 50). The optical switch 5022 may be toggled by the controller 5002 depending on the desired mode. In implementations in which the laser cleanup filter (i.e., filter 5020) is integrated into the optical switch 5022, there may be an optical component in the optical switch 5022 that passes through laser light to the imaging path, and not reflect it into the spectroscopy path. This may be useful for calibration and other purposes in which a small fraction of the steered laser light passes through to the image sensor, for the purpose of XY calibration in the scanning system, and potentially focusing of the laser system on the film 5016 via spot size imaging.

In Raman spectroscopy or measurement mode, the optical switch 5022 diverts the inelastically scattered light 5018 to a tube lens 5024, which directs light into a spectrometer 5026. By virtue of the steering system, the SERS subsystem 5000 may build up a hypercube of spectral data on a "pixel" (XY dimension) basis, in which each pixel has a spectrum (such as the one represented by graph 5028) associated with it. In the imaging mode, the SERS subsystem 5000 allows imaging of the same region. For example, imaging light 5030 may be acquired using an illumination source (not shown), in which light passes through a biological sample on the film 5016, is collected by the objective 5014, and then passes through filters 5012 and 5020. The optical switch 5022 is switched to allow the imaging light 5030 to pass through and is focused by a tube lens 5032 onto an image sensor 5034. The image sensor 5034 is triggered by the controller 5002 and produces a pixel image 5036. In some implementations, the illuminating wavelength for imaging may be configured to not require an optical switch, but rather accomplish the splitting of spectroscopy light from imaging light using a bandpass or dichroic filter.

The combination of spectroscopy and imaging capabilities allows imaging of cell cultures and acquisition of corresponding spatially-resolved Raman spectra, which supports a number of system modalities. For example, the SERS subsystem 5000 may acquire an image of the cell culture using one of several imaging modalities (including reflection, transmission, fluorescence, etc.) and also acquire a spatial SERS map of the cell culture. The SERS measurement may be made both before and after a clearing function of the laser (which may include clearing of biofouling on the film and/or poration of the cells for analysis of intracellular contents by SERS). The clearing function and SERS measurement may be performed on all or part of the imaged area. For example, the clearing and measurement may be performed only in regions of interest that are generated by image processing of the imaging data. The two image sources may then be combined for use in a predictive model (e.g., run by a computing subsystem) that makes predictions on success or fate of certain cell regions. Finally, the clearing laser may be used to lyse cells that are deemed not progressing along the desired trajectory.

In some implementations, the SERS subsystem 5000 may be used to train imaging-based algorithms using SERS training data, in which SERS has been pre-correlated with cell fates, phenotypes, etc. For example, one model may have been trained with spatial SERS data (medium throughput, inexpensive) and then corresponding transcriptomic data (low throughput, expensive). Then the SERS subsystem 5000 may be used to correlate spatial features in the image data to transcriptomic profiles via the SERS measurement.

Figure 51:
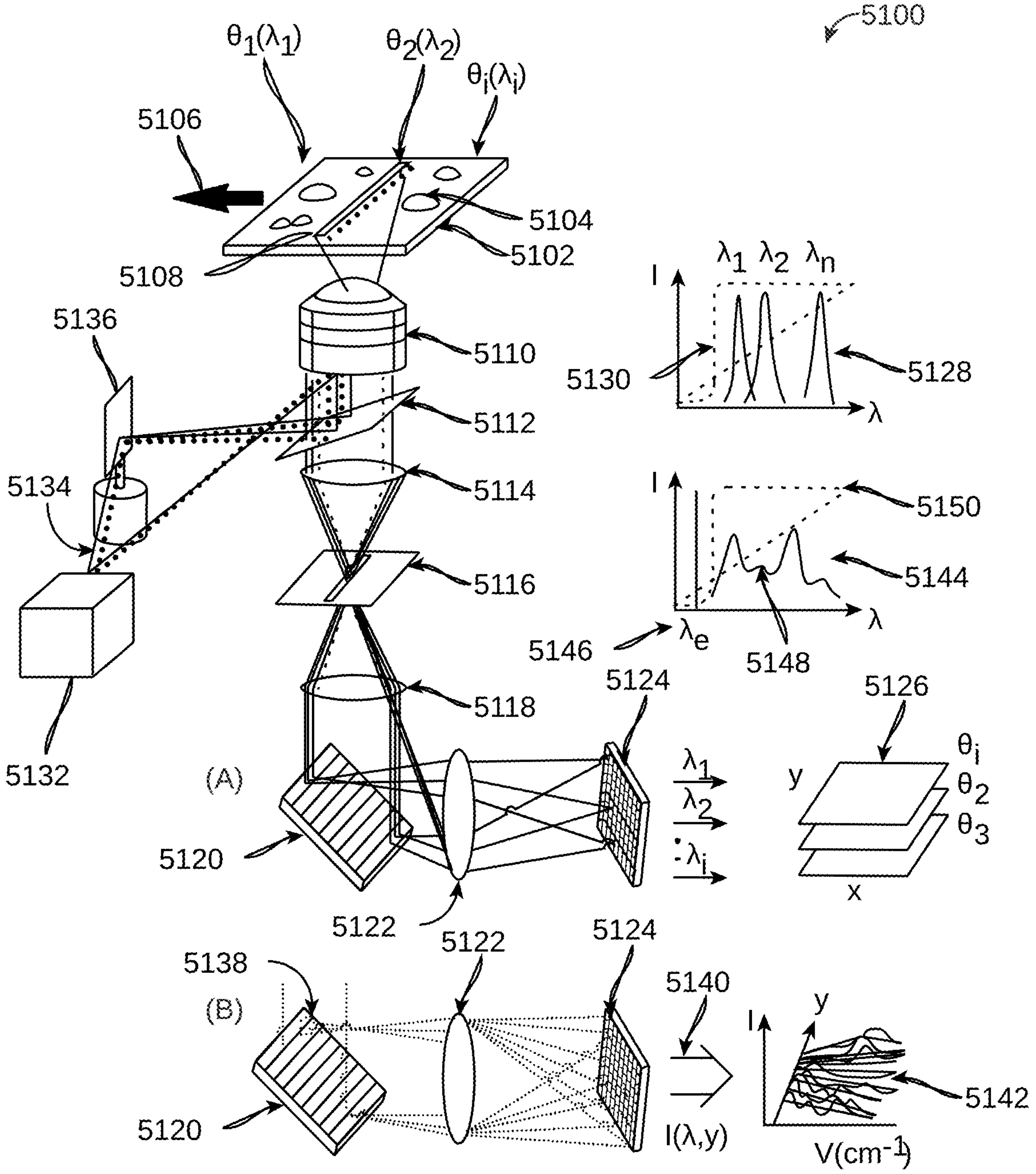
FIG. 51 is a block diagram of another example SERS subsystem for use in a cell culture system in accordance with various implementations.

FIG. 51 is a block diagram of another example SERS subsystem 5100 for use in a cell culture system (e.g., cell culture system 4500) in accordance with various implementations. The SERS subsystem 5100 includes a semi-transparent SERS and laser-absorbing film 5102 situated inside a cell culture container with cells 5104 settling or adhering to the surface with the film 5102. The cell culture container may be translated relative to the optical subsystem of the SERS subsystem 5100, indicated by arrow 5106. As continuous translation of the cell culture container occurs, a single linear region of interest (ROI) 5108 is interrogated by the optical subsystem in either or both an imaging mode and a measurement mode. The imaging mode may be suitable for quantitative phase image (QPI) reconstruction, and the measurement mode may use SERS to measure the local spatial biochemical content of the cell culture, with the potential addition of biofouling clearing functions, cell poration, and cell lysis functions as described herein.

When the SERS subsystem 5100 is in imaging mode, illumination for transmission imaging may be provided at multiple wavelengths, each one of which corresponds to a unique distribution of illumination angles $\theta_1$ through $\theta_1$. Illumination of a sample at multiple known angle distributions may be used to reconstruct the phase of the sample using differential phase contrast (DPC) or Fourier Ptychography algorithms. The use of wavelength multiplexing allows single-shot acquisition of multiple illumination conditions within the ROI 5108 during continuous motion. For each wavelength/angle distribution, some light is diffracted into an objective 5110, passes through a Raman filter 5112, is focused by lens 5114 through a slit 5116 that defines the ROI 5108 and prepares the light for spectral analysis, and then re-collimated by a lens 5118. The collimated light is then diffracted by a grating 5120, which is shown as a reflective grating in FIG. 51 but may also be a transmission grating or dispersive prism.

After the collimated light is dispersed by wavelength by the grating 5120, it is focused using tube lens 5122 onto an image sensor 5124. The linear ROI 5108 is imaged onto the image sensor 5124 at multiple rows, each corresponding to one of the illumination wavelengths, and therefore corresponding to a specific known illumination angle distribution. The image sensor 5124 may be a machine vision CMOS image sensor that is configured to only image selected rows, and if the number of selected and digitized rows is small compared to the overall number of rows, the image sensor 5124 may run at very high frames rates, since data conversion and output is generally the bottleneck, not exposure time. As a result, the optical subsystem may be translated at high speed relative to the sample, with the images (one per illumination condition per wavelength) being built up row by row into 2D planes 5126. The resulting stack of 2D planes 5126 correspond to different illumination conditions and may be used directly by a model, for example a deep learning network, or the 2D planes 5126 may be processed into a representation of phase delay and amplitude by methods such as differential phase contrast or Fourier Ptychography. Graph 5128 shows a representation of different imaging wavelengths $\lambda_1$-$\lambda_n$ used to encode illumination angles in a plot of intensity versus wavelength. The dashed line 5130 indicates the transmission of the Raman filter 5112, which is configured to reflect excitation/clearing laser light and prevent it from interfering with image sensing.

When the SERS subsystem 5100 is in measurement mode, a laser source 5132 (e.g., a 532 nm nanosecond pulsed laser) emits an excitation beam 5134 at an energy sufficient for SERS measurements. The excitation beam 5134 is scanned across the linear ROI 5108 using a scanner 5136 and reflected towards the objective 5110 by the Raman filter 5112. The excitation beam 5134 is focused on the film 5102, where it produces scattered light, including inelastic scattered light (shown in dashed lines) which is captured by the objective 5110, passes through the Raman filter 5112, focused by the lens 5114 through the slit 5116, and then is recollimated into a beam 5138 that impinges on the diffraction grating 5120. This beam path is the same path taken by the imaging light when the SERS subsystem 5100 is in imaging mode.

The beam 5138 is diffracted by wavelength by the diffraction grating and focused by the lens 5122 onto the imaging sensor 5124. The beam wavelengths are spread continuously along the vertical axis of the imaging sensor 5124 (the horizontal axis corresponds to position along the linear ROI 5108), so an output 5140 of the imaging sensor 5124 is Raman intensity as a function of wavelength and Y axis (where Y is perpendicular to the motion of the sample relative to the optical subsystem). In measurement mode, the light scanning uses a continuous section of the imaging sensor 5124 rather than discrete rows (as opposed to the imaging mode) and the signal levels are likewise significantly lower than in imaging mode, so the motion of the sample relative to the optical subsystem should be slower if high spatial resolution was desired.

The composite wavelength data for a single linear ROI is shown by graph 5142. These images are compiled per X location as the SERS subsystem 5100 scans to form a "data cube" with X, Y, and frequency dimensions. In measurement mode, the SERS subsystem 5100 may be used to measure cell media, accumulated biofilms or other compounds, cell components, or intracellular components that have been extracted using the methods described above. Graph 5144 shows a spectrum of the SERS subsystem 5100 operating in measurement mode, and includes the excitation wavelength 5146, the inelastically scattered light spectrum 5148, and the transmission of the Raman filter 5150 (which excludes the excitation wavelength from the measurement system).

In some implementations, the SERS subsystem 5100 may have additional functionalities or modes. For example, the laser 5132 may emit laser pulses at higher energy levels to clear biofouling from the surface of the film 5102 prior to measurement of media, or after measurement of biofilm, or both. In another example, the laser 5132 may emit laser pulses to reversibly porate or lyse cells on or near the film 5102 for the purpose of measuring cell contents using the SERS subsystem 5100. In another example, the laser 5132 may emit laser pulses to reversibly porate cells for the purpose of delivering compounds into them (e.g., intracellular delivery). In another example, the laser 5132 may emit laser pulses to lyse cells for the purpose of removing them from the cell culture, thereby selectively expanding other cells in the cell culture, which may be done based on measurements made by the imaging mode and/or spectroscopy modes described herein.

Cell Culture Membrane with Laser Activated Film

Porous membranes may be utilized for certain cell culture operations, including but not limited to expansion, differentiation, co-culture, maturation, filtration, selective migration, and harvest of cell output. In the implementations disclosed herein, such porous membranes may also include a laser-activated layer (such as the films disclosed with reference to FIGS. 40-44) for processing supported cells via laser illumination.

In implementations disclosed herein, the cell culture system may utilize a porous membrane or sheet made of an optically-clear material, typically a foil with a thickness on the order of tens of microns (often a polymer such as polyester or polycarbonate). The pores in this membrane may have a uniform diameter distribution and density of pores per unit area, with pores sized so as to allow transport of certain substances and cell components but not others. Membranes may be formed from a range of materials, including but not limited to polydimethylsiloxane (PDMS), thermoplastic polymers, polyester, polycarbonate, polystyrene, polyethylene glycol, and other materials. They may be formed by known processes including but not limited to track etching, photo nano imprint lithography, nanoimprint lithography, polymer self-assembly, 3D printing techniques, or electro spinning.

There may be an optical coating or film applied to at least once side of the membrane, in which the optical film absorbs laser radiation for the purpose of affecting cells locally. The film may be semi-transparent, or transparent in some wavelength ranges, to allow imaging of cells on or near the surface of the membrane. The film may be resonantly absorbing so as to absorb laser radiation more strongly at one wavelength, while allowing wavelengths for imaging to be passed through with higher transmission. The film may be composed of metallic nanoislands or nanospheres that are attached to the surface of the membrane. The film may contain fiducial markings for the purpose of ascertaining spatial location in XY (in the plane of the membrane) and/or Z (axially perpendicular to the membrane) planes.

Figure 52:
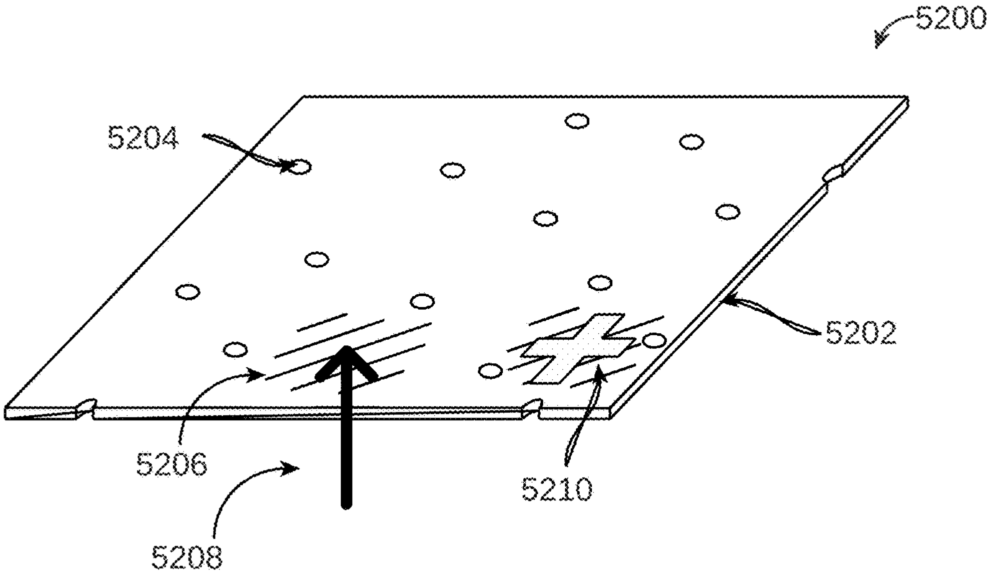
FIG. 52 is a diagram of a porous membrane for use in a cell culture container in accordance with various implementations.

FIG. 52 is a diagram of a porous membrane 5200 for use in a cell culture container in accordance with various implementations. The membrane 5200 may be composed of a sheet 5202 of material, which may be a polymer such as polyester or polycarbonate. The membrane 5200 has pores 5204 that allows transport of media, factors, or cell products but prevent cells from passing through the membrane 5200. The membrane 5200 may be spun material with defined pore sizes, or in other cases a track-etched membrane in which radiation and etching is used to define average pore size and density (for example ipCELLCULTURE™ track-etched membrane filters from it4ip SA, Belgium).

The membrane 5200 may also include an optical film 5206 that is designed to absorb laser radiation 5208 for the purpose of affecting cells growing on the membrane 5200. For example, the laser radiation 5208 may be converted by the film 5206 to heat to locally disrupt or destroy cells thermally. In some implementations, pulsed laser radiation 5208 may be absorbed by the film 5206 and cause rapid formation of explosive microbubbles which disrupt or destroy cells mechanically. In either case, cells may be permanently destroyed through necrosis or apoptosis, or experience temporary membrane disruptions/poration that allows intracellular delivery of molecules, or extraction of cellular components for analysis or downstream use. The membrane 5200 and film 5206 may be optically clear and transparent in at least one wavelength range so that high-quality cell imaging may be performed within this wavelength range. In such a case, the film 5206 may further include fiducial marks 5210 for the purpose of registration and focus for imaging and laser operations. In some implementations, the film 5206 may be flat. In some implementations, the optical film may be disposed on the opposite face of the membrane than where the cells will attach. In this case, incident pulsed laser radiation is absorbed by the film to cause rapid formation and subsequent collapse of explosive microbubbles, which impart forces through the pores of the membrane to the cell layer on the opposite side to disrupt or destroy cells mechanically or to temporarily porate cell membranes for the purpose of delivering or extracting intracellular compounds. In this case, the compounds may be introduced or extracted in the liquid on either the cell-bearing side or non-cell-bearing side of the membrane.

Figure 53:
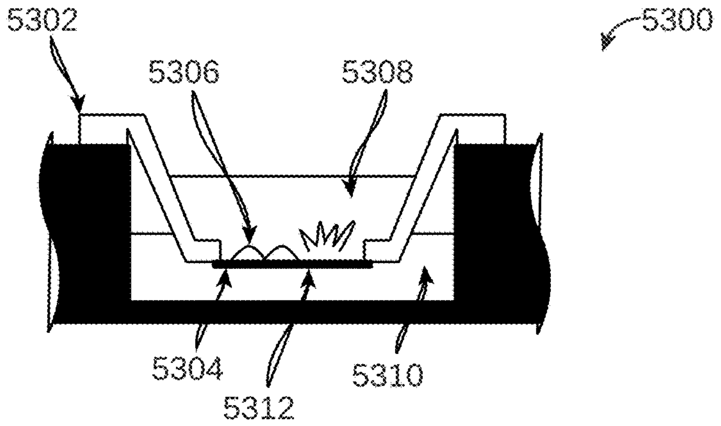
FIG. 53 is a diagram illustrating use of a porous membrane in a multi-well plate in accordance with various implementations.

FIG. 53 is a diagram illustrating use of a porous membrane in a multi-well plate 5300 in accordance with various implementations. A well insert frame 5302 is placed into a well of the multi-well plate 5300. The well insert frame 5302 supports a membrane 5304 including a laser film (as described with reference to FIG. 52), which supports the growth of cells 5306. The membrane 5304 also separates a top media compartment 5308 from a bottom compartment 5310. The separated media compartments 5308, 5310 may be used to influence cell behavior or differentiation, or to allow for cases where cells excrete directionally (for example, retinal pigment epithelial cells that expel waste, and form bubbles under a cell sheet if not placed on a porous membrane or support). The membrane with film 5304 may support imaging of the cells 5306 growing on the surface of the membrane 5304, and a laser source 5312 may be used to selectively destroy or disrupt the cells 5306. FIG. 53 illustrates an example using pulsed laser induced explosive microbubble formations to lyse or porate cells, but manipulation of cells through the membrane 5304 is not limited to the approach shown in FIG. 53.

Furthermore, in configurations with two compartments separated by a porous membrane such as illustrated in FIG. 53, electrical measurements may be made between the two liquid compartments. Such measurements may include, for example, a transepithelial/transendothelial electrical resistance (TEER) measurement which can measure the integrity and properties of a sheet of cells grown on the membrane. Such a measurement may be combined with image analysis to correlate image characteristics with electrical properties and may further be combined with laser processing to help elucidate spatial relationships between cell image characteristics and electrical measurements by selectively destroying or temporarily porating cells using a laser system and the laser film on the membrane.

Figure 54:
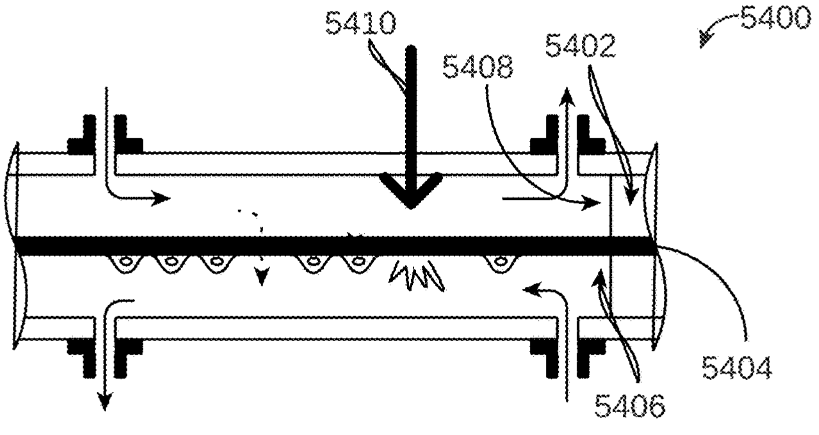
FIG. 54 is a diagram illustrating use of a porous membrane in a cell culture container in accordance with various implementations.

FIG. 54 is a diagram illustrating use of a porous membrane in a cell culture container 5400 in accordance with various implementations. The cell culture container 5400 includes a frame 5402 that holds in place a membrane 5404. The membrane separates the cell culture container 5400 into a lower chamber 5406 and upper chamber 5408. Cells may be cultured on either (or both) sides of the membrane 5404. Both chambers 5406, 5408 may have ports for the purpose of flowing in and out liquid such as cell media and reagents. Cells growing on the membrane 5404 may be imaged, and then a laser source may be used to illuminate selected areas. In the example shown in FIG. 54, the laser source emits laser pulses 5410 that cause explosive microbubble formation for the purpose of destroying selected cells.

The porous membrane described with reference to FIGS. 52-54 may be used for multiple purposes in a cell culture container. For example, some cells ingest compounds from one side and/or excrete on another. A porous membrane may enable cell excretions to be separated effectively and prevent bubbling of cell sheets. In another example, different cell types may be cultured on opposite sides of the membrane, in which one set of cells is supported by the other. This may include cases in which both cell types are adherent, or one cell type is adherent and another is in suspension, or when both are in suspension.

In another example, exogenous compounds including reprogramming or gene editing constructs or compounds may be delivered through one chamber of a cell culture chamber, which may be optimized for minimum volume. These compounds may then be delivered in close proximity to the cells through the membrane. In some implementations, laser pulses may be used to facilitate intracellular delivery of the compounds. In another example, the membrane may enable directional delivery growth factors or nutrients that may facilitate proper development of cells. In another example, when cell constituents or products such as endogenous factors or exosomes are desired, they may be harvested from the cells through the membrane and efficiently extracted by flowing out of the cell culture chamber. This harvest may be promoted by laser action on the film attached to the membrane.

In another example, a device with a porous membrane equipped with a laser activated film may be used to managed suspension cells in culture, either during an all-suspension process or in a process in which cells become adherent. The membrane may be used to create pressure differentials that pull suspension cells onto the surface, where they may be imaged and laser-processed (e.g., destroyed with a laser process, or temporarily porated to affect intracellular delivery). In another example, the pressure differential method may be used hold non-adherent cells in place while the media in the cell culture chamber is exchanged, similar to a tangential-flow filtration system that retains particles in an active flow. In another example, the membrane may facilitate processes in which cells differentiate or activate and become migratory. The pores in the membrane may be traversed by cells that are to be selected (or de-selected), and factors or nutrients may be used to "pull" a subset of cells across the barrier for harvest or removal. This may be done in conjunction with image- and laser-based cell destruction or delivery operations. In another example, a sheet of cells may be separated from the membrane by flowing a medium containing a cell matrix-disassociating compound into the chamber opposite the cell growth chamber. The compound penetrates the membrane through the pores and detaches the cell sheet from the membrane intact. This technique may be used for cell harvesting or destruction/clearing of an entire sheet of cells.

System for Laser Cell Culture Management

Traditionally, laser sources and subsystems used in laser-based cell culture systems were originally built for industrial cutting and marking processes and were repurposed for biotechnology applications. These lasers are expensive, bulky, and require dedicated power and cooling systems. Moreover, they have a limited lifetime compared to other system components, and redundancy for continuous operation is required in cell manufacturing operations. Thus, what is needed in the art are cheap, small, and efficient laser subsystems that may be incorporated into cell culture systems.

The various implementations disclosed herein include systems and methods for sharing a common laser or lasers in a cell culture system. Sharing lasers among a plurality of cell culture containers and/or across a plurality of cell culture processes may enable a reduction in size, cost, and cooling requirements for the laser system as compared to traditional laser systems. In addition, there is also increased redundancy and fast switchover to a new laser source if one laser fails.

Figure 55:
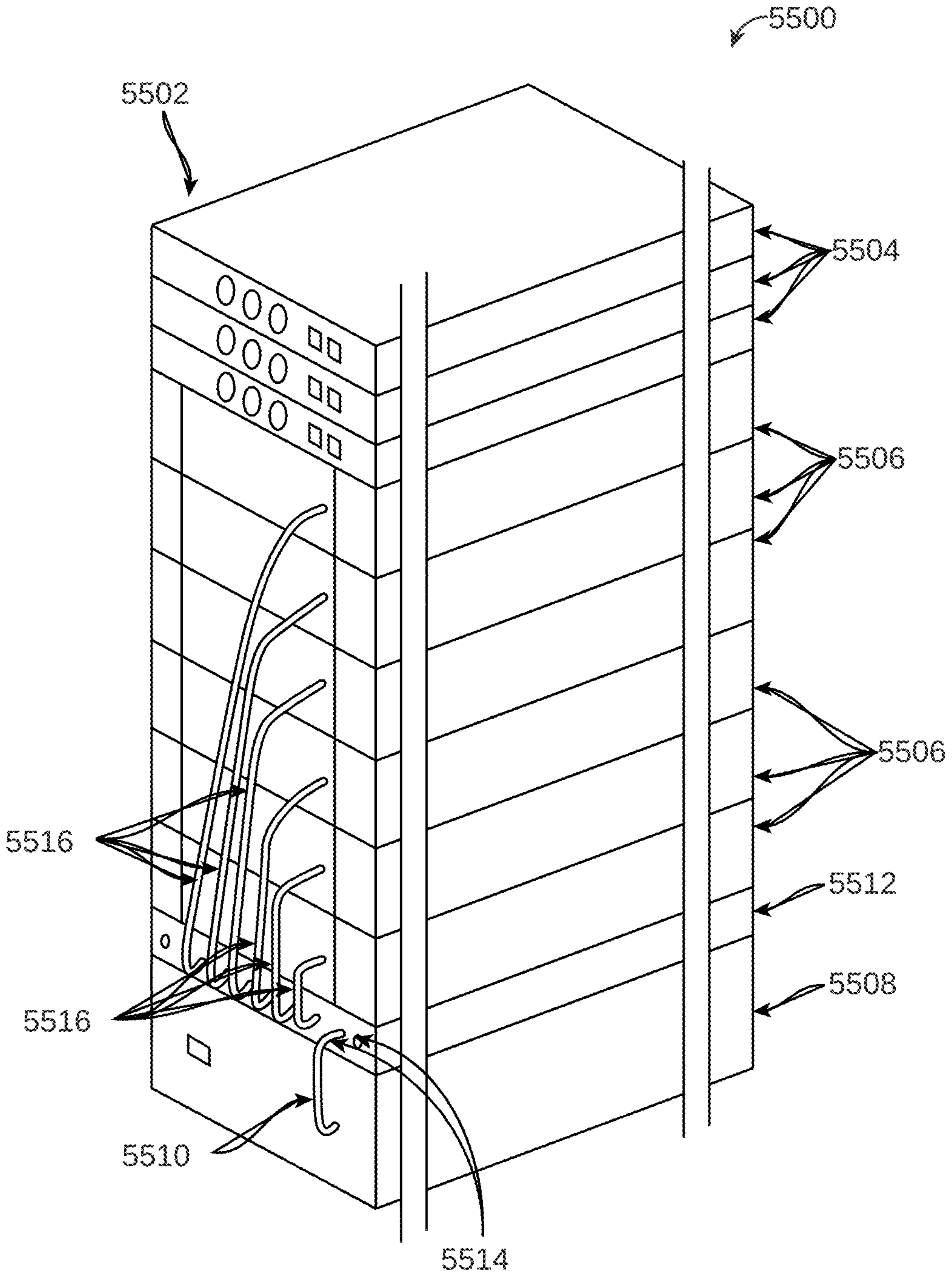
FIG. 55 is a diagram illustrating a cell culture system with shared laser resources in accordance with various implementations.

FIG. 55 is a diagram illustrating a cell culture system 5500 with shared laser resources in accordance with various implementations. The cell culture system 5500 may be embodied in a standard server rack format, as disclosed with reference to FIGS. 29-35. For example, the cell culture system 5500 may include several modules located within a server rack frame 5502. The cell culture system 5500 may include one or more computing subsystems 5504 (e.g., computing subsystem 110) co-located with cell process modules to provide image processing, laser patterning, or other computation, storage, and communication services.

The cell culture system 5500 may include a plurality of cell process modules 5506 configured to accept cell culture containers (e.g., cell culture containers 104) with live cell cultures and monitor and manage these cell cultures. For example, the cell process modules 5506 may be configured to accept cassette-based cell culture containers, or alternatively cell culture container formats such as microwell plates, flasks, or roller bottles. The cell process modules 5506 may be configured to maintain environmental conditions (temperature, gas concentrations, etc.) and may manage media and reagent exchange in the cell culture containers. The cell process modules 5506 may also perform imaging and other measurements of the cell cultures in the cell culture containers.

The cell process modules 5506 may be further configured to perform laser-based operations on the cell cultures in the cell culture containers. These operations may include destruction of cells, whether of specific cells as determined by an imaging subsystem, or pre-programmed areas/volumes of cells (e.g., to maintain a certain cell density or to harvest materials from a cell-based process). These cell operations may also include laser-driven intracellular delivery of compounds into live cells or extraction of intracellular components from live cells. These cell operations may be performed in a variety of ways, including but not limited to direct action of the laser on the cells or cell membranes, thermal action of the laser on the cells via an absorbing material, or mechanical action in which laser energy is converted into a mechanical energy such as a microbubble formation. The absorption mechanism by which the laser light is converted into thermal or mechanical energy may be direct plasma formation in the case of short-pulse high-intensity systems. In other cases, conversion may be accomplished through the use of an absorbing material, including but not limited to cell media, dye or particles in the cell media, nanoparticles, labels, or beads that either permeate the cell culture or attach based on specific receptors/structures, or layers of material specifically configured to absorb laser radiation.

To perform these cell operations, laser power in pulsed or continuous wave (CW) form is utilized, sometimes with very specific attributes such as wavelength, power, pulse energy, and duration. As a result, the laser sources for cell operations may be expensive and/or bulky systems that include supporting components for air or liquid cooling, power supplies, and monitoring and control systems. In addition, for high reliability it may be desirable to have backup lasers so that if one laser experiences degradation or malfunction, another laser may be immediately brought online so cell culture management processes are not interrupted.

The implementations disclosed herein overcome the limitations of cost, space, complexity, and reliability that are inherent to cell culture management process modules that each contain their own dedicated laser subsystems by enabling centralization and sharing of a common laser subsystem. The cell culture system 5500 includes a laser subsystem 5508 mounted on the server rack. In the configuration shown in FIG. 55, the output of the laser subsystem 5508 may patched via an optical fiber cord 5510 into an optical multiplexer 5512. The optical multiplexer 5512 accepts two laser inputs 5514 (one of which is connected in the example shown in FIG. 55) and provides laser power for cell process module use on a number of outputs (e.g., eight possible outputs as shown in FIG. 55), six of which are in use as shown in FIG. 55 by optical fiber patch cords 5516. In this manner, a single laser subsystem may be shared among a plurality of cell process modules 5506, significantly reducing the space requirements, cost, and complexity of each cell process module 5506.

Figure 56:
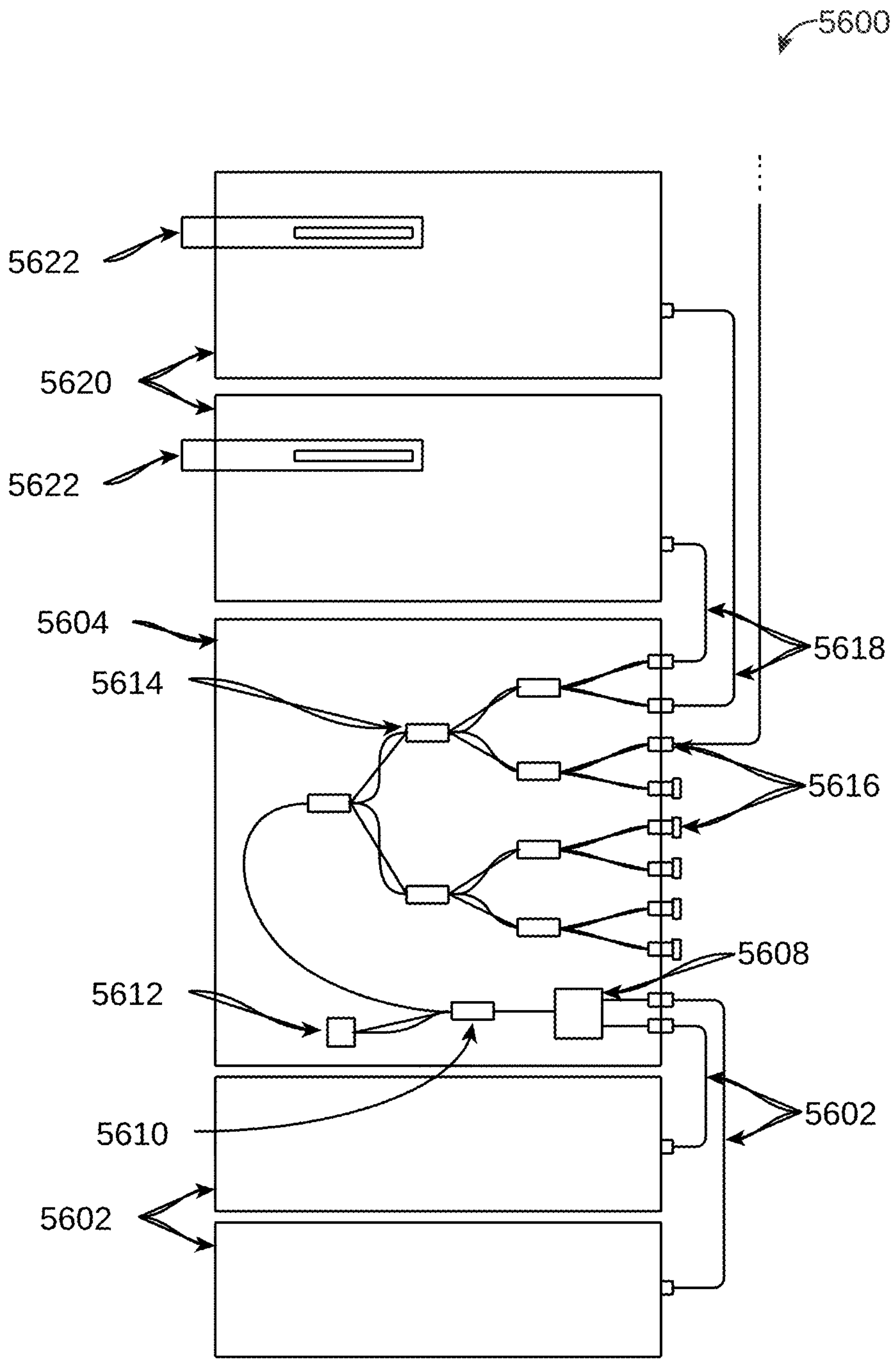
FIG. 56 is a diagram illustrating another cell culture system with shared laser resources in accordance with various implementations.

FIG. 56 is a diagram illustrating another cell culture system 5600 with shared laser resources in accordance with various implementations. The cell culture system 5600 may include two laser subsystems 5602 for redundancy, but in general the cell culture system 5600 may include any number of laser subsystems. In some implementations, the laser subsystems 5602 may be used to provide different illumination characteristics. For example, a 532 nm nanosecond-pulsed laser may be used provide high peak power pulses for cell lysing operations based on explosive microbubble formation, whereas a CW laser may provide narrow wavelength, stable 532 nm illumination output for Raman spectroscopic measurements, or high continuous power output for thermal operations on the cells or other cell culture components.

In some implementations, it may be desirable to deliver a specific polarization of light to the cell process modules and so the laser subsystem 5602 may be configured to output polarized light (e.g., at a specification of 100:1) and may include polarization-maintaining components such as optical fibers and optical couplers or splitters. A multiplexer 5604 may be configured to accept laser inputs from the laser subsystem 5602 via patch cables 5606 to panel connectors on the multiplexer 5604. In a typical server rack configuration, the patch cables 5606 may be arranged in the rear portion of the server rack along with power cables, tubing for heating/cooling, and tubing for gas distribution to keep the front clear for loading/unloading of cell culture containers.

The multiplexer 5604 may include an optical switch 5608 to select one of the laser inputs. A fiber tap 5610 may be used to divert a small amount of light to a monitor photodiode 5612. The monitor photodiode 5612 may be used to monitor laser power, pulse frequency, etc. to ascertain whether the currently-selected laser is functioning properly, or to detect degradation in function, and to allow switchover to a backup laser. The multiplexer 5604 may include a communications connection to the backup laser module to turn power on and go through a warmup process before switchover, or the backup laser may be running continuously, or kept in "warm" mode and switched over instantaneously.

The majority of the laser power then passes into a distribution subsystem 5614, which may be configured to evenly split the laser power among the cell process modules in the cell culture system 5600. The laser subsystems 5602 may be configured to produce a sufficient amount of laser power so that when it is divided each cell process module still receives sufficient laser power to perform cell operations. The distribution subsystem 5614 may include a series of evanescent fiber couplers with 50/50 output ratios to split the laser light into a number of output ports (eight in the example shown in FIG. 56, but in general there may be any number of output ports). In other implementations in which the ratio of laser power provided to the cell process modules to laser output is higher, the fiber couplers may be replaced by 1×2 optical switches, which may either be mechanical switches or waveguide-based switches such as Mach-Zehnder interferometer-based switches. The splitting or switching function shown in FIG. 56 may also be performed in free space, using 50/50 beam splitters or mechanical optical switches (including a 1×8 switch) for example.

The light outputted by the multiplexer 5604 may be outed to fiber connector ports 5616, which have delivery optical patch fibers 5618 attached when in use and are covered with absorbing terminator caps for eye safety when not in use. In some implementations when switchover redundancy is not required, the multiplexer 5604 multiplexer may be integrated into a single unit with the laser source. The optical patch fibers 5618 deliver laser light to cell process control modules 5620, where the light is used to process cell cultures in cell culture containers 5622. An example implementation of using a laser to perform cell operations on cell cultures may utilize a nanosecond laser source such as the Spectra-Physics SPFL 532 fiber laser, which produces 40 microjoule pulses (5 nsec) at 500 kHz. The cell process modules 5620 may only require ~50 nJ of pulse energy to form explosive microbubbles for cell deletion when using a plasmonic absorber film in the cell culture container. In this configuration, and taking into consideration an ample optical loss budget for connectors, couplers, and cell culture process module components, a single laser unit may be shared by sixteen process control modules (picking a power of 2 accommodated by most optical splitting schemes). This light may be delivered via a single-mode polarization-maintaining (PM) fiber such as ThorLabs PM-S405-XP PANDA fiber to maximize the amount of usable light (and minimize additional components) in the cell process modules 5620. For 50:50 splitting, 1×2 50:50 PM fiber couplers such as the ThorLabs PN530R5F1 may be used, and for monitoring purposes a 99:1 PM coupler such as the PN530R1F1 may be used.

Figure 57:
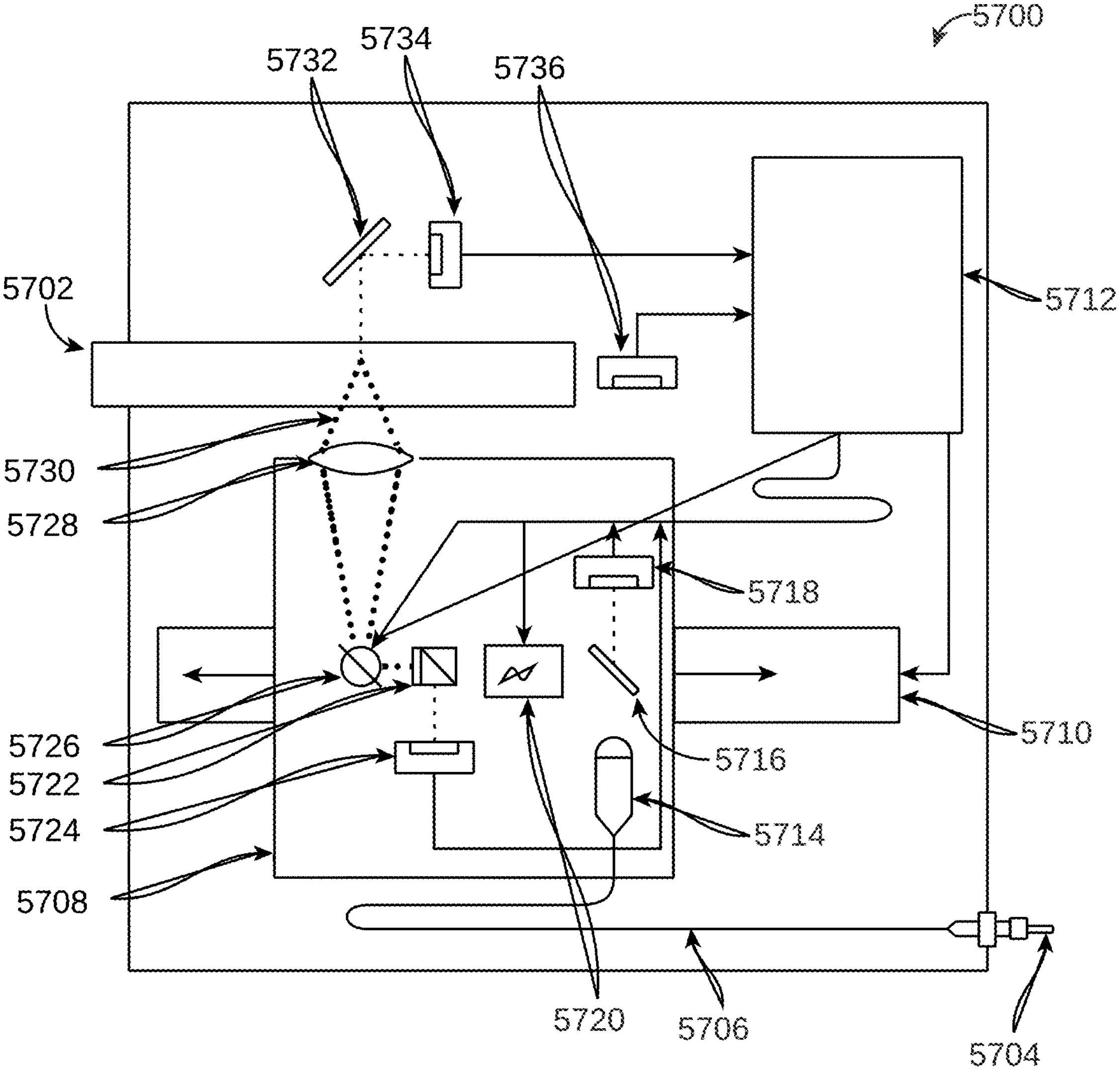
FIG. 57 is a diagram illustrating a cell process module utilizing shared laser resources in accordance with various implementations.

FIG. 57 is a diagram illustrating a cell process module 5700 utilizing shared laser resources in accordance with various implementations. The cell process module 5700 is configured to manage a cell culture in a cell culture container 5702, which may be a cassette with on-board media and reagents, or a standalone container such as a flow cell, a microwell plate, a flask, a dish, a roller bottle, or other container for cell cultures. The cell process module 5700 may manage temperature, pH, media exchange, reagents, etc., of the cell culture containers 5702. The cell process module 5700 may also be configured to use an imaging subsystem (which may be integrated with the laser processing system described herein) to image the cell culture (e.g., cell imaging subsystem 112).

Laser light may be delivered to the cell process module 5700 via an optical fiber connector 5704. A fiber 5706 may be connected to the optical fiber connector 5704 to a moving portion 5708 of an optical engine that moves freely along at least one axis, drive by a translation stage 5710 that simplifies the relay of laser light onto the moving assembly. A controller 5712 may be configured to coordinate coordinates multiple operations of the cell process module 5700, including monitoring photodiodes, motion and scanning, and laser pulse or power modulation. On the moving portion 5708, a fiber collimator 5714 produces a collimated free-space beam (shown as a dotted line in FIG. 57). A beam splitter 5716 allows a small percentage of light (e.g., 1%) to pass to a photodiode 5718.

The photodiode 5718 may be configured to measure the delivered laser pulse energy (or power in the continuous wave case) in real time for the purpose of adjusting the power or energy delivered to a sample. Moreover, in pulsed laser systems, the photodiode 5718 may be configured to feed electronics or firmware that acquires pulse timing from the optical signal, and coordinates internal component timing using this pulse train. This configuration takes advantage of Q-switched pulsed lasers or other lasers that provide a pulsed output with regular intervals, such that once a module is "locked on" to the timing of the pulses, it may synchronize its internal components reliably to the incoming laser pulses. For example, once there is a lock onto the pulse timing, an optical modulator 5720 (for example, an acousto-optic modulator) may modulate pulses on a pulse-to-pulse basis to tailor energy from point to point in the cell culture. The modulator 5720 may also provide steering of the beam along an axis. For example, when using an acousto-optic modulator, RF power controls the amount of light passing to the cell culture, whereas RF frequency may be used to change the output angle of the light to a small degree, allowing high-speed steering along one axis.

The modulated pulses then pass through a combined polarization beam splitter and wave plate 5722 which is configured to divert reflected laser light to a reflected-light monitoring photodiode 5724. The photodiode 5724 may be used to monitor the state of the cell culture container 5702, or coating applied to the cell culture container 5702. The photodiode 5724 may also be used to detect fiducial markings on the cell culture container 5702 or film within the cell culture container 5702 during laser scanning or imaging operations. The photodiode 5724 may also be used to detect focus using reflected laser light. The modulated laser light then is steered by a steering component 5726 that provides steering along at least one axis. The steering component 5726 may include a galvanometric mirror assembly, a spinning polygonal mirror, an acousto-optic deflector, a resonant electrostatically-driven mirror, or other light-steering components and their combinations. The steering axis may be configured such that after the beam passes through one or more lenses 5728 configured to focus light onto a region 5730 within the cell culture container 5702, the beam is steered roughly perpendicularly to the axis of motion of the moving portion 5708 of the optical engine as it is translated by the translation stage 5710.

The motion of the translation stage 5710, the modulation of the beam, and the scanning of the optical engine are all coordinated by the controller 5712. Another axis of motion which adjusts the axial position of the optics relative to the cell culture (the "focus" or "Z" axis) may be simultaneously controlled by positioning the lens 5728 or the cell culture container 5702, or by use of an adjustable lens within the lens assembly (not shown). The laser light that passes through the cell culture container 5702 may be captured on the opposite side. In the implementation shown in FIG. 57, a dichroic or laser band beam splitter 5732 may be used to divert light having the laser wavelength while passing through other light, for example light for illuminating the cell culture for imaging purposes (not shown). This assembly may move in unison with the moving portion 5708 of the optical engine to keep illumination and detection aligned with scanning portions. The laser light from the beam splitter 5732 is received by a photodiode 5734 which may be configured to monitor the transmitted light in real time to estimate the amount of light absorbed or reflected. This may be used to tailor the laser power in the cell process module 5700 to adjust to conditions in the cell culture container 5702. It may also be used to detect fiducial markings within the cell culture container 5702 to ascertain or track XY position or Z focus.

An additional reference photodiode 5736 may be positioned outside of the area of the cell culture container 5702, and with components near the focus plane of the optical engine. For example, a pinhole aperture may be used in combination with a detector to measure the laser power emitted through the entire system, measure the laser spot shape, measure laser spot position, and measure the focus position of the lens system, all for the purpose of tracking in semi-real time to make adjustments to laser power, focus and other beam handling parameters, and steering.

Laser Patterning of Biocoatings for Cell Culture

It may be advantageous for several reasons to utilize biocoatings in cell culture containers used in cell culture systems. For example, biocoatings may help foster cell adhesion, proliferation, expansion, reprogramming, differentiation, etc. In another example, biocoatings may prevent adsorption of proteins onto a surface, or adhesion of cells to a surface. The biocoating may also be patterned for a number of uses. For example, being able to pattern a biocoating in situ during an active cell culture, may obviate the need to move cell cultures from one container to another container for the purpose of presenting different surface coating properties, areas, patterns, etc., and thereby prevent cell death, contamination, and other negative effects of cell passaging/transfer. There is a need in the art to accomplish in situ biocoating patterning in a manner that is not harmful to cells.

The various implementations disclosed herein include systems and methods for patterning biocoatings inside cell culture containers using laser energy absorbed by a laser-absorbing film that is disposed on the surface of the cell culture container, or a foil that is inside of the cell culture container. The laser-absorbing film may be semi-transparent and have wavelength-selective absorption characteristics. In some implementations, the laser-absorbing film may be a plasmonic film as described herein. In some implementations, the biocoating may be spatially-selectively removed by laser exposure of the laser-absorbing film. In some implementations, the laser energy may be pulsed and the energy is converted into mechanical form with an explosive microbubble expansion and collapse that dislodges biocoatings from the laser film. In alternate implementations, the laser energy may be pulsed or continuous wave (CW) and the energy is converted to thermal form which denatures and/or detaches the biocoating from the laser film.

In some implementations, the biocoating may be deposited on the surface of the laser-absorbing film to support adherent cell culture. In some implementations, the biocoating may be composed of collagen, gelatin, poly-1-lysine (PLL), laminin (including but not limited to LN521 and LN111), albumin, vitronectin, fibronectin, and hyaluronic acid (HA), as well as functionalized materials such as PEG with RGD peptide (extracellular matrix cell binding sites) or other short peptides/laminins that bind cell integrins or other receptors. In some implementations, the biocoating may support adhesion and growth for certain cell types but not other cell types. Biocoatings that prevents adhesion of cells or proteins to the surface (sometimes referred to as an "anti-fouling" or "fouling-resistant" coating) include but are not limited to hydrophilic polymer branches such as poly (ethylene glycol) (PEG), zwitterionic polymers, poly(hydroxyfunctional acrylates), poly(2-oxazoline)s, poly(vinylpyrrolidone), poly(glycerol), peptides and peptoids. In some implementations, the biocoating may enable selective adhesive cell capture, including antibody-functionalized biocoatings or aptamer-containing biocoatings. In some implementations, the biocoating may be re-applied in situ in a cell culture process after laser ablation. For example, laminin may be added to cell culture media and re-coats surfaces that were temporarily cleared of laminin, so spatial regions that were made "off-limits" to some cell types (such as iPSCs) temporarily are again suitable for cell adhesion and proliferation.

In some implementations, the biocoating may be laser-ablated in a fixed pattern to form specific regions for cell attachment and/or growth. In some implementations, the ablation may be tailored based on known and/or predicted characteristics of the cell culture. For example, the expected reprogramming or differentiation efficiency for a specific line or patient may be predicted, and the biocoating laser patterning is performed accordingly (for example, taking into account total area for cell adhesion/proliferation, number of islands/regions for cell adhesion/proliferation, size of islands/regions, etc.). In some implementations, the biocoating may be laser-ablated based on dynamic cell culture data. This data may include data derived from imaging of an adherent or semi-adherent cell culture, and processed versions of such image data including but not limited to cell locations, morphology, behavior phenotype, proliferation, motility, etc., as well as aggregate behavior of cells in clusters or colonies. The data may also include data derived from spectroscopic measurements, including but not limited to cell media spectral measurements, spectral measurements of a plasmonic laser film, and/or surface-enhanced Raman spectral measurements. In some implementations, the biocoating may be ablated in a gradient fashion so that the thickness or surface coverage of the biocoating varies based on location. Non-uniform thickness biocoatings may be useful for selecting certain cell types (e.g., those that bind deposited proteins more tightly and remain attached to sparsely coated surfaces). In some implementations, the presence, absence, or density of one or more biocoatings is measured via spectroscopic methods, including but not limited to detecting plasmonic resonance peak wavelength and amplitude, and SERS.

Although multiple techniques are contemplated in this disclosure, there are some potential advantages to using pulsed lasers in combination with a thin laser absorbing film to remove biocoatings with explosive microbubbling and cavitation in contrast to other laser, thermal, or UV-based laser techniques. For example, this enables high spatial resolution in patterning the biocoating due to a very small, affected area, well-defined by the laser beam spot and imparted energy. There is also low collateral damage to nearby cells. The laser-absorbing film and short pulse also localize heating spatially and temporally, and the wavelength of light used may be selected to be in a range that is not harmful to cells (which is not possible with UV light-based patterning).

Figures 58A, 58B, 58C, 58D, 58E, 58F:
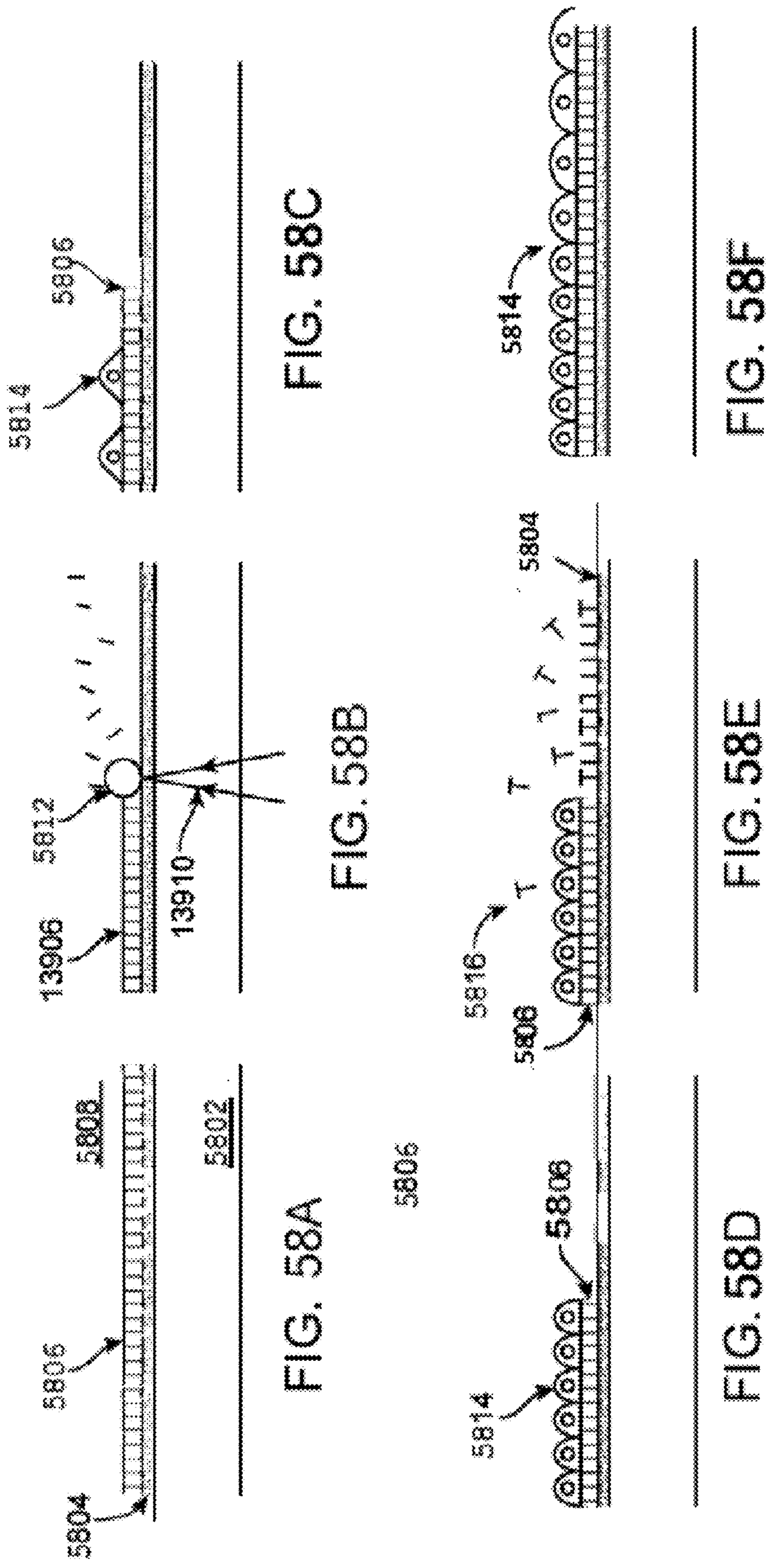
FIGS. 58A-F are diagrams depicting patterning of a matrix biocoating in accordance with various implementations.

FIGS. 58A-F are diagrams depicting patterning of a matrix biocoating in accordance with various implementations. The biocoating may allow for cell attachment and proliferation, and may for example be a laminin coating supporting iPSC reprogramming and/or expansion. FIG. 58A depicts a substrate 5802, which may for example be a window of a cell culture container (e.g., cell culture container 104) or a foil that is disposed inside of a cell culture container. The substrate 5802 bears a laser-activated film 5804, which may be one of several types described herein. A biocoating 5806 to support cell adhesion, health, and proliferation is deposited on top of the laser-activated film 5804. The biocoating 5806 may be pre-applied to the substrate 5802 and then assembled into the cell culture container. In alternate implementations, it may be deposited from liquid in the intact cell culture container, for example laminin deposited overnight from liquid at 4° C. Within the cell culture container, cell media 5808 is filled into the space above the substrate 5802.

FIG. 58B depicts laser-based patterning of the biocoating 5806. In this example, a pulsed laser beam 5810 is used to trigger explosive microbubbles 5812 that expand and collapse, ablating the biocoating 5806 in the process. The ablation of the biocoating 5806 may be measured spectroscopically or through wavelength-selective imaging as described herein. FIG. 58C depicts preferential adhesion of cells to the biocoating 5806 in the present example. Cells 5814 adhere and proliferate regions coated with the biocoating 5806, but not in ablated regions where the biocoating is absent. The ablation patterning may be performed in advance of cell seeding, with patterning parameters set for the cell type, experiment, and incoming cell characteristics (for example. the anticipated yield, efficiency, growth rate, etc., of a cell sample based on known characteristics as pre-measured by assays, or based on patient characteristics or demographics). In alternate implementations, this patterning may be done dynamically based on the observed spatial distribution, growth rate, phenotypic characteristics, media consumption rate, or other observable characteristics of the cell culture.

FIG. 58D depicts confinement of the cells 5814 to the region with the patterned biocoating 5806. Such patterning may help control the cell culture process, including for example limiting mixing between different (potentially clonal) cell populations or ensuring a uniform high cell density is achieved within certain areas as part of a differentiation or reprogramming protocol. It also allows for microscopic or spectroscopic observation of cells growing within a defined area and/or shape. In some implementations, the uncoated region may be amenable to proliferation for some cell types but not others. For example, in a cell culture process in which iPSCs are being reprogrammed from fibroblasts, after emergence of iPSC colonies it may be useful to isolate these on islands of patterned laminin or similar biocoating that supports iPSC health. If cells are observed proliferating beyond the borders of the islands it indicates that there are still fibroblasts in the region. In cases in which iPSCs proliferate faster than fibroblasts and push them out, as can be observed in many fibroblast sheets during iPSC reprogramming, the laser removal of any cells that proliferate beyond the boundary of the islands can effectively clear the island of fibroblasts over time.

FIG. 58E depicts a re-application of cell-supporting biocoating that is possible in some example implementations. A biocoating material 5816 may be introduced into the cell media 5808 and adheres to the surface of the film 5804 that is not currently covered by the biocoating 5806. The successful deposition of the biocoating material 5816 may be tracked by spectroscopic means as described herein. FIG. 58F depicts the subsequent proliferation of the cells 5814 across the freshly-biocoated regions on the substrate 5802. Thus, different stages of cell culture, reprogramming, differentiation, expansion may be performed in different spatial patterns within the same cell culture container rather than transferring cells from container to container for different portions of the process.

Figures 59A, 59B, 59C, 59D, 59E, 59F:
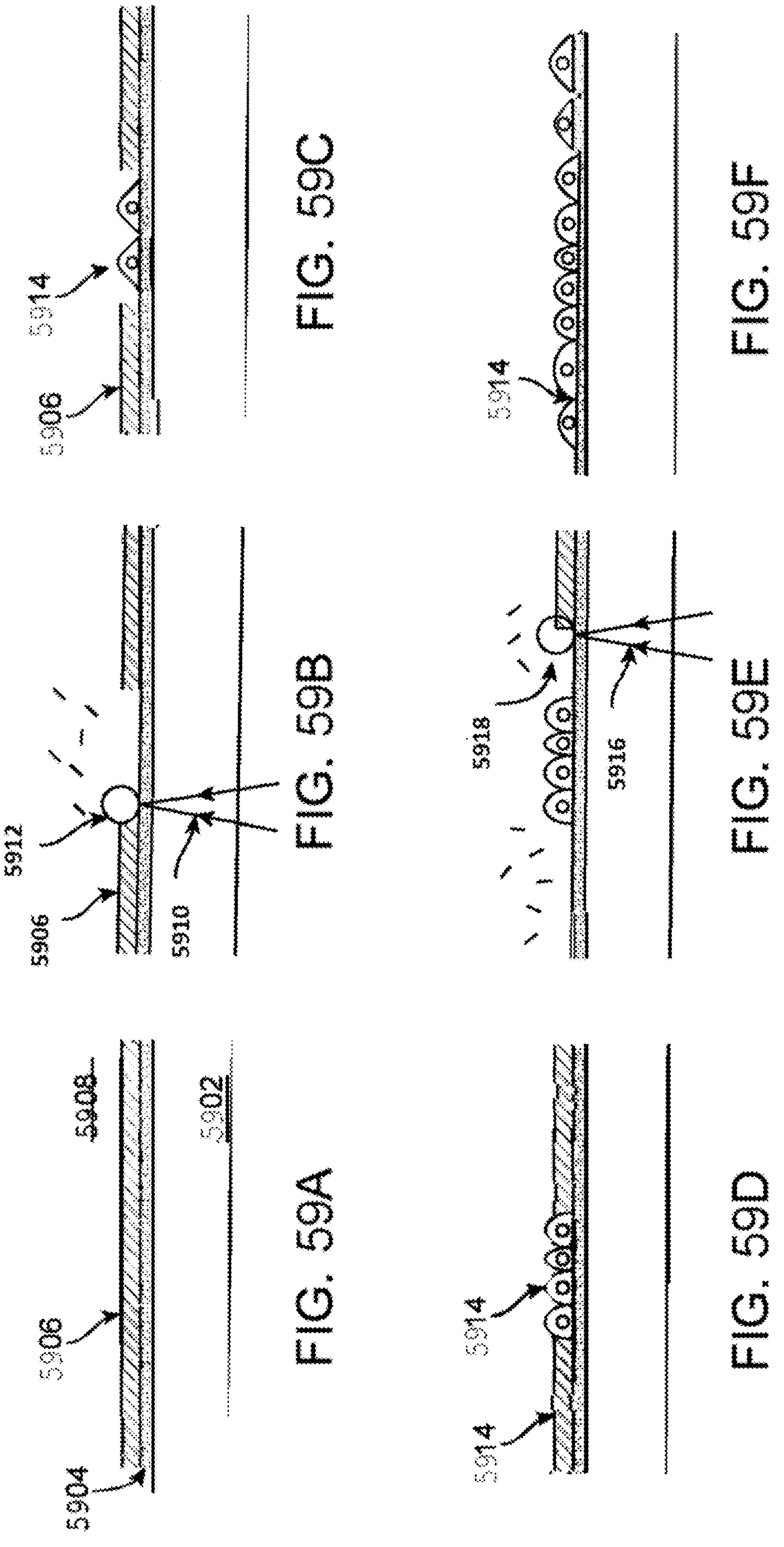
FIGS. 59A-F are diagrams illustrating laser patterning of biocoating for the purposes of confining cell growth in accordance with various implementations.

FIGS. 59A-F are diagrams illustrating laser patterning of biocoating for the purposes of confining cell growth in accordance with various implementations. The cell growth may be limited to specific regions for specific portions of a cell culture process. The process depicted in FIGS. 59A-F may be the inverse of the process depicted in FIGS. 58A-F. Namely, a biocoating may be used to define areas where cells should not grow rather than areas where cells should grow. FIG. 59A depicts a substrate 5902, which may for example be a window of a cell culture container (e.g., cell culture container 104) or a foil that is disposed inside of a cell culture container. The substrate 5902 bears a laser-activated film 5904, which may be one of several types described herein. An anti-fouling biocoating 5906 is deposited on top of the laser-activated film 5904. Within the cell culture container, cell media 5908 is filled into the space above the substrate 5902.

FIG. 59B depicts laser patterning of the biocoating 5906. In the example shown, a pulsed laser 5910 is focused through the substrate 5902 and interacts with the laser-activated film 5904 to produce explosive microbubbles 5912 that remove the biocoating 5906. This process may leave the biocoating 5906 in regions where cell growth should be excluded, for example surfaces that are not observable by imaging, or where cells cannot be effectively destroyed via laser lysis, in tubing and manifolds, or in regions of a cell culture container that do not offer consistent growth environment (temperature, media flow, dissolved gas concentration, etc.).

FIG. 59C depicts selective cell adhesion of cells 5914, after seeding, into the regions where the biocoating 5906 has been selectively ablated. Due to anti-fouling or anti-adhesive properties of the biocoating 5906, regions coated with the biocoating 5906 are unsuitable for cell adhesion (or, in the case where an additional cell-supporting biocoating is applied, does not allow adsorption of this additional biocoating). However, in regions where the biocoating 5906 has been ablated the cells 5914 may adhere. FIG. 59D depicts the proliferation of the cells 5914 within the patterned region that is absent of the biocoating 5906.

FIG. 59E depicts laser removal of some remaining portions of the biocoating 5906. A pulsed laser pattern 5916 may be used to ablate additional biocoating via microbubbles 5918. As with other laser patterning operations described herein, media may be exchanged following the patterning. This allows the ablated biocoating material to wash away rather than settle back onto the surface of the substrate 5902 and/or cell culture. This washing may be performed using a pipette operation in a dish, plate, or flask, or by media flow within a closed fluidic system. In some implementations, the ablation of the biocoating 5906 may be followed by re-deposition of a cell-supporting biofilm onto the cleared areas. FIG. 59F depicts the subsequent proliferation of the cells 5914 out of the initial confined region and into the newly-cleared regions.

Figures 60A, 60B, 60C, 60D, 60E:
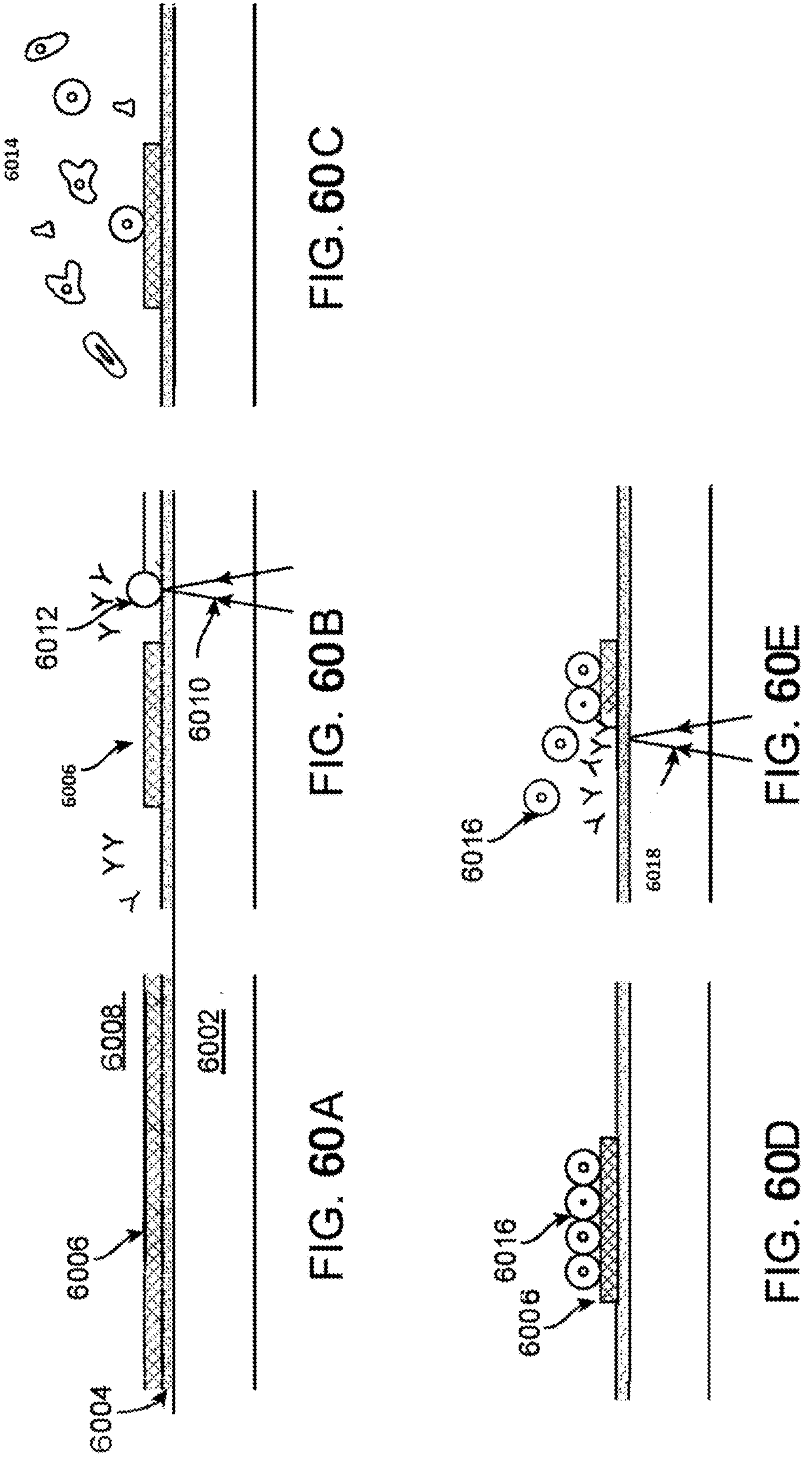
FIGS. 60A-E are diagrams illustrating a biocoating in a cell culture container that binds with specific cells in accordance with various implementations.

FIGS. 60A-E are diagrams illustrating a biocoating in a cell culture container that binds with specific cells in accordance with various implementations. FIG. 60A depicts an optically-clear substrate 6002, which may for example be a window of a cell culture container (e.g., cell culture container 104) or a foil that is disposed inside of a cell culture container. The substrate 6002 bears a laser-activated film 6004, which may be one of several types described herein. A biocoating 6006 is deposited on top of the laser-activated film 6004. The biocoating 6006 may have properties designed to bind with specific cell types. Within the cell culture container, cell media 6008 is filled into the space above the substrate 6002.

FIG. 60B depicts selective laser ablation of the biocoating 6006 using laser pulses 6010 that generate explosive microbubbles 6012, which ablate the biocoating 6006 into the surrounding media 6008 for removal. FIG. 60C depicts the cell media 6008 with a variety of cell types 6014 in suspension. The region of the substrate 6002 that retained biocoating 6006 offers cell-specific receptors that preferentially cause select cell types with the variety of cell types 6014 to adhere to the region.

FIG. 60D depicts expansion of cells 6016 of a selected cell type on the patterned region with the biocoating 6006. For example, a single captured cell 6016 may proliferate (clonally) and be observed for characteristics using imaging, spectroscopic, or fluorescent techniques. FIG. 60E depicts selective laser retrieval or removal of the cells 6016. For example, laser illumination 6018 may be focused on a region of the laser-activated film 6004 to impart energy on it. In some implementations, the laser illumination 6018 may be pulsed to cause formation of microbubbles, which may detach or destroy the biocoating 6006 and remove it from the film 6004 at low enough energies that it preserves the cells 6016. In alternate implementations, the laser illumination 6018 may be continuous to thermally dissociate the biocoating 6006, which in turn releases the cells 6016.

Spatial Transport or Translation of Cell Colonies

During cell culture processes, many cell operations which may benefit from controlled translation of adherent groups/clusters of cells or colonies (hereafter referred to as "colonies") from one location to another on a cell-bearing surface. However, the tools for performing this are currently lacking. Current methods known in the art generally involve manual manipulation of cells, such as opening the cell culture container and either lifting and transferring cells, or scratching away a portion of the cells from the cell culture container. These methods are time-consuming, inaccurate, and requires a potentially sterile cell culture container to be opened. Thus, what is needed in the art is a non-invasive manner for moving and manipulating cell colonies on a cell-bearing surface, which may be computer-automated and monitored in an automated cell culture system.

The systems and methods disclosed herein include a method of translating adherent cell colonies using an automated cell removal tool (CRT), which may be part of a cell editing subsystem (e.g., cell editing subsystem 114). The CRT may be one of a range of tools that can precisely remove cells from an adherent cell culture, in some cases in a non-invasive manner that is compatible with a closed cell culture container to minimize opportunities for contamination or cross-contamination. Additionally, CRTs may be employed to remove or pattern biofilms on the surface of the cell culture container. The CRTs applicable to colony transport/translation and other cell culture operations herein include but are not limited to: automated mechanical tools that may remove or destroy cells and/or pattern biofilms, including magnetically-coupled tools that may be remotely controlled for use within a cell culture container; ultrasonic tools that may remove or destroy cells selectively and/or pattern biofilms; and laser-based or other optical-based tools that may selectively remove or destroy cells, and/or pattern biofilms.

In the case of optical-based or laser-based tools, these CRTs may selectively destroy or remove cells through optical effects, or may selectively remove or destroy cells through thermal effects either by direct absorption in cells and/or surrounding media, or through the use of absorbing materials, or may selectively remove or destroy cells through mechanical effects resulting in rapid bubble formation and/or collapse due to local heating (e.g., with heating either directly from absorption by media or cells), or through the use of an absorber. Where absorbers are used in conjunction with optical sources, the absorber may be in the cell media, on the surface of cells (e.g., Gold nanoparticles), or deposited on the surface of the cell culture container. CRTs may function by damaging cells in a manner where they subsequently die and can be removed, or by directly removing cells from the cell culture by mechanical force and/or de-adhering them from the cell culture container surface, which may be achieved by damaging or removing a biofilm, or by breaking connections between the cell and the cell culture surface (including any intervening biofilm). In the case of direct cell damage, the CRT may act on the cells by lysing the cells, by thermal damage, by mechanical damage to the cell membrane or other cellular components, by photochemical damage to cell components, or by other means that cause cell death via apoptosis, necrosis, autophagy, or paraptosis.

Examples implementations of cell editing subsystems, biofilms, cell removal/management, and cell operations described herein may describe a CRT that includes a pulsed laser and a laser-absorbing ("laser-activated") film deposited on the surface of the cell culture container. This film may further be pattern with registration/fiducial markings for spatial reference by imaging and laser. However, references to a pulsed laser and laser-activated film are only examples of CRTs and do not limit the various implementations of CRTs that may be used with the systems and methods described herein. Various implementations may additionally utilize biocoatings as described herein with reference to FIGS. 58A-60E, which are also patternable using the laser system, to guide colony translation.

Figure 61:
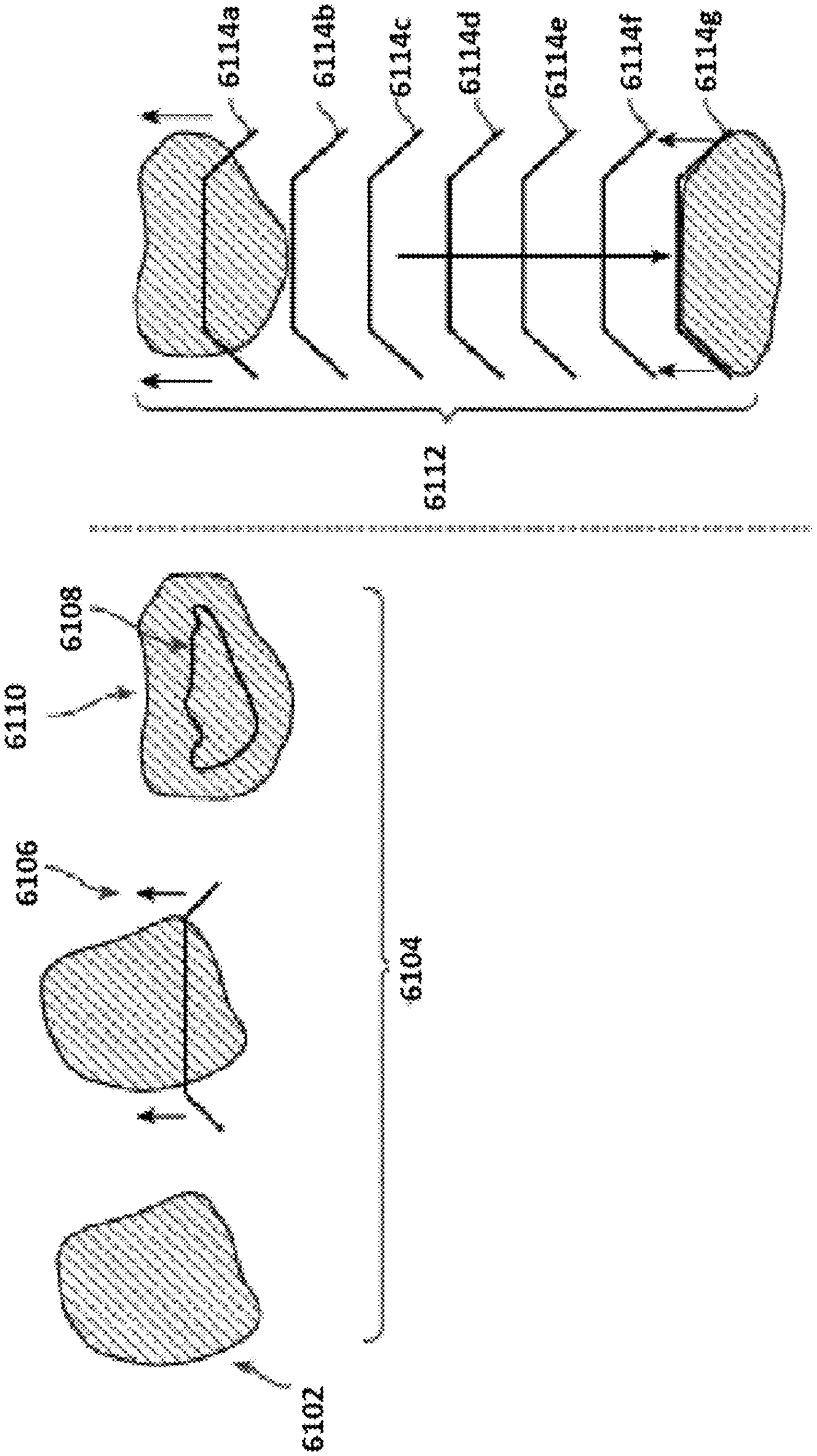
FIG. 61 is a diagram illustrating movement of a cell colony using a laser scanner in accordance with various implementations.

FIG. 61 is a diagram illustrating movement of a cell colony using a laser scanner in accordance with various implementations. FIG. 61 depicts a cell colony 6102 is adhered to a cell-bearing surface of a cell culture container (e.g., cell culture container 104), the surface including a laser-activated film as described herein. Sequence 6104 shows a single step in the laser-driven transport process. A laser scanner (e.g., part of the cell editing subsystem 114 or another laser processing subsystem within a cell culture system) emits laser illumination that is scanned over the "trailing region" of the cell colony 6102, shown as a region 6106 above the cut line as indicated by arrows in FIG. 61. This scanning may remove cells of the cell colony 6102 in the region 6106 from the cell-bearing surface but retains cells outside the region 6106 shown as retained cells 6108. After washing detached/removed cells away, the retained cells 6108 may proliferate and expand into translated cell colony 6110. As can be seen in FIG. 61, the center of mass of the translated cell colony 6110 has been translated "downwards" in the orientation of FIG. 61 as compared to the original cell colony 6102.

Sequence 6112 illustrates repeated application of the single sequence 6104. A first line 6114*a* shows where a cell colony is divided to scanned-away cells (above the line 6114*a*) and retained cells (below the line 6114*a*). As the retained cells proliferate into a new region, the process is repeated with additional scanning lines 6114*b-f* in a sequential manner, thus translating the cell colony to a final position. This sequence of operations may be done "blind," in which the initial position of the cell colony is known, either because of other patterning within the cell culture container or from a single timepoint imaging, and the series of laser scanning operations is applied with prior knowledge of the cell proliferation/colony expansion rate. Cell colonies that do not expand sufficiently quickly may be eliminated entirely by this process, so it may serve as a filtering mechanism. In alternate implementations, the steps may be performed in conjunction with imaging that locates the colony prior to each new laser translation step, and the laser-removed region (and timing of the laser removals) is tailored according to the observed colony size and location, a target location for the cell colony, and potentially a time series knowledge of colony behavior.

Figure 62:
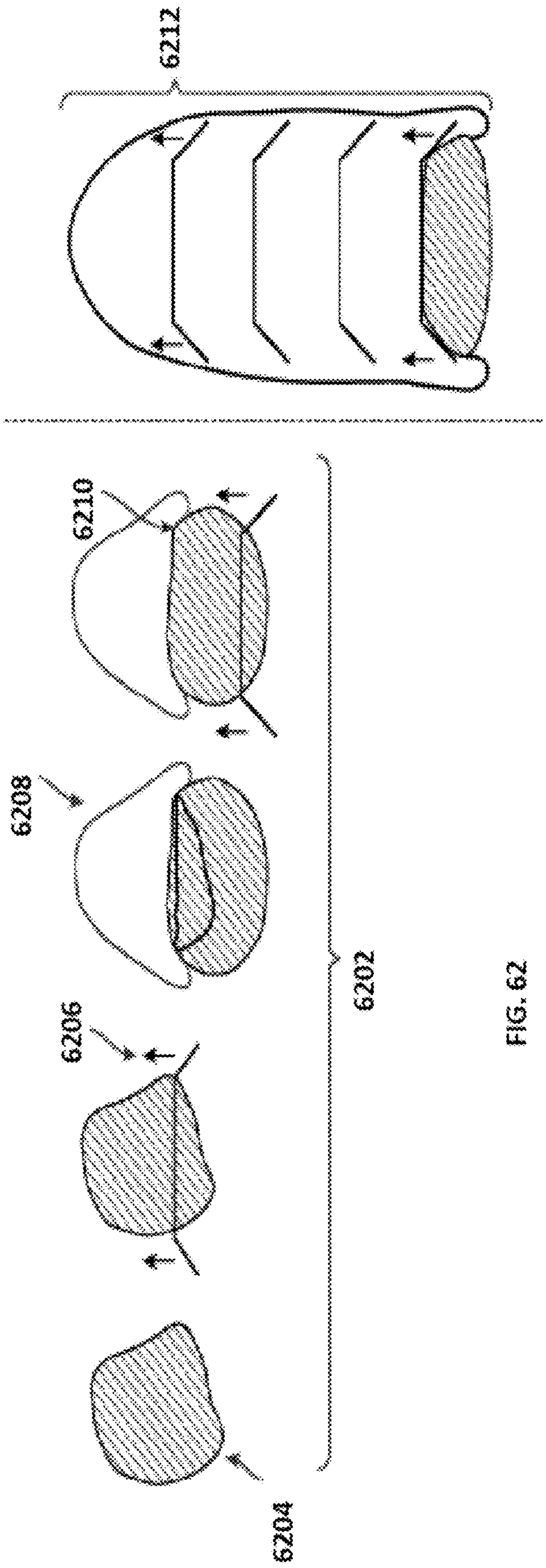
FIG. 62 is a diagram illustrating movement of a cell colony using a laser scanner and a biocoating in accordance with various implementations.

FIG. 62 is a diagram illustrating movement of a cell colony using a laser scanner and a biocoating in accordance with various implementations. The biocoating may promote cell health and proliferation. For example, the biocoating may include laminin and the cell colony be an iPSC colony, for which laminin (for example) is used sustain iPSCs on the cell-bearing surface. Sequence 6202 illustrates a single step in the cell colony transport process. A cell colony 6204 may grow on a cell-bearing surface including a laser-activated film and a biocoating. A laser scanning operation may be performed on cells above cut line 6206 to remove them from the cell-bearing surface. The laser removal may be accomplished, for example, by a pulsed laser system striking a laser-absorbing coating to produce cavitation bubbles at the cell-bearing surface. The cavitation bubbles lyse the cells in the targeted region of the cell colony 6204 and may also ablate biocoating from the cell-bearing surface. Both the cell debris and biocoating materials are washed away, leaving an uncoated region 6208 that is not hospitable to cell colony attachment and/or growth. The retained cells 6210 proliferate preferentially into areas that still are coated with the biocoating, thus expanding downwards in FIG. 62. Additional laser scanning steps may then be performed to continue translation of the cell colony, shown as sequence 6212.

Figure 63:
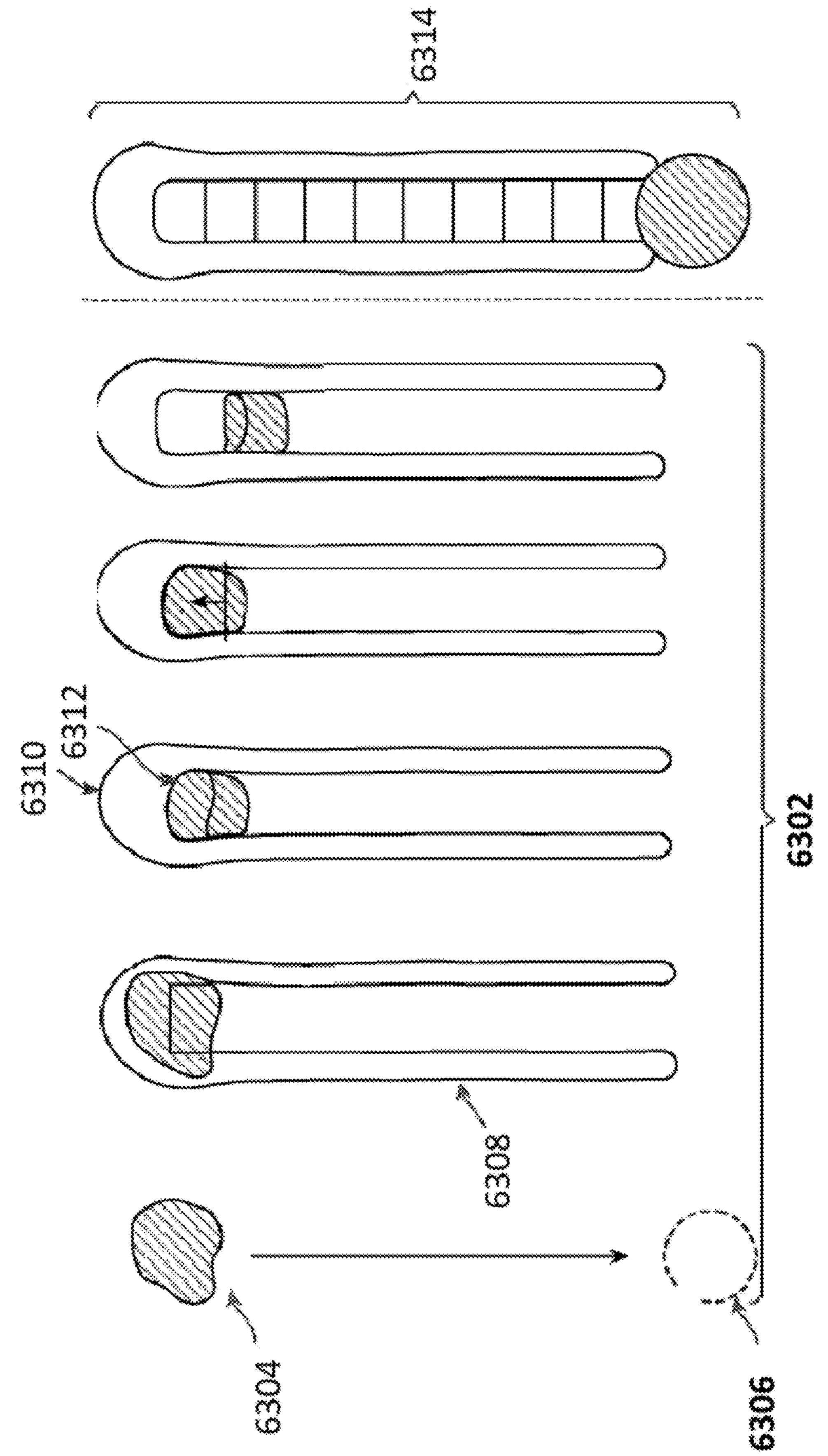
FIG. 63 is a diagram illustrating another example of movement of a cell colony using a laser scanner and a biocoating in accordance with various implementations.

FIG. 63 is a diagram illustrating another example of movement of a cell colony using a laser scanner and a biocoating in accordance with various implementations. In this example, laser scanning of a cell-supporting biocoating may be used to pattern "rails" that guide cell colony transport, as the cell colony is translated using selective laser destruction of cells. Sequence 6302 shows a single step of the translation process. A cell colony 6304 may grow on a cell-bearing surface including a laser-activated film and a biocoating, and the cell colony 6304 needs to be moved to location 6306. A region 6308 is laser-scanned to perform the first colony translation "step" along the translation path by ablating part of the cell colony 6304 above a cut line, but at the same time establish two "rails" that will guide and confine colony growth along the path to minimize subsequent laser operations. The result of this scan is a region 6310 where the biocoating has been ablated and that inhibits proliferation of the cells. The retained cells 6312 expand downwards within the rails.

Repeated applications of laser scanning translate the cell colony downwards, within the confines of the rails, resulting in sequence 6314. A series of laser scans (with associated cut lines shown in FIG. 63) leaves the upper regions where the cell colony once grew uncoated with biocoating, preventing the cell colony from growing back upwards. In the example shown in FIG. 63 as well as other implementations in which a biocoating is patterned, the removal of biocoating may be confirmed via spectroscopic or imaging means. In some implementations, biocoatings may be reapplied after transport operations. For example, laminin may be re-added via cell media to re-coat all regions that have been ablated.

Figure 64:
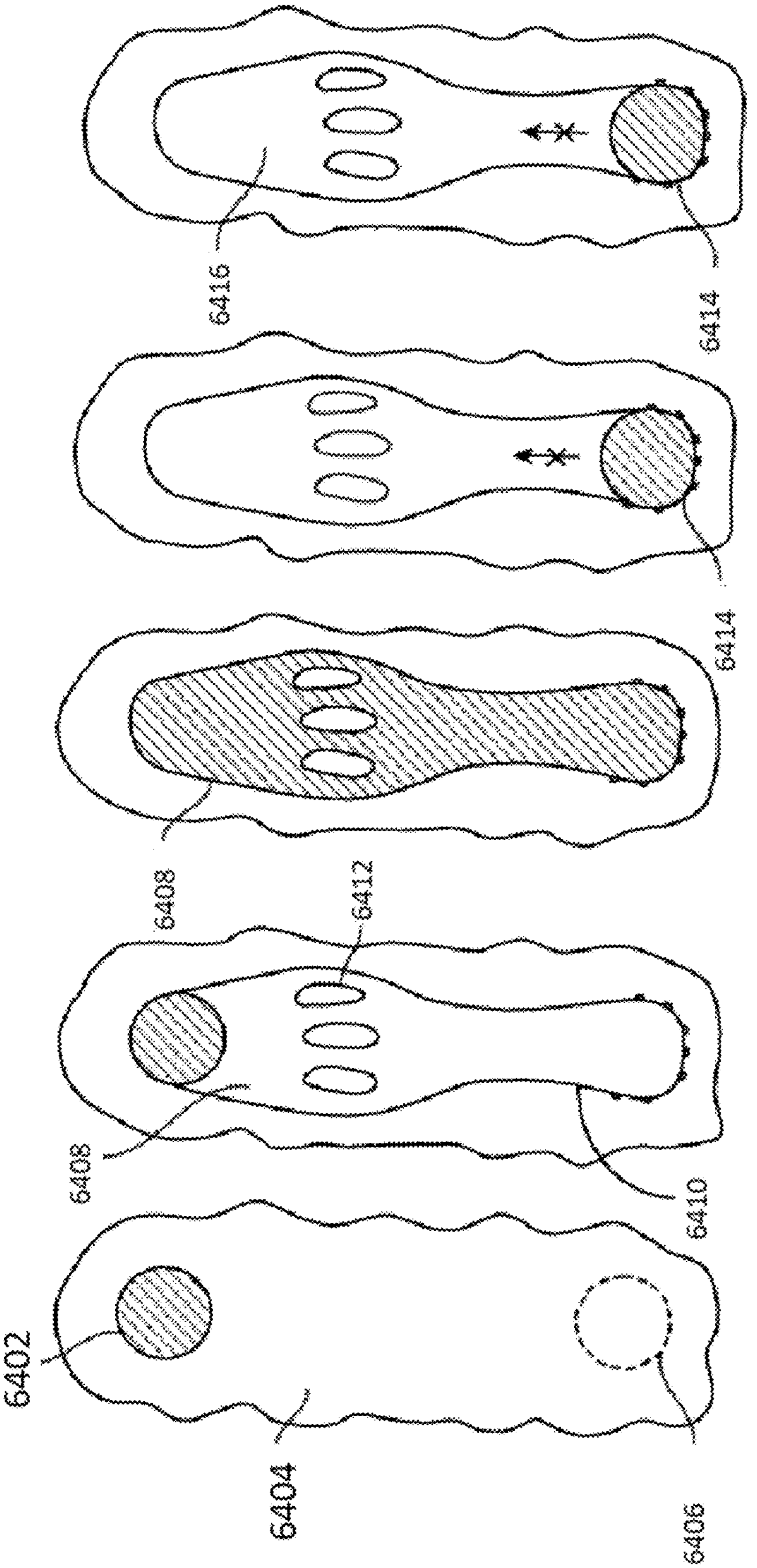
FIG. 64 is a diagram illustrating another example of movement of a cell colony using a laser scanner and an anti-fouling biocoating in accordance with various implementations.

FIG. 64 is a diagram illustrating another example of movement of a cell colony using a laser scanner and an anti-fouling biocoating in accordance with various implementations. In this example, an anti-fouling/anti-stick biocoating may be applied to the majority of the surface of the cell culture vessel and is selectively laser-removed from the surface for the purpose of transporting cell colonies. A cell colony 6402 is growing in a region that does not contain anti-fouling biocoating 6404 is therefore able to proliferate. Cells may be seeded onto a surface that bears a laser-activated film and the anti-fouling biocoating 6404, in which the biocoating has been pre-patterned with open circular regions not containing the biocoating so that cells only adhere to these regions. Cells may then proliferate inside these regions to achieve a certain local density at the beginning of a cell differentiation process, for example.

When a certain local density has been achieved, it may be desirable to move the cells to a new location 6406. A laser scanning patterning process may be applied, leaving a region 6408 that is uncoated with the biocoating. The region 6408 may now be suitable for cell growth and proliferation. In alternate implementations, another biocoating configured to support cell growth (that does not adhere to the anti-fouling biocoating 6404) may coated onto the region 6408 via cell media addition. The region 6408 may have various features useful for preferentially selecting certain cell or colony types, compositions, or functionality. For example, expansions or constrictions 6410 in the path may select for certain growth patterns or rates. Likewise, obstacles 6412 may preferentially select for certain cell characteristics in the cells that are ultimately transported to the target location, or split or generate replicates of target cell colonies. In the example shown in FIG. 64, cells are allowed to grow across the entire region 6408. Laser removal of cells may then be performed to remove cells in the region 6408 except for cells located in the desired location 6406, resulting in translated cell colony 6414. In some implementations, the initially ablated region 6408 may be recoated with a second, cell adhesion promoting biocoating 6416 (e.g., laminin) prior to cell proliferation. Subsequent laser removal of cells with the exception of cells in the target destination region 6406 also ablates the second biocoating 6416, thus restricting the location of the translated cell colony 6414.

Figure 65:
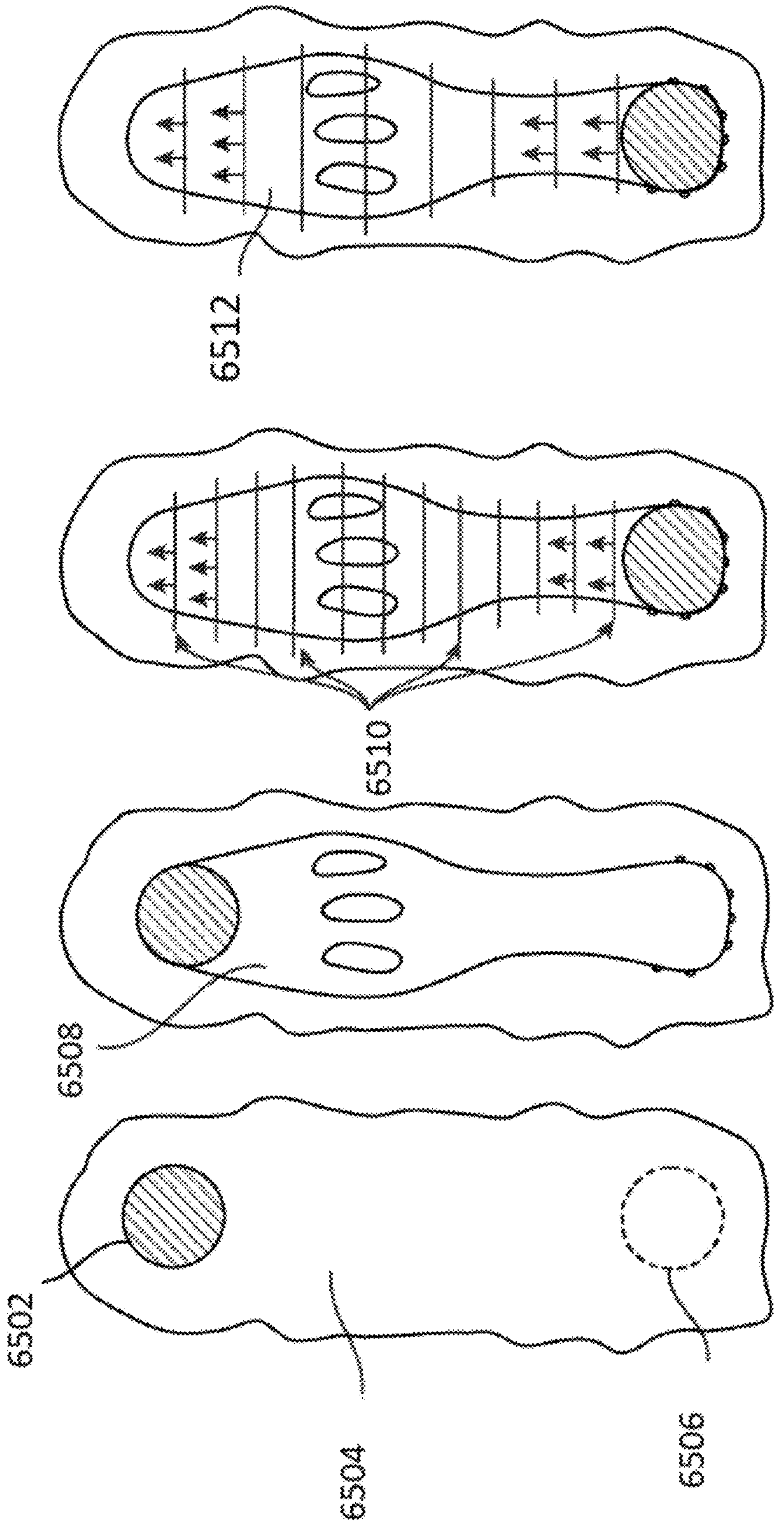
FIG. 65 is a diagram illustrating another example of movement of a cell colony using a laser scanner and an anti-fouling biocoating in accordance with various implementations.

FIG. 65 is a diagram illustrating another example of movement of a cell colony using a laser scanner and an anti-fouling biocoating in accordance with various implementations. The example shown in FIG. 65 may be an alternate implementation to the example shown in FIG. 64. A cell colony 6502 may grow on a cell-bearing surface including a laser-activated film and an anti-fouling biocoating 6504, and the cell colony 6502 needs to be moved to location 6506. A patterned biocoating ablation step removes the biocoating 6504 from a region 6508, clearing a path for cell growth. A series of laser cuts 6510 may be made to translate the cell colony within the region 6508 to the location 6506, as described with reference to FIGS. 61-62. In some implementations, the region 6508 may be re-coated with a cell-supporting biocoating 6512 before the laser cuts 6510 are applied. The laser cuts may translate the cell colony and remove the biocoating 6512 at the same time.

Figure 66:
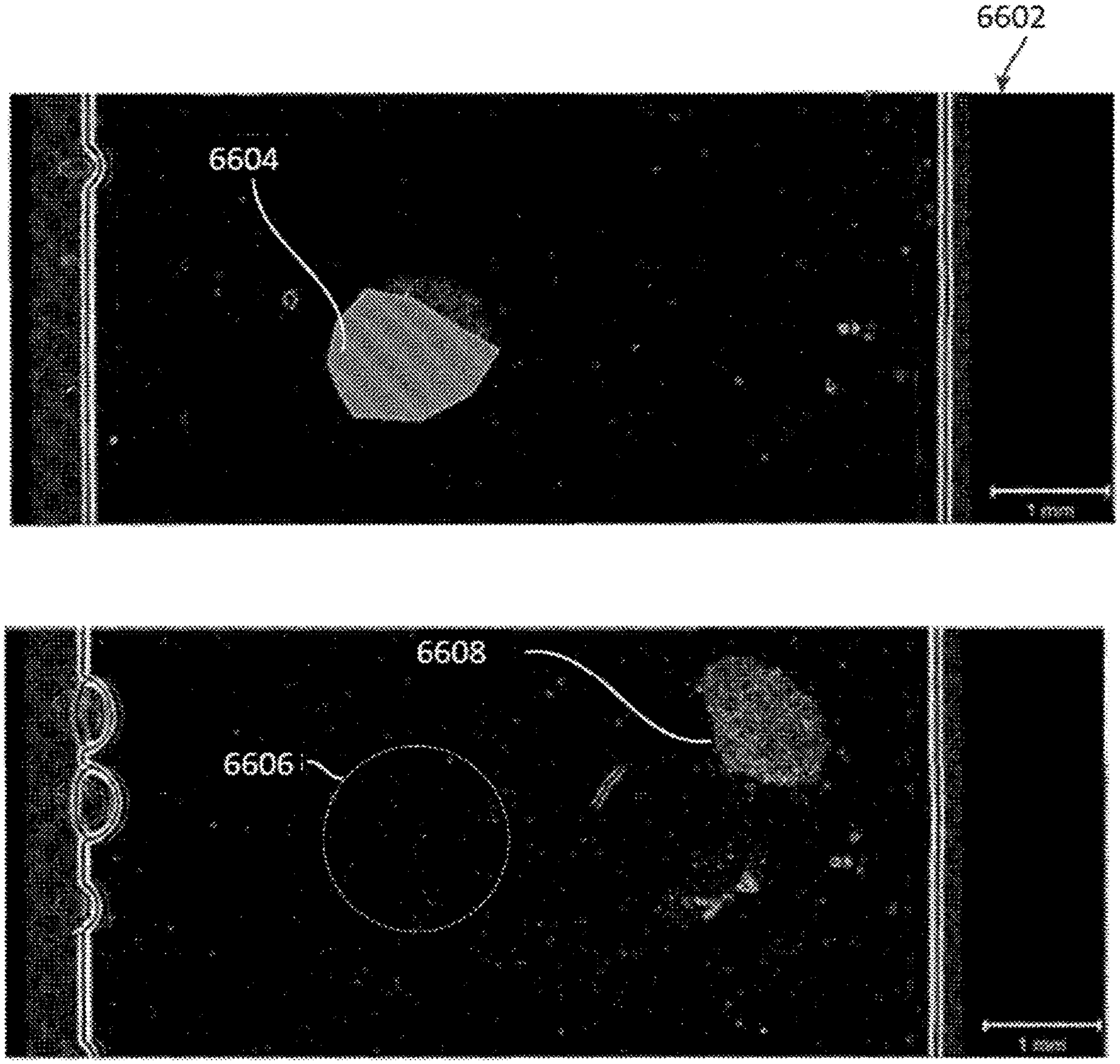
FIG. 66 are images illustrating movement of a cell colony using a laser scanner in accordance with various implementations.

FIG. 66 is a series of images illustrating movement of a cell colony using a laser scanner in accordance with various implementations. FIG. 66 shows an example as applied to the transport of an iPSC colony in a cell culture container. The cell colony is adhered to a transparent surface of a cell culture container 6602 that is equipped with a plasmonic laser-activated film, enabling a pulsed laser to create explosive microbubbles. The cell culture container surface has further been coated with a biocoating of laminin, which supports iPSC health and proliferation. In a sequence of five patterned laser scans, portions of both the cell colony and the laminin biocoating are removed to translate the cell colony several millimeters across the cell culture container. In a first step, a first laser scanning region 6604 is scanned across the majority of the iPSC colony in its original position. The cells in the scanned region 6604 are lysed and washed away, and the underlying laminin biocoating is likewise ablated. The non-scanned cells of the cell colony survive and proliferate preferentially into regions that are still biocoated. After a series of scanning and proliferation steps, the colony has been translated from its original location 6606 to its final location 6608.

Cell Removal Tool Splitting and Distribution of Cell Colonies

During cell culture processes for adherent cells, it may be desirable to split cell colonies. Prior art approaches to colony splitting include using mechanical tools such as pipette tips to "cut" colonies apart in an open cell culture container. This may be done in conjunction with subsequent treatment with enzymes such as Trypsin to lift the resulting colony fragments off the cell culture surface and redistribute them, often into new cell culture containers. However, this process places significant stress on the cells, introduces human error into the process, and the sub-colonies cannot be tracked over time due to random relocation. Moreover, these processes require the opening of cell culture containers, with the possibility of contamination or cross-contamination.

Various implementations disclosed herein include systems and methods for using pulsed laser illumination of a semi-transparent laser-activated film to split and redistribute cell colonies in situ. It should be understood that the laser-activated film and pulsed laser described with reference to the following examples is merely one example of a CRT compatible with the systems and methods herein, and that other implementations of CRTs are also contemplated herein. Using this method, colonies may be redistributed for observation of individual sub-colonies, for expansion, or for optimizing reprogramming or differentiation protocols. In some implementations biocoatings may also be present on the film, the biocoating configured to support cell proliferation (both universally for cell culture processes, or specifically for certain cell types), and anti-fouling biocoatings that prevent cell adhesion and proliferation. The systems and methods disclosed herein may be performed in an "open-loop" manner, in which a series of laser operations is used in a pre-set pattern, in conjunction with cell seeding, washing, and media/reagent changes. In alternate implementations, it may be performed in a "closed-loop" manner, in which cell location, density, phenotype, or other data are tracked via imaging, spectroscopy or other subsystems, and this information is used to guide the splitting and redistribution of cells.

Figure 67:
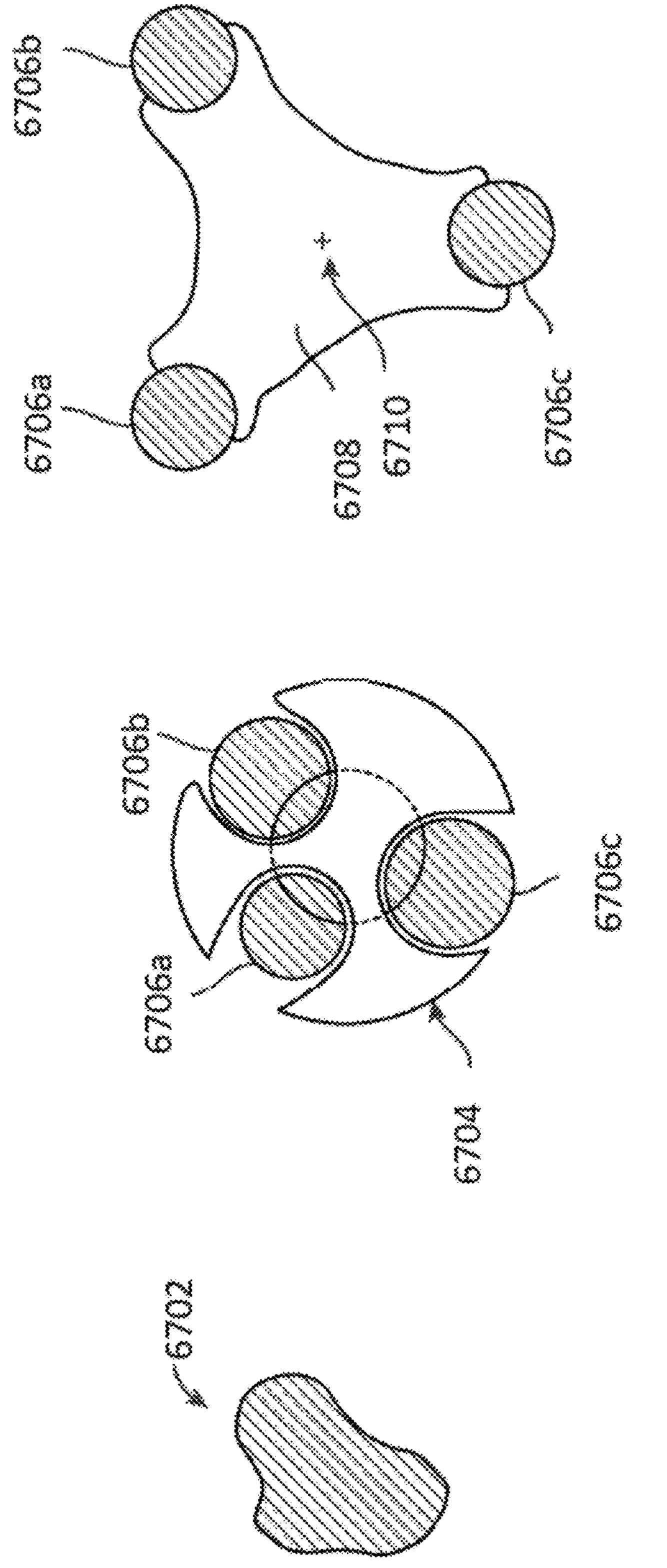
FIG. 67 are diagrams illustrating splitting of cell colonies in accordance with various implementations.

FIG. 67 is a series of diagrams illustrating splitting of cell colonies in accordance with various implementations. FIG. 67 depicts a cell colony 6702 growing on a transparent substrate in a cell culture container. The substrate may be coated with a laser-absorbing film, and then coated with a laser-ablatable biocoating that supports cell proliferation. The cell colony 6702 should be redistributed or sectioned for observation of the individual pieces. A laser processing subsystem (e.g., cell editing subsystem 114) may laser scan a pattern 6704 to remove portions of the cell colony 6702 and the biocoating, leaving three sub-colonies 6706*a-c*. The sub-colonies 6706*a-c* may then expand preferentially into regions still coated with the biocoating (e.g., areas of the substrate that were not laser scanned. The sub-colonies 6706*a-c* may be transported via a series of laser operations (described with reference to FIGS. 61-66), leaving an uncoated region 6708, and the three sub-colonies 6706*a-c* some distance from the original colony center 6710.

Figure 68:
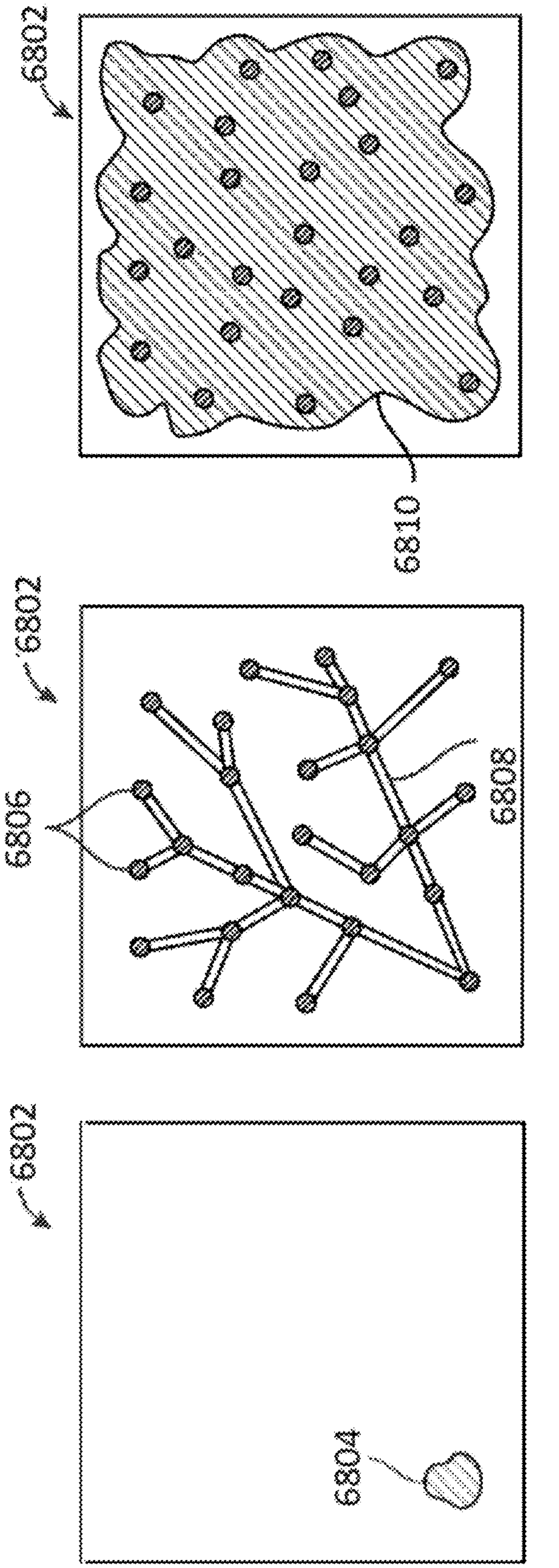
FIG. 68 are diagrams further illustrating splitting of cell colonies in accordance with various implementations.

FIG. 68 is a series of diagrams further illustrating splitting of cell colonies in accordance with various implementations. FIG. 68 depicts a cell colony 6804 growing on a transparent substrate in a cell culture container 6802. The substrate may be coated with a laser-absorbing film, and then coated with a laser-ablatable biocoating that supports cell proliferation. The cell colony 6802 may be, for example, an iPSC colony that was selected from a plurality of iPSC colonies emerging during a reprogramming process. Other cell colonies, and any cells that were not reprogrammed, may have previously been laser-removed, leaving only the single clonal colony 6804. In these cases, a biocoating, for example laminin, may have been re-applied to the scanned regions via addition from cell media. In this example reprogramming process, colony selection may be followed in prior art processes by extended passaging of the cells from container to container to clear reprogramming vectors, allow telomeres to form properly, etc. Then the cells are expanded in a cell culture container to make the final output cell product.

By contrast, in the various implementations disclosed herein the clonal colony may be sequentially split and redistributed over the cell culture container surface without passaging, enabling a single-container sterile-sealed process that allows for continuous quantitative observation and tracking, management. In the example shown in FIG. 68, after splitting cell colony 6804 sub-colonies 6806 may be split and translated along paths 6808 until the sub-colonies 6806 are roughly uniformly distributed in the cell culture container 6802. The translation paths 6808 may be the most direct path, or in other cases indirect paths to coordinate timing and potentially extend timing during the cell culture process and for measurement or cell editing operations. The sub-colonies 6806 may be maintained for a period of time in place by a laser processing subsystem configured to laser-remove cells and maintain proper density of the sub-colonies 6806, again to allow time for vector clearance or cell maturation.

Prior to, during, and after this process, the cell-supporting biocoating may be replenished in the ablated regions, for example through the addition of laminin to the cell media. The total number of cell divisions through the process may be calculated from time-series images and/or estimates of the mean cell density and total area removed throughout the cell culture process. Finally, the sub-colonies 6806 are allowed to expand to confluence, resulting in expanded cell colony 6810. This expansion may still be laser-managed to prevent over-dense areas from forming. However, this problem may be minimized by uniform distribution of the sub-colonies 6806. Thus, through this process a single clonal colony may be vector-cleared, matured, and expanded over the entire cell culture container growth surface in situ, and in some cases without opening the cell culture container 6802. This enables an aseptic process that may be parallelized in multiple cell culture containers in a dense space, for example on a rack-mounted system.

Figure 69:
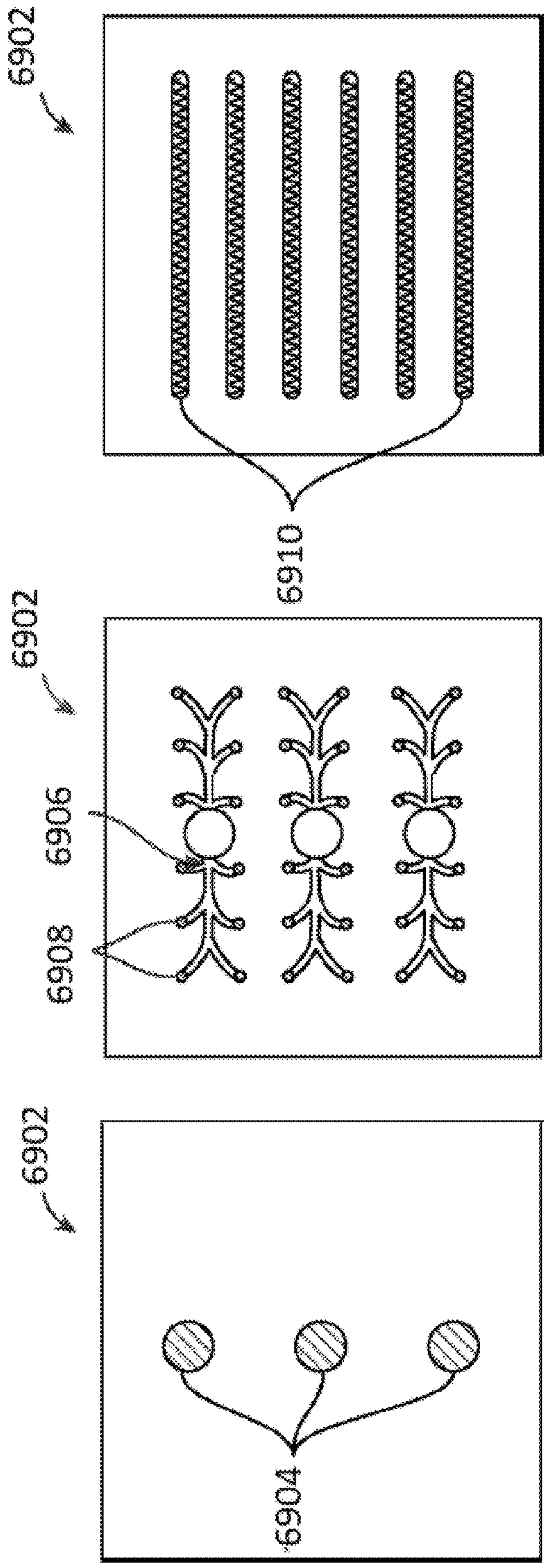
FIG. 69 are diagrams further illustrating splitting of cell colonies in accordance with various implementations.

FIG. 69 are diagrams further illustrating splitting of cell colonies in accordance with various implementations. The example depicted in FIG. 69 is a multi-stage cell differentiation process that has been optimized by two using different spatial configurations for cells inside cell culture container 6902. The cell culture container 6902 may include a transparent substrate for growing adherent cell cultures. The substrate may include a laser-activated film and/or a biocoating that promotes cell growth. For example, pluripotent cells are first seeded and confined to circular regions 6904 where they acclimate and proliferate during a first stage, and any spontaneous differentiation that occurs may be managed via laser ablation of the differentiating cells. After the acclimation phase, which may also include an initial differentiation protocol but leaves cells in a rapidly-dividing state, the colonies are sequentially divided and translated as indicated by the ablated biocoating track 6906, into sub-colonies 6908.

These sub-colonies 6908 are then allowed to selectively proliferate into linear sections 6910 which are optimized for the overall differentiation process. For example, the linear sections 6910 for cell growth may be preferential in the example of pluripotent stem cells because they are healthiest in clusters, but differentiation often occurs initially at the edges of pluripotent colonies. Thus, by creating the linear sections 6910 that the pluripotent stem cells are initially confined to, the differentiated cells have ample room to grow out from the linear sections 6910.

Method for In Situ Cell Colony Clonalization

Some cell culture processes involve adherent or semi-adherent cell clusters or colonies that form by proliferation of cells. In some cases, there may be only a single clonal population in the cluster or colony, while in other cases there may be a polyclonal population. In many cell culture processes, it is desirable to produce a monoclonal product. Monoclonality may be achieved by various methods in post-processing. For example, single cells may be seeded in containers, but is often highly stressful for adherent cell types. In another example pieces of cell colonies may be repeatedly transferred to new containers, but this process is both stressful on the cells and labor-intensive. Both these post-processing approaches also require transfers from one container to another, which introduces the possibility of contamination or cross-contamination between samples handled in the same facility. To avoid contamination, one would need to build expensive facilities and implement extensive sterilization and cleaning procedures after each run. Additionally, the post-process approach to clonalization may add significant time to the total cell process.

Thus, what is needed in the art are methods that ensure the isolation and growth of clonal cell colonies in a cell culture container that does not require container-to-container transfers. Such methods should also not extend the duration of the total cell culture process significantly and allow for in situ observation of monoclonal cell colonies arising from the cell culture process for the purpose of data collection, human observation, machine learning predictions, selection of specific colonies for further expansion or analysis, and other applications.

Various implementations disclosed herein include systems and methods of using a sequence of laser cell deletion operations on a proliferative adherent cell cluster or colony to ensure clonality of that cluster or colony. It should be understood that the laser-activated film and pulsed laser described with reference to the following examples is merely one example of a CRT compatible with the systems and methods herein, and that other implementations of CRTs are also contemplated herein. The systems and methods disclosed herein do not require cells to be detached from a cell culture container surface or transferred to another container, so they maintain their natural adherent state, do not experience the stress of transfer in liquid and re-attachment, and in some cases avoid open-container processes that are prone to contamination or sample cross-contamination. The systems and methods disclosed herein also take advantage of a geometric approach that ensures clonality for cell populations that form orderly, clean borders upon collision of two sub-populations and display minimal mixing. This assumption holds true for many cell types that grow in dense colonies, such as iPSCs.

The various implementations disclosed herein may be performed with open-loop targeting when approximate cell colony locations are known, for example when a cell culture container has been pre-patterned with a biocoating that allows cell attachment and proliferation only in some regions. In this example, the systems and methods disclosed herein utilize a series of laser patterning steps and anticipates cell colony regrowth patterns to eventually clonalize the cell colony. The systems and methods disclosed herein may also be performed closed-loop with image-derived cell colony data (including but not limited to the geometry of the colony borders) to actively tailor laser scanned areas to the shape, size, and re-growth rate of the cell colony. Neither of these methods requires any knowledge of polyclonality or monoclonality, nor borders between polyclonal areas within the cell colony, to achieve the end result of monoclonality.

Advantages of the systems and methods disclosed herein include the in situ formation of cell colonies that are highly likely to be clonal and therefore likely to exhibit characteristics, either as individual cells or as an entire colony, that are more strongly reflective of the likely quality or functionality of the cell colony when compared to a cell colony that is a mix of clones. For example, a monoclonal cell colony that is karyotypically abnormal may exhibit a clearly higher or lower proliferation rate than karyotypically normal cell colonies, may display unusual cell morphology, and has poor stability of the molecular state of cells. These attributes may also be difficult to discern in a polyclonal setting. If only one subpopulation of a polyclonal colony is karyotypically abnormal, this may not be evident from image-based time series data. This may result in an unusable cell product, or worse, a cell product that produces a false positive in downstream quality control testing because only a small percentage of cells are karyotypically abnormal, and in the worst case may lead to adverse patient outcomes.

The systems and methods disclosed herein may in some cases be combined with other steps of a cell culture process disclosed herein, for example the observation of cell colony behavior (e.g., cell division rate, area growth rate, mobility, density, phenotype based on morphology, etc.), the clearing of reprogramming or other vectors, and the transport of a cell colony from one location to another.

Figure 70:
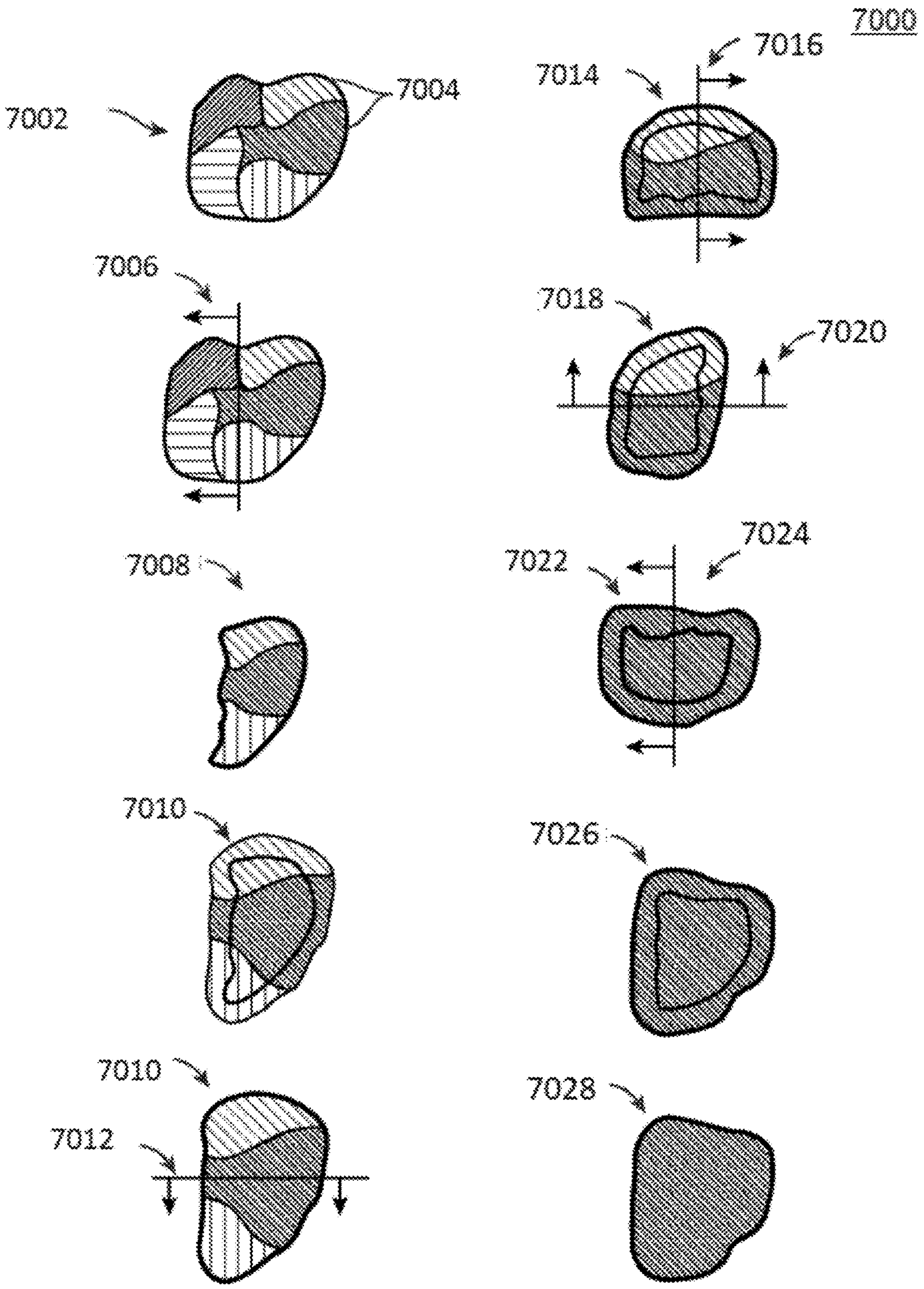
FIG. 70 are diagrams illustrating a process for forming a clonal cell colony in accordance with various implementations.

FIG. 70 is a series of diagrams illustrating a process 7000 for forming a clonal cell colony in accordance with various implementations. The process 7000 may involve repeated cycles of cell ablation of one or more colonies followed by expansion of the remaining cells. FIG. 70 depicts an initial cell colony 7002 that may be composed on multiple clonal sub-populations 7004, as indicated by different patterns. The clonal sub-populations 7004 may have arisen, for example, from an original cluster of cells or from a process that produces highly-proliferative cells. An example of this is an iPSC reprogramming process that generates multiple clonal iPSC colonies that may collide into contiguous polyclonal colonies. In a first step, approximately half of the initial cell colony 7002, as indicated by arrows to the left of cutline 7006, may be scanned by a laser system to destroy the cells, and the cells or cell debris are subsequently washed away. In some implementations, more or less than 50% of the cell colony 7002 may be ablated in each of the laser removal operations in the process 7000. For example, over 65%, 75%, or 85% of the initial cell colony 7002 may be ablated in each laser removal step. In alternate implementations, the percentage of the initial cell colony 7002 that is ablated in each step may be determined by information obtained from imaging of the initial cell colony 7002, including but not limited to its size, shape, density, and growth rate.

A first intermediate cell colony 7008 is left after the first laser ablation step. The first intermediate cell colony 7008 may have fewer clonal sub-populations 7004 than the initial cell colony 7002. In the example shown in FIG. 70, the cells in the first intermediate cell colony 7008 may proliferate uniformly in all directions, including in the direction where cells were previously ablated, and may grow into second intermediate cell colony 7010 by a later timepoint. At this timepoint (which may be determined by known growth rates, or by tracking of colony growth via imaging) another laser ablation may be performed on the second intermediate cell colony below cut line 7012. After this laser ablation and washing step, a subset of the original plurality of clonal sub-populations 7004 (e.g., two clonal sub-populations) may still be present remain in third intermediate cell colony 7014. The third intermediate cell colony 7014 may expand to a certain size (which may be determined through imaging) before another laser ablation and washing step is applied on cells to the right of cutline 7016, resulting in fourth intermediate cell colony 7018.

The fourth intermediate cell colony 7018 may expand to a certain size (which may be determined through imaging) before another laser ablation and washing step is applied on cells above cut line 7020, resulting in fifth intermediate cell colony 7022. The fifth intermediate cell colony 7022 may expand to a certain size (which may be determined through imaging) before another laser ablation and washing step is applied on cells to the right of cutline 7024, resulting in sixth intermediate cell colony 7026. Further expansion and laser ablation rounds may be applied to the sixth intermediate cell colony 7026 until a monoclonal cell colony 7028 is achieved. Repeated ablations, particularly ablations of a majority of the cells in a colony, reduce the probability of polyclonal sub-populations in the resultant colony and therefore increase the probability that the colony is clonal (or at least has fewer polyclonal sub-populations). The number of rounds of expansion and ablation until a monoclonal population is achieved may depend on several factors such as number of clonal sub-populations, cell types, and rate of growth. Thus, by taking advantage of the geometric nature of expanding, dense cell populations that maintain clean borders, and a series of orthogonal cuts that remove growths in certain directions, the implementations disclosed herein allows in situ generation of a monoclonal population using the precision afforded by laser-activated film cell removal.

In the case of closed-loop (image-guided) operation, each laser cut may be made through the "center" of the cell colony, which may for example be calculated as the center of mass (from either the covered area, or the covered area multiplied by local cell density), or by other geometric measurements. The cut line may be a straight line, or in other implementations the cut line may be a curve. For example, the cut line may be configured to resect more of the population away from the center of the cell colony, where sub-clone boundaries may move more rapidly depending on relative proliferation rates. In alternate implementations, cell density changes and/or cell motion may be calculated from time series images and the cut line may be calculated dynamically to account for proliferation of different regions, in which high-proliferating regions may "push" the cut line away to minimize steps-to-clonality despite dynamic internal sub-clone boundaries. In some implementations, the number of iterations may be reduced by image analysis of the cell colony to identify likely monoclonal clusters and define laser cuts that try to isolate a monoclonal cluster. A model of cell colony growth dynamics, which may be informed by time series imaging of the cell colony, may track the "flow" of cell proliferation within the cell colony, and estimate when all remaining cells are descended from a single cell in the original cell colony.

Figure 71:
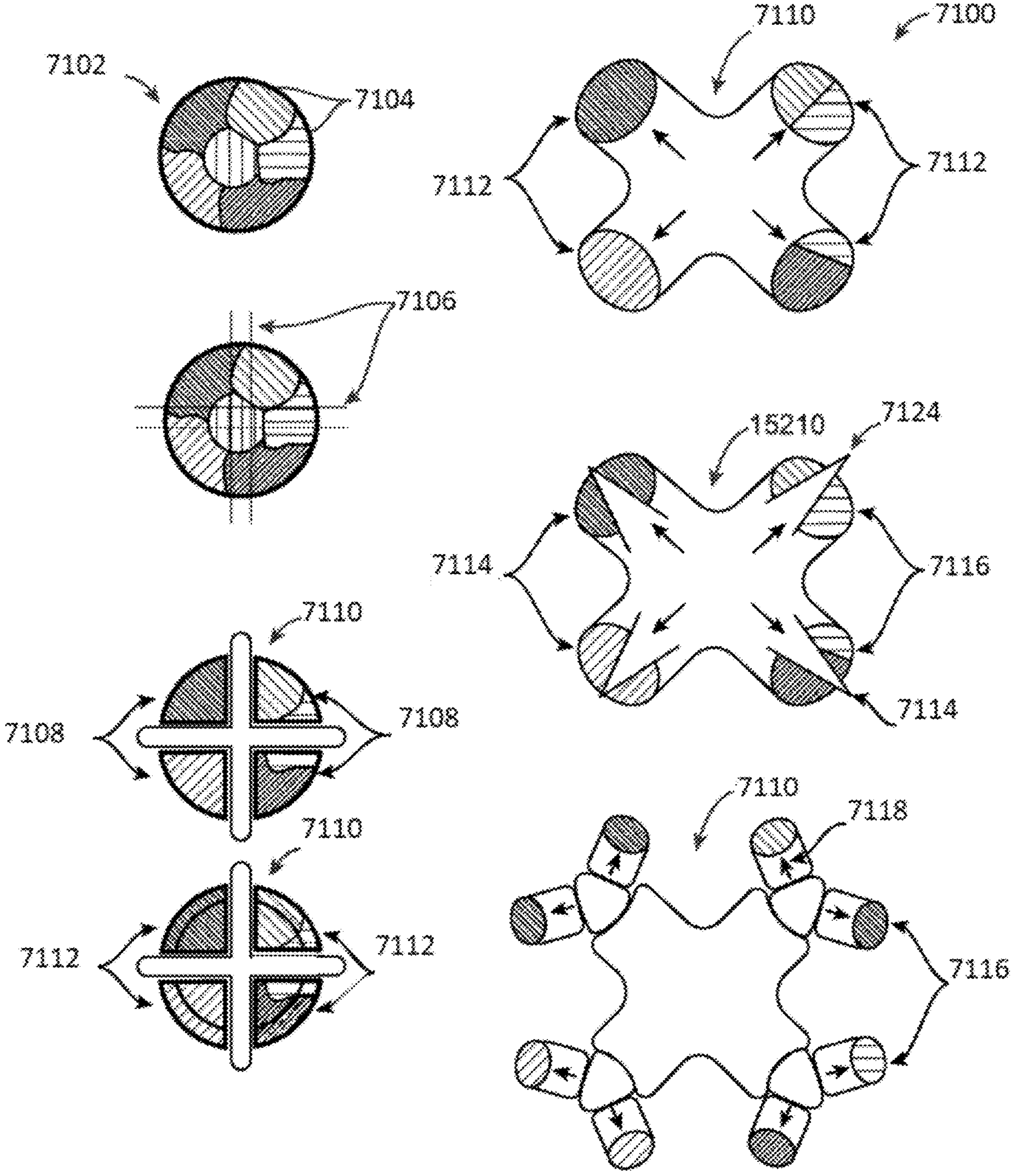
FIG. 71 are diagrams illustrating another process for forming a clonal cell colony in accordance with various implementations.

FIG. 71 is a series of diagrams illustrating another process 7100 for forming a clonal cell colony in accordance with various implementations. The process 7100 may involve repeated cycles of colony splitting, expansion, and translation. FIG. 71 depicts an initial cell colony 7102 composed of a plurality of clonal sub-populations 7104 that are shaped into an array by a series of laser splitting and translation processes. This may be aided by the ablation of a cell-supporting biocoating that is initially applied to the cell culture container surface, and is ablated as part of the splitting and translation processes. As described with reference to FIGS. 58A-60E, biocoatings may allow for more efficient splitting and translation due to a higher rate of cell proliferation into the biocoated areas compared to the regions where the biocoating has been laser-ablated, either during the cell removal process or when the biocoating specifically targeted for ablation in certain regions to optimize the clonalization process.

The process 7100 may be used, for example, in cases in which a small initial growth region is used to allow precursor cells to achieve a certain density and cell count during the cell culture process. For example, this may be used in an iPSC reprogramming process starting from fibroblast cells. In this example, a certain fibroblast density may be required before cells transition into the pluripotent state. However, when this transition occurs the density of iPSC colonies within the region may be high and the iPSC clonal regions may be difficult or impossible to separate. It is desirable to split this region into multiple clonal sub-colonies, separated by a distance that allows them to maintain clonality during a period of expansion. The sub-colonies may be monitored by an operator or by an imaging system and computing system (e.g., cell imaging subsystem 112, computing subsystem 110) and down-selected (i.e., selecting a subset of colonies and removing the rest) according to human or machine learning predictions of iPSC success.

In the example shown in FIG. 71, two cut regions 7106 may be established to define areas of laser ablation within the regions 7106, and the initially cell colony 7102 may be divided into a plurality of first intermediate sub-colonies 7108, with a clear region 7110 between them to keep them separated during regrowth. Cell-supporting biocoating may have also been removed from the region 7110. In some implementations, the biocoating ablation may be extended beyond the cell removal region defined by cut regions 7106 to further separate growth regions of the resulting first intermediate sub-colonies 7108. The first intermediate sub-colonies 7108 may expand over time into second intermediate sub-colonies 7112 while avoiding the region 7110. Laser translation methods as disclosed with reference to FIGS. 61-66 may be used to translate the second intermediate sub-colonies 7112 further apart and expand the biocoating-ablated region 7110. In implementations in which cells other than those requiring the biocoating emerge from the second intermediary sub-colonies 7112 (e.g., residual fibroblasts in an iPSC reprogramming process, in which fibroblasts do not require a laminin or similar biocoating for proliferation), they may proliferate back into the region 7110 and laser clean-up operations may be performed to remove them. This process may gradually clear each sub-colony 7112 of fibroblasts as well.

The process 7100 may further include a second colony splitting operation in which wedge-shaped scan regions 7114 are defined and laser ablation is applied to the regions 7114 to divide the second intermediate sub-colonies 7112 into smaller third intermediate sub-colonies 7116. The cut direction of the regions 7114 may be roughly orthogonal to the previous translation direction for optimal progression towards clonal sub-colonies. The third intermediate sub-colonies 7116 may subsequently be translated further apart from each other as shown by arrows 7118, which also expands the biocoating-ablated region 7110. Further colony splitting and translation operations may be performed to create a set of sub-colonies that are each clonal (due to probabilistic reduction of the number of polyclonal sub-populations for each ablation step), and that may subsequently be observed for prediction of function, phenotype, karyotype, etc. The process 7100 may be used with a range of sub-colonies created per splitting step. For example, each cell splitting operation in the process 7100 divides a colony into two sub-colonies (or in other examples into three sub-colonies or four sub-colonies). In some implementations, the number of sub-colonies created may vary depending on the physical location of the original cell colony with respect to the cell culture container boundaries.

Figure 72:
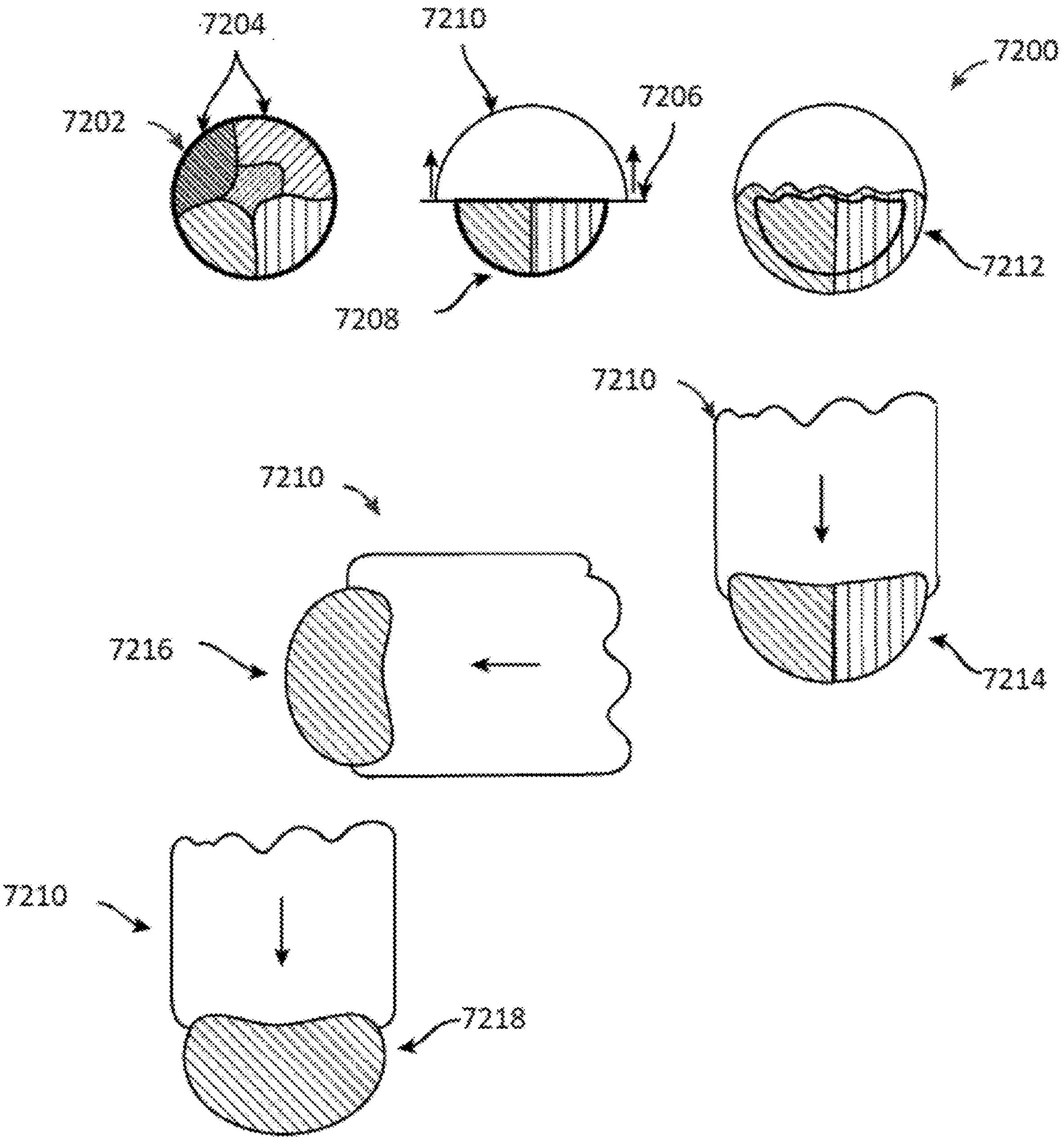
FIG. 72 are diagrams illustrating another process for forming a clonal cell colony in accordance with various implementations.

FIG. 72 are diagrams illustrating another process 7200 for forming a clonal cell colony in accordance with various implementations. The process 7200 may involve repeated laser translation and expansion of a colony to clonalize it in situ. The process 7200 takes advantage of the fact that cells and sub-clones in the trailing edge of the cell colony are preferentially ablated.

FIG. 72 depicts an initial cell colony 7202 composed of a plurality of sub-clones 7204. A first laser cell removal scan is done above the cut line 7206, resulting in first intermediate cell colony 7208 and a cell-supporting biocoating-ablated region 7210. The first intermediate cell colony 7208 preferentially grows in areas other than the region 7210 due to the absence of the cell-supporting biocoating and expands into second intermediate cell colony 7212. Additional cell laser scanning/biocoating ablation steps may be applied to the upper portion of the colony, and the resultant colonies may regrow preferentially away from the ablated region (shown by intermediate cell colonies 7214, 7216, and 7218). The biocoating-ablated region 7210 expands into a "track" as the ablation and expansion steps are repeated. Repeated laser ablation and expansion steps, which are configured to translate the cell colony in the process, may result in a monoclonal colony (due to probabilistic reduction of the number of polyclonal sub-populations for each ablation step). The process 7200 may be combined with colony translation (described with reference to FIGS. 61-66) for the purpose of repositioning the cell colony within the cell culture container, or when there are a plurality of cell colonies to distribute them around the cell culture container. In general, aspects of the clonalization processes described with reference to FIGS. 70-72 may be combined. For example, clonalization by splitting, clonalization by translation, and in-place clonalization may be combined in various sequences to produce one or more clonal colonies as part of a cell culture process. In other implementations, the process may maintain multiple separated cell colonies in a cell culture container, translating them locally, in a square-spiral pattern for example, to simultaneously clonalize each cell colony, mature it (for example during reprogramming), and potentially observe its characteristics such as proliferation and cell morphologies for the purpose of ranking or selecting (clonal) cell colonies.

Methods for Cell Colony Management Using Cell Removal Tools

Detaching and/or dissociating adherent cell clusters and colonies into single-cell or clumped suspensions is a highly variable process that often results in low yields due to incomplete detachment, variable clump size and resulting low viabilities, damage due to enzymes used for dissociation, and generally high heterogeneity in cell and cell colony behavior in these processes. To hasten this process, mechanical patterning is sometimes used, for example the use of pipette tips to crudely scratch cells away and form a "grid" of cells out of a stem cell colony before clumped transfer. Such mechanical manipulation not only is crude, leaving a lot of collateral damage, but is not tailored for real-time cell and cell colony conditions, both colony-to-colony and intra-colony. Finally, these methods rely on open-container operations that introduce the possibility of contamination and patient cross-contamination.

Figure 73A:
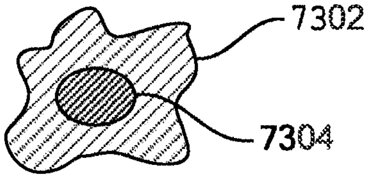
FIGS. 73A-D are diagrams illustrating a process for laser management of cell colony uniformity in accordance with various implementations.

Various implementations disclosed herein include systems and methods for configuring adherent cell clusters and cell colonies for consistent dissociation using patterning by a laser on a laser-activated film patterned on a cell growth surface (e.g., a transparent surface of a cell culture container). It should be understood that the laser-activated film and pulsed laser described with reference to the following examples is merely one example of a CRT compatible with the systems and methods herein, and that other implementations of CRTs are also contemplated herein. For example, FIG. 73A-D are diagrams illustrating a process for laser management of cell colony uniformity in accordance with various implementations. FIG. 73A depicts a cell colony 7302 having a gradation of cell densities, as illustrated by an inner higher-density region 7304. It may be desirable to continue to grow the cell colony 7302 in a managed manner to achieve uniform cell density. This may be useful in different scenarios, for example to set the stage for a cell reprogramming or differentiation process, for a harvesting step, etc.

Figure 73B:
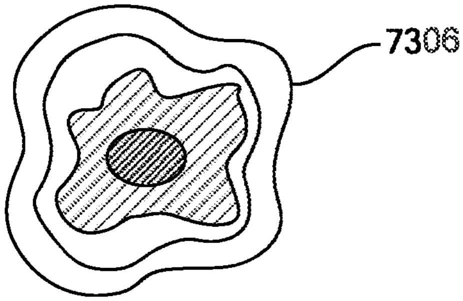

FIG. 73B depicts a barrier region 7306 surrounding the cell colony 7302. The barrier region 7306 may be formed by laser-ablating a biocoating supporting cell proliferation that is on the cell growth surface. The barrier region 7306 provides a barrier to colony growth at different distances from the existing cell colony border. In some implementations, the barrier region 7306 may be calculated from one or more of cell colony density characteristics, overall colony proliferation characteristics, or local growth rates as measured by an imaging subsystem (e.g., cell imaging subsystem 112) and computed by a computing subsystem (e.g., computing subsystem 110). In the example shown in FIGS. 73A-D, the aim is to constrain colony expansion to create a more uniform cell distribution. In some implementations, the barrier region 7306 may contact or even encroach on existing cell regions. For example, the various implementations may be combined with colony splitting methods as described with reference to FIGS. 67-69.

Figure 73C:
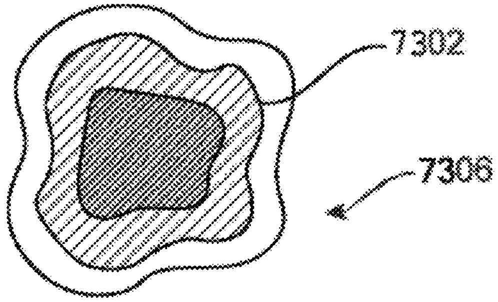
Figure 73D:
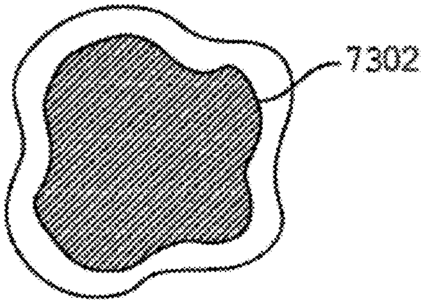

FIG. 73C depicts the cell colony 7302 after it has expanded to the barrier region 7306 and further expansion outwards is inhibited or slowed. At this point, the cell colony 7302 begins to densify internally. The different amount of "expansion space" for different regions around the perimeter of the cell colony 7302, defined by the shape of the barrier region 7306, dictates when this internally densification commences. Thus, the barrier region 7306 may be used to variably control the densification of the cell colony 7302 based on location to create uniform cell density. Having a specially designed shape for the barrier region 7306 aids in targeting specific locations for higher rates of densification compared to circular or rectangular shaped barriers because regions of the expanding cell colony that reach this barrier first begin to densify early. This approach may be combined with selective de-densification of internal regions of the cell colony 7302 by laser cell ablation. FIG. 73D depicts the cell colony 7302 after densification and a uniform density has been achieved as compared to the variable density illustrated in FIG. 73A. The uniform cell colony may subsequently be used to harvest cells or cell clumps, or to commence a reprogramming or differentiation process that has an ideal local starting density.

Figure 74A:
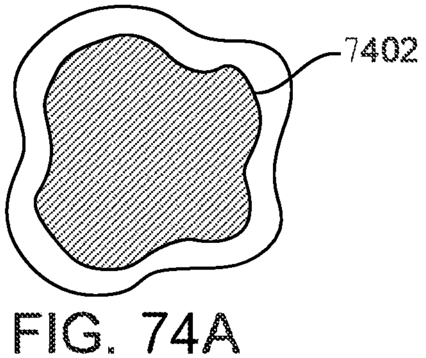
FIGS. 74A-E are diagrams illustrating a process for harvesting portions of a cell colony in accordance with various implementations.
Figure 74B:
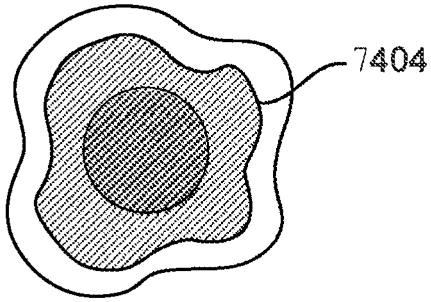

FIG. 74A-E are diagrams illustrating a process for harvesting portions of a cell colony in accordance with various implementations. FIG. 74A depicts an adherent cell colony 7402 that has been growth-constrained via a laser-patterned growth pattern, similar to the approach described with reference to FIGS. 73A-D. In some implementations, a standardized growth barrier such as a circular or rectangular barrier may be used (with or without modification to reflect the dynamics of the specific cell colony). The purpose of the barrier is to achieve the largest possible area of a uniform, but also critical cell density, where "critical" is used in this case to mean a density where cells begin to separate from the underlying substrate due to mechanical effects, cell excretion, and/or consumption of a layer of material under the cells. FIG. 74B depicts the formation of a dome 7404 from the cell colony 7402, where cells separate from the substrate as a result of increased density.

Figure 74C:
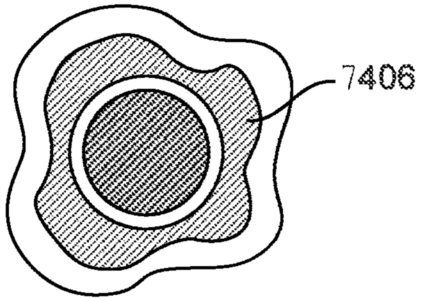
Figure 74D:
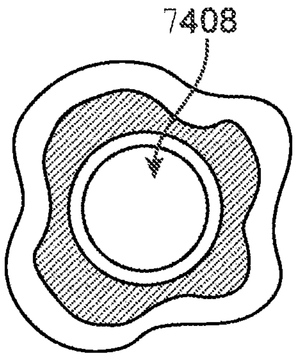

FIG. 74C depicts use of a laser ablation along cut line 7406 around the perimeter of the dome 7404, used to detach the dome 7404 from the adhered portions of the cell colony 7402. This laser pattern may follow the edges of the domed area as identified by cell imaging and computing subsystems (e.g., cell imaging subsystem 112, computing subsystem 110). The distinction between detached dome areas versus attached areas may also be measured using spectral signatures of the laser activated film, as described herein. FIG. 74D depicts the result after laser ablation and detachment of the dome 7404, leaving an empty region 7408. The detached cell sheet composing the dome 7404 may be removed via washing in a pipette-based system, flow in a fluidic system, or gravity where the cell-adherent surface is inverted.

Figure 74E:
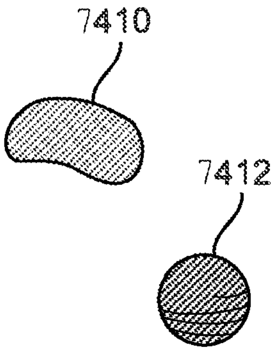

FIG. 74E depicts examples of the extracted cell sheet after removal. In some cases, the sheet may retain its planar nature, as shown by cell sheet 7410, and may be transferred to another growth surface where it re-adheres. In other cases, the cell sheet may fold or curl to form a 3-dimensional structure such as the one shown by cell sheet 7412. This may be used in situations when subsequent processes require 3D structure (e.g., the cells form a spheroid and then an organoid or embryoid body). In this manner, highly consistent 3D structures may be formed from previously adherent colonies, potentially after imaging-based screening of the 2D colonies. Various initial colony confinement geometries may be employed, and then subsequent cut patterns employed, both to create unique folded 3D geometries, and to respond dynamically to initial 2D cell colony shape, growth rates, and cell characteristics. In some implementations, the identification and laser separation of cell domes or bubbles described herein may be performed without the initial confinement of a group or colony of cells, although this confinement may be used in some cases to hasten formation of these domes or to achieve them with higher predictability, yield, and/or consistency. This folding process may be accelerated by adding high concentrations of matrices (e.g., laminin) to the cell media.

FIG. 75A-D are diagrams illustrating a process for sampling portions of a cell colony in accordance with various implementations. This sampling may be done on a live, adherent cell colony without the use of enzymes such as trypsin to release the sample cell clusters, or with minimal use thereof. This process may be used to retrieve a viable cell sample, with intact cells, from a specific colony and regions within that colony. The samples may be used to run in-process assays, including but not limited to qPCR, RNA sequencing, and DNA sequencing. In other implementations, the retrieved cell clusters may be used to seed a new cell culture.

Figure 75A:
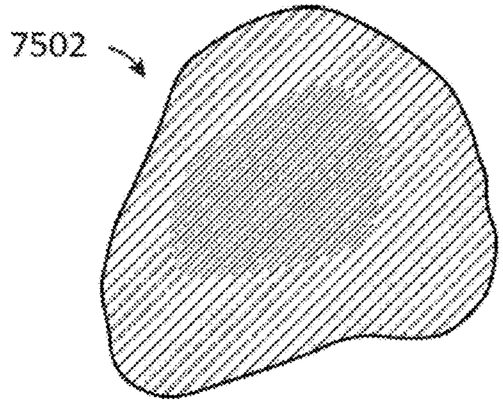
FIGS. 75A-D are diagrams illustrating a process for sampling portions of a cell colony in accordance with various implementations.
Figure 75B:
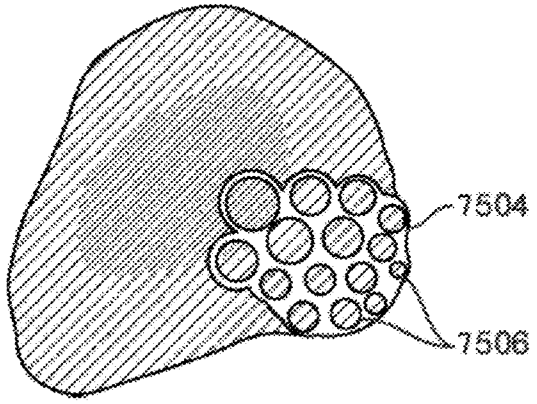
Figure 75C:
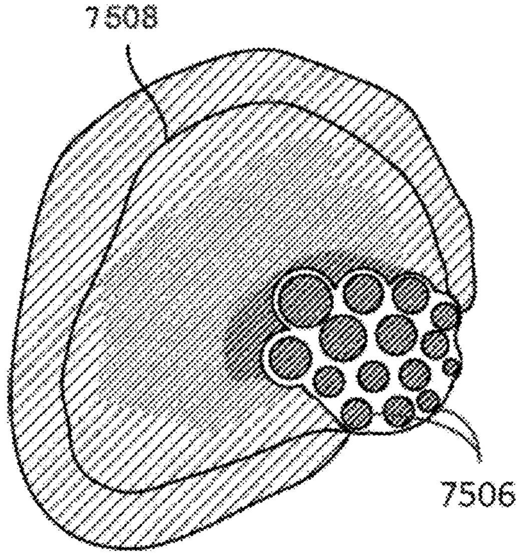

FIG. 75A depicts an initial cell colony 7502 having a range of cell densities and/or other properties that may be observable via imaging. A region of the cell colony 7502 may be selected for non-destructive retrieval. FIG. 75B depicts a scan pattern 7504 and laser ablation applied to the cell colony 7502, which results in the ablation of a cell growth-supporting biocoating (shown in shading), as well as a series of cell clusters 7506. The geometry of the cell clusters 7506 may be designed to sample specific regions, but also to scale based on cell density, growth rate, and maturity, with the goal of reaching a "critical point" simultaneously. FIG. 75C depicts expansion of the cell colony 7502 after ablation, past the original colony boundary 7508. However, the cell clusters 7506 are inhibited from propagating beyond their original boundaries because of the absence of the cell growth-supporting biocoating surrounding the cell clusters 7506. This forces a buildup of cell density internally within the cell clusters 7506, with the cell densities approaching a common critical point.

Figure 75D:
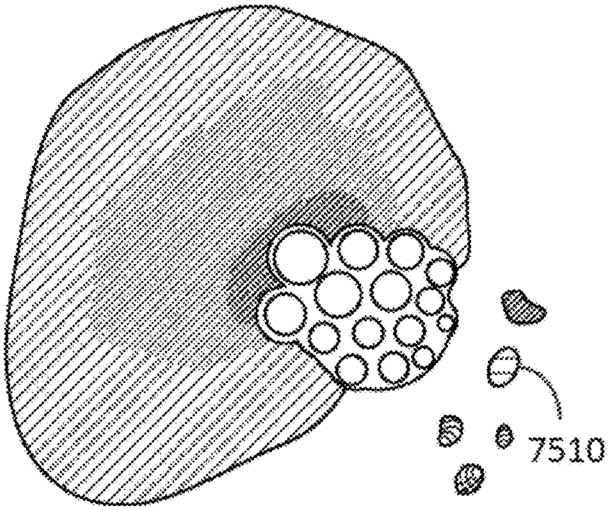

FIG. 75D depicts the cell colony 7502 after the critical point for the cell clusters 7506, at which point individual cell sheets 7510 from the plurality of cell clusters 7506 may have detached. The process depicted in FIGS. 75A-D allows detachment with little or no use of an enzyme such as trypsin to hasten detachment because of the mechanical forces at work in the dense cell clusters 7506. The cell sheets 7510 may be harvested from the cell culture container for analysis or seeding into another container, or used for analytical profiling of the cell colony while it continues to grow. In some implementations, a small amount of mechanical action (e.g., washing, vibration of the substrate, additional laser pulse hits around the borders of the cell clusters 7506 (which cause explosive microbubbles) or under the cell sheets), may be used to detach the cell clusters 7506. In alternate implementations, a low concentration (low enough to keep the main colony regions intact and attached while detaching small clusters) and/or short duration exposure to dissociation enzymes may separate the cell clusters 7506. Additionally, a laser system may be used to help detach the cell clusters by forming bubbles under the cell cluster and/or detaching or denaturing the extracellular matrix (ECM) underlying the cell clusters. This allows minimum disruption of the main cell colony while detaching a subset of the cells. The use of a laser system in conjunction with a laser-activated film allows the method to be performed with high precision and minimum loss of collateral cells, and also allows patterning of arbitrary, non-rectilinear shapes. For example, the various implementations described herein may utilize cell islands or clusters that are circular, elliptical, triangular, or hexagonal among other shapes, to optimize the mechanical forces for cell sheet separation. The patterns may also follow cell orientation. In some implementations, the separation between cell clusters may be less than 100 microns, less than 50 microns, or less than 25 microns. In some implementations, the remaining cell clusters may be as small in diameter as less than 200 microns, less than 100 microns, or less than 50 microns.

Figure 76A:
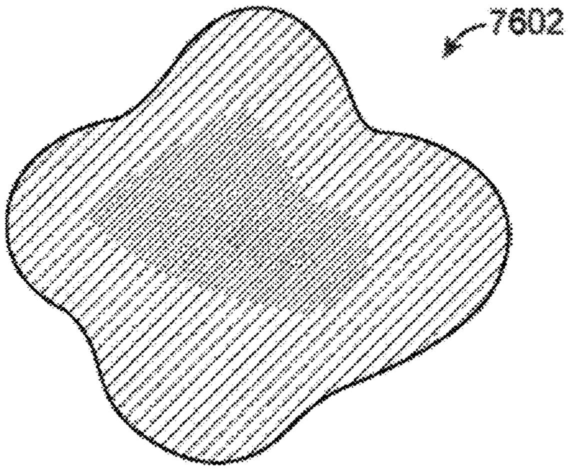
FIGS. 76A-C are diagrams illustrating a process for dissociating a cell colony in accordance with various implementations.
Figure 76B:
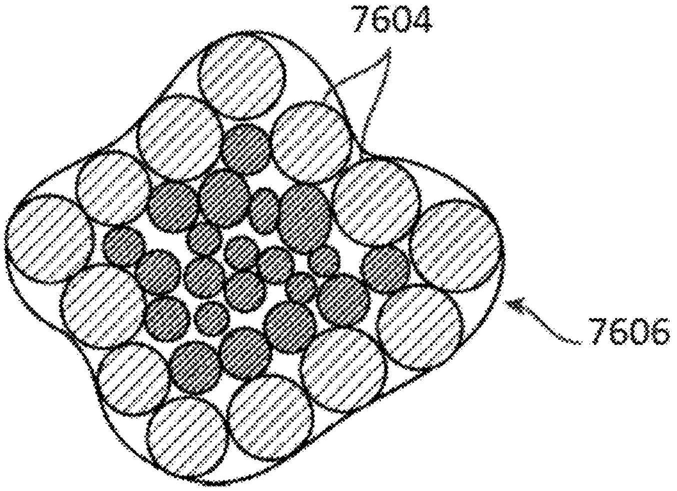
Figure 76C:
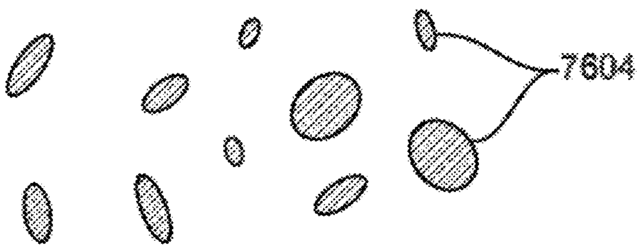

FIG. 76A-C are diagrams illustrating a process for dissociating a cell colony in accordance with various implementations. The dissociation may be performed with minimal use of dissociation enzymes, which in turn minimizes impact on cell health and viability. FIG. 76A depicts a cell colony 7602, which may have variations in internal conditions such as cell density, cell morphology, local cell organization, cell maturity, cell phenotype, etc. With significant intra-colony variability, as well as colony-to-colony variation in area, shape, density, etc., it is difficult to use a single process for colony dissociation that does not damage some cells and leave others undissociated or still adhered. In addition, dissociation may result in cell clumps of a reasonably narrow distribution when it comes to clump cell count.

FIG. 76B depicts separation of the cell colony 7602 into a plurality of cell clusters 7604, taking into account colony area and intra-colony variations in cell density and other characteristics. The cell clusters 7604 may have varying shape and size to optimize de-adhesion from the cell culture surface and/or resulting clump properties in suspension such as total cell count. The cell colony 7602 may be imaged and a computing subsystem (e.g., computing subsystem 112) may determine local density and other properties (potentially as a time series to calculate division rate, etc.) to generate a cut pattern 7606 that when implemented by a laser processing system divides the cell colony 7602 into the cell clusters 7604.

The cut pattern 7606 may be based on structural details of the cell colony 7602. For example, if cells are oriented in a specific manner (such as muscle cells, for example), the cut pattern 7606 may be configured to retain orientation in the resulting cell clusters 7604. In another example when there are heterogeneous regions in the cell colony 7602, these regions may be cut into different cell clusters 7604, or cut in a manner to include multiple characteristic regions in every cell cluster 7604. In another example, the cut pattern 7606 may be combined with laser ablation of cells or regions that are deemed (via an imaging subsystem and computing subsystem) to be unlikely to result in good cells/tissue. The cut pattern 7606 may include any number of shapes optimized to create the appropriate mechanical and/or chemical propagation characteristics within the remaining cell clusters, to maximize the viable cell yield from the process, and to allow uniform clumps or clusters to be released. The shapes contemplated herein may include but are not limited to circular, hexagonal, triangular, rectangular, or various other tiling patterns, for example patterns that maximize perimeter. Tessellated patterns with non-straight edges may also be used for fine control of edge to area relationships or for optimal lift-off.

The cell colony 7602 is then dissociated such that the individual cell clusters 7604 are released from the cell growth surface and into suspension, as depicted in FIG. 76C. The de-adherence itself may accomplished in a number of ways, including but not limited to one or more of the following: use of enzymes or other biochemical means to loosen cell-substrate adhesions (the concentration/duration of which may be minimized by various techniques disclosed herein), washing by cell media agitation over the surface of the islands (e.g., using a pipette, or using flows in a fluidic chamber), mechanical shaking by ultrasonic or other transducers, or local shockwaves from additional pulsed laser operations on the peripheries of or under the cell clusters 7604, resulting in explosive microbubble expansion and collapse. In other implementations, the cell cluster size, combined with the cell density, soon results in spontaneous detachment of the cell clusters 7604. The detached cell clusters 7604 may be re-seeded, either in the same cell culture container (for the purpose of re-distribution of a colony over the entire cell growth surface), or into another cell culture container. In some implementations, the detached cell clusters 7604 may be harvested for downstream processing or assays. In other implementations, the detached cell clusters 7604 may be processed further in suspension for large-scale expansion, differentiation, etc.

In Situ Cell Removal Tool Sorting of Adherent Cells

Many cell culture processes, such as cell reprogramming, differentiation, trans-differentiation, and/or gene editing, result in a heterogenous population of cells as measured by function or phenotype. In cases when bulk biochemical methods such as media composition changes are not sufficient to select for or against specific cell types, cell sorting processes are employed to alter the population fractions of cells. These sorting or enrichment techniques almost universally require dissociating adherent cells into suspension, where they may then be sorted via methods such as flow sorting or magnetic bead sorting. The process of dissociation, flowing cells, labeling cells, and sorting often destroys many cells, particularly sensitive cell types, or alters their state/function. Thus, there is a need in the art for better approaches to sorting adherent cell populations by phenotype or function in situ in cell culture, and to accomplish this even within aseptically sealed cell culture containers and systems.

Various implementations disclosed herein include systems and methods of using a combination of differentials in cell proliferation and/or mobility based on phenotype and/or function, together with a laser-based cell removal system, to sort, purify, or enrich adherent cell populations in situ. It should be understood that the laser-activated film and pulsed laser described with reference to the following examples is merely one example of a CRT compatible with the systems and methods herein, and that other implementations of CRTs are also contemplated herein. The systems and methods disclosed herein may be combined with methods for transporting, splitting, and clonalizing cell populations described herein to produce a cell population with a desired composition.

As populations of cells are reprogrammed, differentiated, or gene edited, these cell culture processes may alter the behavior of the resulting cells from the standpoint of proliferation (which is a combination of rate of division and rate of propagation of a colony across a surface, i.e., density of cells as they divide) and migration (where cells are motile on a surface). The differential in these characteristics between cell phenotypes/functionality levels may be accentuated in the presence of biological, chemical, or mechanical cues or obstacles within a liquid environment. The systems and methods disclosed herein utilizes these differentials between cell phenotypes or functionalities, which result in uneven spatial distributions of cells from an original mixed cell population, together with laser removal of a fraction of the cell population based on at least spatial position. The laser may preferentially remove unwanted cell phenotypes/functionalities in favor or desirable cell phenotypes/functionalities to enrich desirable phenotypes/functionalities. This process may be iterative and/or include multiple stages as cells differentiate/reprogram, or multiple stages of cues/obstacles that cause different differential spatial distributions.

In some implementations, the systems and methods disclosed herein may be run with various cues or obstacles that amplify differentials in cell propagation or motility. These may include, but are not limited to: biocoatings, or lack thereof, including spatial patterns in these biocoatings as described herein; surface microscale features such as roughness, oriented grooves, micro posts, etc.; obstacles such as constrictions or posts in a fluidic chamber or channel; chemometric gradients; or additional cell populations that act as attractants.

Figure 77A:
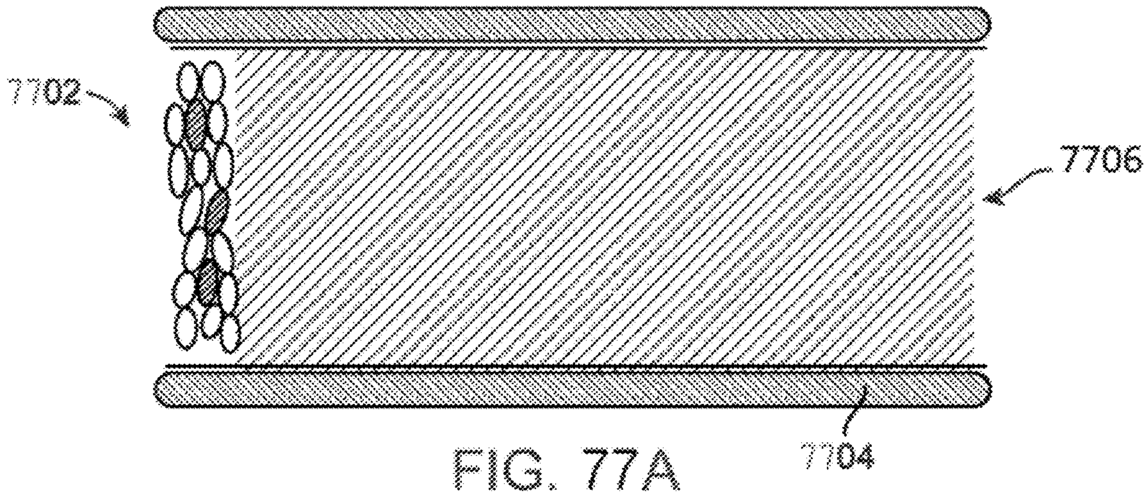
FIGS. 77A-C are diagrams illustrating a process for sorting cells in a cell colony in accordance with various implementations.
Figure 77B:
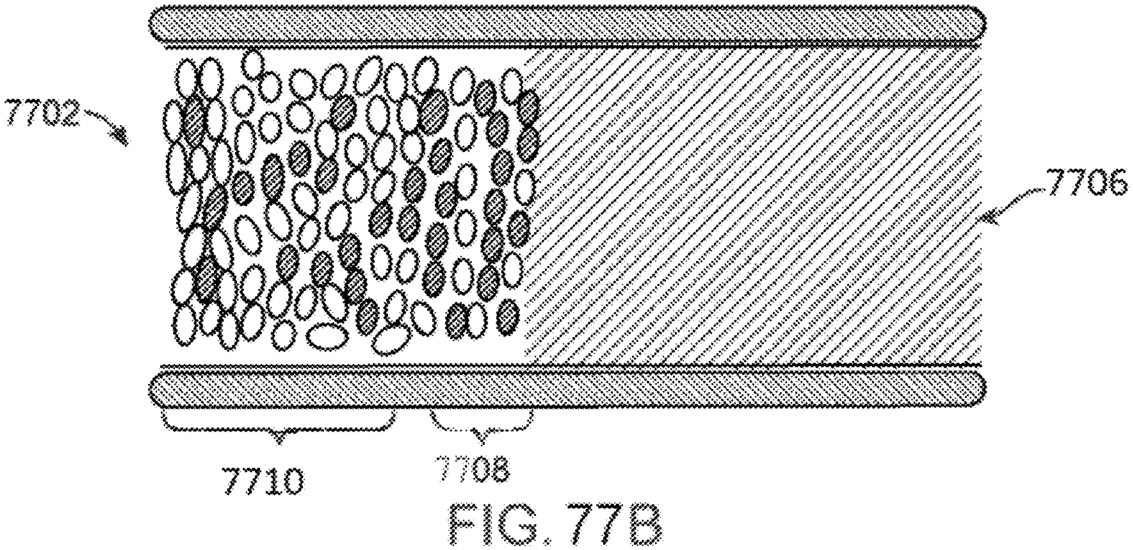
Figure 77C:
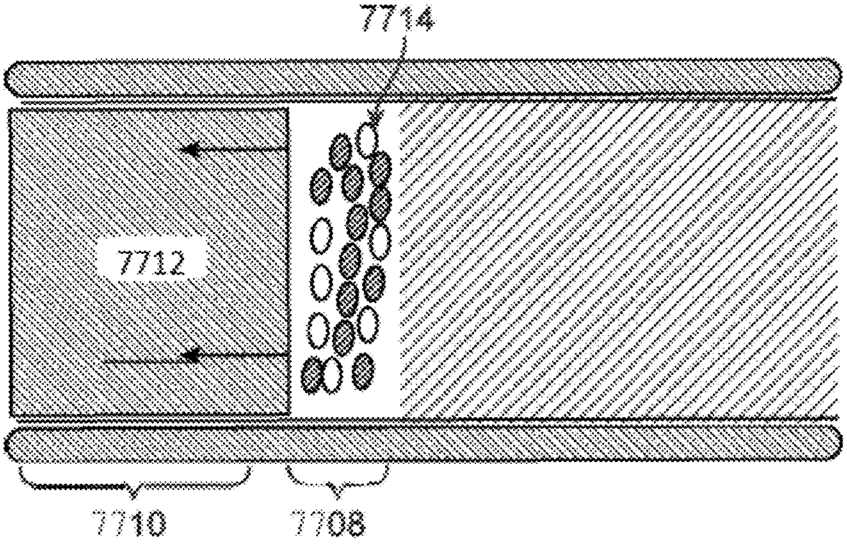

FIG. 77A-C are diagrams illustrating a process for sorting cells in a cell colony in accordance with various implementations. In the example shown in FIGS. 77A-C, the process is applied in a linear region to a heterogeneous cell population in which one cell type exhibits a higher proliferation rate under conditions that are set within the region. Although the example shown involves a linear "channel," in general there are a wide range of adherent surface geometries that are applicable, including but not limited to: linear regions; radial propagation from an origin colony, curved paths including but not limited to spiral paths that maximize propagation length within a given area, etc.

FIG. 77A depicts a cell colony 7702 composed of two different phenotypes in this example (in general, the cell colony may have any number of different phenotypes). The phenotypes may arise, for example, from a reprogramming or differentiation process. For example, the cell colony 7702 may include fibroblasts that are in the process of being reprogrammed into iPSCs, in which the iPSCs will divide and proliferate at a higher rate than the fibroblasts. The objective in this case is to purify or enrich the population of cells towards the cell type that proliferates more rapidly. The cell colony 7702 may be confined to a channel region 7704. In some implementations, the channel region 7704 may be defined by physical borders of a cell culture container such as a microfluidic channel. In other implementations, the channel region 7704 may be defined by biocoated regions of a cell growth surface, for example regions coated with an anti-fouling biocoating as described herein that inhibits cell attachment outside the channel region 7704. Within the channel region 7704 is a propagation region 7706 that may contain a range of "accelerants" for the desired cell type, and/or "obstacles" for the undesirable cell type. These may be coupled with other factors such as chemometric gradients. For example, the propagation region 7706 may be biocoated or microstructured to preferentially support proliferation of the desired cell type.

FIG. 77B depicts expansion of the cell colony 7702 into the propagation region 7706. In this example, the darker cells (the desired cell type) divide and propagate at a higher rate than the lighter cells (the undesired cell type). Thus, the leading growth region 7708 of the cell colony 7702 has a higher percentage of cells of the desired type than a trailing region 7710. FIG. 77C depicts laser ablation of the trailing region 7710, leaving behind an ablated space 7712. Cell growth supporting biocoating may also be ablated from the ablated space 7712, making it unsuitable for furth cell growth. The retained cell colony 7714 is enriched with cells of the desirable cell type compared to the original cell colony 7702 through propagation and then laser removal of trailing regions.

The process illustrated in FIGS. 77A-C may be iterated along a path (e.g., a linear path defined by the channel region 7704) to produce a progressively purer population of the desired cell type. This process may be combined with in situ laser colony transport, redistribution, splitting, and/or clonalization as described herein. While this example uses a simple open-loop process to accomplish this sorting, the method may be combined with imaging of the cell culture (e.g., using cell imaging subsystem 112) and detection via a computing subsystem (e.g., using computing subsystem 11) to tailor the laser ablation area for each iteration. For example, a cell culture system may monitor actual progression of the cell propagation and laser cut accordingly. In other implementations, the cell culture system may make predictions of the cell composition of the remaining cells and continue the process until a target purity or enrichment level is achieved, or accelerate or decelerate the process to coincide with other desired timing for a protocol.

Figure 78A:
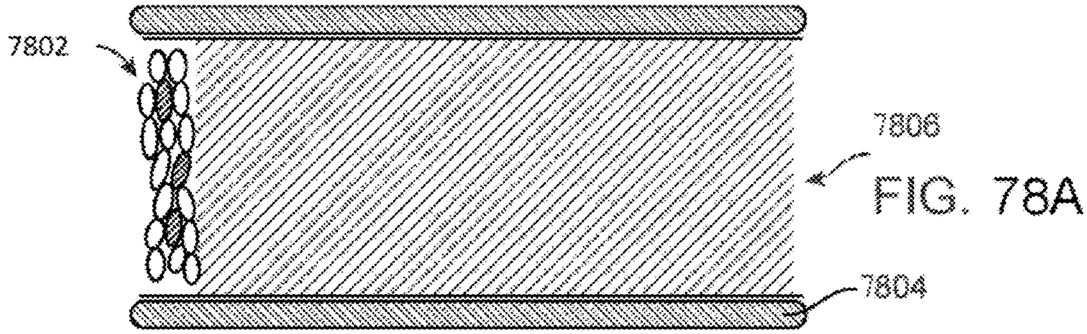
FIGS. 78A-D are diagrams illustrating a process for purifying cells in a cell colony in accordance with various implementations.

FIG. 78A-D are diagrams illustrating a process for purifying cells in a cell colony in accordance with various implementations. For example, the process may involve using a differential in cell motility between phenotypes to purify a cell population. FIG. 78A depicts an initial cell population 7802 that is heterogeneous. For example, the cell population 7802 may be formed during a cell differentiation process, in which white cells in FIG. 78A represent the desirable cell type. The cell population 7802 may be confined to a channel region 7804, which may be linear as depicted in FIG. 78A but in general may encompass a variety of other shapes. In some implementations, the channel region 7804 may be defined by physical borders of a cell culture container such as a microfluidic channel. In other implementations, the channel region 7804 may be defined by biocoated regions of a cell growth surface, for example regions coated with an anti-fouling biocoating as described herein that inhibits cell attachment outside the channel region 7804. Within the channel region 7804 is a propagation region 7806 that is configured to attract undesirable cell types. For example, the propagation region 7806 may be coated with a biocoating that promotes high mobility. Alternatively, or in addition, a chemoattractant specific to the undesirable cell type may be used to form a chemical gradient within the propagation region 7806.

Figure 78B:
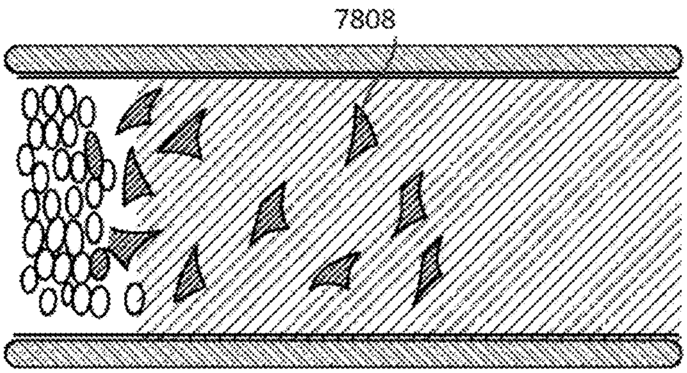
Figure 78C:
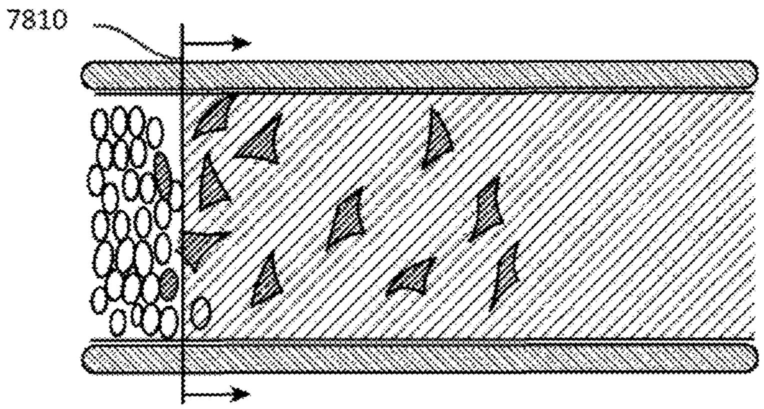

FIG. 78B depicts preferential movement of cells 7808 of the undesired cell type into the propagation region 7806 as a result of their inherent motility and/or the preferential conditions created in the propagation region 7806. FIG. 78C depicts laser ablation of cells to the right of laser cut line 7810, thus removing the undesired cells 7808. This may be performed with a complete scan of the entire propagation region 7806, or by cell-by-cell targeting based on an imaging subsystem and computing subsystem output (e.g., cell imaging subsystem 112 and computing subsystem 110). In some implementations, additional predictions of phenotype or function per cell may be made using the imaging subsystem and computing subsystem, and only a subset of cells eliminated using the laser processing subsystem (e.g., cell editing subsystem 114). This prediction may be based on a variety of data including but not limited to cell mobility and morphology.

Figure 78D:
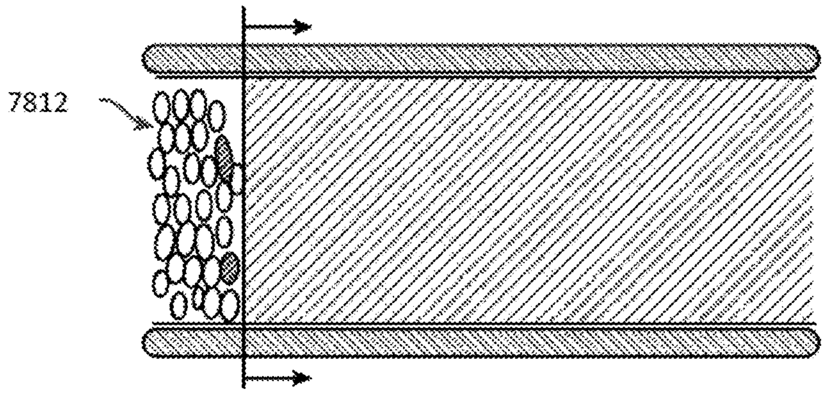

FIG. 78D depicts a remaining cell population 7812 after laser ablation of the undesired cells 7808. Because the more mobile undesired cells 7808 moved away from the desired cells and were eliminated using laser destruction, the composition of the remaining cell population 7812 favors the desired cell type. The process illustrated in FIGS. 78A-D may be performed iteratively, and in some implementations may be used in conjunction with other laser translation or colony division methods to move different cell regions to the outer edge of a cell population and allow cells to propagate away for the purpose of removal. While the example shown in FIGS. 78A-D shows the elimination of the more motile cells, in general the process may also be used to purify a population where the more motile cells are selected for by ablating the cells that do not move into the propagation region 7806.

Methods for In Situ Clonal Processing and Selection

Gene-edited cell line generation has generally been performed via transfection of a starting cell population with molecular components to drive the desired genetic change. This is achieved using engineered DNA nucleases such as transcription activator-like effector nucleases (TALENs), zinc finger nucleases (ZFNs), or Cas9 proteins with a target-specific single guide RNA (sgRNA) molecule. See, e.g., Doudna, Jennifer, "The Promise and Challenge of Therapeutic Genome Editing," Nature, February 2020, 578 (7794): 229-236, which is hereby incorporated by reference in its entirety. The nucleases may be introduced into cells in a DNA plasmid or mRNA encoding for them (see, e.g., Kehler, James et al., "RNA-Generated and Gene-Edited Induced Pluripotent Stem Cells for Disease Modeling and Therapy," J. Cell. Phys. Vol. 232, Issue 6, June 2017, 1262-1269, which is incorporated by reference in its entirety), or as direct proteins (or in the case of CRISPR, ribonucleoproteins). For knock-ins, in which a new sequence is introduced into the genome or a portion of an existing sequence is altered to a particular desired sequence, a homology DNA plasmid containing the desired sequence is co-transfected with these components to act as a template during homology directed repair (HDR) of the target site.

Due to inefficiencies in the delivery of gene-editing tools and stochasticity in the editing process, typically only a small fraction of transfected cells carry the desired edit. This necessitates a clonal selection and screening process, in which single cells are isolated, proliferated, and profiled to find a clonal population with the desired edit and otherwise desired functional phenotypic properties.

Because intended gene edits often occur at a low frequency in the transfected cell population, it is common practice to introduce a selection marker cassette in addition to the intended edit that allows for enrichment of cells with successful knock-ins. These selection marker cassettes often include a constitutive promoter such as EF1-alpha or PGK driving the expression of either a fluorescent protein, such as mEGFP or mCherry, or an antibiotic resistance-inferring protein such as NeoR. See, e.g., Long, Yicheng et al., "Targeted Mutagenesis in Human iPSCs using CRISPR Genome-Editing Tools," Methods, July 2021, 191:44-58 (the "Long" reference), which is hereby incorporated by reference in its entirety. A successful knock-in edit will introduce these cassettes in addition to the intended edit, resulting in the edited cells being distinguishable by either fluorescence signal recording (either via FACS or microscopy) or exposure to a predetermined dose of antibiotics.

Once cells with the successful edits are enriched with the selection marker, it is often desirable to remove this insert from the cells' genome. To accomplish this, the selection marker cassette (otherwise known as a resistance cassette) is often flanked with paired recombination sequences (such as loxP sequences) that are oriented in the same direction. To excise the selection marker cassette, cells are transfected with either the recombinase protein or a plasmid encoding this protein that targets the cassette sites (e.g., Cre in the case of loxP). For fluorescence selection markers, there may be a second selection round for successful removal of the selection cassette by sorting for cells without a fluorescence signal.

Overall, the process of knock-in-based gene editing may be stressful for cells beyond the gene edit itself, as the repeated single-cell passaging and fluorescence-assisted cell sorting or exposure to antibiotics for clone enrichment may have adverse effects on the genomic integrity and cell state stability of the edited cells. For example, the process of single-cell seeding for clonality may be stressful on cells, resulting in low survival rate and/or alteration of cell properties and health. In addition, single-cell seeding may have low efficiency due to low survival rates and low optionality in selection per run. Repeated passaging of cells is also stressful because it interrupts cell processes, may cause genomic instability, and interrupts observations of cell populations. The processes known in the prior art also typically require open-well operations, increasing the possibility of contamination, and requiring expensive containment and sterility equipment and procedures in clinical processes.

Low efficiency of the gene editing process necessitates the starting cell population to have self-renewal capabilities to ensure sufficient expansion and selection of correctly edited cells. This makes human induced pluripotent stem cells (hiPSCs) a valuable starting material for the basis of gene-edited cell therapies. See, e.g., Blassberg, Robert, "Genome Editing of Pluripotent Stem Cells for Adoptive and Regenerative Cell Therapies," GEN Biotechnology, February 2022, 77-90, which is hereby incorporated by reference in its entirety. For example, a recent study has demonstrated successful targeted gene editing concurrent to reprogramming of patient cells into hiPSCs, effectively shortening the total timeline for gene-edited iPSC generation. See, e.g., Neumayer, Gernot et al., "A scalable, GMP-compatible, autologous organotypic cell therapy for Dystrophic Epidermolysis Bullosa," bioRxiv preprint, Mar. 1, 2023, available at https://www.biorxiv.org/content/10.1101/2023.02.28.529447v1.full, which is hereby incorporated by reference in its entirety.

Thus, there is a need in the art for a process by which cells may be maintained, clonalized, evaluated, and selected all in their natural physiological state (in colony form), without single-cell plating and without frequent passaging (e.g., continuously adhered to a cell culture surface during the cell culture process). This would also potentially allow the process to be automated or semi-automated and occur within closed containers that maintain sterility and eliminate cross-contamination concerns.

The systems and methods disclosed herein include methods that may be performed on cells that are adherent and proliferative post gene-editing and entirely on intact multi-cell clusters or colonies that are initially polyclonal. These kinds of cells include, but are not limited to, iPSCs, mesenchymal stem cells, neural stem cells, HEK-293 cells, and MDCK cells. In this process, cell colonies are observed via imaging and colony growth and proliferation are managed using a cell removal tool to progressively clonalize the cell colonies. This process may be performed on multiple colonies within a single cell culture chamber of a cell culture container, maintaining separation between the colonies to maintain clonality. This method may be combined with observation of clonal colony characteristics to make a selection of which colonies to retain and which to remove. This process may also be combined with active enrichment toward properly edited cells and/or proper phenotype cells during the in situ clonalization process.

An example implementation of the systems and methods disclosed herein includes a process in which cells may be continuously managed through reprogramming, gene editing, clonalization, clone tracking, and clone selection. This continuous process does not utilize mechanical colony transfer or passaging steps so that the cell culture is continuously adhered to a cell culture surface throughout the process. This process maintains cells in a physiological manner for maximum cell health, process consistency, and product traceability. Furthermore, the process is compatible with a system with sealed cell culture containers because it does not require passaging of cells from container to container.

In some implementations, the process may include reprogramming of a clonal human iPSC sample from somatic cells, with appropriate quality control (QC) testing to ensure high quality in terms of pluripotency, identity, karyotypic profile, etc. The resultant iPSCs may then be clump passaged into one or more cell culture containers, which in some implementations may be appropriately pre-coated with an extracellular matrix such as Laminin 521.

After adherence of the cell clumps or clusters in the one or more cell culture containers and establishment of new colonies, the process may include managing the surface area or cell density of the cell colonies. For example, the process may include selective removal of cell clusters/clumps using one of a number of CRTs to ensure proper spacing between colonies for long-term in situ maintenance. The cell removal method may be one that does not require opening of the cell culture container. For example, the cell culture container may include a transparent window with an absorbing coating or film on the cell culture surface. Pulsed laser energy may be directed to the cell clumps/clusters to be removed, and the absorbing coating or film may absorb the optical energy and convert it into mechanical energy (e.g., creation of microbubbles) to dislodge cells from the coating/film. In some implementations, the laser may also be used to shape cell colonies or manage their internal density to optimally configure them for the gene editing process.

The process may then include gene-editing the iPSCs in the same cell culture container, and may also include adding selection marker cassettes that indicate whether a cell has been successfully gene-edited. For example, the iPSCs may be transfected using lipofection, for example using Lipofectamine Stem Cell Reagent to deliver CRISPR-Cas9 plasmid or RNP, along with guide RNA, and homology-directed repair plasmid including LoxP-flanked cassette with an mCherry gene to report successful edits. See, e.g., the Long reference, and Giacolone, Joseph et al., "CRISPR-Cas9 Based Genome Editing of Human Induced Pluripotent Stem Cells," Curr. Protoc. Stem Cell Biol. February 2018, 44:5B.7.1-5B.7.22, which is hereby incorporated by reference in its entirety. In some implementations, delivery of gene editing constructs may be achieved by electroporation, by laser-induced bubble poration of cell membranes, or by a range of other intracellular delivery techniques known to those skilled in the art.

The process may then include iterative proliferation and colony management of cell colonies by selective removal of portions of the colony (e.g., using laser-based cell management or other selective cell removal tools). Laser management may be useful to manage colony density to maintain healthy conditions for iPSC proliferation and pluripotency. Laser management may also be used to derive clonal colonies by sequential spatial sectioning of the initially polyclonal (post gene-editing) proliferating colony. In some implementations, laser management may be guided by imaging of selection marker cassettes (e.g., mCherry fluorescent reporter genes) that indicates successful gene editing (e.g., sectioning the colony to preferentially leave higher fluorescence-expressing sectors of each colony intact). In some implementations, laser management may be guided by measurements of cell proliferation and morphology in different sectors of each colony, preferentially leaving sectors that match functional, pluripotent iPSCs.

Once clonal colonies have been established based on measurements of repeated sectioning and proliferation and prior models of clonality, the process may include laser removal of any clonal colonies not expressing selection marker cassettes such as mCherry. In some implementations, the process may include shaping colonies or managing their internal density using the laser to configure them optimally for the Cre recombinase transfection. The process may also include transfecting the iPSCs with Cre recombinase using Lipofectamine. Where successful, the recombinase removes the selection marker cassette (e.g., a LoxP-flanked cassette including the mCherry reporter).

In some implementations, the colony clonalization steps may be repeated, but this time biasing the colony sectioning process towards cell sections that do not contain any selection marker cassettes (e.g., mCherry reporters). In other implementations, this repeated sectioning and clonalization may not be necessary. For example, the initial sectioning process may simply be used to arrive at a colony that is entirely mCherry reporting, if this can be accurately imaged.

The process may also include managing the iPSC colony to track now-clonal colony morphology, proliferation rates, density, and other features to score each colony based on a model for iPSC functionality, stability and genomic integrity. iPSC colony management may also be used to avoid collisions between clonal colonies, or collisions of colonies with container walls, regions where ECM has been depleted, etc., as colonies are repeatedly sections and regrown.

The process may then include laser down-selection to the top-ranked cell colony in the cell culture container based on the tracking data described herein, and a model that has been trained using prior in-process colony behavior and post-harvest clonal assay data for multiple runs. The process may then include expanding the selected clonal colony across the cell culture container to generate enough cells for down-stream processes and characterization.

Figures 79A, 79B, 79C, 79D, 79E, 79F, 79G:
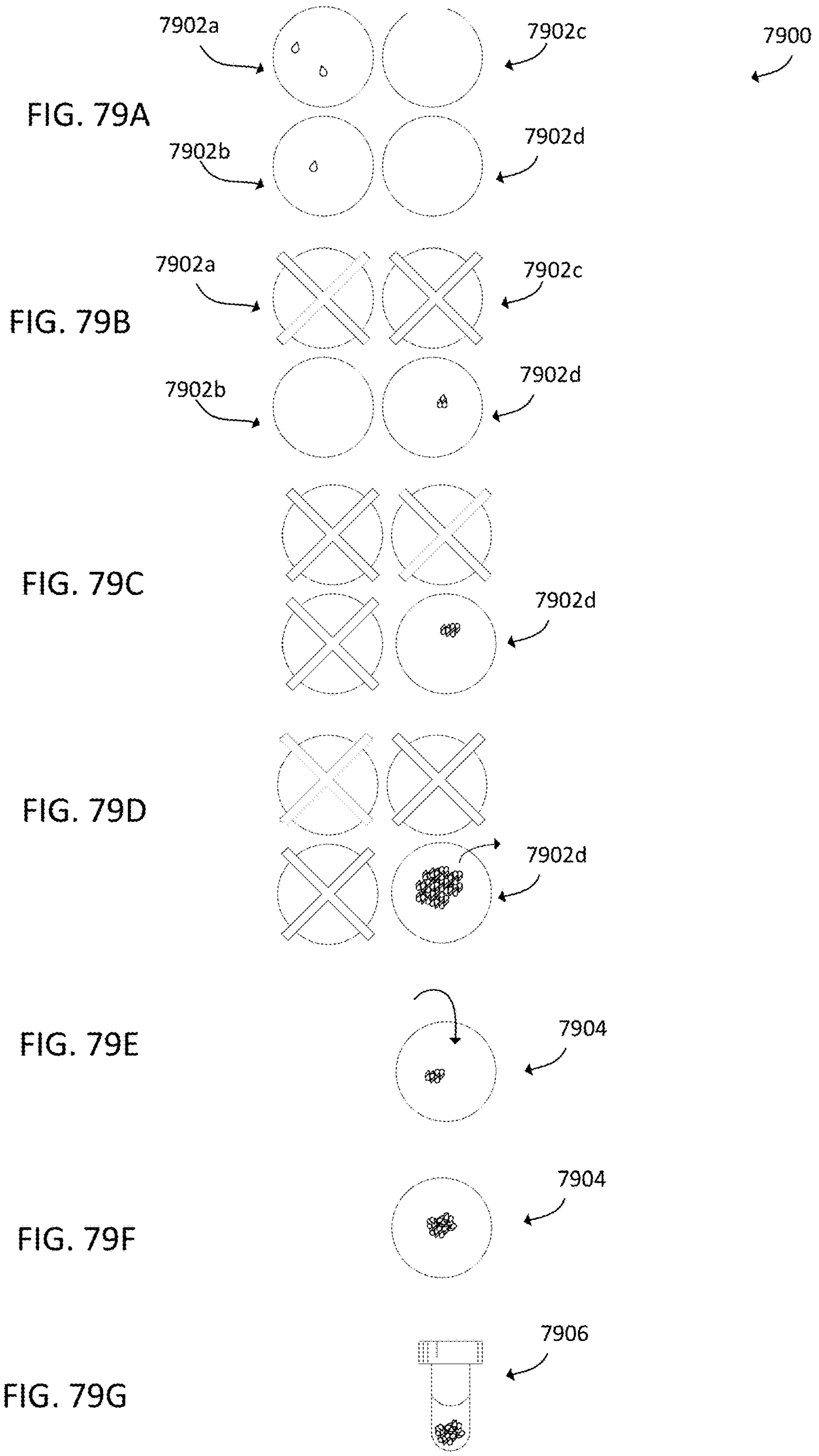
FIGS. 79A-G are diagrams illustrating a prior art process for gene-edited clonal cell screening and selection.

FIGS. 79A-G are diagrams illustrating a prior art process 7900 for gene-edited clonal cell screening and selection. The process 7900 centers on placing a single source cell into each cell culture container to ensure clonality. FIG. 79A shows four cell culture chambers 7902*a-d* into which cells have been seeded after a gene editing step. The cell culture chambers 7902*a-d* may be, for example, single wells in a well plate. In practice, many techniques that attempt to place single cells into cell culture containers produce a range of outcomes. For example, limiting dilution of single cell suspensions produces a Poisson-distributed cell population over a range of cell culture containers. Similarly, use of flow sorting machines produces a range of results and can additionally be stressful on cells, lowering survival rates.

FIG. 79B shows viable and non-viable chambers after attachment and acclimation of cells. Two cell culture chambers 7902*a* and 7902*c* have been eliminated from contention at this point because of either multiple cells per well (cell culture chamber 7902*a*) or (ii) no cells in well (cell culture chamber 7902*c*). Efforts have been made to address the "multiple cells per well" situation in the prior art. For example, in PCT Publication No. WO2020176798A1, a laser system is used to remove all but one single cell in a chamber, thereby allowing lower dilution of cell suspensions while losing fewer containers to "no cell" conditions. However, none of these solutions address a fundamental limitation of these systems—many cell types, including stem cells such as embryonic stem cells (ESCs) and induced pluripotent stem cells (iPSCs), do not fare well in single-cell configurations. The stress of not being part of a cell colony or cluster often leads to cell death, as depicted in cell culture chamber 7902*b* in FIG. 79B. In other cases, a cell may survive but the stress from enzyme and/or mechanical dissociation, suspension in single-cell format, and seeding in single-cell format may alter cell expression and phenotype in a manner that leads to non-viable cell populations.

FIG. 79C illustrates a single viable cell culture chamber 7902*d* after some cell death resulting from single-cell handling and plating stresses. Cell culture chamber 7902*d* is the only chamber remaining with a viable cell colony for observation. FIG. 79D shows the remaining cell colony in cell culture chamber 7902*d* growing but also reaching high density in its interior. For cell types such as ESCs and iPSCs, high cell density lowers proliferation rates, and can additionally trigger spontaneous cell differentiation. As a result, for extended clone growth and observation, it is necessary to passage cells to a fresh cell culture chamber, typically using chemical and/or mechanical dissociation, removal of dissociation reagent using centrifugation, resuspension in media, and re-plating of a fraction of cells into a fresh container.

FIG. 79E shows a fraction of the clonal cell colony from cell culture chamber 7902*d* plated into a new cell culture chamber 7904 (shown schematically as a single cluster). The re-plating and reattachment process is stressful for cells, and typically causes them to pause proliferation for some time before resuming their growth. The passaging process is also known to induce significant variability into clonal populations and is seen as the potential cause of karyotypic abnormalities that arise from associated stress. For extended observation of clones, or where reprogramming vectors must be cleared, or where cells must mature, the passaging process must be applied multiple times, with associated stresses. Moreover, the passaging process inherently requires transfer from chamber to chamber, and often centrifugation steps, and therefore is highly incompatible with a closed cell culture process desirable for clinical-grade cell processing.

FIG. 79F shows a final population of cells in cell culture chamber 7904 ready for harvest and analysis. FIG. 79G shows the resulting clonal cell population harvested in a tube 7906, ready for expansion and/or analysis. Such analysis could include analysis for proper gene editing, measurement of pluripotency, genetic analysis including karyotyping, among other tests. Note the low overall yield from the process 7900, the extensive stresses the cell sample has experienced over the process from single-cell handling and passaging, and the low optionality in picking clones, simply going with a single cell per well and running all the way through.

FIGS. 80A-F are diagrams depicting a method 8000 for in situ clonalization of a cell colony by repeated sectioning in accordance with various implementations. The method 8000 may be performed by a cell culture system as described herein. The method 8000 may be performed with a bias applied to preferentially result in a clonal population expressing a desired (and observable) characteristic, which may be observed in situ by imaging. The characteristic may be, for example, expression of a fluorescent protein that is contained in the same selection marker cassette used for gene editing (in some cases multiple fluorescent proteins associated with different selection marker cassettes if doing multiple edits). In other examples, the characteristic may be the absence of the selection marker cassette after the selection marker cassette should have been removed, for example by use of Cre recombinase. In some implementations, the characteristic may be observable label-free features of the cell, such as its morphology, proliferation rate, or spectral features such as those obtained by transmission, autofluorescence, or vibrational spectroscopy.

Figure 80A:
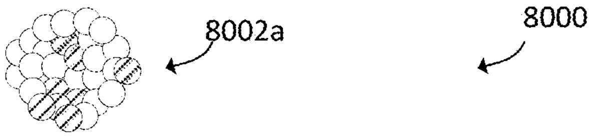
FIGS. 80A-F are diagrams depicting a method for in situ clonalization of a cell colony by repeated sectioning in accordance with various implementations.

FIG. 80A shows a polyclonal cell colony 8002*a* with a heterogenous population with respect to a desired characteristic, such as those disclosed above. In the example shown in FIG. 80A, darker cells express this characteristic while lighter cells do not. The cell colony 8002*a* may be composed of a cell type (such as iPSCs) that generally proliferates rapidly and is adherent.

Figure 80B:
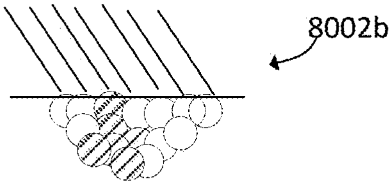

FIG. 80B shows sectioning/removal of a portion of the cell colony 8002. Cell removal may be achieved by a variety of cell removal tools disclosed herein. For example, the cell culture chamber in which the cell colony 8002*b* grows may include a transparent window with an absorbing coating or film on the cell culture surface. Pulsed laser energy may be directed to the cell clumps/clusters to be removed, and the absorbing coating or film may absorb the optical energy and convert it into mechanical energy (e.g., creation of microbubbles) to dislodge cells from the coating/film. The cell removal method and tools utilized in the present implementations may be those that do not require opening of a sealed cell culture chamber. Cells that have been removed from the cell culture surface may be washed away to remove dead and/or detached cells from the cell culture chamber. Using imaging or other analysis techniques, a computing subsystem may determine which part of the cell colony

8002*b* to remove to maximize the proportion of remaining cells expressing the desired characteristic (e.g., a particular gene edit).

Figure 80C:
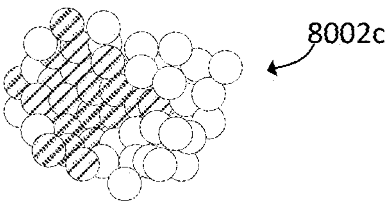

FIG. 80C shows the cell colony 8002*c* after the cell removal operation shown in FIG. 80B, when there has been time for the cell colony 8002*c* to proliferate. The cell removal operation may result in a higher proportion of cells having the desired characteristic, which then proliferate at a relatively higher fraction compared to the undesired cells. Thus, the cell colony 8002*c* may have larger and more contiguous regions of cells with the desired cell characteristic as compared to cell colony 8002*a*.

Figure 80D:
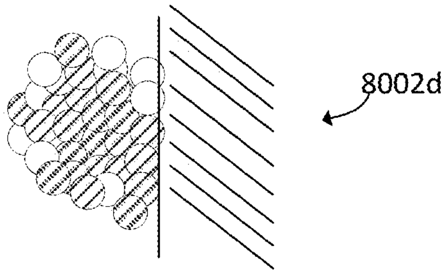

FIG. 80D shows the application of a further cell sectioning/removal step, resulting in cell colony 8002*d*. Again, the sectioning may be optimized to maximize the proportion of remaining cells expressing the desired characteristic. In addition to this enrichment, the method 8000 may accomplish a number of other goals, such as maintaining a healthy density for the cells, avoiding collisions of the cell colony with other colonies or with cell culture chamber features (such as walls), and slowly clonalizing the population by effectively "zooming in" to a single cell in the original colony because that single "source" cell continuously proliferates into a larger region and maintains intact border relationships with populations originating from neighboring source cells.

Figure 80E:
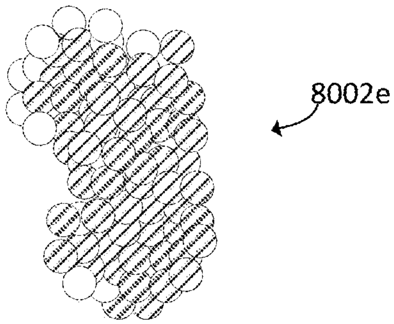
Figure 80F:
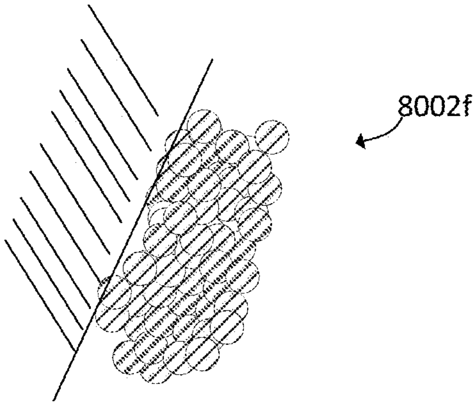

FIG. 80E shows the cell colony 8002*e* after the cell removal operation shown in FIG. 80D, when there has been time for the cell colony 8002*e* to proliferate. Cell colony 8002*e* may have a higher proportion of cells with the desired characteristic than cell colony 8002*c*. FIG. 80F shows another cell sectioning/removal step, resulting in cell colony 8002*f*. After a number of iterations of cell sectioning and proliferation, the resultant cell colony may have cells that all or almost all express the desired observable characteristic. The cell colony population may be nearing clonality as well, although an excess of sectioning steps may be used to have a high confidence of clonality (e.g., so that all remaining cells in the colony are descended from a single source cell in the original colony). In this manner even a CRT with much less precision and/or a much larger affected area than a single cell may be used to clonalize a proliferative colony of cells, effectively removing all contributions from cells other than one in the original colony.

FIGS. 81A-F are diagrams depicting a method 8100 for selection and expansion of a plurality of gene-edited cells in accordance with various implementations. The method 8100 may be applied, for example, to a population of adherent cells that have been previously gene edited and require clonal selection based on phenotypic characteristics, with minimum stress on the cell population that could cause genetic or epigenetic instabilities, or loss of pluripotency. The method 8100 may be performed by a cell culture system as described herein.

Figure 81A:
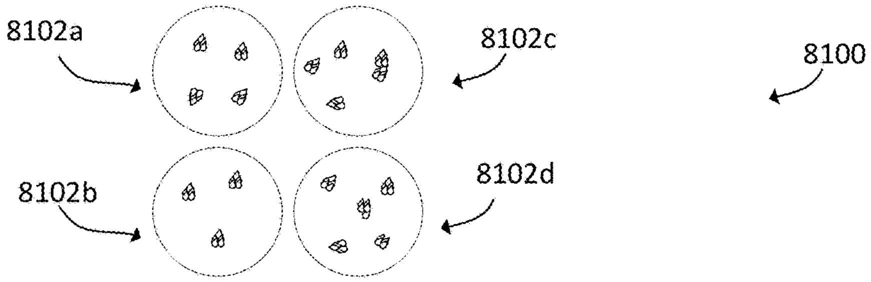
FIGS. 81A-F are diagrams depicting a method for selection and expansion of a plurality of gene-edited cells in accordance with various implementations.

FIG. 81A shows cell culture chambers 8102*a-d*, into which gene-edited cells have been clump passaged. Clump passaging may be preferable to single-cell passaging for cell health and survival. Seeding may be performed to achieve a target colony density, such that cell colonies may be managed in parallel, without collision, for the duration of the process. In the case where there is an excess density of initial clumps, either globally in the cell culture chamber or locally in a region within the chamber, this may be identified through imaging and a cell removal tool (e.g., laser removal) may be used to remove colonies and de-densify the cell culture chamber or region within the chamber. In some implementations, cells may be seeded in single-cell suspension, for example when being seeded directly after some transfection operations (e.g., electroporation, cell squeezing). In such cases, cell seeding may be performed at a density sufficiently high to promote rapid formation of multi-cell colonies so as to foster early return to a healthy growth environment. After formation of clusters, cells may be removed using the cell removal tool in order to define well-bounded, well-spaced cell colonies for management.

Figure 81B:
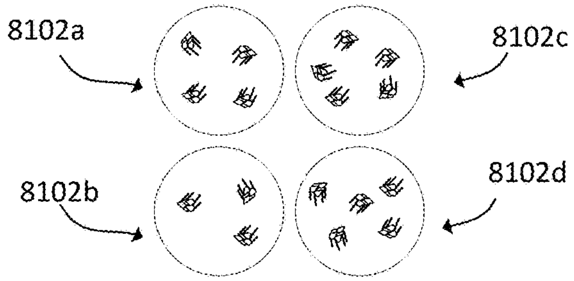

FIG. 81B shows the cell culture chambers 8102*a-d* after a first round of laser management of the cell colonies grown within. As the cell colonies proliferate, laser management may be used to remove a portion of each colony to maintain low density, progressively clonalize the colony by repeated sectioning, and potentially enrich the colony for an observable characteristic, as described with respect to FIGS. 80A-F. The observable characteristic may include, but is not limited to, fluorescent reporter expression, phenotype as determined by cell/cell neighborhood morphology or dynamics (such as proliferation rate or mobility), or cell health as determined by cell/cell neighborhood morphology or dynamics (such as proliferation rate or mobility). In implementations in which an antibiotic resistance gene has been added to an editing cassette to facilitate purification of the population for cells that have had correct edits applied, the present implementation may serve to optimize the process. A balancing act is required to add sufficient antibiotic to remove non-edited cells, while not killing or damaging properly-edited cells. In the implementations disclosed herein, a lower amount of antibiotic may be used and imaging data may be analyzed to determine cells or colonies whose health is declining as a result of the antibiotic addition, and these may be removed preemptively using the CRT.

Figure 81C:
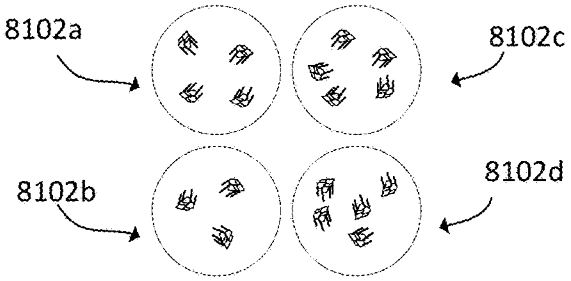

FIG. 81C shows the cell culture chambers 8102*a-d* after a subsequent round of laser management. Rounds of laser management, proliferation, and monitoring may be repeated until colony clonality is achieved, either by a geometric/probabilistic model or by direct observation of cell "flows" within each colony during proliferation and subsequent sectioning. In addition to density management, clonalization, and potentially enrichment of the colonies, laser management may be used to prevent collisions between cells colonies (to maintain clonality), to prevent collisions of the colonies with the sidewalls of the cell culture chamber and to move colonies towards areas with fresh extracellular matrix. During this process, cell colonies may be preemptively removed if their characteristics do not match desired clone characteristics.

Figure 81D:
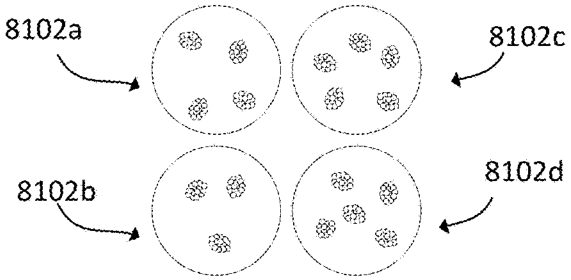

FIG. 81D shows the cell culture chambers 8102*a-d* after repeated rounds of continuous laser management, clonalization, and potential enrichment. The cell colonies may be allowed to expand freely for a period of time for observation. An imaging and computing system of the cell culture system may collect time series data during laser management and free expansion, which results in a large number of statistics that may be collected for each cell colony. This information may include, but is not limited to, colony morphology, cell morphology, spontaneous differentiation propensity, observable characteristics linked to successful gene editing, proliferation rate, area expansion rate, colony density, growth into fresh matrix versus depleted matrix (if the cell removal process depletes the extracellular matrix), and overall velocity across the container growth surface.

Figure 81E:
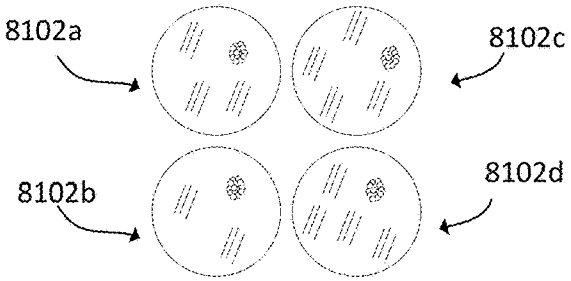

FIG. 81E shows the cell culture chambers 8102*a-d* each containing a single clonal colony after a clonal downselection process. In some implementations, this downselection may be made using a machine learning model that has been previously built and informed by the colony characteristics collected as disclosed herein, as well as assays on the resulting clonal cell populations (e.g., for pluripotency, proper editing, karyotypic and genomic integrity, etc.). During process development or optimization, cell colonies may be chosen at random during the model training phase, such that a range of characteristics and their assay outcomes may be captured. In other implementations, an active learning process may be used wherein clonal colonies are selected based on their characteristics to optimally enhance model training. In other words, the model may select colonies whose characteristics fall into regions of the characteristics space that are both sparsely filled and considered of importance. After clonal downselection, the selected clone may be expanded in the cell culture chamber, either by free growth of the colony or by replating via clumped passaging, or some combination thereof.

Figure 81F:
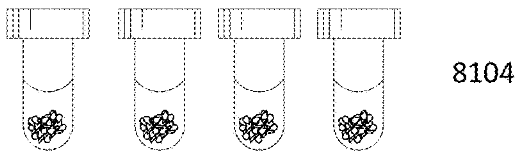

FIG. 81F shows the output of the method 8100 in the form of four clonal cell populations, each stored in separate tubes 8104. The method 8100 described herein may have higher process efficiency than the conventional process described with respect to FIGS. 79A-G. The method 8100 may also have higher optionality with respect to selection of clones, and the vast amount of data that may be accumulated per intact clone and evaluated for the purpose of selecting clones for downstream analysis and processing. The lack of passaging steps in the method 8100 means that disruption of cell behavior and health is minimized, which minimizes instabilities affecting iPSCs.

Figure 82:
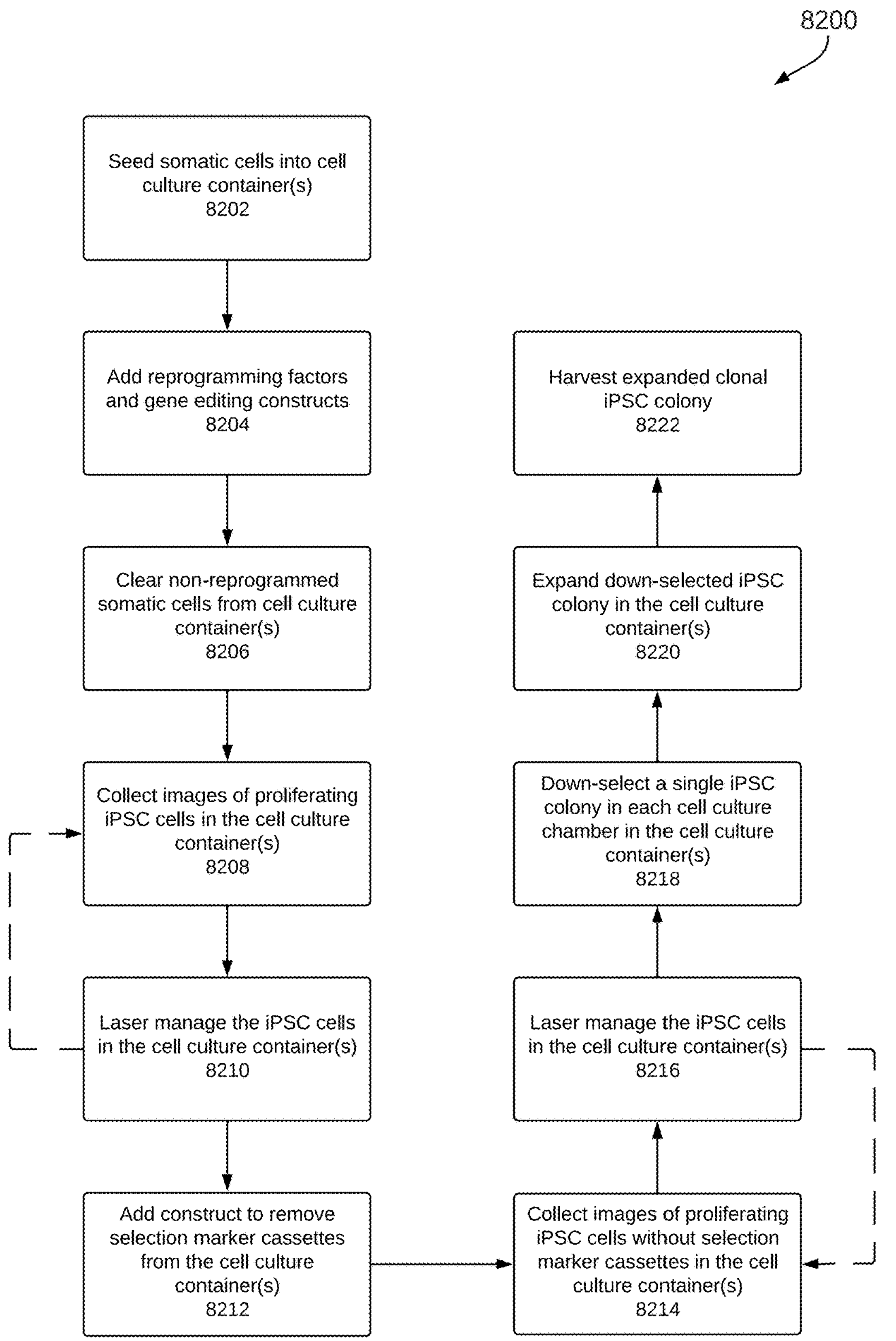
FIG. 82 is a diagram depicting a method for iPSC reprogramming and gene editing in accordance with various implementations.

FIG. 82 is a diagram depicting a method 8200 for iPSC reprogramming and gene editing in accordance with various implementations. In the method 8200, the reprogramming of somatic cells to iPSCs and one or more gene editing steps may be performed simultaneously, reducing the overall number of steps. The method 8200 may enable multiple cell colonies may be tracked, density managed, enriched for desired characteristics (e.g., correct gene editing, desired iPSC features), and ultimately down-selected to a single clone that may be expanded. The cell culture may remain continuously adhered to the cell culture surface during all or a majority of the method 8200, avoiding any damage or negative effects to cells caused by repeated passaging that is performed in the prior art. The method 8200 may last over the course of many days, for example over at least 7 days, over at least 10 days, over at least 20 days, over at least 30 days, over at least 45 days, and over at least 60 days. During the course of the method 8200, the cell population may double a number of times, for example at least 10 doublings, at least 20 doubling, at least 30 doublings, at least 40 doublings, or at least 100 doublings. The population doubling times may be, for example, 48 hours or less, 36 hours or less, 24 hours or less, 20 hours or less, or 18 hours or less. The method 8200 may be performed by a cell culture system as disclosed herein.

In block 8202, somatic cells from a patient may be seeded into one or more cell culture containers at an appropriate cell density. Each cell culture container may include one or more cell culture chambers (e.g., well plates, closed cassette chambers) that are sealable. Each cell culture chamber may include a transparent or semi-transparent surface on which cells may adhere. This cell culture surface may also include a laser film as disclosed herein. This laser film may be configured to enable light-based cell imaging (e.g., within an imaging wavelength range emitted by an imaging subsystem) and light-based cell removal (e.g., within a removal wavelength range emitted by a cell removal tool, the removal wavelength range different from the imaging wavelength range).

In block 8204, reprogramming factors and gene editing constructs may be added to the one or more cell culture containers. The reprogramming factors are used to reprogram the somatic cells into iPSCs. The reprogramming factors and gene editing constructs may be added simultaneously, or at different timepoints. After some time has elapsed, iPSC-like cell colonies may emerge from the somatic cells. In some implementations, the somatic cells may be reprogrammed and gene-edited before being seeded into the one or more cell culture containers.

In block 8206, the cell culture system may clear non-reprogrammed somatic cells from the one or more cell culture containers. The non-reprogrammed somatic cells may be cleared using a media change, washing, and/or removal by the cell removal tool. In block 8208, the cell culture system may collect images of the remaining reprogrammed iPSC cells as they proliferate in the one or more cell culture containers. iPSC colonies that emerge from the somatic cells may be clonal or polyclonal and may have properly gene edited cells and non-edited cells within each of them. Properly-edited cells may be observable by the imaging subsystem.

In block 8210, the cell culture system may perform laser management of the iPSC cells in the one or more cell culture containers. Laser management may be performed by a cell removal tool (e.g., pulsed laser system that, in conjunction with the laser film, uses mechanical energy to remove cells from the cell culture surface as disclosed herein). Laser management may achieve a number of goals, such as maintaining healthy cell densities, enriching properly-edited cells, clonalizing iPSC colonies, avoiding collisions between colonies and other colonies or cell culture chamber walls, and moving colonies to regions with fresh extracellular matrix (as disclosed herein). Some cell colonies may be removed in this process if they do not possess properly-edited cells, or do not show pluripotent cell markers. The steps illustrated by blocks 8208 and 8210 may be repeated a number of times until the laser management goals are achieved. For example, the cell culture system may clonalize the cell colonies by repeated imaging of the cell colonies as they expand to determine the cell density and then removing, using the CRT, portions of each cell colony if the cell density exceeds a threshold amount. Each cycle of removal may result in an increase in the percentage of cells in each cell colony that are clonal (i.e., originate from the same origin cell).

The cell density thresholds that above which may trigger CRT removal of portions of cell colonies may be, for example, 750,000 cells/cm$^2$, 500,000 cells/cm$^2$, 400,000 cells/cm$^2$, 300,000 cells/cm$^2$, or 250,000 cells/cm$^2$. Cell density may also be calculated in terms of multiples of the initial cell density (e.g., 1.5, 2, 2.5, 3, 5, or 5 times the initial cell density, either measured at single timepoints or mean values over time periods). In some implementations, metrics other than cell density may be used to determine when to remove cells. For example, colony surface area may be measured through imaging and portions of cell colonies may be removed if the colony surface area exceeds a threshold amount (e.g., an increase in surface area that is 5, 10, 20, 30, 50, or 100 times the initial surface area). In another example, cell count may be measured through imaging and portions of cell colonies may be removed if the cell count exceeds a threshold amount (e.g., an increase in cell count that is 5, 10, 20, 30, 50, or 100 times the initial surface area).

In block 8212, a construct to excise the selection marker cassettes containing reporter gene (and/or antibiotic resistance gene) from the cells may be added to the one or more cell culture containers. For example, this may be transfection of the cells with Cre recombinase using Lipofectamine. When successful, the recombinase removes the LoxP-flanked cassette including the fluorescent reporter and/or antibiotic resistance gene. After application of the selection marker cassette removal constructs, desired cells in which cassettes have been successfully removed may be distinguishable from cells in which the cassettes have not been successfully removed by the imaging subsystem.

In block 8214, the cell culture system may collect images of the remaining iPSCs (which no longer have the selection marker cassettes) in the one or more cell culture containers, and in block 8216 the cell culture system may perform laser management of the iPSCs in the one or more cell culture containers. The process illustrated in blocks 8214 and 8216 may be similar to the process illustrated in blocks 8208 and 8210 and may be iterated a number of times until the laser management goals are achieved. These goals may include maintaining healthy cell densities, enriching properly-edited cells, clonalizing iPSC colonies, avoiding collisions between colonies and other colonies or cell culture chamber walls, and moving colonies to regions with fresh extracellular matrix (as disclosed herein). During this time, the cell colonies may remain continuously adhered to the cell culture surface of the one or more cell culture containers, avoiding the repeated passaging performed in conventional cell culture processes.

In block 8218, the cell culture system may down-select a single iPSC colony in each of the one or more cell culture chambers in the one or more cell culture containers. The downselection may be performed by the cell removal tool by removing all but one colony in each cell culture chamber. The decision of which colony to retain may be made based on accumulated data throughout the method 8200 collected by the cell culture system, along with a machine learning model that processes the accumulated data to make a selection decision. For example, there may be a contiguous record of colony characteristics accumulated through imaging and analysis of the iPSC colonies in blocks 8208-8216, with no loss of tracking due to passaging. This provides a very rich time series for model-based selection of the best clonal cell colony in each cell culture chamber.

In block 8220, the down-selected iPSC colony may be expanded. Expansion may be monitored using an imaging subsystem and managed by the cell removal tool (e.g., splitting and spreading out the clonal colony while maintaining healthy density), or by inclusion of a clump harvest and re-plate step, either into the same cell culture chamber or a new chamber in which an end-to-end single container process is desired.

In block 8222, the clonal iPSC cell colony population may be harvested. The harvested cells may be used for further analysis, expansion, cryopreservation and/or downstream processes such as differentiation into a target tissue. Thus, the method 8200 enables automated or semi-automated gene-edited iPSC clonal colony manufacturing along with contiguous data tracking and colony selection yield, while allowing the entire process to be performed in the minimum number of cell culture containers, making it compatible with high-volume clinical production.

Methods for Proliferative Cell Maintenance

Proliferative cells overgrow the capacity of their cell container and must be "passaged" to maintain a healthy density. For proliferative adherent cells, cells must be passaged before they become overcrowded on the cell growth surface. In some cases, overcrowding simply starves cells of nutrients and dissolved gas such as oxygen, or causes excessive buildup of waste products. In other cases, overcrowding leads to an undesirable reduction in cell proliferation rate. In yet other cases, overcrowding may lead to undesirable phenotypic changes.

An example of a highly-proliferative cell type that is sensitive to density is an iPSC. Healthy iPSCs divide roughly every 18 hours. As part of the iPSC reprogramming process, consistent sustained cell division is required for a number of subprocesses, including but not limited to dilution or resetting of epigenetic markers such as DNA methylation markers associated with the differentiated state of the source somatic cell, extension of telomeres, selective expansion of genetically- and epigenetically stable subpopulations, clearance of reprogramming vectors such as Sendai vector or episomal vectors, and long-term observation of populations for markers of proper pluripotency and genetic and epigenetic stability. As a result, consistent, healthy cell proliferation is a major goal of the stabilization phase of iPSC reprogramming.

The process for maintaining proliferative adherent cells, and iPSCs in particular, has barely changed in the past decades, despite known shortfalls of the traditional "passaging" process. An example prior art method of cell maintenance includes enzymatic and/or mechanical cell detachment, retrieval using a pipetting system, centrifugation to remove enzymes, and re-seeding onto a fresh surface, with a target density, cell cluster size, and uniformity. This process is known to be stressful to cells, and iPSCs in particular. It also favors subpopulations that may not be genetically stable or desirable. The process may be performed every 3-6 days, typically, and total process durations may be weeks or even months long and may not necessarily result in the expansion of the total number of cells. Each cycle of the passaging process results in three proliferation phases for the cells: a "lag" phase during which proliferation is slowed or near zero while cells attach to the growth surface, a "log" phase in which cells proliferate freely, unconstrained by available growth surface or by cell density effects, and then deceleration of proliferation into a "stationary" phase in which cell density effects slow proliferation.

Efforts continue to reduce the stress of this cell passaging process. See, e.g., Takahashi, Kazutoshi et al., "A stress-reduced passaging technique improves the viability of human pluripotent cells," Cell Rep. Methods February 2022, 2(2):100155, which describes minor modifications to the iPSC passaging process to reduce cell stress. However, the nature of traditional cell passaging, which includes repeated, highly-unphysiological cell detachment and re-adhesion, makes it difficult to avoid inducing cell stress during the process.

Furthermore, traditional cell passaging has a number of other key disadvantages. For example, the process does not allow continuous monitoring of cell populations in situ by imaging or other means, since cells are redistributed every few days into a new cell culture container. For example, image-based behavior tracking of cell colonies can only be performed for several days at a time. This limits the data that may be collected on colonies, and therefore the quality of predictions that can be made for colony outcomes. In addition, most passaging processes mix together all cell material in a cell culture container, meaning a container with multiple clonal or subclonal colonies are mixed together in the transfer process. Mechanical clonal colony transfer tools are available but have low yield and are typically made to do 1-to-1 or 1-to-many transfers, not N-to-N traceable transfers.

Traditional cell passaging that involves repeatedly passaging from container to container is also highly incompatible with closed, aseptic systems that are ideal for clinical production. Passaging is usually performed with liquid handling or clone transfer equipment together with open containers. As a result, the process is prone to contamination or cross-contamination. Furthermore, the process is performed on an entire cell culture container, or in the case of multiwell plates usually all wells simultaneously, based on the "average" conditions across the container or multiple containers (e.g., wells). As a result, each cell colony within the container or containers may be at a very different state in terms of density, expansion, etc. Therefore, despite a careful balancing act, a high degree of variability is imparted. For example, regions that reach high density earlier may slow their cell division rates or even begin spontaneous differentiation compared to lower density regions.

Lastly, the re-plating process has inherent variability in terms of the cell clump sizes, local clump density, and the number of clumps. This may result in over-dense situations in some areas of a cell culture container (or multiple attached containers) early in a growth phase, while other regions are still sparse. Clumps with few cells may remain in the "lag" phase for longer periods after re-plating. Conversely clumps with more cells, or where clumps are in close proximity, may reach high density earlier in the process and begin to decelerate their proliferation in the "stationary" phase. The negative effects of high cell density, even if localized within a region of the cell culture container, include reduced proliferation rates as well as gradual reduction of pluripotency markers, as described in Wu, Jincheng et al., "Increased Culture Density Is Linked to Decelerated Proliferation, Prolonged Gi Phase, and Enhanced Propensity for Differentiation of Self-Renewing Human Pluripotent Stem Cells," Stem Cells and Development, 2015, 24(7):892-902.

As a result of these and other factors, including human judgement and variability in process steps, a large amount of the variability and inconsistency in iPSC reprogramming (or similarly, gene editing and clone selection) processes results from the repeated passaging process that is required. Similar problems are found in passaging processes for other proliferative adherent cells, including but not limited to embryonic stem cells (ESCs), mesenchymal stem cells (MSCs), neural stem cells (NSCs), HEK-293 cells, MRC-5 cells, WI-38 cells, PER.C6 cells, and MDCK cells. Further, the same challenges exist in some phases of cell differentiation processes (e.g., from ESCs, iPSCs, or other source cells) in which cells proliferate quickly, and differentiation efficiency can be highly dependent on local cell density. Further, the challenges generally exist for adherent cells with density-dependent growth inhibition, including but not limited to: endothelial cells, epithelial cells, fibroblasts, keratinocytes, mesenchymal stem cells, hepatocytes, smooth muscle cells, astrocytes, chondrocytes, and adipocytes.

The systems and methods disclosed herein include a method for managing adherent, proliferative cell colonies of the types described above using a CRT for long periods of time in a single cell culture container in a consistent manner. The cell colonies may be continuously adhered to the cell culture surface during the cell culture process, avoiding repeated passaging that may damage cells. Moreover, the method may be maintained for long periods of time in the "log" phase of growth, which represents the maximum proliferation rate for the cell type. The system and methods disclosed herein maintain a healthy cell colony size and density throughout the process to maintain cell health, minimize stresses on cells from passaging, maximize the number of cell divisions per unit time as a result of removal of "lag" and "stationary" phases, and allow long-term continuous observation of colony characteristics such as cell morphology, colony morphology, cell proliferation rate, colony density, colony movement into regions with fresh and depleted ECM, and other parameters which may be used by a computing subsystem to adjust colony management and/or make predictions of colony health in terms of epigenetic and genetic characteristics and stability. These predictions may be made using models trained using previous observations of time-series colony behavior in the disclosed cell culture system, in addition to assays performed on cells after being processed by the cell culture system.

The implementations disclosed herein may be applied to iPSCs (among other cells) during reprogramming and/or gene editing to speed up and/or make more consistent the stabilization and characterization of cell colonies or entire cell populations for one or more purposes. These purposes include, but are not limited to, dilution or resetting of epigenetic markers such as DNA methylation markers associated with the differentiated state of the source somatic cell, extension of telomeres, selective expansion of genetically- and epigenetically stable subpopulations, clearance of reprogramming vectors such as Sendai vector or episomal vectors, and long-term observation of populations for markers of proper pluripotency and genetic and epigenetic stability. The implementations disclosed herein may reduce the time required to clear reprogramming vectors from iPSCs. For example, the methods disclosed herein may reduce the overall time to achieve vector clearance by maintaining cells in a "log" growth phase. In addition, the vector clearance time is likely to be more consistent for many other cell processes.

Figure 83:
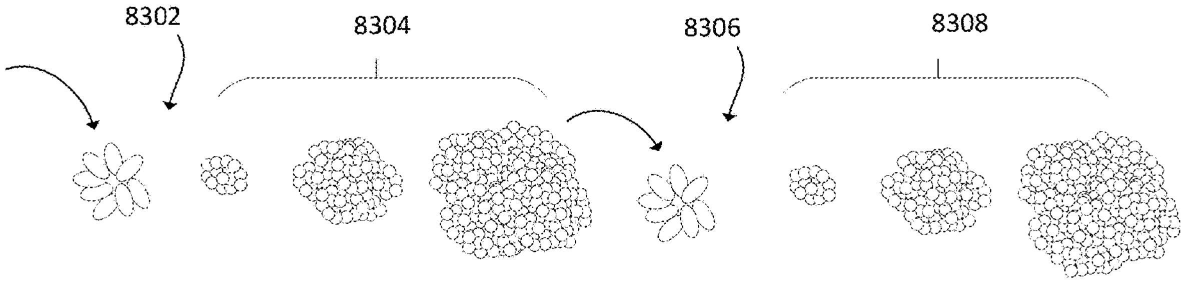
FIG. 83 illustrates a diagram of a conventional clumped cell passaging process in the prior art.

FIG. 83 illustrates a diagram of a conventional clumped cell passaging process in the prior art. A cell clump 8302 is plated into a cell culture container from suspension. The shape and cell count of the cell clump 8302 is usually highly variable, as is the positioning of the cell clump 8302 relative to other cell clumps that are seeded into the cell culture container as they settle onto the cell culture surface. In this early stage, the cells are recovering from passaging and lower or arrest their proliferation rate as a result of the associated stresses (the "lag" phase). The "lag" phase can last various amounts of time depending on the clump size and other conditions. Some cell clumps may never recover and die during the lag phase.

After attachment to the cell culture surface, the cell clump 8302 begins to proliferate as shown in sequence 8304, with its boundaries moving outwards towards fresh ECM and its internal regions showing increasing cell density. At some point, which will vary from colony to colony and container to container, even within the same process run, the density of cells in regions of the cell colonies reaches a point where cell proliferation starts to slow. In the example shown in FIG. 83, the center of the cell clump after sequence 8304 has reached a high density and proliferation has slowed. This slowdown reduces the overall cell division rate for the cell culture sample. In addition, prolonged high density may cause iPSCs to spontaneously differentiate and lose their pluripotent properties.

To avoid this, the cell clump is passaged into a new cell culture container, resulting in smaller cell clump 8306. Each source cell colony or clump may result in multiple new clumps, interrupting any image-based tracking of the population that may be underway. Each cell colony in the cell culture container may be at a different state of proliferation as this clump passaging is performed, resulting in various levels of stresses and various compositions/states of cell clumps going into the new cell culture container. The lag-log-deceleration process is then repeated in the new cell culture container as indicated by sequence 8308. Each iteration proliferation and passaging steps introduces additional stresses on the cells being cultured, which may result in loss or damage to a large number of cells, as well as lower quality output cells. This reduces the efficiency of the cell culture process as many cells are rendered unusable.

Figure 84:
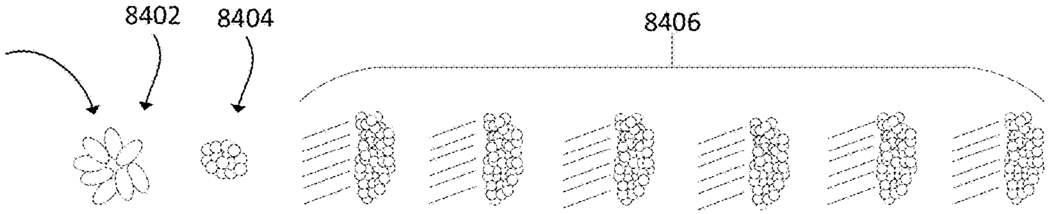
FIG. 84 illustrates a diagram of continuous management of a cell clump using a cell removal tool in accordance with various implementations.

FIG. 84 illustrates a diagram of continuous management of a cell clump using a cell removal tool in accordance with various implementations. This continuous management aids in promoting uniform conditions and continuous log phase proliferation during the cell culture process. A cell clump 8402 is plated onto a cell culture growth surface of a cell culture container. The cell clump 8402 forms into a cell colony 8404 that is well-adhered to the cell culture growth surface (e.g., ECM). Subsequently, however, the process deviates from the prior art process illustrated in FIG. 83.

The cell colony 8404 proliferates but is continuously "trimmed" by a cell removal tool (CRT) as shown by sequence 8406. The CRT may be a cell editing subsystem of a cell culture system as disclosed herein. For example, the cell removal tool may be a pulsed laser that targets a semi-absorptive surface on the cell culture container (e.g., a laser film as disclosed herein). The semi-absorptive surface may be configured to absorb optical energy from the laser pulses within certain wavelength ranges (the removal wavelength range) while allowing transmission of light in other wavelength ranges (e.g., imaging wavelengths). The laser pulses cause the formation of microbubbles whose expansion and collapse cause the destruction and/or removal of selected cells from the cell culture growth surface. The CRT may be image-guided to target specific regions of the cell colony 8404, for example regions with the highest cell density. The cell culture system may have an imaging subsystem that is configured to capture image data of the cell colony 8404 (and other colonies in the cell culture container) and a computing subsystem that determines which regions of the cell colony 8404 to be removed by the CRT. In some implementations, the CRT may target cells in a specific portion of the cell colony 8404 to move or translate the cell colony around the cell culture surface via cell proliferation as disclosed herein. The cell colony 8404 may be moved, for example, to fresh ECM regions or to prevent collisions with other cell colonies or cell culture chamber walls. Continuous colony management enables a consistent colony size range and colony density range to be maintained throughout the cell culture process, which in turn helps maintain cell health and keeps the cell colony in the "log" phase of growth with the maximum healthy cell division rate. In addition, this method maintains the cells that become the ultimate cell product in continuous, physiologically-compatible conditions (e.g., remaining attached to and proliferating across an ECM surface) rather than subjecting them to repeated dissociation, suspension handling, and re-plating.

Figure 85:
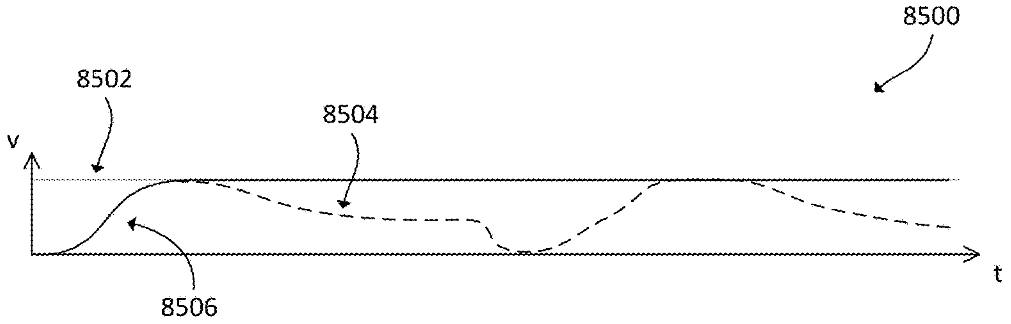
FIG. 85 is a graph comparing the proliferation rate of cells using a conventional passaging process versus continuous management in accordance with various implementations.

FIG. 85 is a graph 8500 comparing the proliferation rate of cells using a conventional passaging process versus continuous management in accordance with various implementations. The time spans shown in the graph 8500 correspond to the processes illustrated in FIGS. 83-84. The horizontal axis of the graph 8500 represents time while the vertical axis represents cell division rate. A horizontal line 8502 represents the inherent division rate for the cell phenotype when unconstrained by resources or cell density. For example, for healthy iPSCs the inherent division rate is roughly 1 division per 18 hours.

The dashed plot 8504 shows the division rate for two cycles of the conventional passaging process as described with reference to FIG. 83. After a lag phase, the growth rate accelerates to the inherent division rate (the "log" phase). However, as the densities of the cell colonies grow and/or colonies collide, the division rate decelerates, necessitating a passaging step. The cycle is then repeated for every passaging step. Note that for a significant portion of the overall process, the cell division rate is below the optimal (maximum) rate of line 8502. Moreover, since every cell colony is a different size and emerges from different conditions, one can expect a wide spread in these growth profiles, resulting in unpredictable processes.

The solid plot 8506 shows the division rate for two cycles of cells undergoing continuous management as described with reference to FIG. 84. Because the cell colony is kept in a relatively constant state (e.g., constant size, density, etc.), a continuous "log" phase may be achieved and the cell division rate may be maintained near the maximum rate (shown by the line 8502) for much of the process. In addition, the ability of the cell culture system to use imaging and the CRT to shape cell colonies allows it to maintain all cells in a very consistent manner. This creates higher predictability in the process and sets the stage for process improvements possible only with a consistent biological signal.

Figure 86:
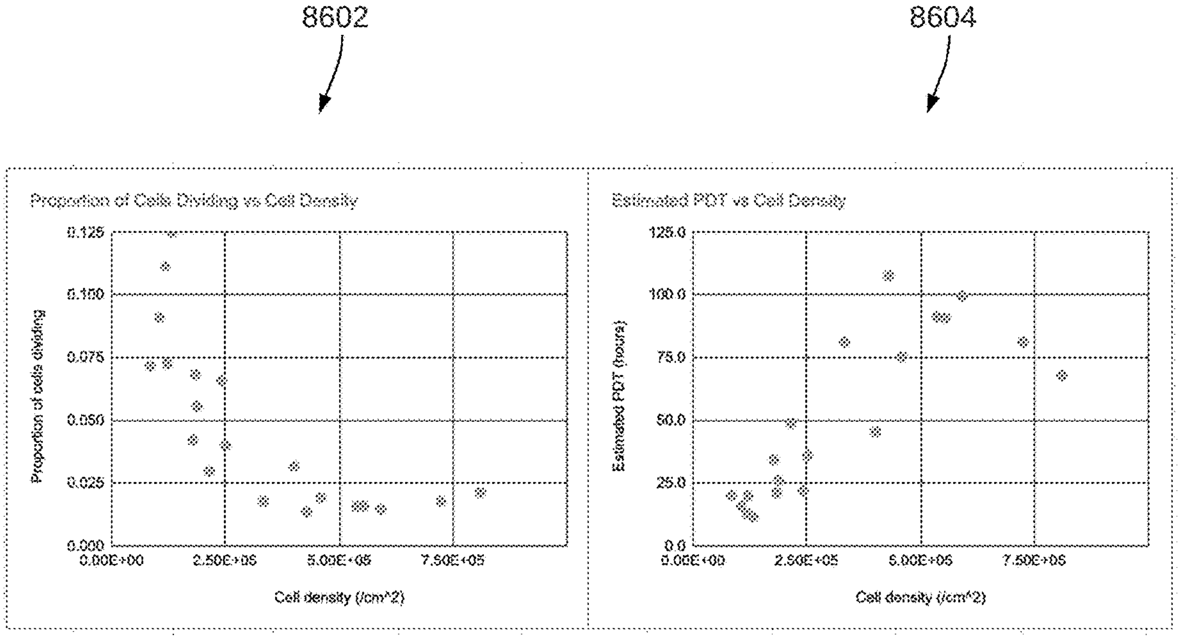
FIG. 86 illustrates graphs showing cell growth metrics as a function of local cell density in accordance with various implementations.

FIG. 86 illustrates graphs showing cell growth metrics as a function of local cell density in accordance with various implementations. Graph 8602 shows the observed fraction of iPSCs dividing (vertical axis) as a function of local cell density (horizontal axis) within a single cell culture. The data points were obtained by selecting random image patches of iPSC culture that had been fluorescently labelled with a nuclear stain, counting the number of cells in each patch and dividing by patch area to calculate cell density, and counting the number of cells in the process of dividing as evidenced by nuclear shape. A clear inverse proportional relationship may be seen in the trend, confirming prior literature such as the Wu reference. In other words, the graph 8602 confirms that as cell density increases, cell division rates drop dramatically.

Graph 8604 shows calculated population doubling times (PDT) on the vertical axis as a function of cell density on the horizontal axis, based on the data in the graph 8602. A minimum PDT of 18 hours, often given as the healthy cell division rate for unconstrained iPSCs, was used as a baseline from which to calculate PDTs. The relative PDTs between low (~125,000/cm$^2$) and medium (~500,000/cm$^2$), still considered "healthy," density conditions show a 5× increase in PDT, meaning 5× fewer cell divisions per unit time, and a 5× reduction in cell division-related processes including vector clearance as cell density increases.

Figure 87:
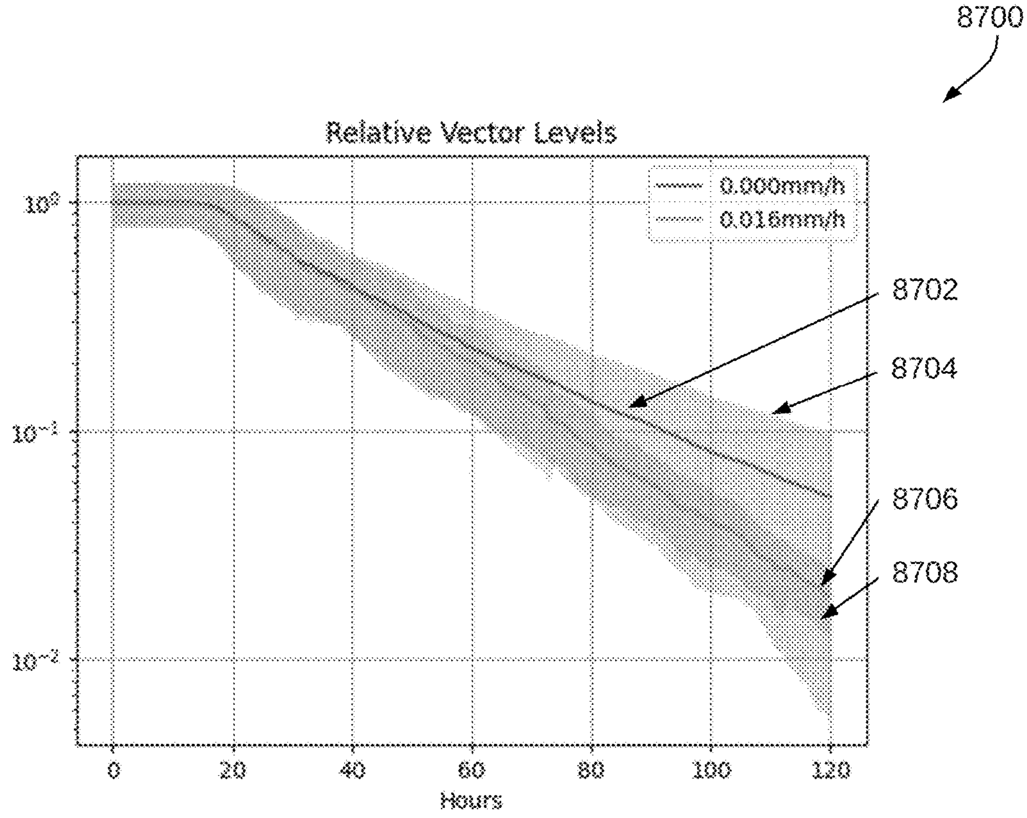
FIG. 87 illustrates a graph showing simulated vector clearance during a single passaging step in accordance with various implementations.

FIG. 87 illustrates a graph 8700 showing simulated vector clearance during a single passaging step in accordance with various implementations. The graph 8700 compares unmanaged cell colony growth to cell colony growth that is continuously managed using a CRT mechanism to "push" the colony across ECM and continuously reduce its density as it proliferates, as described with reference to FIG. 84. The vertical axis is a log representation of the relative reprogramming vector level, while the horizontal axis shows time in hours. Initial vector levels for cells in the colony are set at a mean of 1 ($10^0$), with a distribution around the mean as indicated by the gray regions.

Line 8702 shows the mean vector levels for the unmanaged proliferating iPSC colony. After a brief "lag" phase where proliferation is halted, vector per cell is diluted by cell division. However, as the colony's density increases in its central regions, PDT in these regions increases, with the result that vector clearing starts to slow on a log scale (i.e., cells are no longer uniformly in a "log" growth phase). Moreover, the range of vector load per cell diverges rapidly within the population, as shown by lighter gray region 8704. The same initial colony managed using a CRT that continuously removes cells from the colony, and in the process translates the colony over fresh ECM at 0.016 mm per hour, shows more rapid vector clearing as indicated by line 8706. Moreover, the range of vector loads per cell remains tight across the population as indicated by darker gray region 8708.

The graph 8700 shows only a 5-day span equivalent to a single passaging step. For conventionally passaged cells, the process is repeated, with both the slowing from "lag" phase and then deceleration repeated multiple times. Note that because of the rapid divergence in vector levels, a wide range of overall clearing times is possible, depending on which cells are passaged into a new container during each cycle. On the other hand, for the CRT-managed colony the colony management process may continue the clearing at a constant ("log") rate, extending the line 8706 and distribution in the region 8708 indefinitely. Moreover, because the colony is maintained for long periods of time in the same cell culture container, observation of its characteristics over time, including the estimated number of cell divisions, is feasible, with uniform conditions over the population and over time. This allows observation of the inherent characteristics of the colony, with minimum noise from overgrowth, varying vector levels, and passaging.

Continuously-Sampled Cell Culture

Many biological processes require long time periods and at the same time are performed with cells that proliferate, sometimes rapidly. Cells may also be sensitive to cell density, both because of resource competition (e.g., competing for nutrients, dissolved oxygen) or waste effects, and also because many cells are sensitive to crowding. When these cells experience higher density and contact inhibition, they may slow their division rate and therefore the cell culture process may also slow down. Higher density or lower division rates of cells may also cause unwanted differentiation, or mis-differentiation of cells.

Systems and methods disclosed herein disclose management of cell density issues with continuous in-place cell colony management using spatially-selective CRTs to eliminate the problem of constantly moving cells from one container to another ("passaging") for the purpose of "diluting" or reducing cell density. This in-place ("non-passaged" or "passage-free") cell management method provides advantages in terms of consistency of cell conditions and the ability to fit into closed-container systems that are not compatible with cell passaging (e.g., the closed cassettes disclosed herein). In addition, in-place cell management also isolates cell cultures from contamination or cross-contamination and can offer higher media efficiencies. However, one aspect that is attractive in passaging-based cell cultures is that there is often excess cell material generated from each passaging step. This may be used to expand the overall number of cells, or to sample the cell material for quality, etc.

The systems and methods disclosed herein include a process, with multiple potential implementations, for simultaneously managing an adherent cell culture using CRTs and periodically sampling cell material for downstream analysis or other processes. The process uses CRT-based cell operations or manipulations (including, for example, cell colony density maintenance, splitting, translation, and isolation) to continuously maintain a cell colony while extracting live cell samples in the form of sub-colonies. Many cell colonies may be simultaneously maintained and sampled in this manner. This may be used during extended cell processes in which periodic sampling for cell process progress or cell quality is desired. It may also be used to generate cell samples for harvest over extended periods without moving cells from one container to the next.

Figure 88:
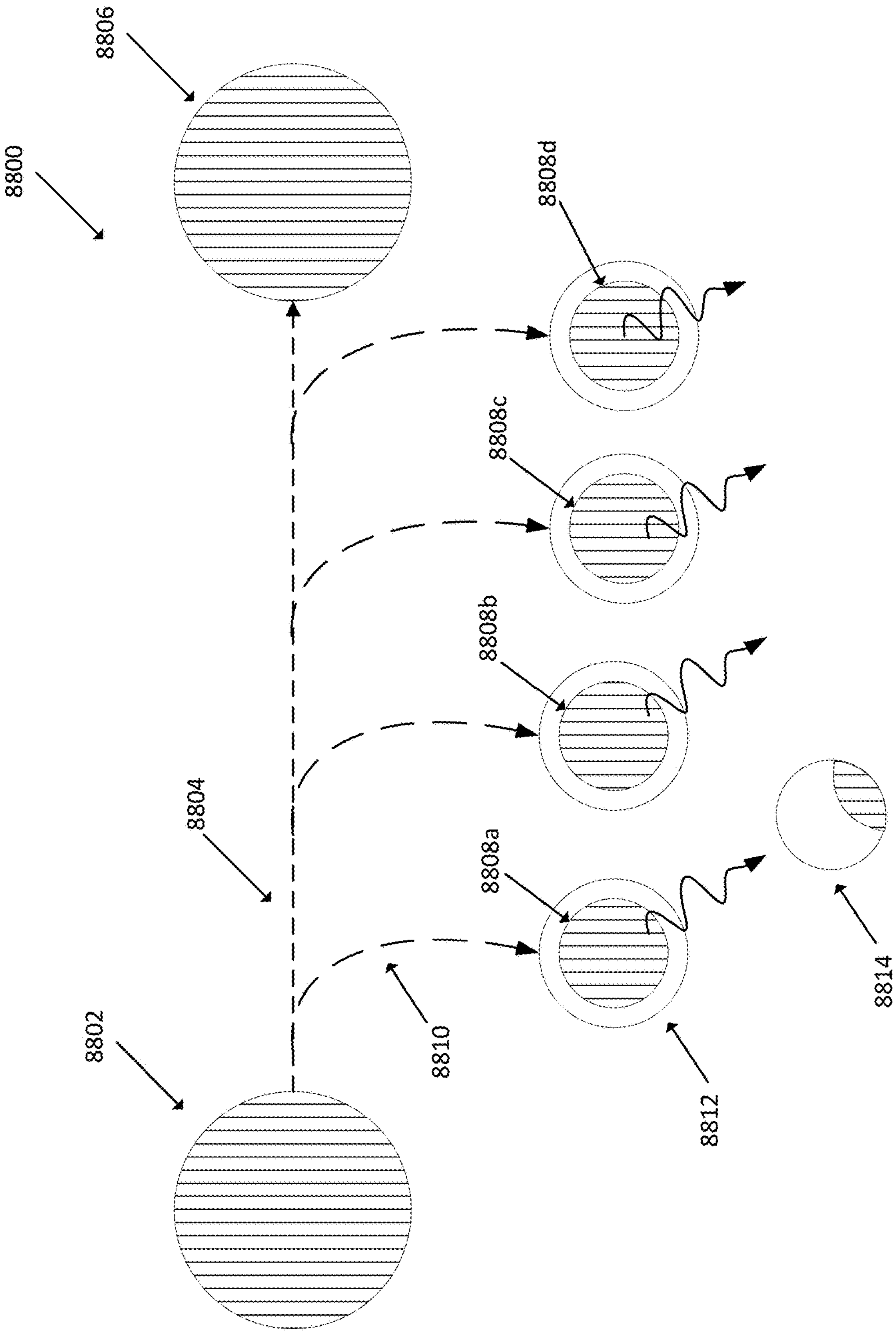
FIG. 88 is a diagram illustrating an example of continuously sampled cell culture management in accordance with various implementations.

FIG. 88 illustrates a diagram 8800 showing an example of continuously sampled cell culture management in accordance with various implementations. The diagram 8800 shows a cell colony 8802 that is continuously managed along a translation path 8804 to a final destination 8806 using translation methods described herein (e.g., with reference to FIGS. 61-66). The translation path 8804 may be straight as shown in FIG. 88 or may follow a range of other shapes or paths, including in-place management with minimal or no translation. In some implementations, the translation path 8804 may be configured to selectively expand portions of the original cell colony 8802, or to clonalize the cell colony 8802.

During translation, the cell colony 8802 may be managed for size, surface area, density, and/or other characteristics. For example, during the translation and maintenance process, sub-colonies 8808*a-d* may be split off the cell colony 8802. For example, the CRT may separate sub-colony 8808*a* from the cell colony 8802 and translate the sub-colony 8808*a* along translation path 8810. The sub-colony 8808*a* may then be isolated from fresh ECM via removal of the ECM in a "moat" 8812 by the CRT. For example, the CRT may be a pulsed laser that acts on a laser-absorbing coating on the cell culture surface that ablates the ECM. The ECM may be, for example, Laminin supporting cell growth and proliferation and the cells may be iPSC cells. Once the sub-colony 8808*a* is isolated in this manner, it grows dense and may also grow into a 3-dimensional shape rather than stay 2-dimensional in shape on the cell culture surface.

The sub-colony 8808*a* eventually detaches from the cell culture surface partially or completely, and may be washed away as indicated as shown by sample 8814. The sample 8814, which may be in the form of a semi-2D sheet, or a spheroid mass, may be used downstream for a range of purposes, including but not limited to seeding new cell cultures, performing assays on the cells to assess the quality of the original cell colony 8802, or beginning a cell differentiation process (e.g., those that begin with a spheroid of pluripotent cells). The sub-colony separation, translation, isolation, and harvest may be performed repeatedly along the translation path 8804, resulting in additional sub-colonies 8808*b-d*. This may be done for the purpose of monitoring progression of a process (such as reprogramming, differentiation, transdifferentiation, vector clearing, epigenetic remodeling, clonalization, etc.), or for continuously generating cell material for a downstream process.

Figure 89:
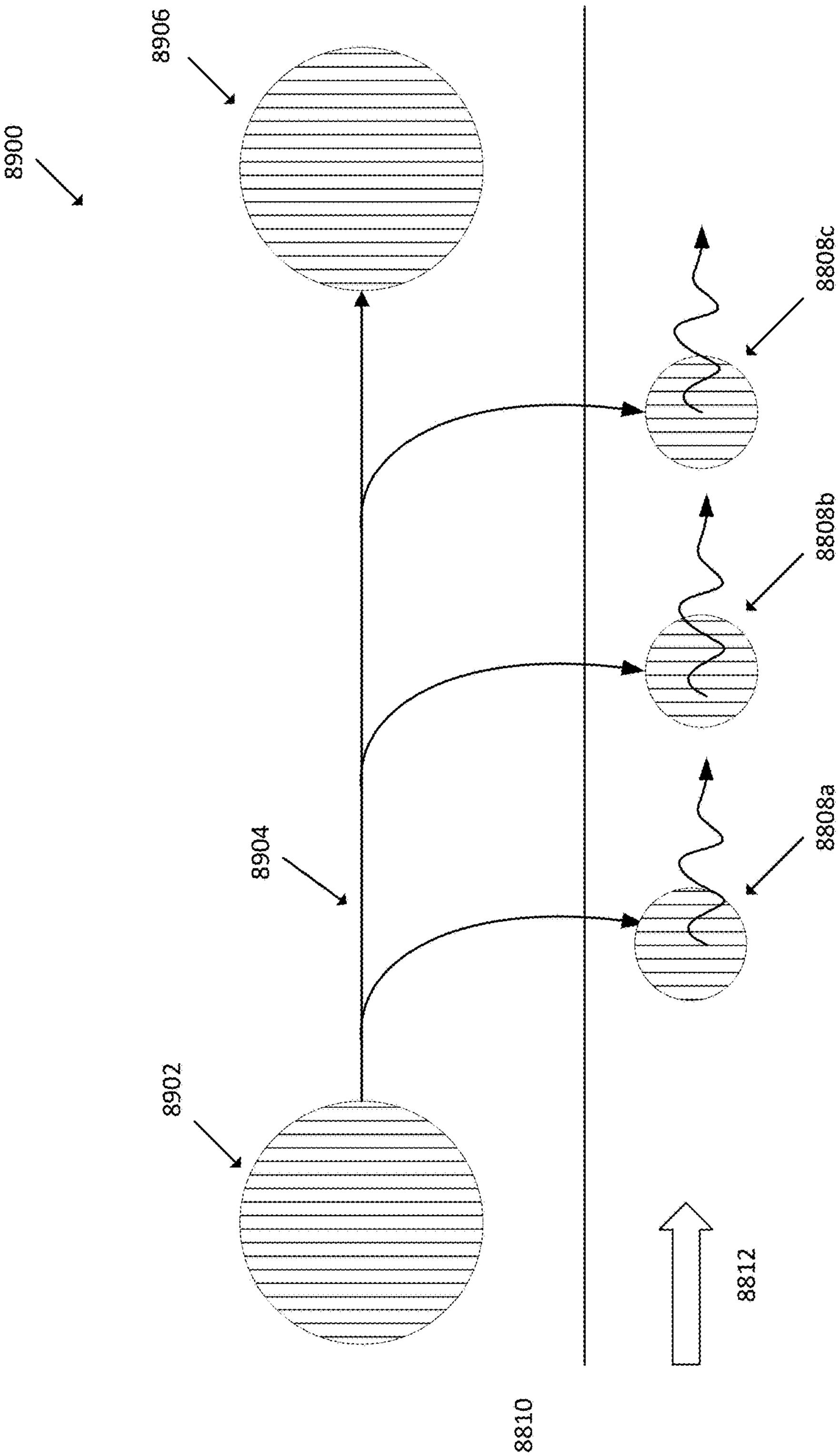
FIG. 89 is a diagram illustrating another example of continuously sampled cell culture management in accordance with various implementations.

FIG. 89 is a diagram 8900 illustrating another example of continuously sampled cell culture management in accordance with various implementations. The diagram 8900 shows an initial cell colony 8902 that undergoes a continuous management cell culture process 8904 using CRT-based cell management, resulting in ending cell colony 8906. The cell culture process 8904 may include one or more iterations of expansion, translation, pruning, or other cell operations. During the cell culture process 8904, sub-colonies 8908*a-c* may be divided from the initial cell colony 8902 and translated away using CRT-enabled methods as disclosed herein. The sub-colonies 8908*a-c* may be translated across a boundary 8910 into a "sampling" region 8912. The conditions in the sampling region 8912 may make it easier for the sub-colonies 8908*a-c* to be sampled (e.g., harvested/washed away for downstream processing). For example, the sampling region 8912 may be exposed to a higher liquid flow rate, allowing the sampled sub-colonies 8908*a-c* to be washed downstream. In another example implementation, the cell culture surface conditions (such as ECM concentration) may be different in the sampled region 8912, allowing easier harvest of the sampled sub-colonies 8908*a-c*.

Figure 90:
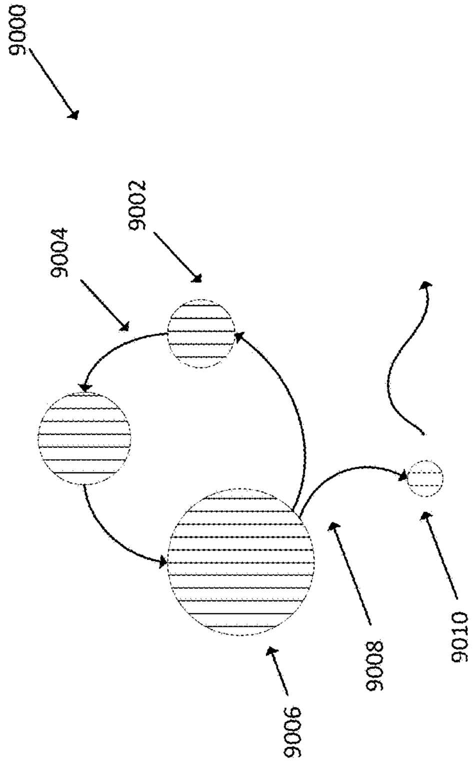
FIG. 90 is a diagram illustrating another example of continuously sampled cell culture management in accordance with various implementations.

FIG. 90 is a diagram 9000 illustrating another example of continuously sampled cell culture management in accordance with various implementations. The diagram 9000 shows a cell culture process that maintains a cell colony indefinitely while continuously producing samples from the cell colony. Such a process may be used in a range of applications, including biomanufacturing, biosensing, assays for cell genetic or epigenetic stability, drug screening, long-term cell sample maintenance, continuous production of cells for research or therapeutic applications, etc.

In this implementation, a cell colony 9002 is managed through a CRT-based cell culture process 9004 in a controlled manner (e.g., controlling for features such as cell density, colony size, cell population doubling time, colony morphology, etc.) such that it grows to a larger cell colony 9006. Sub-colony 9010 may be extracted from the larger cell colony 9006 via a splitting and translation sub-process 9008. After separation the sub-colony 9010 may be harvested/retrieved for downstream use. In this manner, proliferative cells may be maintained indefinitely while producing material continuously for use in monitoring the cell colony and/or using in downstream processes.

In some implementations, patient pluripotent stem cells may be maintained in a live state, without becoming overly dense, inside of a compact closed fluidic system, with samples extracted periodically to measure pluripotency and genomic integrity, or to expand for downstream processes (e.g., differentiation into therapeutic cell doses). In this and other implementations, a large number of cell colonies may be maintained and harvested in this manner. In some implementations, the cell colonies may be continuously monitored by imaging, analysis of surrounding media, spectroscopy, or other means to detect deviation from desired conditions. Such deviations may be corrected using parameters in the cell culture process (e.g., media, CRT removal parameters, etc.) or cell colonies may be removed entirely via the CRT to ensure the output of the system (e.g., harvested sub-colonies) remains high quality.

Figure 91:
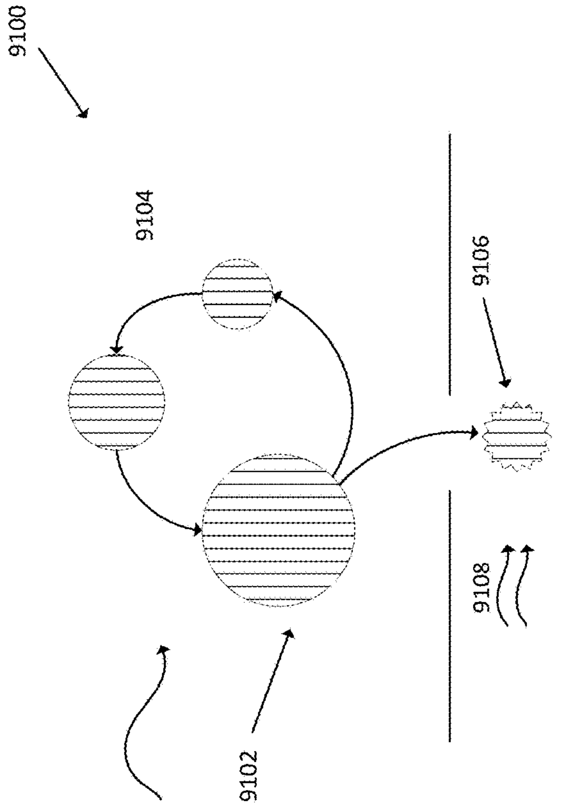
FIG. 91 is a diagram illustrating another example of continuously sampled cell culture management in accordance with various implementations.

FIG. 91 is a diagram 9100 illustrating another example of continuously sampled cell culture management in accordance with various implementations, in which a cell culture process may maintain a cell colony continuously for the purpose of producing a steady stream of differentiated cells for downstream use. A cell colony 9102 may be maintained in a stable state in a maintenance region 9104, and periodically a sub-colony 9106 may be split from the cell colony 9102 and translated into a differentiation region 9108. After splitting the sub-colony 9106, the cell colony 9102 may be allowed to expand again.

The maintenance region 9104 may have certain types of fluid media supplied within it, such as stem cell media, the differentiation region 9108 may have different fluid media supplied within it. The fluid media in the differentiation region 9108 may include, for example, factors for directed differentiation and/or support of differentiated cells of the target type. Additionally, the differentiation region 9108 may have other features to promote targeted cell differentiation, such as surface coatings, topology, stiffness, stretching, etc. Differentiated cells deriving from the sub-colony 9106 may be harvested for downstream use. In some implementations, the two regions in the diagram 9100 may be defined by different fluidic channels in a micro- or millifluidic flow system. In such implementations, many alternating channels may be used to create many niches for both source cell and output cells, and the ability to independently vary media and flow conditions in these regions.

In summary, the methods disclosed herein enable sampling of a cell colony or cluster without interrupting the overall cell culture process (e.g., expansion of iPSCs after reprogramming). The methods may include maintaining a cell colony in a stable state, for example in a proliferative state. The cell colony may be maintained in the relatively same area or may be translated across a cell culture surface. Imaging and computing resources (e.g., cell imaging subsystem and computing subsystem of a cell culture system) may determine whether a portion of the cell colony should be sectioned off for harvesting. A CRT is configured to split one or more sub-colonies from the cell colony and translate them away from the cell colony. In some implementations, the sub-colonies may be translated into a different region of the cell culture chamber, where harvesting the sub-colonies is easier. This enables sampling of the cell colony anytime throughout the cell culture process for a variety of reasons, including for analysis or harvesting of output cell products.

Spatially-Selective Colony Expansion

In various cases, it may be desirable to harvest or retrieve live material from certain parts of cell cultures or colonies. For example, certain regions of a cell colony may exhibit desirable characteristics as determined by cell differentiation patterns, imaging of cell or cell region morphology, spectroscopic measurements, fluorescent markers that have been applied to cells or are expressed by particular cells, or behavioral features such as mobility or proliferation rates. However, few tools exist to selectively retrieve material from small regions of cell cultures or colonies.

The systems and methods disclosed herein provide methods for selective expansion of a region of a cell culture or cell colony so that cells from that region may be easily harvested using a CRT. The CRT may have poor resolution and poor accuracy compared to the size of the desired cell region, and therefore to overcome the limitations of the CRT the methods disclosed herein may enlarge the cell region for easier retrieval. The methods disclosed herein may be vaguely analogous to "expansion microscopy" in that continuous expansion of the cell colony (when managed via the CRT to consistently low density) in conjunction with a series of spatially-selective cell removal steps progressively enriches the cell colony for cells descended from the desired region. This may be performed on one or more regions of a colony, and may optionally be performed until each resulting sub-colony is descended from a single cell in the original cell colony (i.e., the sub-colonies are clonal).

The systems and methods disclosed herein may be used to enrich cell cultures for specific phenotypes (such as during cell reprogramming or differentiation) and/or genotypes (such as during cell gene editing), and/or may be used to phenotypically or genetically measure regions of cell cultures or colonies that have been identified in situ using imaging or other non-invasive methods.

Figure 92:
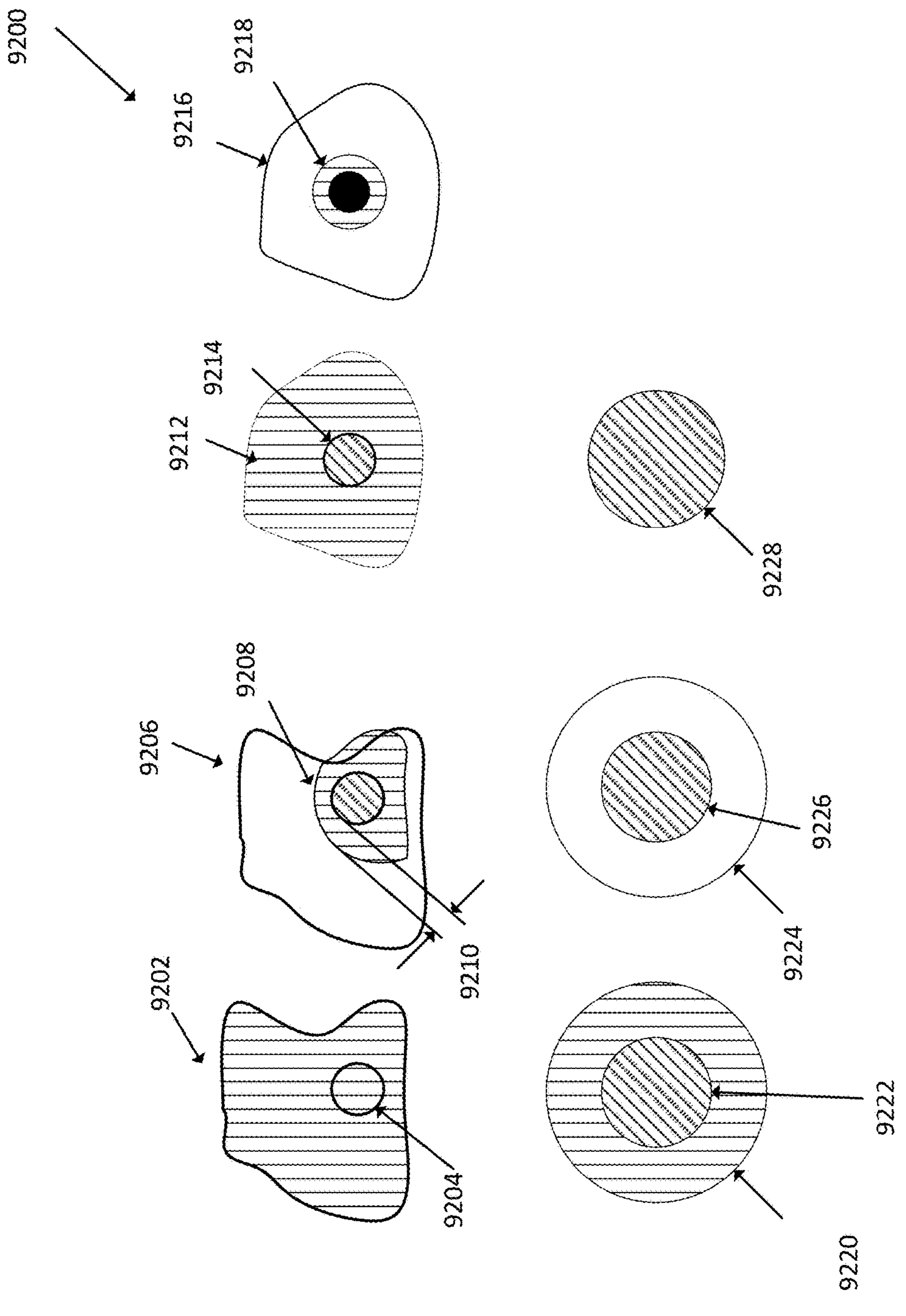
FIG. 92 is a diagram illustrating an example of spatially-selective colony expansion in accordance with various implementations.

FIG. 92 is a diagram 9200 illustrating an example process for spatially-selective colony expansion in accordance with various implementations. The diagram 9200 includes a starting cell colony 9202 that includes a desired spatial region 9204. The population of cells in the spatial region 9204 may have desirable characteristics, for example in terms of clonality, cell quality, or aggregate cell attributes. Cells within the spatial region 9204 may be selectively expanded through a series of cell removal operations that act to enrich the proportion of the remaining cells that derive from the original desired spatial region 9204. The cell removal operations may leave the cell colony 9202 at a lower density that allows for rapid proliferation, followed by proliferation in which all parts of the cell colony 9202 grow, including the area derived from the desired spatial region 9204. The cell removal operations may be performed by a CRT as described herein.

A first cell removal operation may remove a portion of the cell colony 9202, shown by the dotted region 9206. A smaller cell colony 9208 remains that includes the desired spatial region 9204. The cell colony 9208 is larger than the desired spatial region 9204 by a margin 9210 because the CRT does not have the spatial resolution to isolate just the spatial region 9204. For example, the CRT may have an effective resolution of 25 cells, and the spatial region 9204 is the size of 10 cells so that the CRT cannot isolate just that region. Various CRTs may have a range of resolutions, such as 1 cell, 5 cells, 25 cells, or 100 cells. The cell colony 9208 is then allowed to proliferate through a combination of cell division and cell translation, resulting in cell colony 9212 having a larger desired spatial region 9214. A second cell removal operation may be performed, excising region 9216 from the cell colony 9212 and leaving a smaller cell colony 9218 that is enriched (i.e., a higher proportion of cells in the cell colony 9218 are cells originating from the desired spatial region 9214).

Cell colony 9218 may proliferate and expand again, resulting in cell colony 9220 having an even larger desired spatial region 9222. The spatial region 9222 may now be large enough for the spatial resolution of the CRT to isolate it completely without leaving a margin. Thus, a final cell removal operation may excise region 9224, leaving cell colony 9226 that is composed entirely of cells deriving from the original spatial region 9204. The cell colony 9226 may be expanded into cell colony 9228, which is ready for retrieval. Throughout the process shown in FIG. 92, the CRT may be controlled to isolate the desired region purely from a pre-existing model of how cells proliferate and migrate. Alternatively, the cells may be tracked using periodic imaging and an optical flow-type algorithm to track the evolution of the desired regions. In other implementations, the desired region may have an observable characteristic in imaging (whether transmission, fluorescence, spectroscopic, or other imaging) that allows it to be tracked. For example, this process may be combined with techniques described herein for enriching properly gene edited regions of cell cultures/cell colonies that co-express fluorescent markers.

Figure 93:
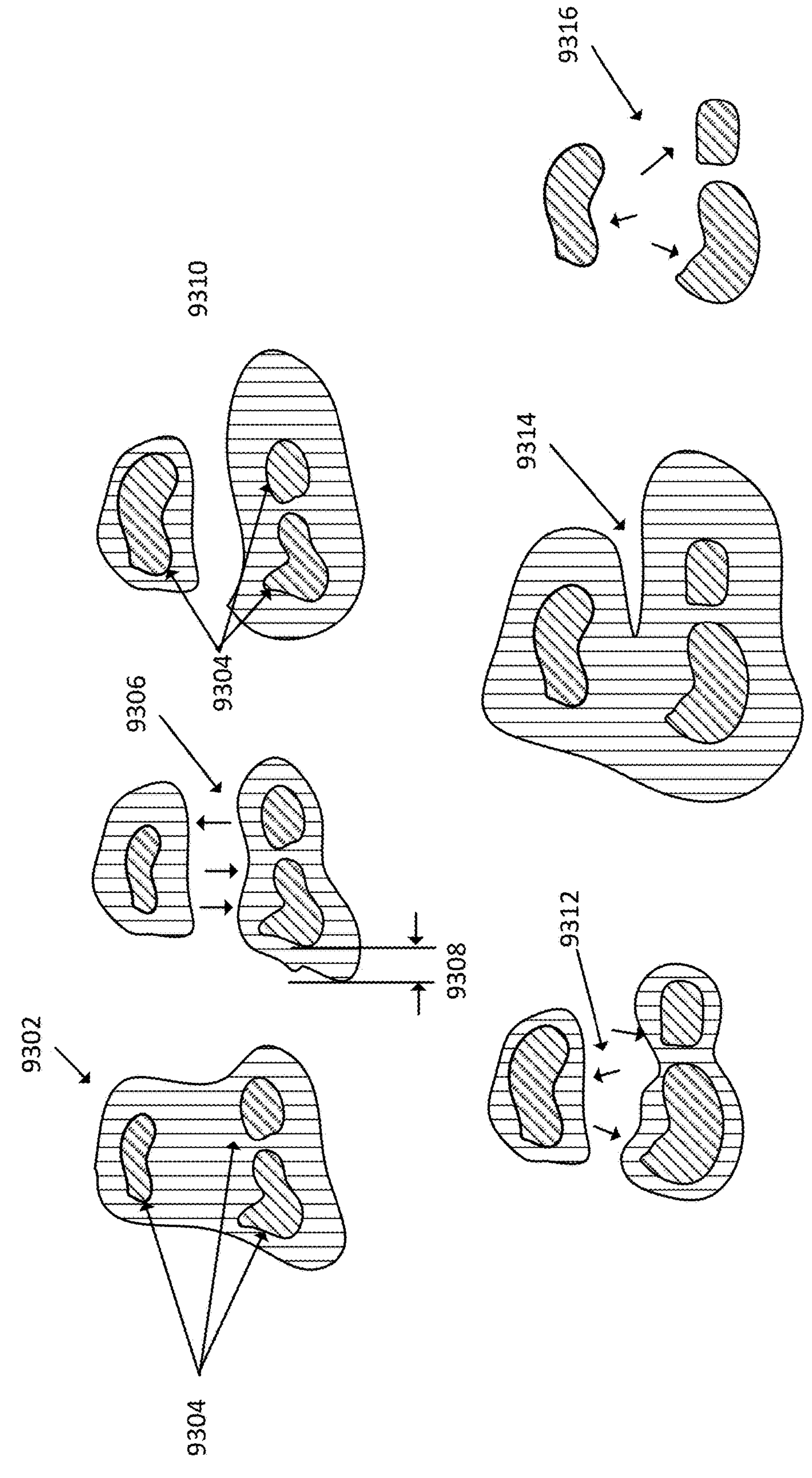
FIG. 93 is a diagram illustrating another example of spatially-selective colony expansion in accordance with various implementations.

FIG. 93 is a diagram 9300 illustrating another example of spatially-selective colony expansion in accordance with various implementations. The diagram 9300 illustrates a process for isolating material from multiple desirable regions 9304 within a starting cell colony 9302. After the desired regions 9304 are identified, a removal pattern 9306 is generated based on the accuracy of the CRT, taking into account a margin 9308 because the size of the desired regions 9304 is smaller than the spatial resolution of the CRT. The removal pattern 9306 may be generated by a computing subsystem of a cell culture system. The CRT is controlled to ablate cells not belonging to the desirable regions plus the margin. The resulting cell colonies 9310 are allowed to expand, with the desirable regions within the cell colonies also expanding their areas.

Another removal pattern 9312 may be generated, that when performed by the CRT further enriches the cell colonies (i.e., increasing the proportion of cells that originate from the original desirable regions 9304 as shown in cell colony 9314). A final cell removal pattern 9316 may be generated that fully isolates cells originating from the original desirable regions 9304 alone. This is because the desirable regions 9304 have expanded large enough that the CRT may fully isolate them without leaving a margin of other cells. In some implementations, the sequence shown in FIG. 93 may be performed until each of the resulting sub-colonies is in itself clonal, the outgrowth of a single cell in the original cell colony 9302. After isolation, these enriched sub-colonies may be processed in various ways, including but not limited to: expanding them in place to form a larger enriched colony, expanding them while translating and managing to form larger independent colonies, downselecting based on observed characteristics including time series characteristics, sampling portions of the colonies for analysis, harvesting the colonies one by one, and/or harvesting all the colonies simultaneously.

In summary, the methods disclosed herein provide a way to expand one or more desirable portions of a larger cell colony when the CRT methods available have a spatial resolution that is larger than the size of the desirable portion. The methods may include identifying portions of a cell colony that are desirable for sampling, harvesting, or otherwise retrieving. For example, imaging and computing resources (e.g., cell imaging subsystem and computing subsystem of a cell culture system) may be used to identify desirable portions. The methods may include removing non-desirable portions of the cell colony using the CRT, leaving the desirable portions and some non-desired portions because the CRT cannot completely isolate the desirable portions. The pruned cell colony is allowed to expand, which also means the desirable portions are expanded as well. Iterative cycles of expansion and removal may be performed until the cells in the cell colony all originate from the desirable portions of the original cell culture.

Dynamic Cell Culture Expansion

Adherent cell expansion of proliferative cells is a constant challenge in cell culture manufacturing, particularly with pluripotent cells that are very sensitive to both over-density and over-passaging (meaning frequent passaging from one container to another). Thus, there is a need in the art for systems and methods of culturing adherent pluripotent cells that can dynamically reduce the density of the culture and minimize the number of passaging steps.

The systems and methods disclosed herein include methods for actively controlling adherent cell expansion using CRTs in a manner that allows a combination of more efficient use of cell culture containers (e.g., higher confluence at harvest) and more consistent density conditions for cells. Instead of repeated passaging, the systems and methods disclosed herein may maintain a cell culture that is continuously adhered to the same cell culture surface throughout the cell culture process and use in situ cell imaging and removal methods to manage the cell culture. While the processes disclosed herein may be applied to the expansion of cells, they may also be applied to cell differentiation processes or other cell processes that would preferably start with uniform, well-controlled cell densities over a cell culture container.

Figure 94:
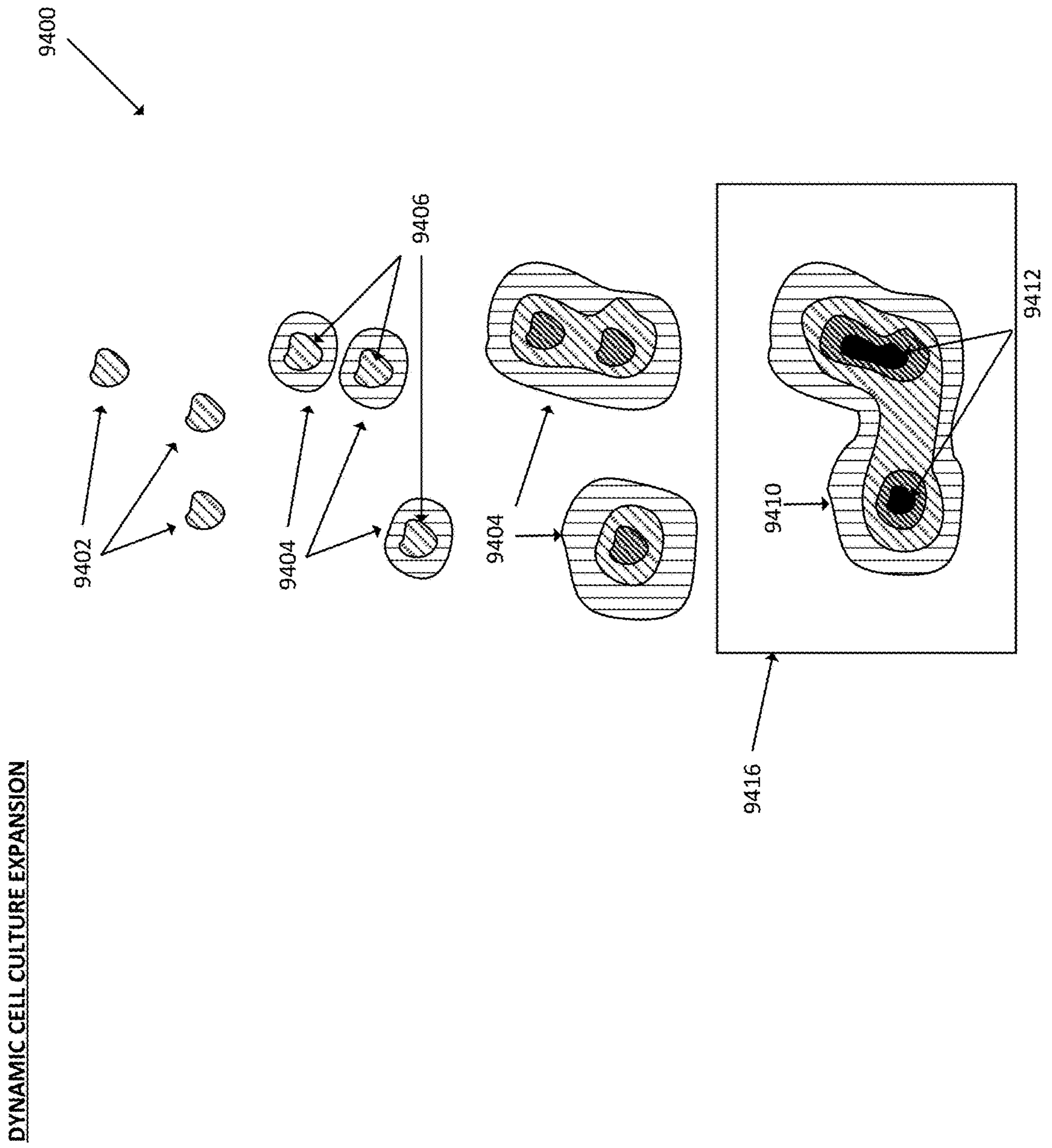
FIG. 94 is a diagram illustrating a conventional process for adherent cell culture expansion.

FIG. 94 is a diagram illustrating a conventional process 9400 for adherent cell culture expansion. The duration of a single round of expansion is typically bounded by a maximum confluence (the percentage of the cell culture surface that is covered by cells). For example, the expansion phase of a cell culture may be stopped at 70-80% confluence. The target confluence at the end of the expansion phase is meant to balance high cell numbers with overcrowding/over-density inside of cell colonies. Over-dense regions may cause contact-inhibited slowdown of cell proliferation as well as other gene expression/regulatory changes that may result in changes in phenotype, including but not limited to spontaneous differentiation of pluripotent cells, or mis-differentiation of cells in a differentiation process. Additionally, the resulting slowdowns (and wide distribution) of cell division rates may slow down and/or make cell processes less effective (such as vector clearance, epigenetic remodeling, telomere extension, etc.).

A cell culture container (e.g., cell culture container 104) may be seeded with an initial configuration of cells 9402, some of which may be arranged in clusters or colonies. The positioning of the seed cells 9402 is typically random, which means sometimes the cells 9402 may be distributed such that certain regions may be denser than others due to liquid flows and settling. The cells 9402 are allowed to proliferate for a period of time, resulting in enlarged cell colonies 9404. The centers 9406 of the cell colonies 9404 are denser than the outer edges due to how cells naturally proliferate. As proliferation continues, the cell colonies 9404 continue to expand and some may merge into larger colonies, shown as cell colonies 9408. The centers of the cell colonies 9408 have become even more dense as compared to the cell colonies 9404. Eventually, the cells reach a target confluence level, shown as cell colony 9410. The cell colony 9410 includes central regions 9412 that have reached an unhealthy cell density, so further expansion is not desired. However, at this point there still may be a significant amount of unused cell culture surface area in cell culture container 9414. As a result of the random distribution of the seed cells 9402, constraints on cell density, and lack of control over cell growth, this conventional process 9400 suffers from low efficiency as well as high variability.

Figure 95:
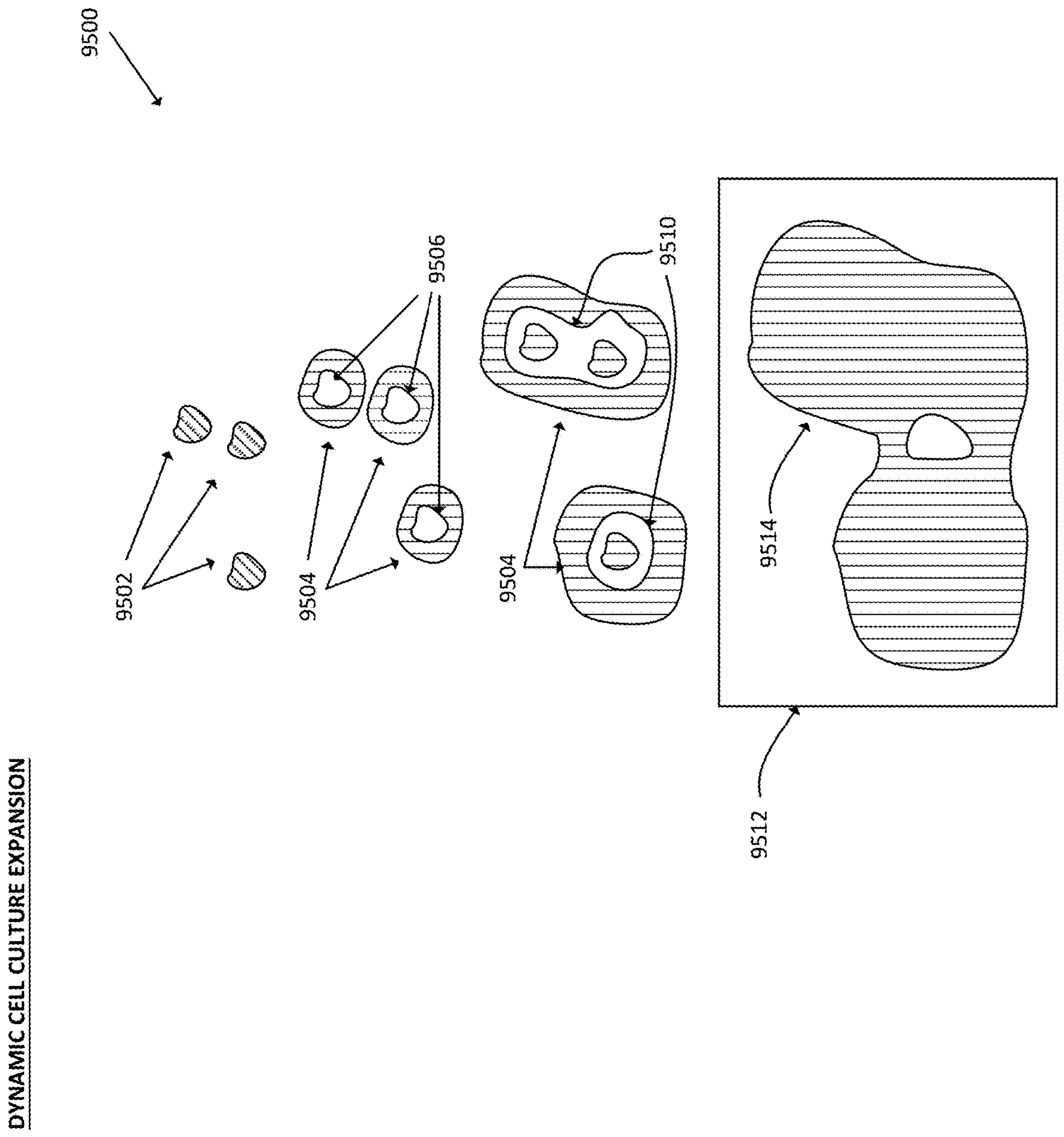
FIG. 95 is a diagram illustrating an example of dynamic cell culture expansion in accordance with various implementations.

FIG. 95 is a diagram 9500 illustrating an example of dynamic cell culture expansion in accordance with various implementations. The process shown in FIG. 95 is an example of a CRT-managed in situ adherent cell expansion process that avoids repeated passaging. A cell culture container (e.g., cell culture container 104) may be seeded with an initial configuration of cells 9502 in a random distribution, some of which may be arranged in clusters or colonies. The cells 9502 may be allowed to proliferate into cell colonies 9504, in which their centers are denser than the outer edges. However, the CRT (in conjunction with imaging and computing resources) may be used to remove or preemptively remove the regions that would become higher density (e.g., the center regions of the cell colonies 9504), as indicated by the removed regions 9506.

As proliferation continues, the cell colonies 9504 continue to expand and some may merge into larger colonies, shown as cell colonies 9508. The CRT may be used again to remove or preemptively remove regions that would become higher density, shown by removed regions 9510. The cell colonies may continue to expand within cell culture container 9512, resulting in cell colony 9514. As compared to the cell colony 9410 in FIG. 94 under the conventional proliferation process, the cell colony 9514 that has been dynamically density managed has a more uniform density distribution (and no regions that are over-dense), and/or a higher confluence (i.e., more used surface area in the cell culture container 9512). Thus, more of the cell culture container can be used, and the there is less variability in the end result due to density differentials experienced by the cells.

Figure 96:
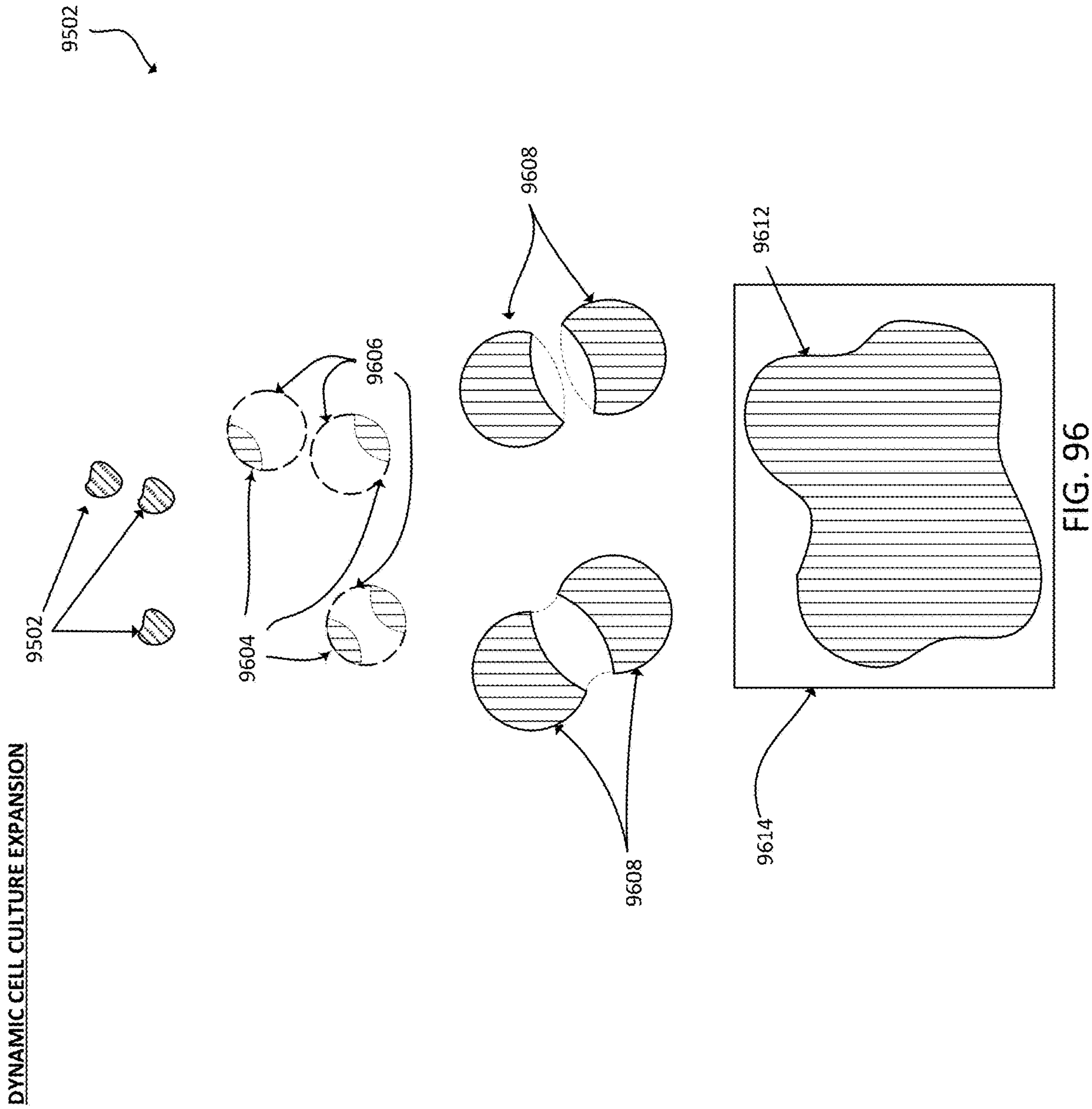
FIG. 96 is a diagram illustrating another example of dynamic cell culture expansion in accordance with various implementations.

FIG. 96 is a diagram 9600 illustrating another example of dynamic cell culture expansion in accordance with various implementations. The process shown in FIG. 96 is another example of a CRT-managed in situ adherent cell expansion process, this time also utilizing cell colony translation and splitting operations described herein to redistribute cell material to achieve even higher efficiency and density consistency. A cell culture container (e.g., cell culture container 104) may be seeded with an initial configuration of cells 9602 in a random distribution, some of which may be arranged in clusters or colonies. The cells 9602 may be allowed to proliferate into cell colonies 9604, with some portions of the cell colonies 9604 denser than other portions. However, the CRT (in conjunction with imaging and computing resources) may be used to remove sections of the cell colonies 9604 or split single colonies into multiple colonies (as indicated by the removed regions 9608) so that the remaining portions may be translated into more open space on the cell culture surface.

As proliferation continues, the remaining portions of the cell colonies 9604 expand into cell colonies 9608, some of which may merge or grow closer to each other. Another cell removal operation may be used to further separate and/or translate the cell colonies 9608, shown by removed regions 9610. The remaining portions of the cell colonies 9608 may continue to expand and merge into cell colony 9612 that fills a large portion of cell culture container 9614 and has a consistent density as compared to the cell colony 9410 in FIG. 94.

In summary, the methods disclosed herein provide a way to dynamically manage cell culture expansion to increase uniform density of the cell culture and surface area utilization of the cell culture container, all while avoiding passaging steps that may stress the cells or introduce imperfections to the cell culture. The method may include monitoring an adherent cell culture as it expands and then repeatedly removing cells using a CRT. The cell culture is adhered to the same cell culture surface throughout the cell culture process, as opposed to repeated passaging in which the cells are moved into different cell culture surfaces in different cell culture containers. In some implementations, the removed cells may be higher density regions of the cell culture. In some implementations, cells may be removed so that the remaining portion of the cell colonies may translate or proliferate into empty regions of the cell culture surface so that they continue to expand without reaching unhealthy levels of cell density. The end result is a more uniform density cell culture that maximizes space usage of the cell culture container. As opposed to conventional cell passaging techniques which target 60, 70, or 80% confluence before passaging and often have non-uniform density distributions (e.g., 10%-90% ranges of 2×, 3×, or even 4× in local cell density), the present implementations enables expansion to greater than 75%, 85% or even 90% confluence with cell density ranges (10%-90%) of less than 2.5×, less than 2×, even less than 1.5×.

The various CRT-enabled cell operations described herein may be used in any combination to assist in various cell culture processes. These cell operations include, for example, translation of a cell colony by removal of a portion of the colony, clonalization of a cell colony by repeated removal of portions of the colony, splitting of a cell colonies into multiple sub-colonies (which may then be translated to spread them out over a cell culture surface), isolation of a desired portion of a cell colony that is below the resolution of the CRT by repeated expansion and removal of portions of the colony, the use and removal of biocoatings to encourage or inhibit cell growth in certain regions of the cell culture surface, and removal and translation/washing of a portion of a cell colony for sampling.

High-Optionality iPSC Reprogramming

Induced pluripotent stem cell (iPSC) reprogramming processes have traditionally been difficult to perform consistently over many runs due to a number of variability factors. In addition, the process is often labor-intensive and requires many container-to-container transfers (i.e., passaging) that exposes cells to contamination or cross-contamination in a multi-patient, multi-clone environment. As a result of the extensive and often inconsistent handling, iPSC outputs from repeated reprogramming and expansion processes may suffer from a range of deficiencies when output cells are tests, including displaying abnormal karyotype, containing excess reprogramming vector, and lack of complete pluripotency needed to differentiate into any target tissue.

In addition, because of the lack of ability to observe colonies over extended periods during the process, it has been difficult to develop systems for making quality predictions in situ. Making such predictions would achieve a higher process yield, rather than the current method of screening output cells using expensive quality control (QC) assays at the end of the process. This also means that the time and resources used to bring the cells all the way through the cell culture process is wasted if the cells don't pass QC at the end. If in situ observation were possible, it would be advantageous to simultaneously screen a large number of candidate iPSC clones for the purpose of maximizing optionality. In machine learning terms, a real-time dynamic imaging, monitoring, and control system would work at the high-precision end of a typical precision-recall curve for a predictive model (i.e., the large number of clone options making a low recall acceptable, therefore getting maximum precision in good clone selection). Thus, there is a need in the art for consistent, repeatable cell culture processes that can monitor and change cell culture conditions dynamically to increase output yield.

The systems and methods disclosed herein include a method for iPSC reprogramming with high consistency, long-term maintenance, and observation of a large number of clones in parallel. The method takes advantage of precision image-guided CRTs and related cell/colony operations as described herein. Unlike conventional iPSC processes, or even CRT-based processes that down-select colonies early in the overall reprogramming process, the systems and methods described herein provide maximal optionality in the form of simultaneously maintained and tracked colonies for the majority of the cell culture process, thereby allowing more precise prediction of clone quality during down-selection. The systems and methods disclosed herein may also be combined with the iPSC gene-editing processes disclosed herein.

Figure 97:
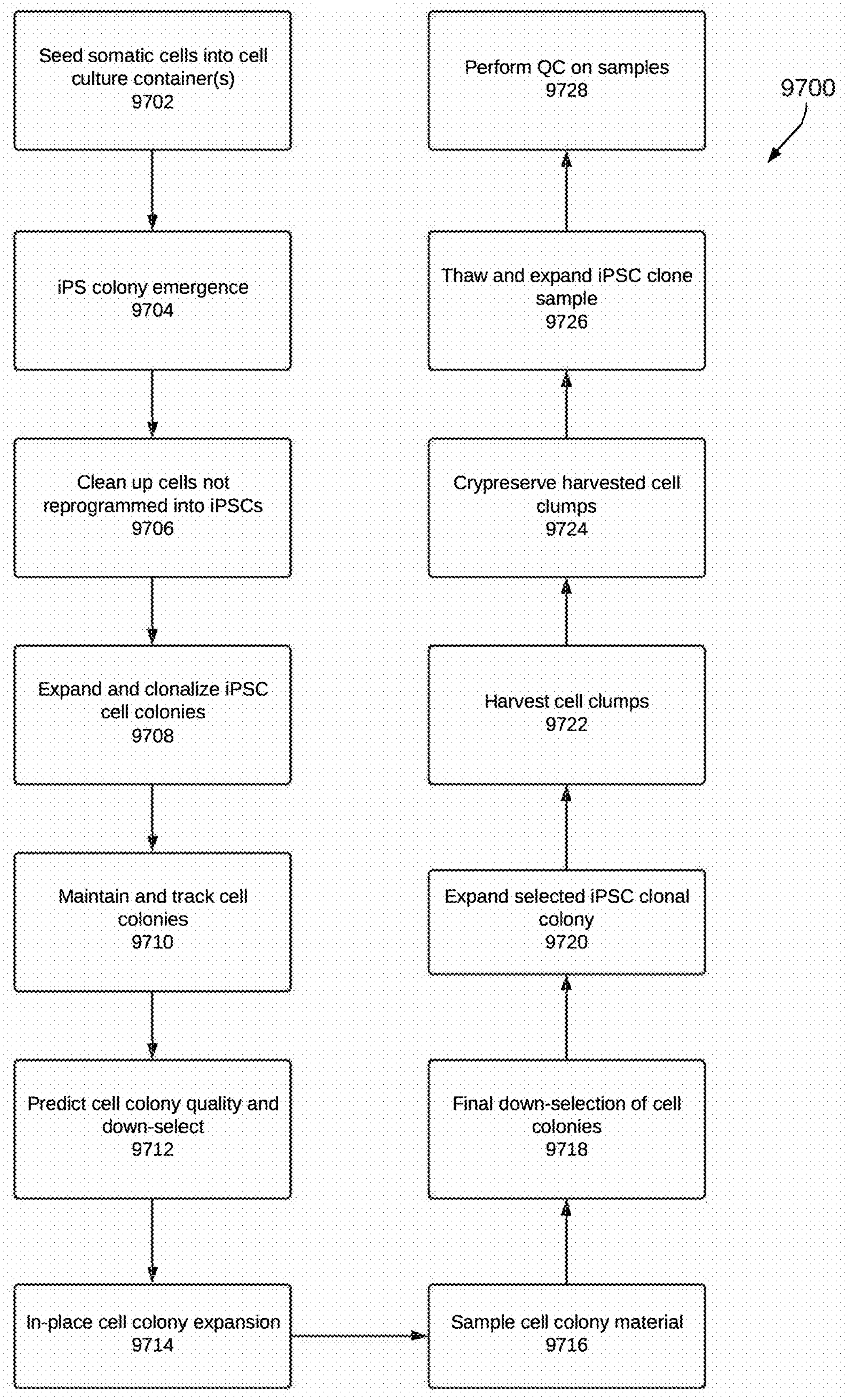
FIG. 97 is a flow chart depicting a method for an iPSC cell culture process in accordance with various implementations.

FIG. 97 is a flow chart depicting a method 9700 for an iPSC cell culture process in accordance with various implementations. The method 9700 may be performed by a cell culture system (e.g., cell culture system 100). The cell culture system may include, among other components, one or more cell culture containers for culturing cells, an imaging subsystem, a computing subsystem, and a cell editing subsystem (which may include various forms of CRTs as described herein). The cell culture containers may include open containers such as well plates, dishes, or flasks, or may be performed in closed fluidic containers (e.g., chambers, cassettes) as described herein. In the example discussed with reference to FIG. 97, the CRT may include a pulsed laser that targets a semi-transparent film on the cell growth surface (various implementations of which are disclosed herein) that is used to kill cells selectively, followed by a wash step that removes the dead cells from the cell culture container. The cell cultures may be continuously adhered to the cell culture surface of the cell culture containers throughout the majority of the method 9700.

The method 9700 begins in block 9702, in which patient somatic cells are seeded or placed into one or more cell culture containers. The cells may have had iPSC reprogramming vectors pre-delivered before seeding, or the vector may be delivered in the initial seeding step in block 9702. An imaging system may be used in this stage to assess cell density, and to re-start the run, or start additional runs, if it is deemed unacceptable. The target cell count may be varied on a per-patient basis, based on a pre-existing model of reprogramming efficiency and iPSC clone yield versus patient demographic, pre-existing conditions, or results of tests or assays. These tests and assays may include but are not limited to profiling of incoming patient somatic cell material (e.g., RNA sequencing, DNA sequencing, ATAC sequencing, and/or DNA methylation sequencing).

As the reprogramming vector acts all or a subset of the somatic cells, iPS-specific media may be introduced and at least a fraction of the somatic cells begin to emerge as pre-iPS cells, represented in block 9704. An imaging subsystem may be used to monitor these emergence events as indicated by changes in cell morphology and/or the formation of small cell colonies. A computing subsystem may analyze the images to determine the correct timing for the beginning of the cleanup phase. In block 9706, the computing subsystem may guide the CRT to clean up somatic cells that have not been reprogrammed into iPSCs. The cleanup phase may include in-place cleanup with image-guided use of the laser cell removal tool, in which the CRT removes cells that do not fit the profile of emerging iPSCs to enrich the cell culture for emerging iPSCs. This laser cleanup may be done in place, or maybe be combined with transfer of cells from one cell culture container to another. In the case of a transfer, a passaging reagent such as ReLeSr (produced by StemCell Technologies) that preferentially dissociates pluripotent stem cells may be used to preferentially transfer emerging iPSCs to a new cell culture container. There, the laser-based enrichment process may be repeated, and the transfer process may be repeated as well, until the cell culture is sufficiently enriched for emerging iPSCs.

Once the cleanup phase is complete, the resulting cell colonies may be processed in place for the remainder of the process 9700 (e.g., remain continuously adhered to the cell culture surface). In some implementations in which multiple clonal populations are desired at the end of the process 9700, the cells may be harvested and then redistributed to a number of independent cell culture containers (each ultimately yielding one clonal population) for the rest of the process 9700.

Then the process 9700 may proceed to iterations of colony expansion, imaging and analysis, and downselection, as represented by blocks 9708-9718. In some implementations, multiple independent growth chambers are used for the steps represented by blocks 9708-9718, with the entire process completed in a single chamber for each clone (e.g., 6 clonal populations coming out of 6 independent growth chambers). Particularly, the steps represented by blocks 9708-9718 may be performed entirely in a single cell culture container (e.g., non-passaged or passage-free culturing), although this process may have a duration over 30 or even over 60 days. During this phase, the iPSCs clear their reprogramming vector (primarily through cell division), remodel epigenetically, elongate their telomeres, and otherwise stabilize into stable, pluripotent iPSCs. Much of this remodeling and stabilization is thought to be driven by processes around cell division. Many of the problems associated with this phase in conventional processes surround the act of "passaging," or moving cells from one cell culture container to another to avoid overcrowding effects. The passaging process puts stress on cells, lowers cell division rates, and causes variability in cell conditions.

The cell culture management represented by blocks 9708-9718 may last over the course of many days, for example over at least 7 days, over at least 10 days, over at least 20 days, over at least 30 days, over at least 45 days, and over at least 60 days. During the course of the cell culture management represented by blocks 9708-9718, the cell population may double a number of times, for example at least 10 doublings, at least 20 doubling, at least 30 doublings, at least 40 doublings, or at least 100 doublings. The population doubling times may be, for example, 96 hours or less, 48 hours or less, 36 hours or less, 24 hours or less, 20 hours or less, or 18 hours or less. The one or more cell culture containers may each maintain a number of colonies, such as 1 colony, 2 or more colonies, 3 or more colonies, 5 or more colonies, 10 or more colonies, 25 or more colonies, or 50 or more colonies.

In the single-container stages of the process 9700, there will typically be multiple colonies per cell culture container. The objective is to simultaneously manage and track these colonies over a long period of time, giving the maximum observation time and therefore highest precision in a predictive model that ranks the cell colonies. Initially, there may be a downselection via CRT of cell colonies simply by spatial criteria. For example, colonies that reside too close to the edge of the cell culture container, or in a region of the cell culture container where fluid flow is unstable or unsuitable may be removed. Likewise, cell colonies that are in very dense clusters near one another, where CRT-based colony translation paths that keep them isolated cannot be computed, may also be removed. Whereas conventional iPSC processes may process multiple clones per patient through the stabilization/vector clearing phase, these clones must be kept in separate cell culture containers. In the present implementations, multiple clones may be processed inside of a single cell culture container throughout the expansion and clearing process. Whereas managing even 2 clones per cell culture container is not possible with conventional processes, the present implementations may allow 2 or more, 3 or more, 5 or more, 10 or more, or even 50 or more colonies to be managed through this entire stage simultaneously before final down-selection. However, there is utility in the present implementations even in the case that 1 colony is managed per well, because of the high consistency afforded, the traceability/trackability of features, and the elimination of passaging steps that disrupt cell processes, expose the sample to contamination, and add consumable and labor costs.

In the first step of the single-container or passage-free portion of the process 9700, the iPSCs in the cell culture container may expand and clonalize in block 9708. During expansion, the cell culture system may perform cell colony maintenance and tracking in block 9710. The clonalization step in block 9708 is done to assure that each cell colony being managed in the cell culture container is a clonal iPSC colony, derived from a single somatic cell. This is to ensure maximally descriptive QC data at the end of the process 9700, but also to maximize the utility of predictive models based on in situ colony tracking. For this reason, it is desirable to clonalize early in the cell culture process. Clonalization via CRT may be performed by various methods disclosed herein. For example, the cell colony may be iteratively downsized via CRT removal of portions of it and then allowed to regrow. This process of culling and regrowth gradually enriches the cell colony for cells descended from a single cell in the original cell colony. The clonalization may be performed by colony translation, splitting, or expansion-selection of a particular region using methods described herein.

After clonalization is complete, further colony maintenance and tracking as represented by block 9710 is performed to maintain iPSC colonies in a consistent state, track their behavior, and additional vector clearing and epigenetic remodeling processes. The maintenance and tracking step may include a number of sub-steps, such as imaging the cell colonies (using a range of imaging techniques, including label-free and quantitative phase imaging techniques); using models and algorithms potentially including deep learning models to map colony areas, map colony cell density, map cell pluripotency, track colonies location over time, and track colony characteristics over time (including but not limited to area, shape, approximate cell count, cell division rate, estimated cumulative number of cell divisions, cell density, cell morphology, level of spontaneous differentiation, etc.); using a model or algorithm to compute which region of the cell colony to remove with the CRT to best maintain its cell density and count, remove spontaneously differentiating cells, clonalize the cell colony, move it into regions with fresh ECM, avoid collisions with other colonies or borders within the cell culture container, or other functions; then use the laser-based CRT to remove these cells. In this manner, cell colonies may be kept in a consistent state relative to one another, even if their growth rates differ, and they may be observed over long periods of time in a similar state.

The cell culture system may track a number of characteristics of the iPSC cell colonies to determine when to perform CRT-based removal of portions of the cell colonies. These characteristics may include, for example, surface area, cell density, and cell count. The cell culture system may initiate cell removal when one or more of the characteristics exceeds a threshold amount. For example, cell density thresholds that above which may trigger CRT removal of portions of cell colonies may be, for example, 750,000 cells/$cm^2$, 500,000 cells/$cm^2$, 400,000 cells/$cm^2$, 300,000 cells/$cm^2$, or 250,000 cells/$cm^2$. Cell density may also be calculated in terms of multiples of the initial cell density (e.g., 1.5, 2, 2.5, 3, 5, or 5 times the initial cell density, either measured at single timepoints or mean values over time periods). In another example, colony surface area may be measured through imaging and portions of cell colonies may be removed if the colony surface area exceeds a threshold amount (e.g., an increase in surface area that is 5, 10, 20, 30, 50, or 100 times the initial surface area). In another example, cell count may be measured through imaging and portions of cell colonies may be removed if the cell count exceeds a threshold amount (e.g., an increase in cell count that is 5, 10, 20, 30, 50, or 100 times the initial surface area).

In block 9712, the cell culture system may perform prediction and down-selection. Prediction may include predicting which cell colonies are high quality, or in other words have the best probability to result in viable clonal iPSC output products at the end of the process 9700 based on imaging and other data. Down-selection means selecting those cell colonies with the highest quality and removing the other colonies. The data accumulated during the colony maintenance and tracking step in block 9710 may be used in the prediction and down-selection step in block 9712. In some implementations, the prediction and down-selection step may be run in parallel to the maintenance and tracking step so that colonies with very low predictions are removed early. In alternate implementations, all cell colonies may be managed through a final prediction and down-selection step. The predictive model may be informed by a variety of data, including the colony tracking data described herein. In some implementations, the down-selection may reduce the number of managed cell colonies, but does not yet reduce them to a single cell colony per desired output clone. For example, the predictive model may be run on 30 candidate cell colonies that have been tracked in the cell container, and all but the top 3 ranked via colonies are removed via CRT down-selection.

In block 9714, the remaining cell colonies may be expanded in-place. Methods including dynamic expansion involving splitting and translation, which is described herein, may be used to expand cell colonies while maintaining optimal conditions for iPSC proliferation and pluripotency.

In block 9716, cell material from each of the candidate cell colonies may be sampled/harvested using harvesting and extraction processes described herein or otherwise known in the art. Multiple methods described herein using the CRT to separate, isolate, and extract cells and/or cell material may be employed. The cell material for a single cell colony may be removed via a liquid step, and may be profiled for properties including but not limited to: karyotype, reprogramming vector clearance, pluripotency, RNAseq profile, DNA profile, etc. While these tests are performed, cell colonies may continue to be managed via the CRT.

In block 9718, the cell culture system performs a final down-selection. The down-selection may be based on the sampled material results from the sampling step in block 9716. The cell culture system may control the CRT to remove all but one candidate clonal iPSC colony. After a single clonal cell colony is isolated in block 9718, a colony expansion step shown in block 9720 is performed to generate the required number of cells for the clone. This step may include in-place expansion managed by the CRT, redistribution of cell material to cover a large portion of a cell culture container (which could be the same cell culture container used in previous steps or a new cell culture container, including multiple cell culture containers if a large number of cells is desired per clone), or combinations thereof, using methods described herein.

Following this expansion into a uniform-density, highly-confluent sheet of cells, in block 9722 the cell culture system may harvest one or more cell clumps from the expanded final iPSC clonal colony. For example, the cell sheet is first "scored" using the CRT to define small sectioned areas of cells that are the optimal size for clump harvesting and cryopreservation. Release of these clumps by various means is followed by harvest of the clumps, either in media that is subsequently replaced by cryoprotectant, or directly in the cryoprotectant solution, such that the clonal iPSC sample may be cryopreserved as shown in block 9724. Typically, multiple cryotubes with 1-2 million cells each will be frozen down for QC, banking, and downstream processes.

A quality measurement cycle may be performed following cryopreservation of clones. The quality measurement cycle may include thawing and then expanding an iPSC clone sample as indicated in block 9726. The expansion may be managed using the CRT-based methods described herein, or by conventional means. One measure of cell viability is measured via the survival through cryo and thawing, and subsequent proliferation. After expansion to sufficient numbers, the clonal population is run through various QC tests (e.g., iPSC assays) as shown in block 9728. If the iPSC samples pass the QC tests, other cryopreserved iPSC tubes may be released for other downstream processing (e.g., for use in iPSC-based cell therapies). The QC test results, even when they are not used for outgoing QC purposes, may used to inform the predictive models of in situ clone behavior. For example, the information may be used to further refine the ability to predict the quality of, and rank, iPSC colonies during the management, tracking, in-place expansion, and material sampling stages of the process 9700, thereby ultimately maximizing the yield of the overall process.

In summary, the method 9700 provides a way for producing an iPSC clonal output product from a somatic cell in a cell culture system that utilizes continuous imaging, monitoring, and cell removal in a passage-free manner. This method avoids the risks posed to cells through multiple passaging steps, allows in-situ monitoring and control of the cell culture in a closed, sealed environment, and generates large amounts of tracking data that may be used to ensure high quality end product and improve machine learning and other automated components of the system in future runs. The result is a high yield of high quality cell outputs that can meet the quality metrics for clinical medical therapies and applications.

Figure 98:
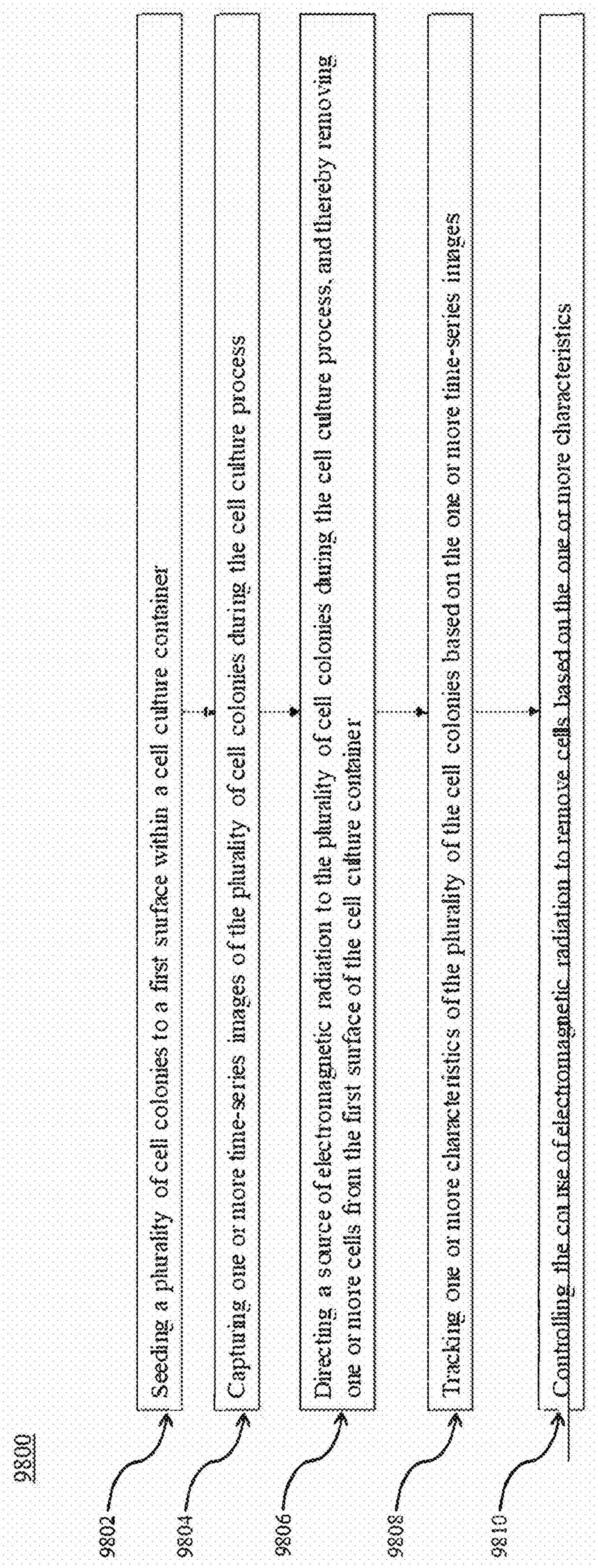
FIG. 98 is a flow chart depicting a method for a cell culture process in accordance with various implementations.

FIG. 98 is a flow chart of an exemplary method 9800 for culturing cells. In block 9802, the method may include seeding a plurality of cell colonies to a first surface within a cell culture container. In block 9804, the method may include capturing one or more time-series images of the plurality of the cell colonies during the cell culture process. In block 9806, the method may include directing a source of electromagnetic radiation to the plurality of cell colonies during the cell culture process, and thereby removing one or more cells from the first surface of the cell culture container. In block 9808, the method may include tracking one or more characteristics of the plurality of the cell colonies based on the one or more time-series images. In block 9810, the method may include controlling the course of electromagnetic radiation to remove cells based on the one or more characteristics.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise, and encompass "at least one." Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "flexible" as used herein refers to an object or material that is able to be bent or compressed without cracking or breaking. The term "semi-flexible" as used herein refers to an object or material that has a portion thereof that is able to be bent or compressed without cracking or breaking.

As used in any implementation herein, a "circuit" or "circuitry" may include, for example, singly or in any combination, hardwired circuitry, programmable circuitry, state machine circuitry, and/or firmware that stores instructions executed by programmable circuitry. An "integrated circuit" may be a digital, analog or mixed-signal semiconductor device and/or microelectronic device, such as, for example, but not limited to, a semiconductor integrated circuit chip.

The term "coupled" as used herein refers to any connection, coupling, link or the like by which signals carried by one system element are imparted to the "coupled" element. Such "coupled" devices, or signals and devices, are not necessarily directly connected to one another and may be separated by intermediate components or devices that may manipulate or modify such signals. Likewise, the terms "connected" or "coupled" as used herein in regard to mechanical or physical connections or couplings is a relative term and does not require a direct physical connection.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

It will be appreciated by those skilled in the art that any block diagrams herein represent conceptual views of illustrative circuitry embodying the principles of the disclosure. Similarly, it will be appreciated that any flow charts, flow diagrams, state transition diagrams, pseudocode, and the like represent various processes which may be substantially represented in computer readable medium and so executed by a computer or processor, whether or not such computer or processor is explicitly shown. Software modules, or simply modules which are implied to be software, may be represented herein as any combination of flowchart elements or other elements indicating performance of process steps and/or textual description. Such modules may be executed by hardware that is expressly or implicitly shown.

Also, various inventive concepts may be embodied as one or more methods, of which an example has been provided. The acts performed as part of the method may be ordered in any suitable way. Accordingly, implementations may be constructed in which acts are performed in an order different than illustrated, which may include performing some acts simultaneously, even though shown as sequential acts in illustrative implementations.

While various implementations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the implementations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific inventive implementations described herein. It is, therefore, to be understood that the foregoing implementations are presented by way of example only and that, within the scope of the appended claims and equivalents thereto, implementations may be practiced otherwise than as specifically described and claimed. In addition, any combination of two or more such features, systems, aspects, articles, materials, kits, and/or methods, if such features, systems, aspects, articles, materials, kits, and/or methods are not mutually inconsistent, is included within the inventive scope of the present disclosure. Particularly, any element of the disclosure and any aspect thereof may be combined, in any order and any combination, with any other element of the disclosure and any aspect thereof.

The above-described implementations can be implemented in any of numerous ways. For example, the implementations may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device. Also, a computer may have one or more input and output devices. These devices can be used, among other things, to present a user interface. Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Implementations of the methods described herein may be implemented using a processor and/or other programmable device. To that end, the methods described herein may be implemented on a tangible, non-transitory computer readable medium having instructions stored thereon that when executed by one or more processors perform the methods. The computer readable medium may include any type of tangible medium, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of media suitable for storing electronic instructions.

The terms "program" or "software" are used herein in a generic sense to refer to any type of computer code or set of computer-executable instructions that can be employed to program a computer or other processor to implement various aspects of implementations as discussed above. Additionally, it should be appreciated that according to one aspect, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various implementations. Also, data structures may be stored in computer-readable media in any suitable form.

Also, various inventive concepts may be embodied as one or more methods, of which an example has been provided. The acts performed as part of the method may be ordered in any suitable way. Accordingly, implementations may be constructed in which acts are performed in an order different than illustrated, which may include performing some acts simultaneously, even though shown as sequential acts in illustrative implementations.

Non-Transitory Computer Readable Storage Medium

In some implementations, the platforms, systems, media, and methods disclosed herein include one or more non-transitory computer readable storage media encoded with a program including instructions executable by the operating system of an optionally networked computing device. In further implementations, a computer readable storage medium is a tangible component of a computing device. In still further implementations, a computer readable storage medium is optionally removable from a computing device. In some implementations, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some implementations, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some implementations, a computer program comprises one sequence of instructions. In some implementations, a computer program comprises a plurality of sequences of instructions. In some implementations, a computer program is provided from one location. In other implementations, a computer program is provided from a plurality of locations. In various implementations, a computer program includes one or more software modules. In various implementations, a computer program includes, in part or in whole, one or more web applications, one or more mobile applications, one or more standalone applications, one or more web browser plug-ins, extensions, add-ins, or add-ons, or combinations thereof.

Software Modules

In some implementations, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various implementations, a software module comprises a file, a section of code, a programming object, a programming structure, or combinations thereof. In further various implementations, a software module comprises a plurality of files, a plurality of sections of code, a plurality of programming objects, a plurality of programming structures, or combinations thereof. In various implementations, the one or more software modules comprise, by way of non-limiting examples, a web application, a mobile application, and a standalone application. In some implementations, software modules are in one computer program or application. In other implementations, software modules are in more than one computer program or application. In some implementations, software modules are hosted on one machine. In other implementations, software modules are hosted on more than one machine. In further implementations, software modules are hosted on a distributed computing platform such as a cloud computing platform. In some implementations, software modules are hosted on one or more machines in one location. In other implementations, software modules are hosted on one or more machines in more than one location.

Databases

In some implementations, the platforms, systems, media, and methods disclosed herein include one or more databases, or use of the same. In view of the disclosure provided herein, those of skill in the art will recognize that many databases are suitable for storage and retrieval of image data, cell types, attribute categories, labels, assay data, or any combination thereof. In various implementations, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some implementations, a database is internet-based. In further implementations, a database is web-based. In still further implementations, a database is cloud computing-based. In a particular implementation, a database is a distributed database. In other implementations, a database is based on one or more local computer storage devices.

What is claimed is:

1. A system for culturing cells, comprising:
- a cell culture container comprising a first surface, the first surface being configured for a plurality of cell colonies to continuously adhere thereto throughout a cell culture process;
- an image sensor configured to capture one or more time-series images of the plurality of cell colonies during the cell culture process;
- a cell removal tool configured to remove one or more cells from the first surface of the cell culture container during the cell culture process; and
- a computing subsystem configured to:
  - track one or more characteristics of the plurality of cell colonies based on the one or more time-series images,
  - provide the one or more characteristics to a machine learning model,
  - receive therefrom an indication of which cells to remove, and
  - control the cell removal tool to remove those cells indicated.

2. The system of claim 1, wherein the cell culture process comprises manufacturing a plurality of clonal induced pluripotent stem cells (iPSCs) from a plurality of somatic cells.

3. The system of claim 2, wherein the cell culture process further comprises:
- reprogramming the plurality of somatic cells to form a plurality of iPSC colonies and wherein
- the computing subsystem is further configured to:
  - maintain a cell density of the plurality of iPSC cell colonies below a first threshold;
  - select a first clonal iPSC cell colony from the plurality of iPSC cell colonies;
  - remove the plurality of iPSC cell colonies from the first surface except for the first clonal iPSC cell colony; and
  - maintain a cell density of the first clonal iPSC cell colony below a second threshold amount while the first clonal iPSC colony expands.

4. The system of claim 3, wherein the first threshold is one of 750,000 cells/cm$^2$, 500,000 cells/cm$^2$, 400,000 cells/cm$^2$, 300,000 cells/cm$^2$, or 250,000 cells/cm$^2$.

5. The system of claim 3, wherein the second threshold is one of 750,000 cells/cm$^2$, 500,000 cells/cm$^2$, 400,000 cells/cm$^2$, 300,000 cells/cm$^2$, or 250,000 cells/cm$^2$.

6. The system of claim 1, wherein the cell culture process has a duration of one of: at least 7 days, at least 10 days, at least 20 days, at least 30 days, at least 45 days, or at least 60 days.

7. The system of claim 3, wherein maintaining the cell density of the plurality of iPSC cell colonies below the first threshold comprises iteratively removing portions of the plurality of iPSC cell colonies and expanding a remainder of the plurality of iPSC cell colonies.

8. The system of claim 3, wherein selecting the first clonal iPSC cell colony is based on the one or more characteristics.

9. The system of claim 8, wherein the first clonal iPSC cell colony has a highest clonal quality among the plurality of iPSC cell colonies based on the one or more characteristics.

10. The system of claim 3, wherein the cell culture process further comprises extracting a portion of the first clonal iPSC cell colony from the first cell culture container.

11. The system of claim 10, wherein the cell culture process further comprises:
- profiling the portion of the first clonal iPSC cell colony; and
- providing a resulting profile to the computing subsystem.

12. The system of claim 1, wherein the cell removal tool comprises a pulsed laser.

13. The system of claim 12, wherein the pulsed laser comprises one or more visible light lasers.

14. The system of claim 12, wherein the first surface comprises a laser film.

15. The system of claim 14, wherein the laser film is semi-transparent and has wavelength-selective absorption.

16. The system of claim 14, wherein the laser film is a plasmonic film.

17. The system of claim 14, wherein the laser film is configured to enable light-based cell imaging.

18. The system of claim 17, wherein the light-based cell imaging is within an imaging wavelength range detectible by the image sensor.

19. The system of claim 18, wherein the laser film is further configured to enable light-based cell removal within a removal wavelength range emitted by the pulsed laser, the removal wavelength range different from the imaging wavelength range.

20. The system of claim 14, wherein the laser film is absorptive of optical energy from the pulsed laser, thereby removing the one or more cells from the first surface.

21. The system of claim 14, wherein the laser film is at least partially absorptive of optical energy from the pulsed laser within a first range of wavelengths and at least partially transmissive of optical energy to the imaging sensor within a second range of wavelengths.

22. The system of claim 1, wherein the one or more characteristics are selected from: cell proliferation rate, cell count, colony surface area, colony area growth rate, colony morphology, and fluorescent marker expression.

23. The system of claim 1, wherein the cell removal tool comprises a continuous wave laser.

24. The system of claim 23, wherein the first surface comprises a laser film and a biocoating and wherein the continuous wave laser is configured to ablate the biocoating.

25. A method for culturing cells, comprising:
- introducing a plurality of cell colonies to a first surface of a cell culture container, the first surface being configured for a plurality of cell colonies to continuously adhere thereto throughout a cell culture process;
- capturing one or more time-series images of the plurality of cell colonies by an image sensor during a cell culture process;
- tracking, by a computing subsystem, one or more characteristics of the plurality of cell colonies based on the one or more time-series images;
- providing the one or more characteristics to a machine learning model;
- receiving therefrom an indication of which cells to remove; and controlling, by the computing subsystem, a cell removal tool to remove the indicated cells from the first surface of the cell culture container during the cell culture process.

26. A computer program product for culturing cells, the computer program product comprising a computer readable storage medium having program instructions embodied therewith, the program instructions executable by a processor to cause the processor to perform a method comprising:

receiving one or more time-series images of a plurality of cell colonies captured during a cell culture process, the plurality of cell colonies continuously adhered to a first surface throughout the cell culture process;

tracking, by a computing subsystem, one or more characteristics of the plurality of cell colonies based on the one or more time-series images;

providing the one or more characteristics to a machine learning model;

receiving therefrom an indication of which cells to remove; and controlling, by the computing subsystem, a cell removal tool to remove the indicated cells from a substrate during the cell culture process.

* * * * *